(12) United States Patent
Sinclair et al.

(10) Patent No.: US 11,477,955 B2
(45) Date of Patent: *Oct. 25, 2022

(54) MACHINE HARVESTABLE ICEBERG LETTUCE

(71) Applicant: Enza Zaden Beheer B.V., Enkhuizen (NL)

(72) Inventors: Jonathan Walker Sinclair, Hollister, CA (US); Sandra Escribano, Enkhuizen (NL)

(73) Assignee: Enza Zaden Beheer B.V., Enkhuizen (NL)

(*) Notice: Subject to any disclaimer, the term of this patent is extended or adjusted under 35 U.S.C. 154(b) by 0 days.

This patent is subject to a terminal disclaimer.

(21) Appl. No.: 17/100,607

(22) Filed: Nov. 20, 2020

(65) Prior Publication Data

US 2021/0112742 A1 Apr. 22, 2021

Related U.S. Application Data

(63) Continuation of application No. 16/224,771, filed on Dec. 18, 2018, now Pat. No. 10,874,071.

(60) Provisional application No. 62/609,261, filed on Dec. 21, 2017, provisional application No. 62/609,269, filed on Dec. 21, 2017.

(51) Int. Cl.
*A01H 6/14* (2018.01)
*A01H 5/12* (2018.01)

(52) U.S. Cl.
CPC ............ *A01H 6/1472* (2018.05); *A01H 5/12* (2013.01)

(58) Field of Classification Search
CPC ................................. A01H 6/1472; A01H 5/12
See application file for complete search history.

(56) References Cited

U.S. PATENT DOCUMENTS

| | | | |
|---|---|---|---|
| 3,731,477 | A | 5/1973 | Coon |
| 5,304,719 | A | 4/1994 | Segebart et al. |
| 5,367,109 | A | 11/1994 | Segebart et al. |
| 5,523,520 | A | 6/1996 | Hunsperger et al. |
| 5,763,755 | A | 6/1998 | Carlone et al. |
| 5,777,196 | A | 7/1998 | Hall et al. |
| 5,850,009 | A | 12/1998 | Kevern et al. |
| 5,948,957 | A | 9/1999 | Chapko et al. |
| 5,959,185 | A | 9/1999 | Streit et al. |
| 5,969,212 | A | 10/1999 | Getschman et al. |
| 5,973,232 | A | 10/1999 | Waycott et al. |
| 5,973,234 | A | 10/1999 | Mueller et al. |
| 5,977,445 | A | 11/1999 | Soper et al. |
| 6,492,579 | B2 | 12/2002 | Olivas et al. |
| 6,689,941 | B2 | 2/2004 | Waycott |
| 6,903,249 | B2 | 6/2005 | Lambalk et al. |
| 7,115,799 | B2 | 10/2006 | De Jong et al. |
| 7,371,930 | B1 | 5/2008 | Knerr |
| 7,371,934 | B1 | 5/2008 | Skrsyniarz et al. |
| 7,427,699 | B1 | 9/2008 | Skrsyniarz et al. |
| 7,501,555 | B2 | 3/2009 | Lambalk et al. |
| 7,579,520 | B1 | 8/2009 | Knerr et al. |
| 7,705,206 | B2 | 4/2010 | Waycott et al. |
| 7,790,948 | B2 | 9/2010 | Lambalk et al. |
| 7,960,617 | B2 | 6/2011 | Knerr |
| 7,977,536 | B2 | 7/2011 | Holland et al. |
| 8,183,437 | B2 | 5/2012 | Waycott et al. |
| 8,188,340 | B2 | 5/2012 | Holland et al. |
| 8,203,034 | B2 | 6/2012 | Waycott |
| 8,212,114 | B2 | 7/2012 | Holland et al. |
| 8,212,115 | B2 | 7/2012 | Holland et al. |
| 8,212,116 | B2 | 7/2012 | Lemont et al. |
| 8,389,810 | B2 | 3/2013 | Ammerlaan |
| 8,404,935 | B2 | 3/2013 | Holland et al. |
| 8,404,936 | B2 | 3/2013 | Skrsyniarz et al. |
| 8,410,338 | B2 | 4/2013 | Conijn et al. |
| 8,450,563 | B2 | 5/2013 | Nannes et al. |
| 8,471,105 | B2 | 6/2013 | Holland et al. |
| 8,471,106 | B2 | 6/2013 | Lemont et al. |
| 8,476,494 | B2 | 7/2013 | Nannes et al. |

(Continued)

FOREIGN PATENT DOCUMENTS

| | | |
|---|---|---|
| WO | WO2000063432 A1 | 10/2000 |
| WO | WO02/078428 A2 | 10/2002 |

(Continued)

OTHER PUBLICATIONS

Rijk Zwaan "Coronita RZ (51-607)" available at: https://rijkzwaan.nl/vind-uw-ras/sla/coronita-rz (undated).
Terranova, "Thinking vegetable seeds?", Nov. 2017.
"Eagle Flores, Frutas & Hortalicas", available at: http://eagleflores.com.br/2018/06/11/post-template-17/, dated Jun. 11, 2018.
Syngenta, "Leafy Salad Range", Jan. 2017, available at: https://www.syngenta.co.uk/file/31761/download?token=yGmwXoFR.
Brazilian National Variety Register, Registration No. 24732, Registration Date of Sep. 9, 2008, available at: https://www.gov.br/agricultura/pt-br/assuntos/imsumos-agropecuarios/insumos-agricolas/sementes-e-mudas/registro-nacional-de-cultivares-201-rnc-1.

(Continued)

*Primary Examiner* — Charles Logsdon
*Assistant Examiner* — Wayne Zhong
(74) *Attorney, Agent, or Firm* — Morrison & Foerster LLP

(57) ABSTRACT

Certain aspects of the present disclosure relate to upright heading iceberg lettuce plants including a space between the base of the head and the top of the ground, wherein the space includes an increased length of core outside of the processing material of the head (i.e., external stem). The increased external stem lengths of the upright heading iceberg lettuce plants of the present disclosure make them suitable for machine harvesting. Other aspects of the present disclosure relate to methods of generating and selecting upright heading iceberg lettuce plants. New upright heading iceberg lettuce varieties designated 'E01E.70111' Lot A, 'E01E.70111' Lot B, 'E01E.70168' Lot A, and 'E01E.70168' Lot B are described.

15 Claims, 80 Drawing Sheets
(56 of 80 Drawing Sheet(s) Filed in Color)

(56) References Cited

U.S. PATENT DOCUMENTS

| | | |
|---|---|---|
| 8,476,495 B2 | 7/2013 | Skrsyniarz et al. |
| 8,476,499 B2 | 7/2013 | Nannes et al. |
| 8,558,063 B2 | 10/2013 | Lemont et al. |
| 8,592,654 B2 | 11/2013 | Conijn et al. |
| 8,692,074 B2 | 4/2014 | Sinclair et al. |
| 8,692,075 B2 | 4/2014 | Lemont et al. |
| 8,766,039 B2 | 7/2014 | Skrsyniarz et al. |
| 8,772,578 B2 | 7/2014 | Ammerlaan |
| 8,772,580 B2 | 7/2014 | Holland et al. |
| 8,809,633 B2 | 8/2014 | Knerr |
| 8,809,634 B1 | 8/2014 | Roca et al. |
| 8,822,763 B2 | 9/2014 | Skrsyniarz et al. |
| 8,847,019 B2 | 9/2014 | Lemont et al. |
| 8,957,284 B2 | 2/2015 | Nannes et al. |
| 8,962,927 B2 | 2/2015 | Nannes et al. |
| 8,962,928 B2 | 2/2015 | Sinclair et al. |
| 8,987,559 B2 | 3/2015 | Winsemius et al. |
| 8,987,560 B2 | 3/2015 | Nannes et al. |
| 8,993,848 B2 | 3/2015 | Skrsyniarz et al. |
| 8,993,849 B2 | 3/2015 | Nannes et al. |
| 8,993,850 B2 | 3/2015 | Lemont et al. |
| 9,000,268 B2 | 4/2015 | Skrsyniarz et al. |
| 9,113,609 B2 | 8/2015 | Lemont et al. |
| 9,179,638 B2 | 11/2015 | Lemont et al. |
| 9,198,394 B2 | 12/2015 | Holland et al. |
| 9,277,726 B2 | 3/2016 | Holland et al. |
| 9,290,774 B2 | 3/2016 | Smits et al. |
| 9,313,994 B2 | 4/2016 | Skrsyniarz et al. |
| 9,320,250 B2 | 4/2016 | Ammerlaan |
| 9,332,725 B2 | 5/2016 | Holland et al. |
| 9,392,765 B2 | 7/2016 | Skrsyniarz et al. |
| 9,491,923 B2 | 11/2016 | Munoz Munoz |
| 9,556,493 B2 | 1/2017 | Roosenboom-Kooijmans |
| 9,572,321 B2 | 2/2017 | Lemont et al. |
| 9,635,828 B2 | 5/2017 | Nannes et al. |
| 9,743,633 B2 | 8/2017 | Holland et al. |
| 9,814,210 B2 | 11/2017 | Ammerlaan |
| 9,961,873 B2 | 5/2018 | Nannes et al. |
| 10,015,948 B2 | 7/2018 | Conijn et al. |
| 10,405,510 B2 | 9/2019 | Vriend |
| 10,506,773 B2 | 12/2019 | Nannes |
| 10,517,248 B2 | 12/2019 | Sinclair |
| 10,542,698 B2 | 1/2020 | Lemont |
| 10,582,681 B2 | 3/2020 | Sinclair et al. |
| 10,757,880 B2 | 9/2020 | Lemont |
| 10,874,071 B2 * | 12/2020 | Sinclair ............ A01H 5/12 |
| 11,089,751 B2 | 8/2021 | Lemont |
| 11,102,943 B2 | 8/2021 | Winsemius |
| 2004/0226060 A1 | 11/2004 | Lambalk et al. |
| 2005/0050596 A1 | 3/2005 | De Jong et al. |
| 2006/0005272 A1 | 1/2006 | Lambalk et al. |
| 2007/0214763 A1 | 9/2007 | Nash |
| 2009/0162515 A1 | 6/2009 | Dufresne et al. |
| 2009/0192040 A1 | 7/2009 | Grobler |
| 2009/0193535 A1 | 7/2009 | Ammerlaan et al. |
| 2009/0271890 A1 | 10/2009 | Lambalk et al. |
| 2010/0083398 A1 | 4/2010 | Holland et al. |
| 2010/0299777 A1 | 11/2010 | Lambalk et al. |
| 2011/0078812 A1 | 3/2011 | Holland et al. |
| 2011/0078813 A1 | 3/2011 | Holland et al. |
| 2011/0083223 A1 | 4/2011 | Holland et al. |
| 2011/0167510 A1 | 7/2011 | Lemont et al. |
| 2011/0191890 A1 | 8/2011 | Ammerlaan et al. |
| 2011/0197295 A1 | 8/2011 | Schryve et al. |
| 2011/0277176 A1 | 11/2011 | Conijn et al. |
| 2011/0296549 A1 | 12/2011 | Holland et al. |
| 2012/0005771 A1 | 1/2012 | Nannes et al. |
| 2012/0005772 A1 | 1/2012 | Nannes et al. |
| 2012/0011611 A1 | 1/2012 | Holland et al. |
| 2012/0011612 A1 | 1/2012 | Skrsyniarz et al. |
| 2012/0011613 A1 | 1/2012 | Skrsyniarz et al. |
| 2012/0042405 A1 | 2/2012 | Lemont et al. |
| 2012/0042406 A1 | 2/2012 | Lemont et al. |
| 2012/0073011 A1 | 3/2012 | Conijn et al. |
| 2012/0222149 A1 | 8/2012 | Nannes et al. |
| 2013/0024984 A1 | 1/2013 | Skrsyniarz et al. |
| 2013/0031663 A1 | 1/2013 | Sinclair et al. |
| 2013/0081149 A1 | 3/2013 | Lemont |
| 2013/0276160 A1 | 10/2013 | Holland et al. |
| 2013/0298270 A1 | 11/2013 | Skrsyniarz et al. |
| 2013/0298271 A1 | 11/2013 | Lemont et al. |
| 2013/0305399 A1 | 11/2013 | Lemont et al. |
| 2013/0305400 A1 | 11/2013 | Lemont et al. |
| 2013/0318646 A1 | 11/2013 | Nannes et al. |
| 2013/0333065 A1 | 12/2013 | Winsemius et al. |
| 2013/0340106 A1 | 12/2013 | Nannes et al. |
| 2013/0340107 A1 | 12/2013 | Nannes et al. |
| 2013/0340108 A1 | 12/2013 | Nannes et al. |
| 2013/0340109 A1 | 12/2013 | Skrsyniarz et al. |
| 2014/0033339 A1 | 1/2014 | Skrsyniarz et al. |
| 2014/0041069 A1 | 2/2014 | Nannes et al. |
| 2014/0041070 A1 | 2/2014 | Vriend et al. |
| 2014/0053289 A1 | 2/2014 | Sinclair et al. |
| 2014/0065286 A1 | 3/2014 | Moor et al. |
| 2014/0123335 A1 | 5/2014 | Ammerlaan |
| 2014/0189904 A1 | 7/2014 | Ammerlaan |
| 2014/0259193 A1 | 9/2014 | Lemont et al. |
| 2014/0259194 A1 | 9/2014 | Lemont et al. |
| 2014/0283159 A1 | 9/2014 | Lemont et al. |
| 2014/0283161 A1 | 9/2014 | Holland et al. |
| 2015/0020225 A1 | 1/2015 | Holland et al. |
| 2015/0150154 A1 | 5/2015 | Holland et al. |
| 2015/0164035 A1 | 6/2015 | Skrsyniarz et al. |
| 2015/0289469 A1 | 10/2015 | Holland et al. |
| 2015/0373942 A1 | 12/2015 | Skrsyniarz et al. |
| 2016/0157455 A1 | 6/2016 | Nannes |
| 2016/0198670 A1 | 7/2016 | Lemont et al. |
| 2017/0099800 A1 | 4/2017 | Holland et al. |
| 2017/0142925 A1 | 5/2017 | Nannes et al. |
| 2017/0251622 A1 | 9/2017 | Sinclair et al. |
| 2017/0258029 A1 | 9/2017 | Conijn et al. |
| 2017/0332594 A1 | 11/2017 | Roosenboom-Kooijmans |
| 2018/0228112 A1 | 8/2018 | Nannes |
| 2018/0242548 A1 | 8/2018 | Lemont |
| 2018/0249669 A1 | 9/2018 | Sinclair |
| 2018/0303054 A1 | 10/2018 | Vriend |
| 2018/0332813 A1 | 11/2018 | Lemont |
| 2019/0029211 A1 | 1/2019 | Lemont |
| 2019/0053456 A1 | 2/2019 | Lemont |
| 2019/0191652 A1 | 6/2019 | Sinclair |
| 2019/0335697 A1 | 11/2019 | Vriend et al. |
| 2020/0053972 A1 | 2/2020 | Sinclair |
| 2020/0084988 A1 | 3/2020 | Winsemius |
| 2020/0221662 A1 | 7/2020 | Skrsyniarz et al. |
| 2020/0375136 A1 | 12/2020 | Lemont |
| 2021/0037737 A1 | 2/2021 | Conijn et al. |
| 2021/0112742 A1 | 4/2021 | Sinclair |
| 2021/0251167 A1 | 8/2021 | Haggard |
| 2021/0345574 A1 | 11/2021 | Nannes et al. |
| 2022/0117183 A1 | 4/2022 | Winsemius |

FOREIGN PATENT DOCUMENTS

| | | |
|---|---|---|
| WO | WO2002078428 A2 | 10/2002 |
| WO | WO2008091996 A2 | 7/2008 |
| WO | WO2011058192 A1 | 5/2011 |
| WO | WO2012065629 A1 | 5/2012 |
| WO | WO2012085085 A1 | 6/2012 |
| WO | WO2020/125925 A1 | 6/2020 |
| WO | WO2020125925 A1 | 6/2020 |

OTHER PUBLICATIONS

Brazilian National Variety Register, Registration No. 25752, Registration Date of Jul. 7, 2009, available at: https://www.gov.br/agricultura/pt-br/assuntos/insumos-agropecuarios/insumos-agricola/sementes-e-mudas/registro-nacional-de-cultivares-2013-rnc-1.

"Eagle Flores, Frutas 7 Hortalicas", available at: http://eagleflores.com.be/2018/06/11/post-template-5, dated Jun. 11, 2018.

Buscador Portal Agricola, entry for "VERODITA Rz [41-115]", available at: https://www.buscador.portaltecnoagricola.com/semillas/esp/producto-semillas/VERODITA%20Rz%20%5B41-115%5D (2021).

(56) References Cited

OTHER PUBLICATIONS

Dave Perie Tweet on "CRISPOL from Nunhems", Jul. 23, 2015, available at: https://twitter.com/lettucedave/status/624373959803277312?lang=en.

Paramount Seeds Lettuce Greenhouse Seeds Shop, available at http://paramoundseeds.com/product-category/greenhouse-production/lettuce/ (undated).

"VERODITA RZ (41-115)", available at: https://www.rijkzwaan.com.au/find-your-variety/lettuce/verodita-rz (undated).

Staatscourant, Officiele uit gave van het Koninkrijk der Nederlanden sinds 1814 [Government Gazette,Official edition of the Kingdom of the Netherlands since 1814], Nr. 37058, Dec. 17, 2014, available at: https://zoek.officielebekendmikingen.nl/stcrt-2014-37058.html.

Anonymous Third Party Submission under 37 CFR1.290, Letter, Form, and Comments, filed on Jun. 30, 2021 in the matter of U.S. Appl. No. 16/224,771, 46 pages.

MARKONCooperative, "Live from the Fields: Seeder in Iceberg Lettuce, Salinas Valley, Ca", YouTube, Sep. 10, 2014, available at: https://www.youtube.com/watch?v=WvvfCXllOcU.

"Lettuce News Magazine for Scandinavia", Rijk Zwaan, Mar. 2017.

Anonymous Third Party Submission under 37 CFR 1.501, Letter, Form, and Comments, filed on Jun. 30, 2021 in the matter of U.S. Pat. No. 10,874,071, 46 pages.

Enza Zaden USA, Inc. Apr. 2021. 'Burgandy'. Vegetable Seed Catalogue USA & Canada 2021, p. 13. Obtained on Sep. 14, 2021. Available online at <https://www.yumpu.com/en/document/view/65574518/vegetable-seed-catalogue-usa-canada-2021>.

Enza Zaden USA, Inc. Apr. 2021. 'Casey'. Vegetable Seed Catalogue USA & Canada 2021, p. 26. Obtained on Sep. 14, 2021. Available online at <https://www.yumpu.com/en/document/view/65574518/vegetable-seed-catalogue-usa-canada-2021>.

Enza Zaden USA, Inc. Apr. 2021. 'Ezbruke'. Vegetable Seed Catalogue USA & Canada 2021, p. 15. Obtained on Sep. 14, 2021. Available online at <https://www.yumpu.com/en/document/view/65574518/vegetable-seed-catalogue-usa-canada-2021>.

Enza Zaden USA, Inc. Apr. 2021. 'Pueblo'. Vegetable Seed Catalogue USA & Canada 2021, p. 22. Obtained on Sep. 14, 2021. Available online at <https://www.yumpu.com/en/document/view/65574518/vegetable-seed-catalogue-usa-canada-2021>.

Bassett, M. J., (1975). The role of leaf shape in the inheritance of heading in lettuce (*Lactuca sativa* L.), Journal of the American Society for Horticultural Science, vol. 100, No. 2, pp. 104-105.

Bennetzen, et al., (1992). Approaches and progress in the molecular cloning of plant disease resistance genes, In Genetic Engineering, vol. 14, Ed. J.K. Setlow, Plenum Press, NY, pp. 99-124.

Bonnier, et al., (1992). New Sources of Major Gene Resistance in Lactuca to Bremia Lactucae, Euphytica 61, pp. 203-211.

DeBolle, et al., (1996). Antimicrobial peptides from Mirabilis jalapa and Amaranthus caudatus: expression, processing, localization and biological activity in transgenic tobacco, Plant Molec. Biol, vol. 31, pp. 993-1008.

DeVries, et al., (1994). Numerical morphological analysis of Lettuce cultivars and species (*Lactuca sect.Lactuca, Asteraceae*), Plant Systematics and Evolution, vol. 193, pp. 125-141.

Dufresne, et al., (2004). Genetic Sequences: How are they Patented?, Nature Biotechnology, vol. 22, No. 2, pp. 231-232.

Enza Zaden USA, Inc. Jan. 2020. 'Pueblo'. Vegetable Seed Catalogue USA & Canada 2020. Available online at <https://webkiosk.enzazaden.com/catalogue-usa-2020/62983894>, Obtained on Jul. 24, 2020. pp. 22 and 23.

Enza Zaden. Aug. 2019. 'Crispenza'. Hydroponic 2019 Brochure: Lettuce Endive Herbs. Available online at <https://webkiosk.enzazaden.com/hydroponic-international-2019/62782367>, Obtained on Jul. 24, 2020. pp. 26 and 27.

Enza Zaden. 'Somerset'. 2019 Seed Catalog. Available online at Khttp://www.enzazaden.us/products-and-services/our-products/Somerset> Obtained on May 6, 2019. 1 page.

Eshed, et al., (1996). Less-Than-Additive Epistatic Interactions of Quantitative Trait Loci in Tomato, Genetics, vol. 143, pp. 1807-1817.

Farrara, et al., (1987). Genetic analysis of factors for resistance to downy mildew (*Bremia tactucae*) in species of lettuce (*Lactuca sativa* and *L. serriola*), Plant Pathology, vol. 36, pp. 499-514.

Farrara, et al., (1987). Identification of New Sources of Resistance to Downy Mildew in *Lactuca* Spp, Hortscience, vol. 22, No. 4, pp. 647-649.

Kessell, et al., (1993). Recessive Resistance to Plasmopara lactucaeradicis Maps by Bulked Segregant Analysis to a Cluster of Dominant Disease Resistance Genes in Lettuce, Molecular Plant-Microbe Interactions, vol. 6. No. 6., pp. 722-728.

Kraft, et al., (2000). Linkage disequilibrium and fingerprinting in sugar beet, Theor. Appl. Genet., vol. 101, pp. 323-326.

Landry, et al., (1987). A Genetic Map of Lettuce (*Lactuca sativa* L.) With Restriction Fragment Length Polymorphism, Isozyme, Disease Resistance and Morphological Markers, Genetics, vol. 116, pp. 331-337.

Lebeda, et al., (1991). Further Investigation of the Specificity between Wild Lactuca of *Interactions* Spp. and Bremia lactucae Isolates from *Lactuca serriola*, Journal of Phytopathology, vol. 133, pp. 57-64.

Maisonneuve, Brigitte, (1987). Utilisation de la culture in vitro d'embryons immatures pour Tes croisements interspecifIques entre *Lactuca sativa* L. et *L. Saligna* L. ou *L. Virosa* L. etude des hybrides obtenus, ("Interspecific hybridization in *Lactuca* sp. using in vitro culture of immature embryos, and study of hybrid offspring"), Agronomie, vol. 7, No. 5, pp. 313-319. English Summary Included.

Maisonneuve, Brigitte, (1991). Inheritance of Resistance to Beet Western Yellows Virus in *Lactuca virosa* L., Hortscience, vol. 26, No. 12, pp. 1543-1545.

Maisonneuve, Brigitte, (2003). Lactuca virosa, a source of disease resistance genes for lettuce breeding: results and difficulties for gene introgression, Eucarpia Leafy Vegetables, CGN2003, pp. 61-67.

Maisonneuve, et al., (1994). Rapid mapping of two genes for resistance to downy mildew from *Lactuca seniote* to existing clusters of resistance genes, Theor Appl Genet, vol. 89, pp. 96-104.

Maisonneuve, et al., (1995). Sexual and somatic hybridization in the genus *Lactuca*, Euphytica, vol. 85, pp. 281-285.

Markoncooperative, Youtube, Uploaded Sep. 10, 2014, "Live from the Fields: Seeder in Iceberg Lettuce, Salinas Valley, CA," Available online at <https://www.youtube.com/watch?v=WvvfCXIIOcU>.

Michelmore, et al., (1984). The inheritance of virulence in Bremia lactucae to match resistance factors 3 4,5,6,8,9,10 and 11 in lettuce (*Lactuca sativa*), Plant Pathology, vol. 33, pp. 301-315.

Michelmore, et al., (1987). Transformation of lettuce (*Lactuca sativa*) mediated by Agrobacterium tumefaciens, Plant Cell Rep, vol. 6, pp. 439-442.

Michelmore, et al., (1993). Molecular Markers and Genome Analysis in the Manipulation of Lettuce Downy Mildew, Advances in Molecular Genetics of Plant-Microbe Interactions, pp. 517-523.

Michelmore, et al., (1998). Clusters of Resistance Genes in Plants Evolve by Divergent Selection and a Birth-and-Death Process, Genome Research, vol. 8, pp. 1113-1130.

National Weather Service Forecast Office, "Salinas, CA 2018 Yearly Climate Chart," downloaded Mar. 18, 2020. URL: <https://www.wrh.noaa.gov/climate/yeardisp.php?stn=KSNS&wfo=mtr&year=2018&span=Calendar+Year>. 2 pages.

National Weather Service Forecast Office, "Salinas, CA Feb. 2018 Monthly Climate Charts," downloaded Mar. 18, 2020. URL: <https://www.wrh.noaa.gov/climate/monthdisp.php?stn=KSNS&year=2018&mon=2&wfo=mtr>. 2 pages.

National Weather Service Forecast Office, "Salinas, CA May 2018 Monthly Climate Charts," downloaded Mar. 18, 2020. URL: <https://www.wrh.noaa.gov/climate/monthdisp.php?stn=KSNS&year=2018&mon=5&wfo=mtr>. 2 pages.

Pang, et al., (1992). Expression of a gene encoding a scorpion insectotoxin peptide in yeast, bacteria and plants, Gene, vol. 116, pp. 165-172.

Paran, et al., (1991). Identification of restriction fragment length polymorphism and random amplified polymorphic DNA markers linked to downy mildew resistance genes in lettuce, using near-isogenic lines, Genome, vol. 34, pp. 1021-1027.

(56) References Cited

OTHER PUBLICATIONS

Paran, et al., (1993). Development of reliable PCR-based markers linked to downy mildew resistance genes in lettuce, Theory of Applied Genetics, vol. 85, pp. 985-993.
Ryder, et al., (1992). Lettuce genetics: Inheritance, linkage and epistasis, J. Amer. Soc. Hort. Sci., vol. 117, No. 3, pp. 504-507.
Ryder, et al., (1999). Inheritance and epistasis studies of chlorophyll deficiency in lettuce, J. Amer. Soc. Hort. Sci., vol. 124, No. 6, pp. 636-640.
Simko et al., (2016). "Non-destructive Phenotyping of Lettuce Plants in Early Stages of Development with Optical Sensors," Front. Plant Sci., 7:1-19.
Stam, Piet, (1993). Construction of integrated genetic linkage maps by means of a new computer package: JoinMap, The Plant Journal, vol. 3, No. 5, pp. 739-744.
Thomas, et al., (1974). Lettuce production in the United States, In Agriculture Handbook No. 221. Agricultural Research Service of the United States Department of Aquiculture, 3 pages.
Unpublished U.S. Appl. No. 16/988,187, filed Aug. 7, 2020, titled "Lettuce Varieties 'Asakgreen', 'Ezelda', 'Casey', 'Crispenza', and Burgandy", (Copy not submitted herewith pursuant to the waiver of 37 C.F.R. § 1.98(a)(2)(iii)).
Waycott, et al., (1994). Differentiation of nearly identical germplasm accessions by a combination of molecular and morphologic analyses, Genome, vol. 37, No. 4, pp. 577-583.
Williams, et al., (1990). DNA polymorphisms amplified by arbitrary primers are useful as genetic markers, Nucleic Acids Research, vol. 18, No. 22, pp. 6531-6535.
Xinrun, et al., (1992). Genotypic effects on tissue culture response of lettuce cotyledons, J. Genet. & Breed, vol. 46, pp. 287-290.
Enza Zaden USA, Inc. Apr. 2021. 'Newcastle' and 'Paonia'. Vegetable Seed Catalogue USA & Canada 2021, p. 22. Obtained on Jan. 11, 2022. Available online at <https://www.yumpu.com/en/document/view/65574518/vegetable-seed-catalogue-USA-canada-2021>.
Enza Zaden. 'Casey'. Products & Services. Available online at <https://www.enzazaden.com/us/products-and-services/our-products/Lettuce/Casey>, Obtained on Mar. 10, 2022. 1 page.
Enza Zaden. 'Newcastle'. Products & Services. Available online at <https://www.enzazaden.com/us/products-and-services/our-products/Lettuce/Newcastle>, Obtained on Jan. 11, 2022. 1 page.
Enza Zaden. 'Paonia'. Products & Services. Available online at <https://www.enzazaden.com/us/products-and-services/our-products/Lettuce/Paonia>, Obtained on Jan. 11, 2022. 1 page.
Robinson et al., (1983). "Chapter 9: The Genes of Lettuce and Closely Related Species," Plant Breeding Reviews, pp. 267-293.
Sharma et al., (2018). "Assessment of genetic diversity in lettuce (*Lactuca sativa* L.) germplasm using RAPD markers," 3 Biotech, 8(1):9, 6 pages.
Unpublished U.S. Appl. No. 17/166,961, filed Feb. 3, 2020, titled ettuce Variety 'Airton', (Copy not submitted herewith pursuant to the waiver of 37 C.F.R. § 1.98(a)(2)(iii)).
Unpublished U.S. Appl. No. 17/330,184, filed May 25, 2021, titled "Lettuce Variety 'E01L.30617'," (Copy not submitted herewith pursuant to the waiver of 37 C.F.R. § 1.98(a)(2)(iii)).
Unpublished U.S. Appl. No. 17/551,123, filed Dec. 14, 2021, titled "Lettuce Variety 'Kailua'," (Copy not submitted herewith pursuant to the waiver of 37 C.F.R. § 1.98(a)(2)(iii)).
Unpublished U.S. Appl. No. 17/579,407, filed Jan. 19, 2022, titled "Lettuce Varieties 'Paonia' and 'Newcastle'," (Copy not submitted herewith pursuant to the waiver of 37 C.F.R. § 1.98(a)(2)(iii)).
Anonymous Third Party Observations Comments filed in the matter of International Patent Application No. PCT/EP2018/085203 on Apr. 16, 2021,62 pages.
Anonymous Third Party Observations Form filed in the matter of International Patent Application No. PCT/EP2018/085203 on Apr. 16, 2021, 5 pages.
Paramount Seeds, Inc. Mar. 2016, 'CRISPOL', Paramount Seeds Brochure, Available online at <https://paramountseeds.com/wp-content/uploads/2014/05/2016_03_Brochure_Lettuce.pdf>, Obtained on Apr. 27, 2021, 2 pages.
Paramount Seeds. 'CRISPOL Romaine-Iceberg Lettuce, Pelleted Seed.' Available online at <https://paramountseeds.com/product/crispol-romaine-iceberg-lettuce/>, Obtained on Apr. 27, 2021, 3 pages.

\* cited by examiner

MACHINE HARVESTABLE ICEBERG LETTUCE

CROSS REFERENCE TO RELATED APPLICATIONS

This application is a continuation of U.S. patent application Ser. No. 16/224,771, filed Dec. 18, 2018, which claims the benefit of U.S. Provisional Patent Application No. 62/609,261, filed Dec. 21, 2017, and U.S. Provisional Patent Application No. 62/609,269, filed Dec. 21, 2017, each of which is hereby incorporated by reference in its entirety.

FIELD OF THE INVENTION

The present disclosure relates to the field of plant breeding. In particular, the present disclosure relates to new and distinctive machine harvestable iceberg lettuce plants (*Lactuca sativa*).

BACKGROUND

Cultivated forms of lettuce belong to the highly polymorphic species *Lactuca sativa* that is grown for its edible head and leaves. As a crop, lettuce is grown commercially wherever environmental conditions permit the production of an economically viable yield. For planting purposes, the lettuce season is typically divided into three categories (i.e., early, mid, and late), with coastal areas planting from January to August, and desert regions planting from August to December. Fresh lettuce is consumed nearly exclusively as fresh, raw product and occasionally as a cooked vegetable.

*Lactuca sativa* is in the Cichorieae tribe of the Asteraceae (Compositae) family. Lettuce is related to chicory, sunflower, aster, dandelion, artichoke, and *Chrysanthemum*. *Sativa* is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce, also known as cutting lettuce, comes in many varieties, none of which form a head, and include the green oak leaf variety. Latin lettuce, also known as grasse-type lettuce, looks like a cross between romaine and butterhead. Stem lettuce has long, narrow leaves and thick, edible stems. Oilseed lettuce is a type grown for its large seeds that are pressed to obtain oil.

While iceberg lettuce is favored by consumers for the crisp texture of its leaves and its taste, iceberg heads are difficult to grow and process. For one, the growth of iceberg lettuce close to the ground, as well as its round shape, means that the heads must be harvested by hand. Machines are unable to cut iceberg varieties at the correct level (i.e. on the stem and sufficiently close to the ground), and so a large proportion of processing material is lost. More upright varieties, such as romaine, can be easily machine harvested because most of their processing material sits well above the ground. For another, the closely packed and tightly wrapped leaves of iceberg varieties mean that moisture is trapped within the iceberg head. This high level of moisture means that iceberg varieties are more susceptible to pathogens than more open varieties such as romaine. Finally, the round shape of iceberg as well as its tightly packed leaves mean that iceberg is primarily used in chopped salads. The iceberg head cannot be cleaned thoroughly enough, and the iceberg leaves are too deeply cupped to be used as individual leaves. In contrast, the open and upright stature of romaine allows easy cleaning and separation of individual leaves.

Lettuce is an increasingly popular crop. As worldwide lettuce consumption continues to increase, and the cost of labor continues to rise, there is a need for a new type of lettuce that combines the qualities of iceberg lettuce with the ability to be machine harvested. In particular, there is a need for a new type of lettuce with an upright stature and crisp-textured leaves that in addition is stable, high yielding, and agronomically sound.

SUMMARY OF THE INVENTION

In order to meet these needs, the present disclosure is directed to upright heading iceberg lettuce. In certain aspects, the present disclosure relates to an upright heading iceberg lettuce plant with a height to diameter ratio greater than or equal to about 1.0, a height of about 1.5 to about 3 times a height of a standard iceberg lettuce plant, a crisp leaf texture, and a closed head. In some embodiments, the upright heading iceberg lettuce plant further includes one or more characteristics from the group of a short core, a low level of internal tipburn, a low level of bottom rot, an increased number of leaves, a fast fill rate of leaves in a head, and a space between a base of a head and a top of a ground. In some embodiments, the space between the base of the head and the top of the ground is achieved by an increased length of core or an increased number of frame leaves outside of the processing material of a head.

Certain aspects of the present disclosure relate to an iceberg lettuce seed, wherein the seed produces an iceberg lettuce plant with an upright stature phenotype. In some embodiments, the upright stature phenotype includes a height to diameter ratio greater than or equal to about 1.0, a height of about 1.5 to about 3 times a height of a standard iceberg lettuce plant, a crisp leaf texture, and a closed head. In some embodiments, the iceberg lettuce plant further includes one or more characteristics from the group of: a short core, a low level of internal tipburn, a low level of bottom rot, an increased number of leaves, a fast fill rate of leaves in a head, and a space between a base of a head and a top of a ground.

Certain aspects of the present disclosure relate to an iceberg lettuce seed containing an upright stature allele at locus A, wherein the seed produces an iceberg lettuce plant with an upright stature phenotype. In some embodiments, the upright stature phenotype includes a height to diameter ratio greater than or equal to about 1.0, a height of about 1.5 to about 3 times a height of a standard iceberg lettuce plant, a crisp leaf texture, and a closed head. In some embodiments, the iceberg lettuce plant further includes one or more characteristics from the group of: a short core, a low level of internal tipburn, a low level of bottom rot, an increased number of leaves, a fast fill rate of leaves in a head, and a space between a base of a head and a top of a ground.

Certain aspects of the present disclosure relate to an iceberg lettuce plant produced from a cross of a first iceberg lettuce plant with a second iceberg lettuce plant, wherein the first iceberg lettuce plant produces an upright heading iceberg lettuce plant with a height to diameter ratio greater than or equal to about 1.0, about 1.5 to about 3 times a height of a standard iceberg lettuce plant, a crisp leaf texture, and a closed head, the second iceberg lettuce plant produces an upright heading iceberg lettuce plant with a height to diameter ratio greater than or equal to about 1.0, about 1.5 to about 3 times a height of a standard iceberg lettuce plant, a crisp leaf texture, and a closed head, and wherein the iceberg lettuce plant produced from the cross has a height to diameter ratio greater than or equal to about 1.0, a height of about 1.5 to about 3 times a height of a standard iceberg lettuce plant, a crisp leaf texture, and a closed head. In one embodiment, the first and second iceberg lettuce plants are 'E01E.70111' Lot A lettuce plants, a sample of 'E01E.70111' Lot A lettuce seed having been deposited under NCIMB Accession Number 42957. In another embodiment, the first and second iceberg lettuce plants are 'E01E.70111' Lot B lettuce plants, a sample of 'E01E.70111' Lot B lettuce seed having been deposited under NCIMB Accession Number 42962. In one embodiment, the first and second iceberg lettuce plants are 'E01E.70168' Lot A lettuce plants, a sample of 'E01E.70168' Lot A lettuce seed having been deposited under NCIMB Accession Number 42958. In another embodiment, the first and second iceberg lettuce plants are 'E01E.70168' Lot B lettuce plants, a sample of 'E01E.70168' Lot B lettuce seed having been deposited under NCIMB Accession Number 42963. In still another embodiment, the first iceberg lettuce plant is an 'E01E.70111' Lot A lettuce plant, a sample of 'E01E.70111' Lot A lettuce seed having been deposited under NCIMB Accession Number 42957. In a further embodiment, the second iceberg lettuce plant is an 'E01E.70168' Lot A lettuce plant, a sample of 'E01E.70168' Lot A lettuce seed having been deposited under NCIMB Accession Number 42958.

Certain aspects of the present disclosure relate to an iceberg lettuce plant produced from a cross of an 'E01E.70111' Lot A plant with a second 'E01E.70111' Lot A plant, a sample of 'E01E.70111' Lot A lettuce seed having been deposited under NCIMB Accession Number 42957, wherein the iceberg lettuce seed produced from the cross produces an iceberg lettuce with a height to diameter ratio greater than or equal to about 1.0, a height of about 1.5 to about 3 times a height of a standard iceberg lettuce plant, a crisp leaf texture, and a closed head.

Certain aspects of the present disclosure relate to an iceberg lettuce plant produced from a cross of an 'E01E.70111' Lot B plant with a second 'E01E.70111' Lot B plant, a sample of 'E01E.70111' Lot B lettuce seed having been deposited under NCIMB Accession Number 42962, wherein the iceberg lettuce seed produced from the cross produces an iceberg lettuce with a height to diameter ratio greater than or equal to about 1.0, a height of about 1.5 to about 3 times a height of a standard iceberg lettuce plant, a crisp leaf texture, and a closed head.

Certain aspects of the present disclosure relate to an iceberg lettuce plant produced from a cross of an 'E01E.70168' Lot A plant with a second 'E01E.70168' Lot A plant, a sample of 'E01E.70168' Lot A lettuce seed having been deposited under NCIMB Accession Number 42958, wherein the iceberg lettuce seed produced from the cross produces an iceberg lettuce with a height to diameter ratio greater than or equal to about 1.0, a height of about 1.5 to about 3 times a height of a standard iceberg lettuce plant, a crisp leaf texture, and a closed head.

Certain aspects of the present disclosure relate to an iceberg lettuce plant produced from a cross of an 'E01E.70168' Lot B plant with a second 'E01E.70168' Lot B plant, a sample of 'E01E.70168' Lot B lettuce seed having been deposited under NCIMB Accession Number 42963, wherein the iceberg lettuce seed produced from the cross produces an iceberg lettuce with a height to diameter ratio greater than or equal to about 1.0, a height of about 1.5 to about 3 times a height of a standard iceberg lettuce plant, a crisp leaf texture, and a closed head.

Certain aspects of the present disclosure relate to an iceberg lettuce plant produced from a cross of an 'E01E.70111' Lot A plant with a second 'E01E.70168' Lot A plant, a sample of 'E01E.70111' Lot A lettuce seed having been deposited under NCIMB Accession Number 42957, and a sample of 'E01E.70168' Lot A lettuce seed having been deposited under NCIMB Accession Number 42958, wherein the iceberg lettuce seed produced from the cross produces an iceberg lettuce with a height to diameter ratio greater than or equal to about 1.0, a height of about 1.5 to about 3 times a height of a standard iceberg lettuce plant, a crisp leaf texture, and a closed head.

In other aspects, the present disclosure provides an iceberg lettuce seed from the plants of any of the above embodiments. In another embodiment, the present disclosure is directed to iceberg lettuce plants grown from the seed of any of the above embodiments. In some embodiments of any of the above embodiments, the iceberg lettuce plant has a height to diameter ratio greater than or equal to about 1.0, a height of about 1.5 to about 3 times a height of a standard iceberg lettuce plant, a crisp leaf texture, and a closed head. In some embodiments, the iceberg lettuce plant further includes one or more characteristics from the group of: a crisp leaf texture, a short core, a low level of internal tipburn, a low level of bottom rot, an increased number of leaves, a fast fill rate of leaves in a head, and a space between a base of a head and a top of a ground.

Lettuce plant parts include lettuce heads, lettuce leaves, parts of lettuce leaves, pollen, ovules, flowers, and the like. In another embodiment, the present disclosure is directed to a plant part of the plants of any of the above embodiments. In another embodiment, the present disclosure is further directed to heads, leaves, parts of leaves, stems, roots, meristems, flowers, pollen, and ovules of the plants of any of the above embodiments. In another embodiment, the present disclosure is further directed to tissue culture of the plants of any of the above embodiments, and to plants regenerated from the tissue culture, where the plant has all the morphological and physiological characteristics of the plants of any of the above embodiments. In one embodiment, the plant regenerated from the tissue culture has all of the morphological and physiological characteristics of an iceberg lettuce plant produced by growing seed designated as 'E01E.70111' Lot A, representative sample of 'E01E.70111' Lot A lettuce seed having been deposited under NCIMB Accession Number 42957. In another embodiment, the plant regenerated from the tissue culture has all of the morphological and physiological characteristics of an iceberg lettuce plant produced by growing seed designated as 'E01E.70111' Lot B, representative sample of 'E01E.70111' Lot B lettuce seed having been deposited under NCIMB Accession Number 42962. In one embodiment, the plant regenerated from the tissue culture has all of the morphological and physiological characteristics of an iceberg lettuce plant produced by growing seed designated as 'E01E.70168' Lot A, representative sample of 'E01E.70168' Lot A lettuce seed having been deposited under NCIMB Accession Number 42958. In another embodiment, the plant regenerated from the tissue culture has all of the morphological and physiological characteristics of an iceberg lettuce plant produced by growing seed designated as 'E01E.70168' Lot B, representative sample of 'E01E.70168' Lot B lettuce seed having been deposited under NCIMB Accession Number 42963. In some embodiments, the present disclosure is directed to a plant part of any of the above embodiments of plants regenerated from tissue culture. In some embodiments, the present disclosure is further directed to heads, leaves, parts of leaves, stems, roots, meristems, flowers, pollen, and ovules of any of the above embodiments of plants regenerated from tissue culture.

In still another embodiment, the present disclosure is further directed to packaging material containing plant parts of the plants of any of the above embodiments. Such packaging material includes but is not limited to boxes, plastic bags, etc. The plant parts of the plants of any of the above embodiments may be combined with other plant parts of other plant varieties.

In another embodiment, the present disclosure is directed to methods of producing an herbicide resistant lettuce plant by introducing a gene conferring herbicide resistance into a lettuce plant produced by growing lettuce seed of any of the above embodiments, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant lettuce plants produced by such methods.

In another embodiment, the present disclosure is directed to methods of producing a pest or insect resistant lettuce plan by introducing a gene conferring pest or insect resistance into a lettuce plant produced by growing lettuce seed of any of the above embodiments, and to pest or insect resistant lettuce plants produced by such methods. In certain embodiments, the gene conferring pest or insect resistance encodes a *Bacillus thuringiensis* endotoxin.

In another embodiment, the present disclosure is directed to methods of producing a disease resistant lettuce plant by introducing a gene conferring disease resistance into a lettuce plant produced by growing lettuce seed of any of the above embodiments, and to disease resistant lettuce plants produced by such methods.

In another embodiment, the present disclosure is directed to methods of producing a lettuce plant with a value-added trait by introducing a gene conferring a value-added trait into a lettuce plant produced by growing lettuce seed of any of the above embodiments, where the gene encodes a protein selected from a ferritin, a nitrate reductase, and a monellin. Certain embodiments are also directed to lettuce plants having a value-added trait produced by such methods.

In another embodiment, the present disclosure provides for single gene converted plants of any of the above embodiments. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring lettuce gene.

In another embodiment, the present disclosure is directed to a method of making iceberg lettuce seeds, by a) crossing the plant of any of the above embodiments with another iceberg lettuce plant, and b) harvesting the seed from the cross. In still another embodiment, the present disclosure is further directed to lettuce plants, lettuce parts from the lettuce plants, and seeds produced therefrom where the lettuce plant is isolated by the breeding method of the disclosure.

In yet another embodiment, the present disclosure is further directed to a method of selecting lettuce plants with an upright stature, by a) crossing a first lettuce plant with a height to diameter ratio greater than or equal to about 1.0, a height of about 1.5 to about 3 times a height of a standard iceberg lettuce plant, a crisp leaf texture, and a closed head with a second lettuce plant with a height to diameter ratio greater than or equal to about 1.0, a height of about 1.5 to about 3 times a height of a standard iceberg lettuce plant, a crisp leaf texture, and a closed head, b) selecting offspring from the cross that have an improved set of characteristics including a height to diameter ratio greater than or equal to about 1.5, a height greater than or equal to about 2 to about 3 times a height of a standard iceberg lettuce plant, a crisp leaf texture, and a more tightly closed head, c) selfing or sibbing the offspring, and d) repeating steps b) and c) for multiple generations to produce inbred lines with the improved set of characteristics. In one embodiment, the characteristics used for selection in step b) further includes one or more characteristics from the group of a short core, a low level of internal tipburn, a low level of bottom rot, an increased number of leaves, a fast fill rate of leaves in a head, and a space between a base of a head and a top of a ground. In another embodiment, the space between the base of the head and the top of the ground is achieved by an increased length of core or an increased number of frame leaves outside of the processing material of the head. In still another embodiment, the present disclosure is further directed to lettuce plants, lettuce parts from the lettuce plants, and seeds produced therefrom where the lettuce plant is isolated by the breeding method of the disclosure.

In a further embodiment, the present disclosure relates to methods for developing lettuce plants in a lettuce plant breeding program using plant breeding techniques including recurrent selection, backcrossing, pedigree breeding, restriction fragment length polymorphism enhanced selection, genetic marker enhanced selection, and transformation. Seeds, lettuce plants, and parts thereof, produced by such breeding methods are also part of the disclosure.

In order to meet these needs, the present disclosure is directed to upright heading iceberg lettuce. In certain aspects, the present disclosure relates to an iceberg lettuce (*Lactuca sativa*) plant containing a genetic determinant that leads to the iceberg lettuce plant having an upright stature, wherein the genetic determinant is as contained in a lettuce plant representative seed of which was deposited with the NCIMB under accession numbers 42957, 42962, 42958, and 42963. In some embodiments, the genetic determinant is homozygously present. In some embodiments, the genetic determinant is heterozygously present. In some embodiments, the upright stature includes one or more characteristics from the group of: a ratio of plant height to diameter greater than about 1, a height of about 1.5 to about 3 times a height of a standard iceberg lettuce plant, a crisp leaf texture, and a closed head. In some embodiments, the lettuce further includes one or more characteristics from the group of: a short core, a low level of internal tipburn, a low level of bottom rot, an increased number of leaves, a fast fill rate of leaves in a head, and a space between a base of a head and a top of a ground.

In certain aspects, the present disclosure relates to an iceberg lettuce (*Lactuca sativa*) plant containing a genetic determinant that leads to the iceberg lettuce plant having an upright stature, wherein the upright stature comprises one or more characteristics from the group of: a ratio of plant height to diameter greater than about 1, a height of about 1.5 to about 3 times a height of a standard iceberg lettuce plant, a crisp leaf texture, and a closed head, and wherein the genetic determinant is as contained in a lettuce plant representative seed of which was deposited with the NCIMB under accession numbers 42957, 42962, 42958, and 42963. In some embodiments, the genetic determinant is homozygously present. In some embodiments, the genetic determinant is heterozygously present. In some embodiments, the lettuce further includes one or more characteristics from the group of: a short core, a low level of internal tipburn, a low level of bottom rot, an increased number of leaves, a fast fill rate of leaves in a head, and a space between a base of a head and a top of a ground.

Certain aspects of the present disclosure relate to the plants of any of the above embodiments, obtainable by crossing a first iceberg lettuce plant with a second iceberg lettuce plant, wherein at least one of the said plants comprises the genetic determinant as comprised in a lettuce plant representative seed of which was deposited with the NCIMB under accession numbers 42957, 42962, 42958, and 42963, or a progeny plant thereof carrying the genetic determinant, and selecting, preferably in the $F_2$ generation, for plants having an upright stature.

Certain aspects of the present disclosure relate to a seed from the plants of any of the above embodiments, wherein the seed contains the genetic determinant as present in seeds of which a representative sample was deposited with the NCIMB under accession numbers 42957, 42962, 42958, or 42963.

Certain aspects of the present disclosure relate to a progeny plant from plants of any of the above embodiments, wherein the plant contains the genetic determinant as present in seeds of which a representative sample was deposited with the NCIMB under accession numbers 42957, 42962, 42958, or 42963. In some embodiments, the genetic determinant is homozygously present. In some embodiments, the genetic determinant is heterozygously present.

Certain aspects of the present disclosure relate to a progeny plant from the seeds of any of the above embodiments, wherein the plant contains the genetic determinant as present in seeds of which a representative sample was deposited with the NCIMB under accession numbers 42957, 42962, 42958, or 42963. In some embodiments, the genetic determinant is homozygously present. In some embodiments, the genetic determinant is heterozygously present.

Certain aspects of the present disclosure relate to a propagation material derived from the plants of any of the above embodiments, wherein the plant contains the genetic determinant as present in seeds of which a representative sample was deposited with the NCIMB under accession numbers 42957, 42962, 42958, or 42963.

Certain aspects of the present disclosure relate to a propagation material derived from the seeds of any of the above embodiments, wherein the plant contains the genetic determinant as present in seeds of which a representative sample was deposited with the NCIMB under accession numbers 42957, 42962, 42958, or 42963.

Certain aspects of the present disclosure relate to a propagation material capable of growing into a plant of any of the above embodiments. In some embodiments, the propagation material is a microspore, pollen, ovary, ovule, embryo, embryo sac, egg cell, cutting, root, root tip, hypocotyl, cotyledon, stem, leaf, flower, anther, seed, meristem, protoplast, callus, or cell.

Certain aspects of the present disclosure relate to tissue culture from the plants of any of the above embodiments. In some embodiments, the tissue culture is from the propagation material capable of growing into a plant of any of the above embodiments. In some embodiments, the propagation material is a microspore, pollen, ovary, ovule, embryo, embryo sac, egg cell, cutting, root, root tip, hypocotyl, cotyledon, stem, leaf, flower, anther, seed, meristem, protoplast, callus, or cell.

Certain aspects of the present disclosure relate to a plant part from the plants of any of the above embodiments. In some embodiments, the plant part is a head, a leaf, or a portion thereof. In some embodiments, the plant part is a head.

In another embodiment, the present disclosure is directed to a method of producing an iceberg lettuce plant with an upright stature phenotype, by a) crossing a lettuce plant of any of the above embodiments with a second iceberg lettuce plant, wherein said second iceberg lettuce plant is a non-upright stature iceberg lettuce plant, to produce progeny; b) using said progeny of a) in a back-crossing breeding program with the iceberg lettuce plant of any of the above embodiments as the recurrent parent for one or more generations, to produce a progeny iceberg lettuce plant with an upright stature phenotype. In some embodiments, the upright stature phenotype includes one or more characteristics from the group of: a ratio of plant height to diameter greater than about 1, a height of about 1.5 to about 3 times a height of a standard iceberg lettuce plant, a crisp leaf texture, a closed head, a short core, a low level of internal tipburn, a low level of bottom rot, an increased number of leaves, a fast fill rate of leaves in a head, and a space between a base of a head and a top of a ground.

In another embodiment, the present disclosure is directed to a method of making iceberg lettuce seeds, by a) crossing the plant of any of the above embodiments with another iceberg lettuce plant, and b) harvesting the seed from the cross. In still another embodiment, the present disclosure is further directed to lettuce plants, lettuce parts from the lettuce plants, and seeds produced therefrom, wherein the lettuce plant is isolated by the breeding method of the disclosure.

In a further embodiment, the present disclosure relates to methods for developing lettuce plants in a lettuce plant breeding program using plant breeding techniques including recurrent selection, backcrossing, pedigree breeding, restriction fragment length polymorphism enhanced selection, genetic marker enhanced selection, and transformation. In some embodiments, the present disclosure relates to plants that have obtained the genetic constitution or gene complex of plants of any of the above embodiments that leads to the upright stature phenotype, either by crossing or by means of molecular biological techniques. In some embodiments, the present disclosure relates to the progeny of these plants that have maintained or acquired the trait of the upright stature of the invention. Seeds, lettuce plants, and parts thereof, produced by such breeding methods are also part of the disclosure.

In certain aspects, the present disclosure relates to an upright heading iceberg lettuce plant including a space between a base of a head and a top of a ground. In some embodiments, said space includes an increased length of core outside of a processing material of a head (i.e., external stem). In some embodiments, the iceberg lettuce plant further includes one or more characteristics selected from the group of a height to diameter ratio of about 1.3 to about 1.5, leaf strength between about 300 to 400 grams, about 40 to 50% overlapping leaves inside the processing material of the head, a short stem inside the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

Certain aspects of the present disclosure relate to an iceberg lettuce seed, wherein the seed produces an iceberg lettuce plant with an upright stature phenotype. In some embodiments, the upright stature phenotype includes a space between a base of a head and a top of a ground. In some embodiments, said space includes an increased length of core outside of a processing material of a head (i.e., external stem). In some embodiments, the upright stature phenotype further includes one or more characteristics selected from the group of: a height to diameter ratio of about 1.3 to about 1.5, leaf strength between about 300 to 400 grams, about 40 to 50% overlapping leaves inside the processing material of the head, a short stem inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

Certain aspects of the present disclosure relate to an iceberg lettuce plant produced from a cross of a first iceberg lettuce plant with a second iceberg lettuce plant, wherein the first iceberg lettuce plant is an upright heading iceberg lettuce plant including a space between a base of a head and a top of a ground, wherein said space includes an increased length of core outside of a processing material of a head (i.e., external stem), the second iceberg lettuce plant is an upright heading iceberg lettuce plant including a space between a base of a head and a top of a ground, wherein said space includes an increased length of core outside of a processing material of a head (i.e., external stem), and wherein the iceberg lettuce plant produced from the cross is an upright heading iceberg lettuce plant including a space between a base of a head and a top of a ground, wherein said space includes an increased length of core outside of a processing material of a head (i.e., external stem). In some embodiments, the first and second iceberg lettuce plants are 'E01E.70111' Lot A lettuce plants, a sample of 'E01E.70111' Lot A lettuce seed having been deposited under NCIMB Accession Number 42957. In some embodiments, the first and second iceberg lettuce plants are 'E01E.70111' Lot B lettuce plants, a sample of 'E01E.70111' Lot B lettuce seed having been deposited under NCIMB Accession Number 42962. In some embodiments, the first and second iceberg lettuce plants are 'E01E.70168' Lot A lettuce plants, a sample of 'E01E.70168' Lot A lettuce seed having been deposited under NCIMB Accession Number 42958. In some embodiments, the first and second iceberg lettuce plants are 'E01E.70168' Lot B lettuce plants, a sample of 'E01E.70168' Lot B lettuce seed having been deposited under NCIMB Accession Number 42963. In some embodiments, the first iceberg lettuce plant is an 'E01E.70111' Lot A lettuce plant, a sample of 'E01E.70111' Lot A lettuce seed having been deposited under NCIMB Accession Number 42957. In some embodiments, the second iceberg lettuce plant is an 'E01E.70168' Lot A lettuce plant, a sample of 'E01E.70168' Lot A lettuce seed having been deposited under NCIMB Accession Number 42958.

Certain aspects of the present disclosure relate to an iceberg lettuce plant produced from a cross of an 'E01E.70111' Lot A plant with a second 'E01E.70111' Lot A plant, a sample of 'E01E.70111' Lot A lettuce seed having been deposited under NCIMB Accession Number 42957, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce plant produced from a cross of an 'E01E.70111' Lot B plant with a second 'E01E.70111' Lot B plant, a sample of 'E01E.70111' Lot B lettuce seed having been deposited under NCIMB Accession Number 42962, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce plant produced from a cross of an 'E01E.70168' Lot A plant with a second 'E01E.70168' Lot A plant, a sample of 'E01E.70168' Lot A lettuce seed having been deposited under NCIMB Accession Number 42958, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce plant produced from a cross of an 'E01E.70168' Lot B plant with a second 'E01E.70168' Lot B plant, a sample of 'E01E.70168' Lot B lettuce seed having been deposited under NCIMB Accession Number 42963, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce plant produced from a cross of an 'E01E.70111' Lot A plant with a second 'E01E.70168' Lot A plant, a sample of 'E01E.70111' Lot A lettuce seed having been deposited under NCIMB Accession Number 42957, and a sample of 'E01E.70168' Lot A lettuce seed having been deposited under NCIMB Accession Number 42958, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce seed from the plants of any of the above embodiments. In another embodiment, the present disclosure is directed to iceberg lettuce plants grown from the seed of any of the above embodiments. In some embodiments of any of the above embodiments, the iceberg lettuce plant includes a space between a base of a head and a top of a ground, and said space includes an increased length of core outside of a processing material of a head (i.e., external stem). In some embodiments, the iceberg lettuce plant further includes one or more characteristics from the group of: a height to diameter ratio of about 1.3 to about 1.5, leaf strength between about 300 to 400 grams, about 40 to 50% overlapping leaves inside the processing material of the head, a short stem inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

Lettuce plant parts include lettuce heads, lettuce leaves, parts of lettuce leaves, pollen, ovules, flowers, and the like. In another embodiment, the present disclosure is directed to a plant part of the plants of any of the above embodiments. In another embodiment, the present disclosure is further directed to heads, leaves, parts of leaves, stems, roots, meristems, flowers, pollen, and ovules of the plants of any of the above embodiments. In another embodiment, the present disclosure is further directed to tissue culture of the plants of any of the above embodiments, and to plants regenerated from the tissue culture, where the plant has all the morphological and physiological characteristics of the plants of any of the above embodiments. In one embodiment, the plant regenerated from the tissue culture has all of the morphological and physiological characteristics of an iceberg lettuce plant produced by growing seed designated as 'E01E.70111' Lot A, representative sample of 'E01E.70111' Lot A lettuce seed having been deposited under NCIMB Accession Number 42957. In another embodiment, the plant regenerated from the tissue culture has all of the morphological and physiological characteristics of an iceberg lettuce plant produced by growing seed designated as 'E01E.70111' Lot B, representative sample of 'E01E.70111' Lot B lettuce seed having been deposited under NCIMB Accession Number 42962. In one embodiment, the plant regenerated from the tissue culture has all of the morphological and physiological characteristics of an iceberg lettuce plant produced by growing seed designated as 'E01E.70168' Lot A, representative sample of 'E01E.70168' Lot A lettuce seed having been deposited under NCIMB Accession Number 42958. In another embodiment, the plant regenerated from the tissue culture has all of the morphological and physiological characteristics of an iceberg lettuce plant produced by growing seed designated as 'E01E.70168' Lot B, representative sample of 'E01E.70168' Lot B lettuce seed having been deposited under NCIMB Accession Number 42963. In some embodiments, the present disclosure is directed to a plant part of any of the above embodiments of plants regenerated from tissue culture. In some embodiments, the present disclosure is further directed to heads, leaves, parts of leaves, stems, roots, meristems, flowers, pollen, and ovules of any of the above embodiments of plants regenerated from tissue culture.

In still another embodiment, the present disclosure is further directed to packaging material containing plant parts of the plants of any of the above embodiments. Such packaging material includes but is not limited to boxes, plastic bags, etc. The plant parts of the plants of any of the above embodiments may be combined with other plant parts of other plant varieties.

In another embodiment, the present disclosure is directed to methods of producing an herbicide resistant lettuce plant by introducing a gene conferring herbicide resistance into a lettuce plant produced by growing lettuce seed of any of the above embodiments, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant lettuce plants produced by such methods.

In another embodiment, the present disclosure is directed to methods of producing a pest or insect resistant lettuce plan by introducing a gene conferring pest or insect resistance into a lettuce plant produced by growing lettuce seed of any of the above embodiments, and to pest or insect resistant lettuce plants produced by such methods. In certain embodiments, the gene conferring pest or insect resistance encodes a *Bacillus thuringiensis* endotoxin.

In another embodiment, the present disclosure is directed to methods of producing a disease resistant lettuce plant by introducing a gene conferring disease resistance into a lettuce plant produced by growing lettuce seed of any of the above embodiments, and to disease resistant lettuce plants produced by such methods.

In another embodiment, the present disclosure is directed to methods of producing a lettuce plant with a value-added trait by introducing a gene conferring a value-added trait into a lettuce plant produced by growing lettuce seed of any of the above embodiments, where the gene encodes a protein selected from a ferritin, a nitrate reductase, and a monellin. Certain embodiments are also directed to lettuce plants having a value-added trait produced by such methods.

In another embodiment, the present disclosure provides for single gene converted plants of any of the above embodiments. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring lettuce gene.

In another embodiment, the present disclosure is directed to a method of making iceberg lettuce seeds, by a) crossing the plant of any of the above embodiments with another iceberg lettuce plant, and b) harvesting the seed from the cross. In still another embodiment, the present disclosure is further directed to lettuce plants, lettuce parts from the lettuce plants, and seeds produced therefrom where the lettuce plant is isolated by the breeding method of the disclosure.

In yet another embodiment, the present disclosure is further directed to a method of making upright heading iceberg lettuce plants, by a) crossing a first upright heading iceberg lettuce plant including a space between a base of a head and a top of a ground, wherein said space includes an increased length of core outside of a processing material of a head (i.e., external stem) with a second upright heading iceberg lettuce plant including a space between a base of a head and a top of a ground, wherein said space includes an increased length of core outside of a processing material of a head (i.e., external stem); b) selecting offspring lettuce plants including a space between a base of a head and a top of a ground, wherein said space includes an increased length of core outside of a processing material of a head (i.e., external stem); c) selfing or sibbing the offspring, and d) repeating steps b) and c) for multiple generations to produce inbred lines with the improved set of characteristics. In one embodiment, the characteristics used for selection in step b) further include one or more characteristics from the group of a height to diameter ratio of about 1.3 to about 1.5, leaf strength between about 300 to 400 grams, about 40 to 50% overlapping leaves inside the processing material of the head, a short stem inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material. In still another embodiment, the present disclosure is further directed to lettuce plants, lettuce parts from the lettuce plants, and seeds produced therefrom where the lettuce plant is isolated by the breeding method of the disclosure.

In a further embodiment, the present disclosure relates to methods for developing lettuce plants in a lettuce plant breeding program using plant breeding techniques including recurrent selection, backcrossing, pedigree breeding, restriction fragment length polymorphism enhanced selection, genetic marker enhanced selection, and transformation. Seeds, lettuce plants, and parts thereof, produced by such breeding methods are also part of the disclosure.

In addition to the exemplary aspects and embodiments described above, further aspects and embodiments will become apparent by reference by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows an exemplary iceberg lettuce cross-section at the bottom left, and an exemplary upright heading iceberg at the center of the image. FIG. 1B shows exemplary cosberg lettuce.

FIG. 8A shows the degree of overlapping of the upper part of the leaves. FIG. 8B shows the number of divisions of the leaf. FIGS. 8C-8E show leaf shapes. FIG. 8F shows leaf venation. FIG. 8G shows head shape in longitudinal section.

FIG. 9A shows an exemplary whole head and vertical cross section of head of cosberg lettuce variety 'Cosmopolitan' from Test 1. FIG. 9B shows an exemplary whole head and vertical cross section of head of cosberg lettuce variety 'Crunchita' from Test 1. FIG. 9C shows an exemplary whole head and vertical cross-section of romaine lettuce variety 'True Heart' from Test 1. FIG. 9D shows an exemplary whole head and vertical cross-section of romaine lettuce variety 'Solid King' from Test 1. FIG. 9E shows an exemplary whole head and vertical cross-section of upright heading iceberg lettuce variety 'E01E.70111' Lot A from Test 1. FIG. 9F shows an exemplary whole head and vertical cross-section of upright heading iceberg lettuce variety 'E01E.70111' Lot B from Test 1. FIG. 9G shows an exemplary whole head and vertical cross-section of upright heading iceberg lettuce variety 'E01E.70168' Lot A from Test 1. FIG. 9H shows an exemplary whole head and vertical cross-section of upright heading iceberg lettuce variety 'E01E.70168' Lot B from Test 1. FIG. 9I shows an exemplary whole head and vertical cross-section of iceberg lettuce variety 'Reliant' from Test 1. FIG. 9J shows an exemplary whole head and vertical cross-section of iceberg lettuce variety 'Steamboat' from Test 1.

FIG. 10A shows an exemplary whole head and vertical cross section of head of cosberg lettuce variety 'Cosmopolitan' from Test 2. FIG. 10B shows an exemplary whole head and vertical cross section of head of cosberg lettuce variety 'Crunchita' from Test 2. FIG. 10C shows an exemplary whole head and vertical cross-section of romaine lettuce variety 'True Heart' from Test 2. FIG. 10D shows an exemplary whole head and vertical cross-section of romaine lettuce variety 'Solid King' from Test 2. FIG. 10E shows an exemplary whole head and vertical cross-section of upright heading iceberg lettuce variety 'E01E.70111' Lot A from Test 2. FIG. 10F shows an exemplary whole head and vertical cross-section of upright heading iceberg lettuce variety 'E01E.70111' Lot B from Test 2. FIG. 10G shows an exemplary whole head and vertical cross-section of upright heading iceberg lettuce variety 'E01E.70168' Lot A from Test 2. FIG. 10H shows an exemplary whole head and vertical cross-section of upright heading iceberg lettuce variety 'E01E.70168' Lot B from Test 2. FIG. 10I shows an exemplary whole head and vertical cross-section of iceberg lettuce variety 'Reliant' from Test 2. FIG. 10J shows an exemplary whole head and vertical cross-section of iceberg lettuce variety 'Steamboat' from Test 2.

FIG. 11A shows an exemplary whole head and vertical cross section of head of cosberg lettuce variety 'Cosmopolitan' from Test 3. FIG. 11B shows an exemplary whole head and vertical cross section of head of cosberg lettuce variety 'Crunchita' from Test 3. FIG. 11C shows an exemplary whole head and vertical cross-section of romaine lettuce variety 'True Heart' from Test 3. FIG. 11D shows an exemplary whole head and vertical cross-section of romaine lettuce variety 'Solid King' from Test 3. FIG. 1E shows an exemplary whole head and vertical cross-section of upright heading iceberg lettuce variety 'E01E.70111' Lot A from Test 3. FIG. 11F shows an exemplary whole head and vertical cross-section of upright heading iceberg lettuce variety 'E01E.70111' Lot B from Test 3. FIG. 11G shows an exemplary whole head and vertical cross-section of upright heading iceberg lettuce variety 'E01E.70168' Lot A from Test 3. FIG. 11H shows an exemplary whole head and vertical cross-section of upright heading iceberg lettuce variety 'E01E.70168' Lot B from Test 3. FIG. 11I shows an exemplary whole head and vertical cross-section of iceberg lettuce variety 'Reliant' from Test 3. FIG. 11J shows an exemplary whole head and vertical cross-section of iceberg lettuce variety 'Steamboat' from Test 3.

FIG. 12A shows an exemplary whole head and vertical cross section of head of cosberg lettuce variety 'Cosmopolitan' from Test 4. FIG. 12B shows an exemplary whole head and vertical cross section of head of cosberg lettuce variety 'Crunchita' from Test 4. FIG. 12C shows an exemplary whole head and vertical cross-section of romaine lettuce variety 'True Heart' from Test 4. FIG. 12D shows an exemplary whole head and vertical cross-section of romaine lettuce variety 'Solid King' from Test 4. FIG. 12E shows an exemplary whole head and vertical cross-section of upright heading iceberg lettuce variety 'E01E.70111' Lot A from Test 4. FIG. 12F shows an exemplary whole head and vertical cross-section of upright heading iceberg lettuce variety 'E01E.70111' Lot B from Test 4. FIG. 12G shows an exemplary whole head and vertical cross-section of upright heading iceberg lettuce variety 'E01E.70168' Lot A from Test 4. FIG. 12H shows an exemplary whole head and vertical cross-section of upright heading iceberg lettuce variety 'E01E.70168' Lot B from Test 4. FIG. 12I shows an exemplary whole head and vertical cross-section of iceberg lettuce variety 'Reliant' from Test 4. FIG. 12J shows an exemplary whole head and vertical cross-section of iceberg lettuce variety 'Steamboat' from Test 4.

FIG. 13A shows exemplary images of the external (left image) and internal (right image) stem length measurement procedures. External stem was measured from the harvest cut point at base of head to the first frame leaf of the head, and internal stem was measured from the first frame leaf of the head to the end of the stem at the center of the head (shown in FIG. 29). FIG. 13N). For FIGS. 13B, 13E, 13H, 13K, and 13N, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar. FIG. 13O). FIG. 13P).

FIG. 14A shows an exemplary image of the lettuce head weight measurement procedure. FIGS. 14B-14F shows ANOVA analysis of the means of lettuce head weight measurement in g from Test 1 (FIG. 14B), Test 2 (FIG. 14C), Test 3 (FIG. 14D), Test 4 (FIG. 14E), and all tests (i.e., Tests 1-4; FIG. 14F). For FIGS. 14B-14F, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIG. 15A shows exemplary images of the lettuce head height (left image) and lettuce head width (right image) measurement procedures. FIGS. 15B-15F show ANOVA analysis of the means of lettuce head height and width measurements in cm from Test 1 (FIG. 15B), Test 2 (FIG. 15C), Test 3 (FIG. 15D), Test 4 (FIG. 15E), and all tests (i.e., Tests 1-4; FIG. 15F). For FIGS. 15B-15F, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIG. 16A shows an exemplary image of a lettuce head cut in half for use in the evaluation of the percentage of overlapping leaves procedure. FIGS. 16B-16F show ANOVA analysis of the means of the percentage of overlapping leaves data from Test 1 (FIG. 16B), Test 2 (FIG. 16C), Test 3 (FIG. 16D), Test 4 (FIG. 16E), and all tests (i.e., Tests 1-4; FIG. 16F). For FIGS. 16B-16F, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIG. 17A shows exemplary images of the leaf thickness measurement procedure. FIGS. 17B-17F show ANOVA analysis of the means of leaf thickness measurement in mm from Test 1 (FIG. 17B), Test 2 (FIG. 17C), Test 3 (FIG. 17D), Test 4 (FIG. 17E), and all tests (i.e., Tests 1-4; FIG. 17F). For FIGS. 17B-17F, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIG. 18A shows exemplary images of the measurement of leaf color using the spectrophotometer procedure. FIG. 18F). FIG. 18K). FIGS. 18L-18P show ANOVA analysis of the means of leaf gloss measurements from Test 1 (FIG. 18L), Test 2 (FIG. 18M), Test 3 (FIG. 18N), Test 4 (FIG. 18O), and all tests (i.e., Tests 1-4; FIG. 18P). For FIGS. 18B-18P, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIGS. 20A-20B show exemplary images of the measurement of leaf strength using the texturometer procedure. FIGS. 20C-20G show ANOVA analysis of the means of measurement of leaf strength using the texturometer procedure from Test 1 (FIG. 20C), Test 2 (FIG. 20D), Test 3 (FIG. 20E), Test 4 (FIG. 20F), and all tests (i.e., Tests 1-4; FIG. 20G). For FIGS. 20C-20G, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIG. 22A shows ANOVA analysis of the means of glucose, fructose, and sucrose measurements in g/l from all tests (i.e., Tests 1-4). FIG. 22B shows ANOVA analysis of the means of total sugar measurements in g/l from all tests (i.e., Tests 1-4). FIG. 22C shows ANOVA analysis of the sweetness factor from all tests (i.e., Tests 1-4). For FIGS. 22A-22C, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIGS. 24A-24B show exemplary images of plant material cutting. FIG. 24C shows exemplary images of plant material disinfection and drying. FIG. 24D shows an exemplary image of plant material weighing and packaging. FIGS. 24E-24F show exemplary images of the process to achieve modified atmospheric conditions (MAP) and the sealed bags with MAP. FIG. 24G shows an exemplary image of packaged plant material in storage.

FIGS. 25A, 25B, 25C, 25D, and 25F show box and whisker charts of the percentage of processing damage data from Test 1 (FIG. 25A), Test 2 (FIG. 25B), Test 3 (FIG. 25C), Test 4 (FIG. 25D), and all tests (i.e., Tests 1-4; FIG. 25F). FIG. 25E shows ANOVA analysis of the means of percentage of processing damage data from all tests (i.e., Tests 1-4). For FIG. 25E, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIGS. 26A, 26B, 26C, 26D, and 26F show box and whisker charts of the percentage of processing damage data from Test 1 (FIG. 26A), Test 2 (FIG. 26B), Test 3 (FIG. 26C), Test 4 (FIG. 26D), and all tests (i.e., Tests 1-4; FIG. 26F). FIG. 26E shows ANOVA analysis of the means of percentage of processing damage data from all tests (i.e., Tests 1-4). For FIG. 26E, the bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

FIG. 27A shows exemplary processed and packaged plant material outside and inside the packaging of cosberg lettuce variety 'Cosmopolitan' after 50 days of storage. FIG. 27B shows exemplary processed and packaged plant material outside and inside the packaging of cosberg lettuce variety 'Crunchita' after 50 days of storage. FIG. 27C shows exemplary processed and packaged plant material outside and inside the packaging of romaine lettuce variety 'True Heart' after 50 days of storage. FIG. 27D shows exemplary processed and packaged plant material outside and inside the packaging of romaine lettuce variety 'Solid King' after 50 days of storage. FIG. 27E shows exemplary processed and packaged plant material outside and inside the packaging of upright heading iceberg lettuce variety 'E01E.70111' Lot A after 50 days of storage. FIG. 27F shows exemplary processed and packaged plant material outside and inside the packaging of upright heading iceberg lettuce variety 'E01E.70111' Lot B after 50 days of storage. FIG. 27G shows exemplary processed and packaged plant material outside and inside the packaging of upright heading iceberg lettuce variety 'E01E.70168' Lot A after 50 days of storage. FIG. 27H shows exemplary processed and packaged plant material outside and inside the packaging of upright heading iceberg lettuce variety 'E01E.70168' Lot B after 50 days of storage. FIG. 27I shows exemplary processed and packaged plant material outside and inside the packaging of iceberg lettuce variety 'Reliant' after 50 days of storage. FIG. 27J shows exemplary processed and packaged plant material outside and inside the packaging of iceberg lettuce variety 'Steamboat' after 50 days of storage.

DETAILED DESCRIPTION

Figure 1A:
FIGS. 1A & 1B show representative lettuce types.

There are numerous steps in the development of novel, desirable lettuce germplasm. Plant breeding begins with the analysis of problems and weaknesses of current lettuce germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of lettuce plant breeding is to develop new, unique and superior lettuce varieties. A breeder can initially select and cross two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial lettuce varieties thus requires the development of parental lettuce varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In order to determine whether a lettuce plant is a plant of the present disclosure, and therefore whether said lettuce plant has the same genetic determinant as plants of the present disclosure, the phenotype of the lettuce plant can be compared with the phenotype of a known plant of the present disclosure. The phenotype can be assessed by, for example, the ratio of height to diameter of the plant, the height of the plant, the crisp leaf texture, and/or the closed head.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs). By using these techniques, it is possible to assess the presence of the alleles, genes, and/or loci involved in the upright stature phenotype of the plants of the present disclosure. For example, performing linkage analysis between characteristics of a population (e.g. 'E01E.70111' Lot A) and genetic information of the same population can provide markers linked to particular characteristics. This analysis can then be performed in offspring of the population to further confirm and improve the marker-characteristic linkage.

The genotype of a plant can also be used to determine the similarity between a plant of the present disclosure and a lettuce plant that may be a plant of the present disclosure. For example, a marker from the genotype of a plant of the present disclosure can be compared to a marker from the genotype of a lettuce plant that may be a plant of the present disclosure. The marker can be defined by a set of DNA-based markers, such as AFLP, RFLP, RAPD, SCAR, CAPS, SSR, or SNP, which are closely linked to the alleles, genes, or loci that are involved in producing the upright stature phenotype of the present disclosure. Another method is to analyze the genotype of an $F_2$ population. In this method, first the plant of the present disclosure is crossed to the plant that may be a plant of the present disclosure. Then, the $F_1$ hybrid offspring of this cross is self-fertilized to produce the $F_2$ population. The phenotype and genotype of the $F_2$ population is then analyzed, for example for the absence of segregation for the upright stature phenotype and associated alleles, genes, or loci. In all of these genetic analyses, phenotypic analyses can also be performed (e.g., by assessing the ratio of height to diameter of the plant, the height of the plant, the crisp leaf texture, the closed head, etc.).

One procedure is to identify the equivalence between genetic information responsible for the upright stature phenotype of the plants of the present disclosure and the genetic information of a plant with an upright stature phenotype. First, the plant to be tested (with the upright stature phenotype, but unknown genotype) is used to make homozygous offspring using methods known to the skilled person (e.g., selfing) so that the genetic information responsible for the upright stature phenotype will be homozygous. Then, the homozygous offspring plant is crossed with a tester plant that carries the genetic information responsible for the upright stature phenotype in homozygous condition. If the plant to be tested has the upright stature phenotype as a result of the same genetic information responsible for the upright stature phenotype of plants of the present disclosure (i.e., the genetic information is equivalent), all progeny plants of this cross and subsequent crosses will express the phenotype. If the upright stature phenotype of the plant to be tested is the result of a different part of the genome (i.e., the genetic information is not equivalent), segregation will occur in the population of offspring from the cross. The tester plant can be any plant that carries the genetic information of the disclosure in homozygous condition, such as plants of which representative seed was deposited under accession number 42957, 42962, 42958, or 42963, plants directly grown from the deposited seeds, or progeny plants that have retained the phenotype.

The deposited seeds contain in their genome the genetic information that encodes the upright stature phenotype. Therefore, the deposited seeds are a source for the genetic information that leads to the phenotype. A skilled person is capable of introducing the upright stature phenotype into any other plant using known techniques. Plants in the $F_1$ generation (i.e., the offspring from the cross between a first parent plant that contains the genetic information responsible for the upright stature phenotype with a second parent plant) may not be able to be identified as plants of the present disclosure (e.g., because of their heterozygous condition). The phenotype is better assessed in an $F_2$ generation (e.g., produced by selfing plants of the $F_1$ generation). One way of assessing the phenotype would be to compare the stature of the $F_2$ progeny plant with the second parent plant (e.g., by assessing the ratio of height to diameter of the plant, the height of the plant, etc.). If the stature of the $F_2$ progeny plant is more upright (e.g., has an increased ratio of height to diameter of the plant, an increased height of the plant, etc.) than that of the second parent plant, the progeny plant is a plant of the invention.

In another embodiment, the present disclosure provides plants that have all of the morphological and physiological characteristics corresponding to the upright stature phenotype of plants of the present disclosure, representative seed of which having been deposited under NCIMB Accession Numbers 42957, 42962, 42958, and 42963, which plants are grown from seeds of a plant of the present disclosure, regenerated from parts thereof, or regenerated from a tissue culture thereof. Plants of the present disclosure should have the morphological and physiological characteristics that correspond with the upright stature phenotype but do not necessarily have all the other characteristics of plants of the deposited seeds. The upright stature phenotype is broadly transferrable over multiple types and varieties.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection.

Molecular markers may also be used to identify and exclude certain sources of germplasm as parental varieties or ancestors of a plant by providing a means of tracking genetic profiles through crosses.

Mutation breeding may also be used to introduce new traits into lettuce varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); *Allard* (1960); *Simmonds* (1979); Sneep, et al. (1979); Fehr (1987); and "Carrots and Related Vegetable Umbellferae," Rubatzky, V. E., et al. (1999).

Definitions

In the description and tables that follow, a number of terms are used. In order to provide a clear and consistent understanding of the specification and claims, including the scope to be given such terms, the following definitions are provided:

Allele. The allele is any of one or more alternative forms of a gene, all of which relate to one traitor characteristic. Ina diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Big Vein virus. Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

Bolting. The premature development of a flowering stalk, and subsequent seed, before a plant produces a food crop. Bolting is typically caused by late planting.

*Bremia lactucae*. An oomycete that causes downy mildew in lettuce in cooler growing regions.

Core length. Length of the internal lettuce stem measured from the base of the cut and trimmed head to the tip of the stem.

Corky root. A disease caused by the bacterium *Sphingomonas suberifaciens*, which causes the entire taproot to become brown, severely cracked, and non-functional.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

Figure 29:
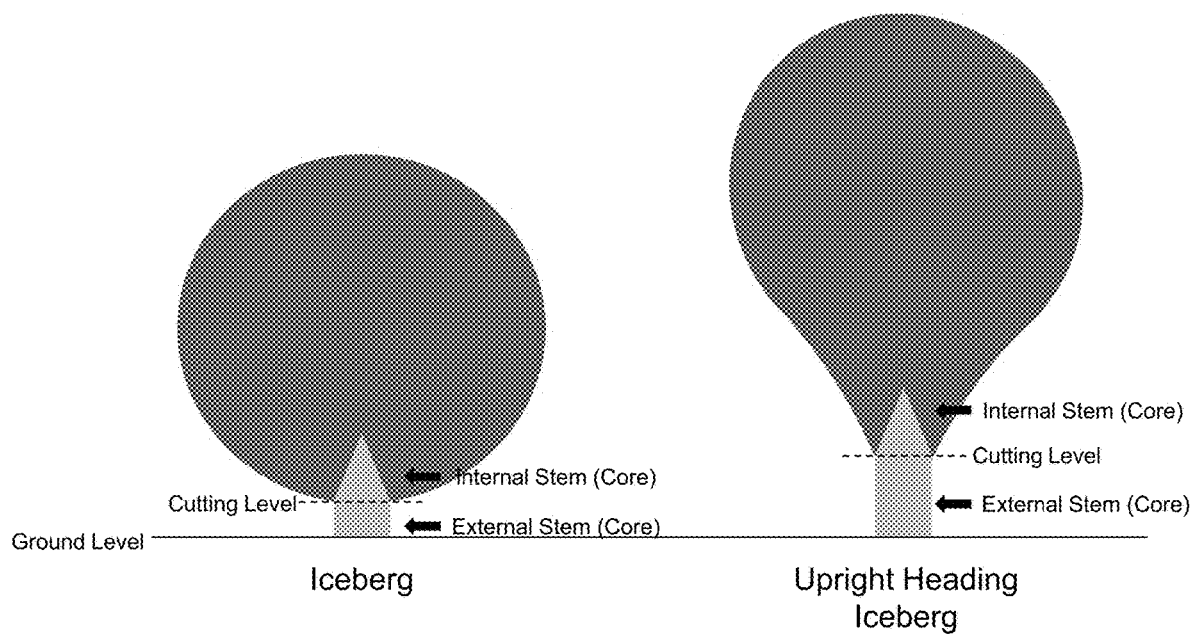
FIG. 29 shows a schematic of the external and internal core measurements on iceberg and upright heading iceberg varieties. Ground level is depicted by a solid line, and cutting level is depicted by a dashed line. The processing material of the head is dark grey, and the stem (i.e., core) is light grey. The internal stem (i.e., core) is measured above the cutting level (labeled and indicated with a thick black arrow), and the external stem (i.e., core) is measured below the cutting level (labeled and indicated with a thick black arrow).

External stem length: External stem (i.e., core) was measured from the harvest cut point at the base of the head the first frame leaf of the head. The location of the external stem (i.e., core) is shown in FIG. 29.

First water date. The date the seed first receives adequate moisture to germinate. This can and often does equal the planting date.

Frame leaves. The leaves that form the base of the plant. Generally not considered a part of the processing material (e.g., head).

Gene. As used herein, "gene" refers to a segment of nucleic acid. A gene can be introduced into a genome of a species, whether from a different species or from the same species, using transformation or various breeding methods.

Head diameter. Diameter of the cut and trimmed head, sliced vertically, and measured at the widest point perpendicular to the stem.

Head height. Height of the cut and trimmed head, sliced vertically, and measured from the base of the cut stem to the cap leaf.

Head weight. Weight of saleable lettuce head, cut and trimmed to market specifications.

Internal stem length: Internal stem (i.e., core) was measured from the first frame leaf of the head to the end of the stem at the center of the head. The location of the internal stem (i.e., core) is shown in FIG. 29.

Lettuce Mosaic virus. A disease that can cause a stunted, deformed, or mottled pattern in young lettuce and yellow, twisted, and deformed leaves in older lettuce.

Maturity date. Maturity refers to the stage when the plants are of full size or optimum weight, in marketable form or shape to be of commercial or economic value.

*Nasonovia ribisnigri*. A lettuce aphid that colonizes the innermost leaves of the lettuce plant, contaminating areas that cannot be treated easily with insecticides.

Quantitative Trait Loci. Quantitative Trait Loci (QTL) refers to genetic loci that control to some degree, numerically representable traits that are usually continuously distributed.

Ratio of head height/diameter. Head height divided by the head diameter is an indication of the head shape; <1 is flattened, 1=round, and >1 is pointed.

Regeneration. Regeneration refers to the development of a plant from tissue culture.

*Rhizoctonia solani*. A soil-borne fungus that causes bottom rot in lettuce.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing or via genetic engineering where essentially all of the desired morphological and physiological characteristics of a line are recovered in addition to the single gene transferred into the line via the backcrossing technique or via genetic engineering.

Tipburn. Means a browning of the edges or tips of lettuce leaves that is a physiological response to a lack of calcium.

Wet date. The wet date corresponds to the first planting date of lettuce.

Upright Heading Iceberg Lettuce Plants and Seeds

Certain aspects of the present disclosure relate to upright heading iceberg plants, and to seeds that produce the upright heading iceberg lettuce plants described herein.

Plants

Certain aspects of the present disclosure relate to an upright heading iceberg lettuce plant with a height to diameter ratio greater than or equal to about 1.0, about 1.5 to about 3 times a height of a standard iceberg lettuce plant, a crisp leaf texture, and a closed head. In some embodiments, the height of the standard iceberg lettuce plant is about 5 inches to 6 inches. In some embodiments, the height of the upright heading iceberg lettuce plant is about 7.5 inches to about 18 inches. In some embodiments, a height of a head of an upright heading iceberg lettuce plant is about 1.5 to about 3 times a height of a head of a standard iceberg lettuce plant. In some embodiments, the height of the head of the standard iceberg lettuce plant is about 5 inches to 6 inches. In some embodiments, the height of the head of the upright heading iceberg lettuce plant is about 7.5 inches to about 18 inches. In some embodiments, the head does not include frame leaves. In some embodiments, the height of the upright heading lettuce plant is dependent on the season in which the upright heading lettuce plant is grown (e.g., winter, spring, summer, fall). In some embodiments, the diameter of the upright heading lettuce plant is dependent on the season in which the upright heading lettuce plant is grown. In some embodiments, the height to diameter ratio is dependent on the season in which the upright heading lettuce plant is grown. In some embodiments, the upright heading lettuce plant may not grow as tall due to sub-optimal growing conditions or a poorly grown field. In some embodiments, the crisp leaf texture is the result of high water content. In some embodiments, the crisp leaf texture is the result of thick leaves. In some embodiments, the crisp leaf texture is due to a combination of factors (e.g., high water content and thick leaves). In some embodiments, the crisp leaf texture is a characteristic that enables specific processing types (e.g., chopping). In some embodiments, the crisp leaf texture is a subjective assessment of texture and/or a pleasant sensation when chewing.

In some embodiments, the iceberg lettuce plant further includes one or more characteristics from the group of a short core, a low level of internal tipburn, a low level of bottom rot, an increased number of leaves, a fast fill rate of leaves in a head, and a space between a base of a head and a top of a ground. In some embodiments, the characteristics above only apply to the processing material (e.g. head). In some embodiments, the characteristics above do not apply to frame leaves. In some embodiments, the short core is short inside the head. In some embodiments, the short core is short outside the head. In some embodiments, core length is the same as in iceberg, romaine, or cosberg types. In some embodiments, core length is shorter than in iceberg, romaine, or cosberg types. In some embodiments, a low level of tipburn means so no visible symptoms. In some embodiments, tipburn is the same as in iceberg, romaine, or cosberg types. In some embodiments, tipburn is less than in iceberg, romaine, or cosberg types. In some embodiments, the level of tipburn is dependent on external conditions (e.g., environment, growing process, etc.). For example, in some embodiments, the upright heading iceberg lettuce plant is about 2 to about 3 times taller than a standard iceberg lettuce plant, has a similar core length to a standard iceberg lettuce plant, and has tipburn tolerance. In some embodiments, a low level of bottom rot means no visible symptoms. In some embodiments, the level of bottom rot is the same as in iceberg types. In some embodiments, the level of bottom rot is less than in iceberg types. In some embodiments, the level of bottom rot is dependent on external conditions (e.g., environment, growing process, etc.). In some embodiments, less bottom rot is due to less contact of the head with the ground. In some embodiments, a low level of bottom rot is due to less contact of the head with the ground than in iceberg types. In some embodiments, the problems associated with bottom rot are avoided because the harvest machine cuts higher on the upright heading iceberg plant than the standard iceberg lettuce plant. In some embodiments, an increased number of leaves means an increased number of leaves in the head. In some embodiments, the iceberg lettuce plant produces an increased number of frame leaves. In some embodiments, an increased number of frame leaves results in the processing material being higher off of the ground. In some embodiments, the fill rate is slower than the fill rate of iceberg lettuce. In some embodiments, the fill rate is similar to the fill rate of iceberg lettuce. In some embodiments, a fast fill rate of leaves in a head is comparable to the fill rate of an iceberg lettuce. In some embodiments, a fast fill rate of leaves is faster than the fill rate of an iceberg lettuce. In some embodiments, a fast fill rate of leaves in a head results in tightly packed leaves at harvest time. In some embodiments, tightly packed leaves at harvest time result in blanched inner leaves that are paler in color than the outer leaves. In some embodiments, a fast fill rate of leaves in a head means that the core remains short and tipburn is reduced. In some embodiments, the space between the base of the head and the top of the ground is achieved by an increased length of core outside of the processing material of a head. In some embodiments, the space between the base of the head and the top of the ground is sufficient for machine harvesting. In some embodiments, the base of the head is a similar distance to the ground as iceberg lettuce, the head is taller, and the bottom of the head is cut off during harvesting (e.g., machine harvesting). In some embodiments, a small proportion of processing material is cut off (i.e., lost) during harvest (e.g., machine harvest). In some embodiments, upright heading iceberg lettuce varieties allow processing of the same amount of product per acre with a machine as can be processed for standard iceberg lettuce varieties using hand labor. In some embodiments, the use of a machine allows significant cost savings in comparison to hand labor. In some embodiments, the processor will be able to harvest less upright heading iceberg lettuce product per acre than standard iceberg lettuce product, and will still be able to make a profit. In some embodiments, the iceberg lettuce plant further has the characteristic of good shelf life, where good shelf life means similar shelf life qualities as a standard iceberg lettuce. In some embodiments, shelf life encompasses odor, rotting, and browning or pinking.

Figure 1B:

An exemplary upright heading iceberg lettuce plant is illustrated in FIG. 1A. A longitudinal cross-section of the upright heading iceberg lettuce plant (FIG. 1A center) is shown next to a longitudinal cross-section of an iceberg lettuce plant (FIG. 1A bottom left). Without wishing to be bound by theory, it is thought that the heading and leaf density of the upright heading iceberg lettuce plant is similar to that of the iceberg lettuce plant. Without wishing to be bound by theory, it is further thought that the upright heading iceberg lettuce plant is both taller and narrower than the iceberg lettuce plant, which means a greater amount of processing material is further away from the ground, and thus the upright heading iceberg lettuce plant is machine harvestable. Exemplary cosberg plants are depicted in FIG. 1B. Without wishing to be bound by theory, it is thought that cosberg plants are generally shorter in stature than upright heading iceberg lettuce plants, not generally suitable for mechanical harvest, and not able to be used to replace product from standard iceberg plants. Without wishing to be bound by theory, it is further thought that cosberg plants do not taste like standard iceberg plants, and also do not have the same crisp texture as standard iceberg plants.

Figure 8A:
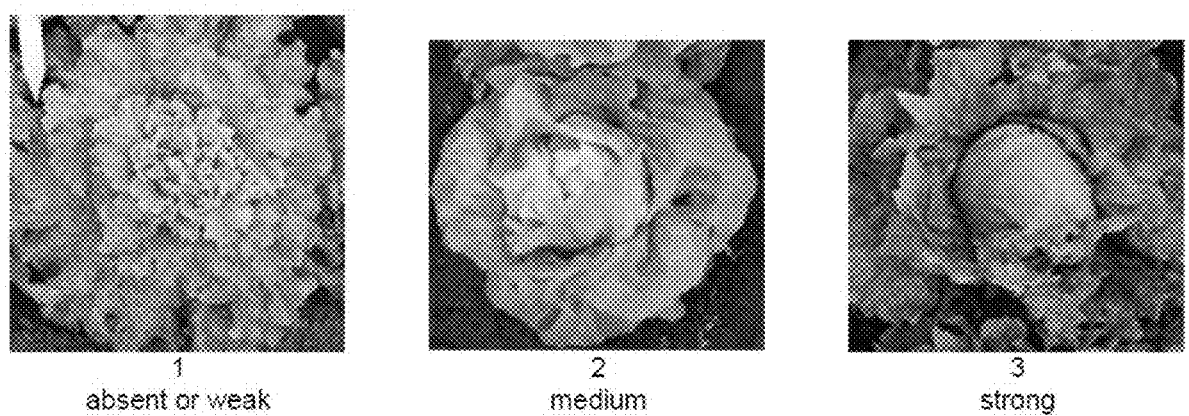
FIGS. 8A-8G show lettuce characteristics.
Figure 8B:
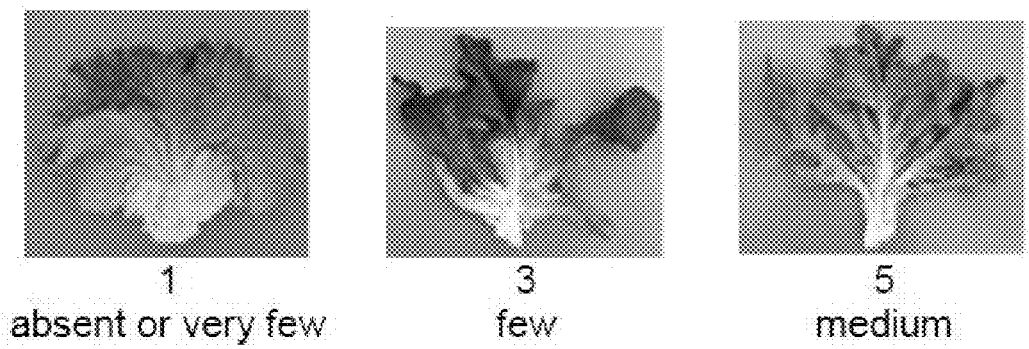
Figure 8C:
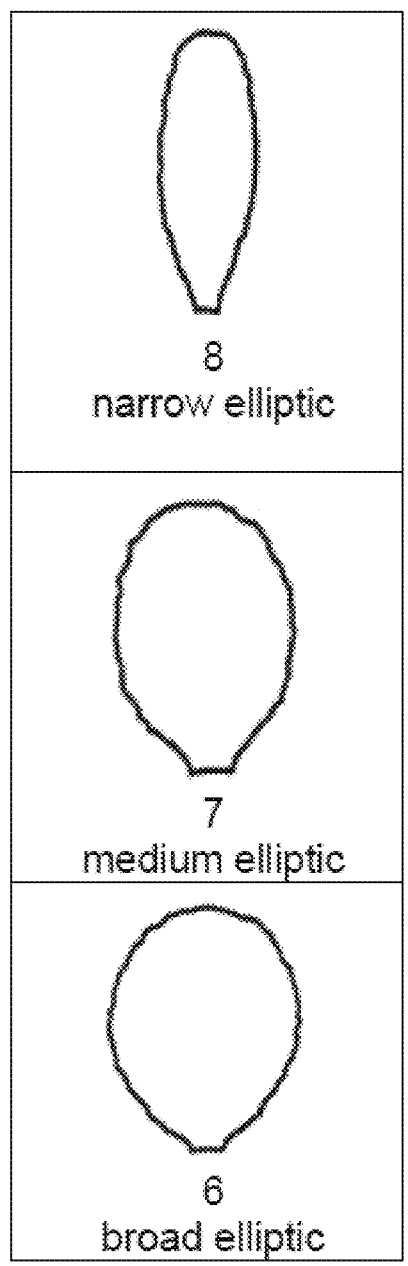
Figure 8D:
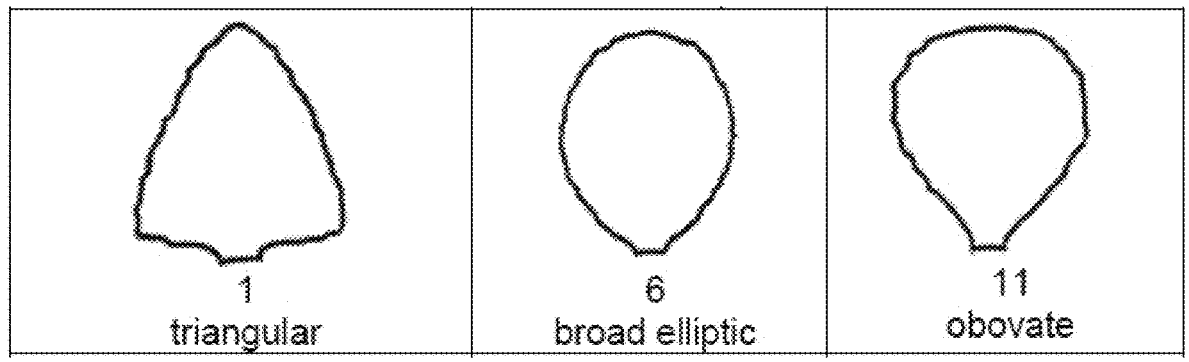
Figure 8E:
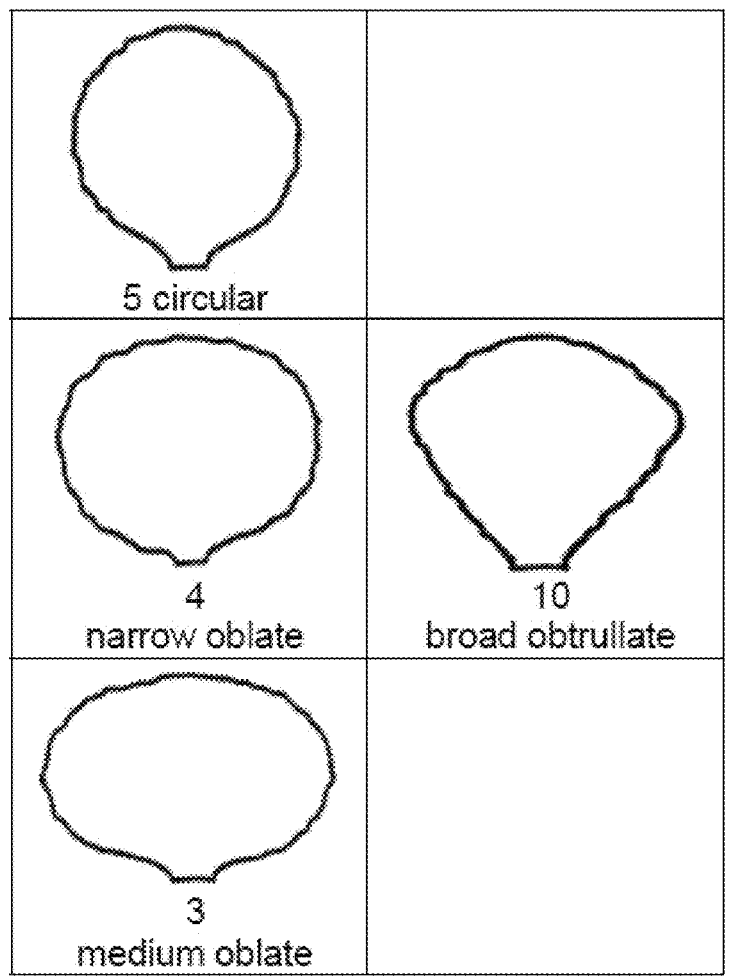
Figure 8F:
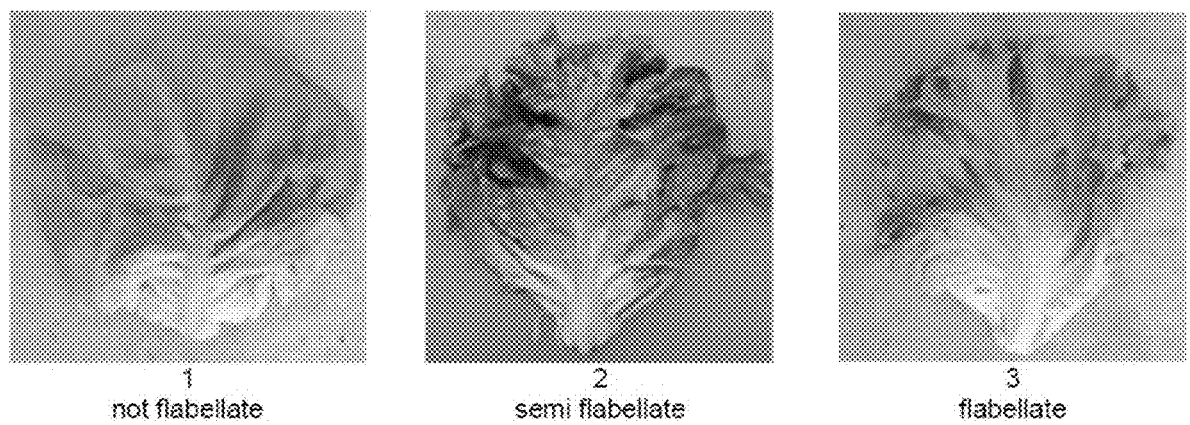
Figure 8G:
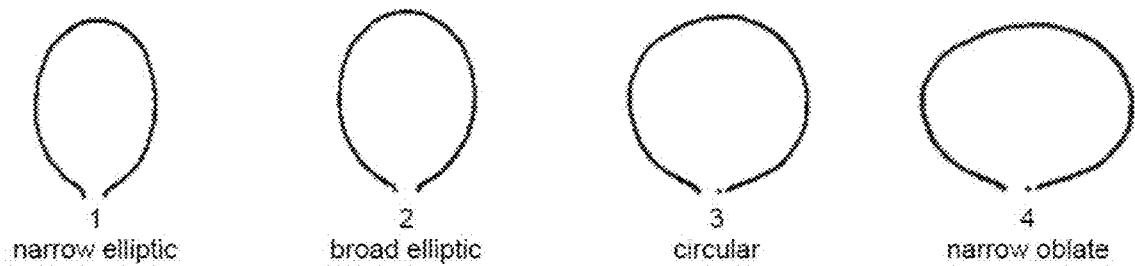
Figure 9A:
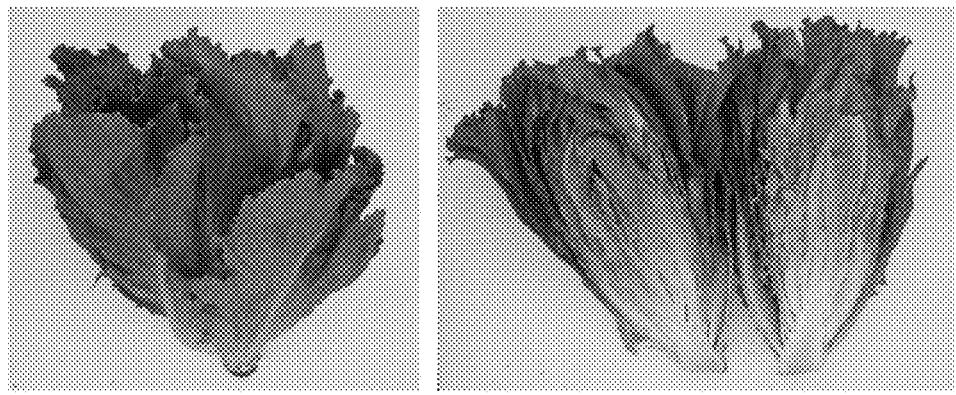
FIGS. 9A-9J show exemplary whole heads and vertical cross-sections of heads of lettuce varieties from Test 1.
Figure 9B:
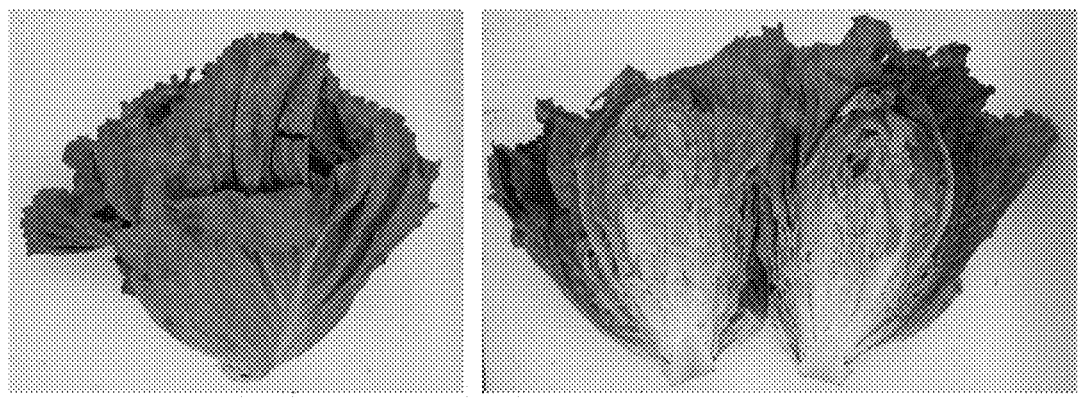
Figure 9C:
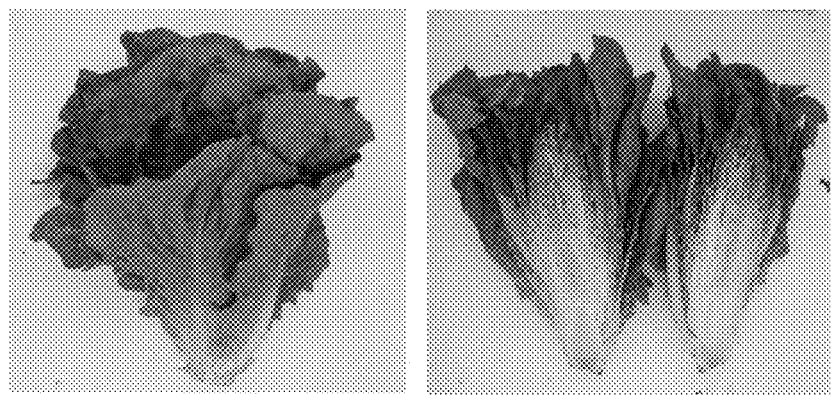
Figure 9D:
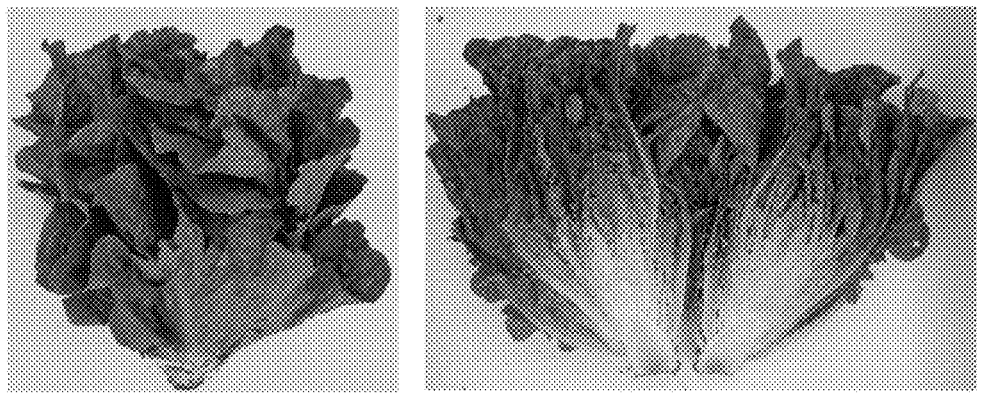
Figure 9E:
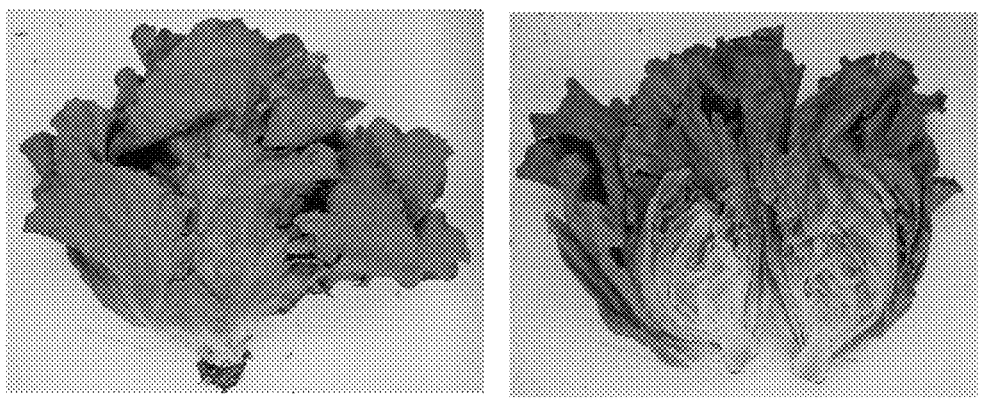
Figure 9F:
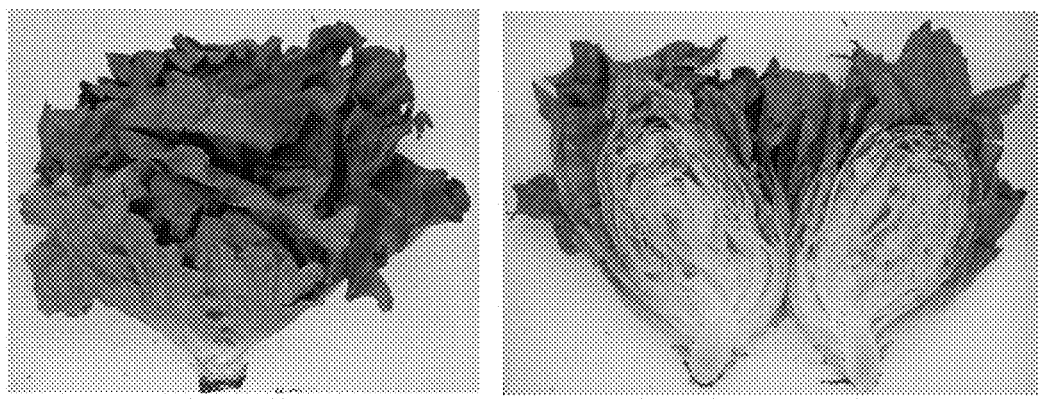
Figure 9G:
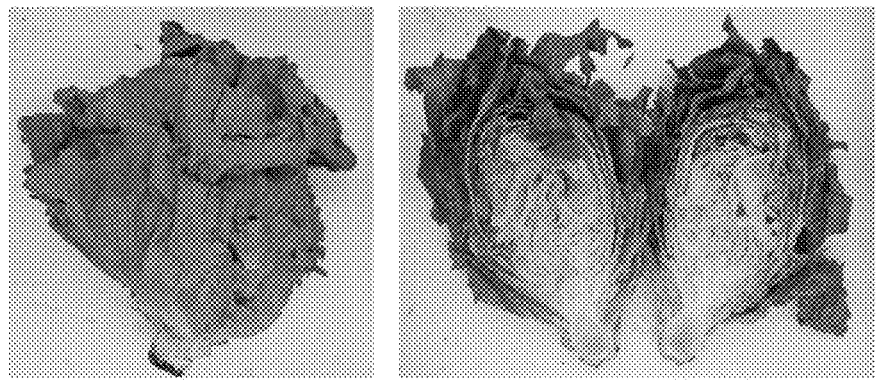
Figure 9H:
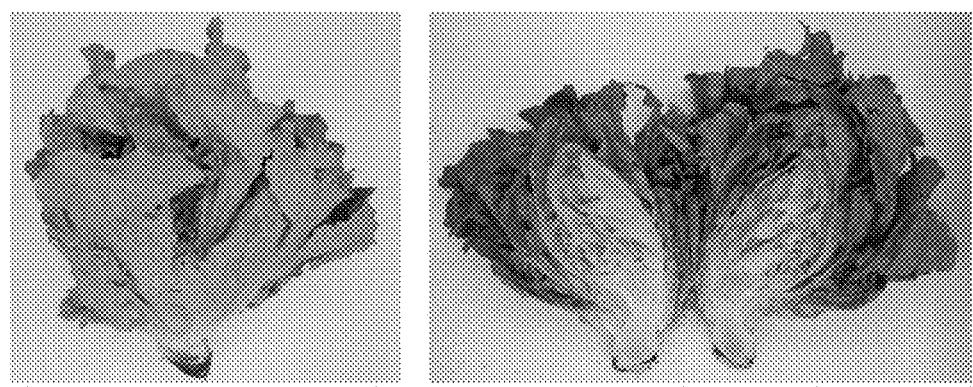
Figure 9I:
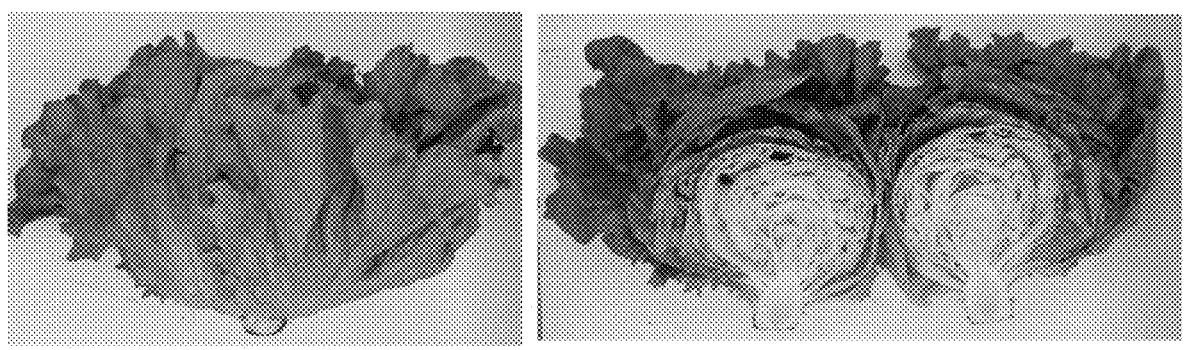
Figure 9J:
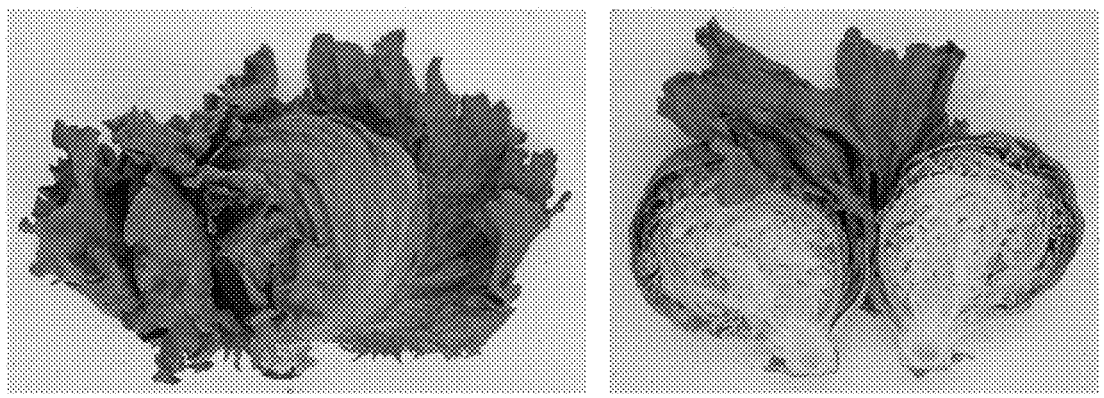
Figure 10A:
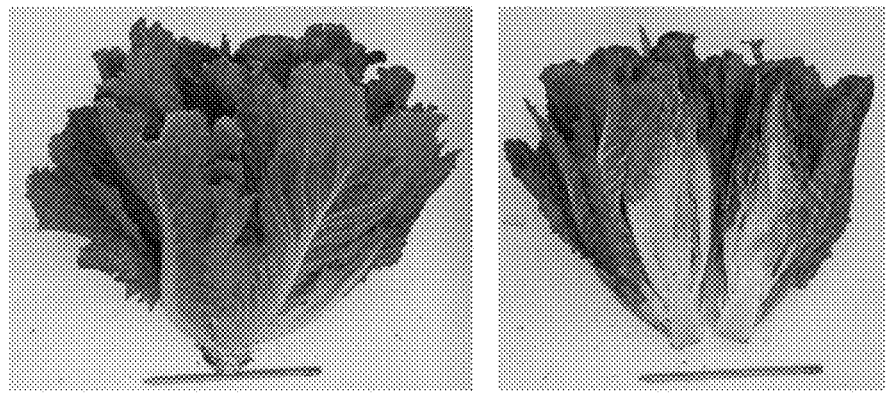
FIGS. 10A-10J show exemplary whole heads and vertical cross-sections of heads of lettuce varieties from Test 2.
Figure 10B:
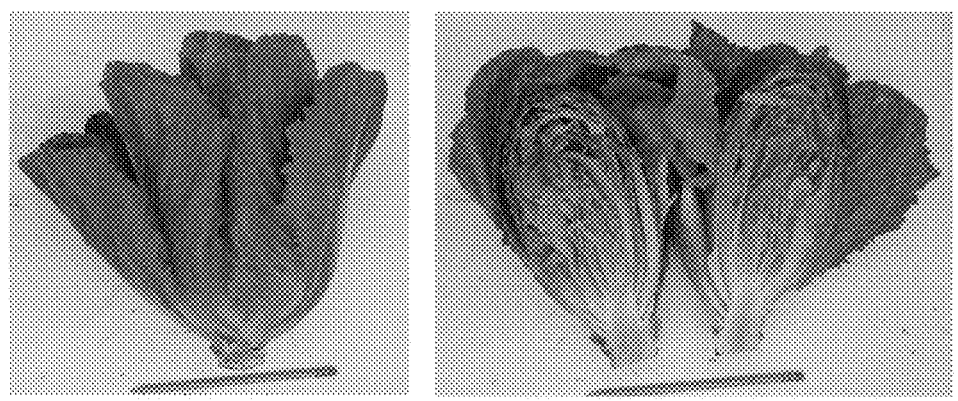
Figure 10C:
Figure 10D:
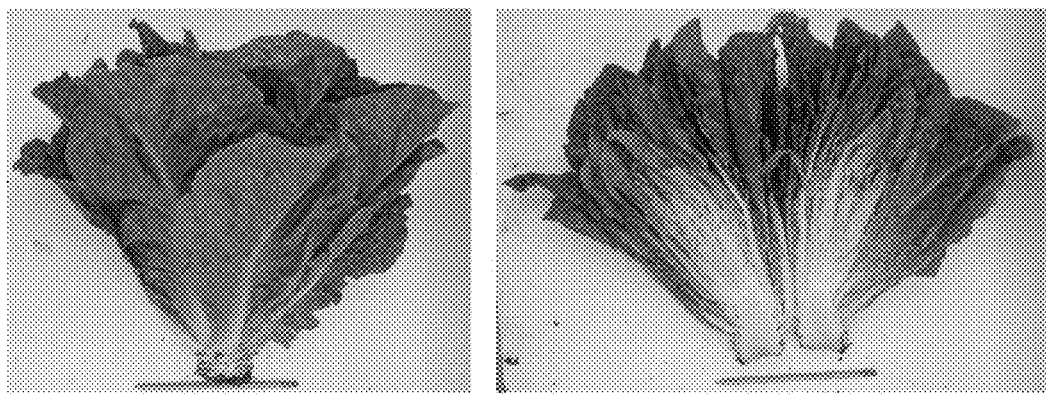
Figure 10E:
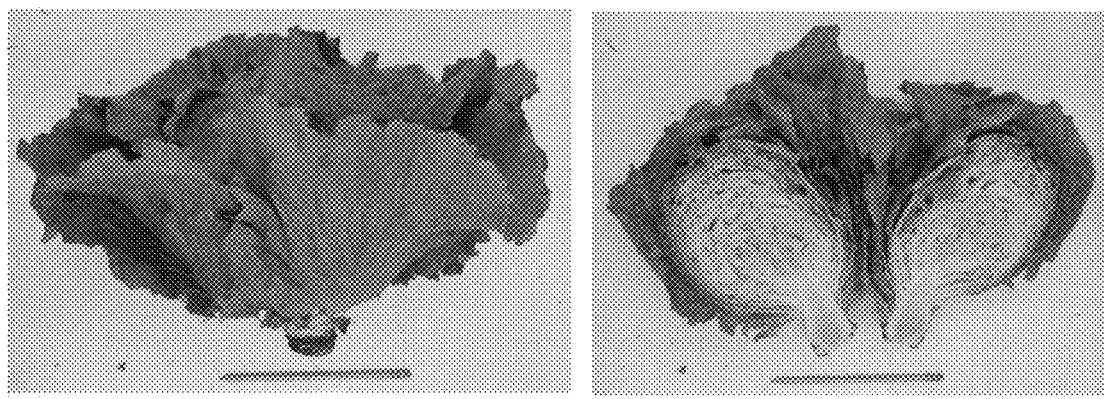
Figure 10F:
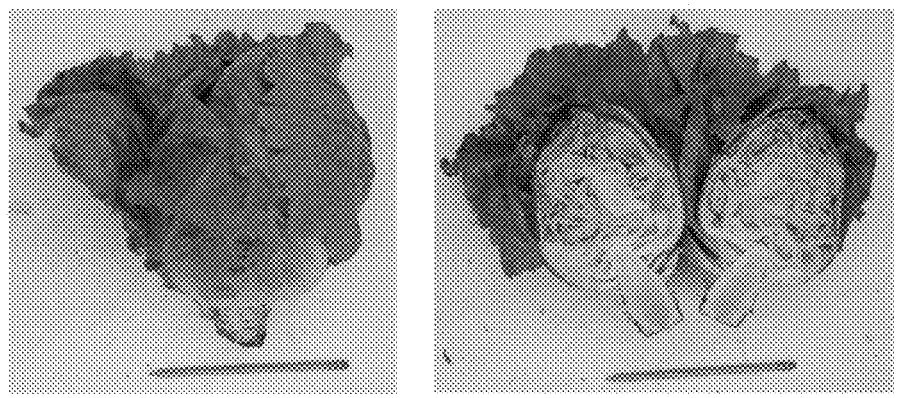
Figure 10G:
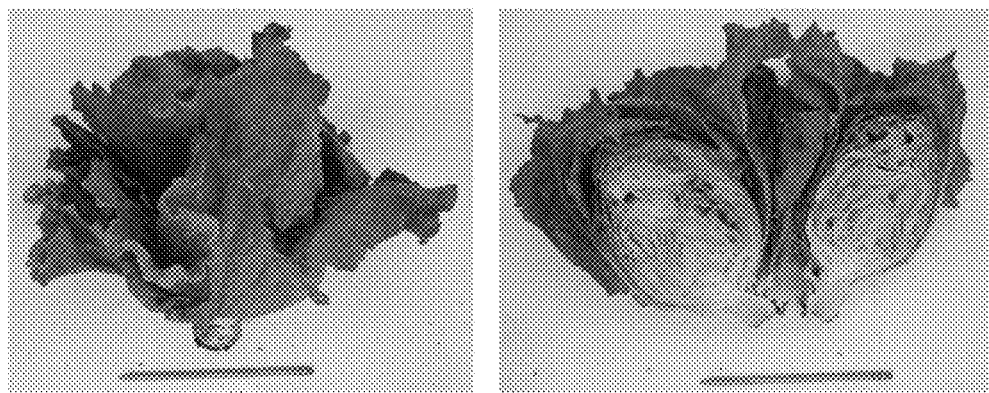
Figure 10H:
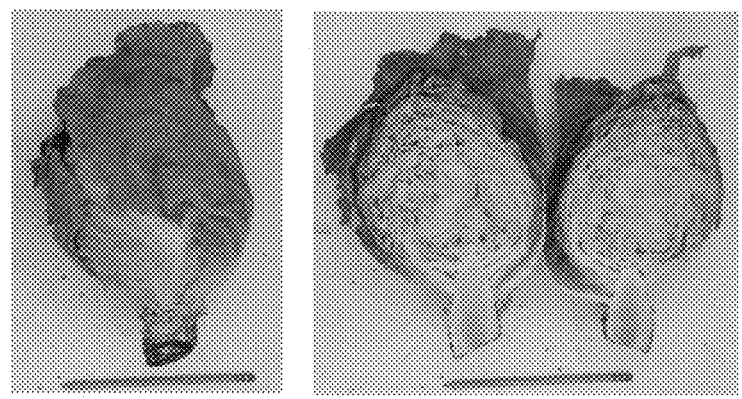
Figure 10I:
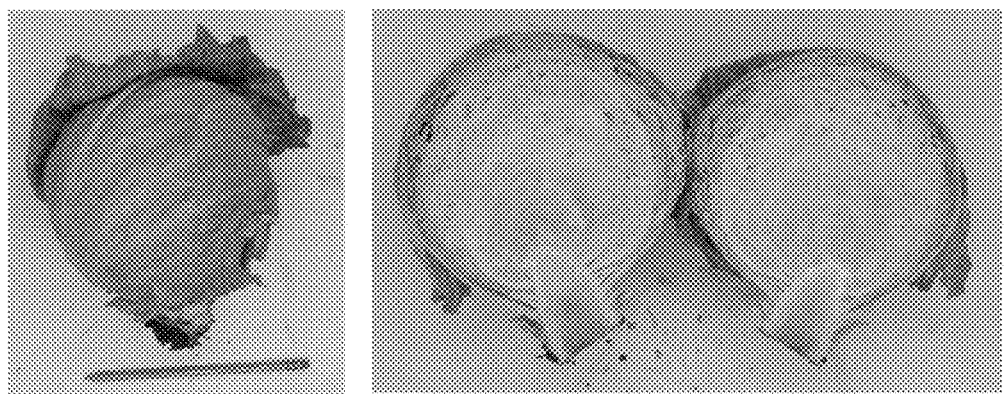
Figure 10J:
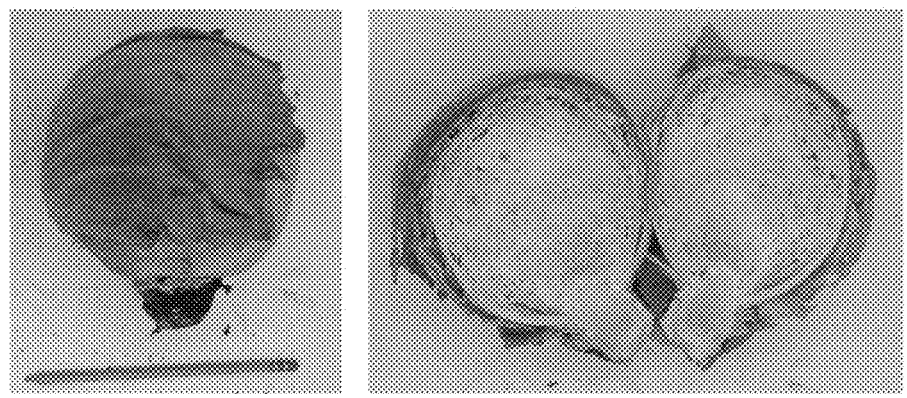
Figure 11A:
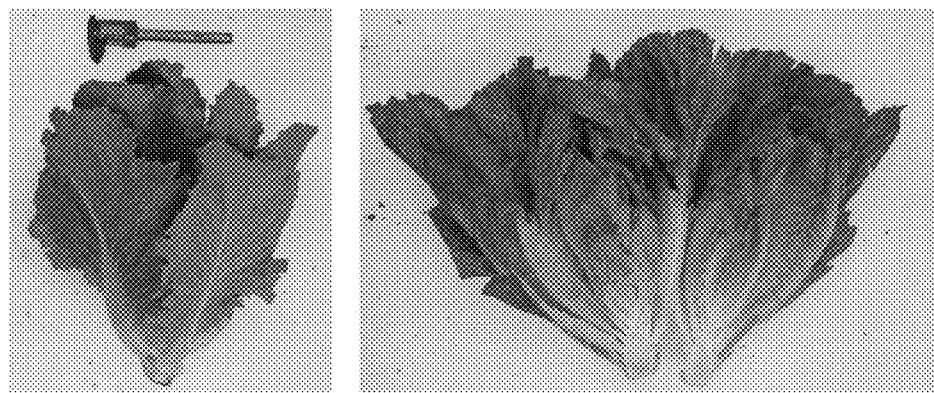
FIGS. 11A-11J show exemplary whole heads and vertical cross-sections of heads of lettuce varieties from Test 3.
Figure 11B:
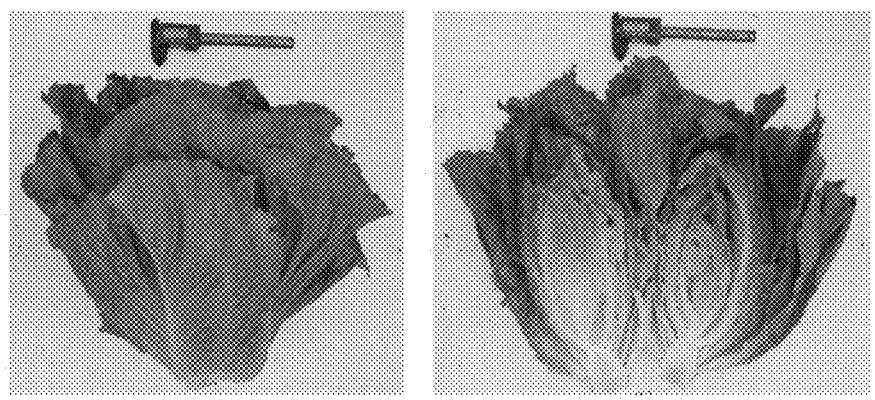
Figure 11C:
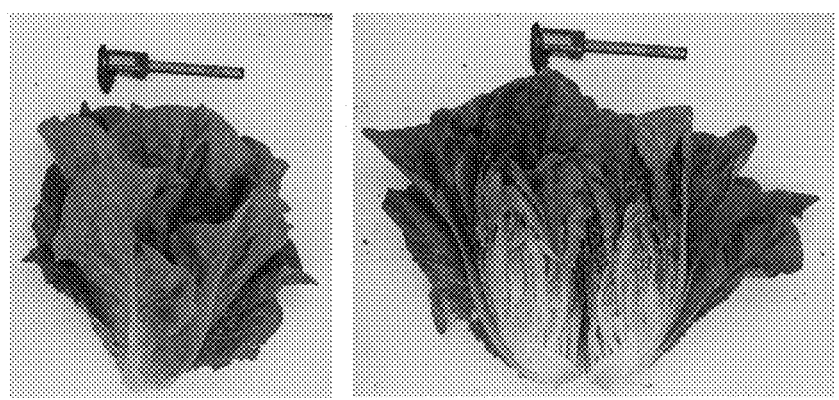
Figure 11D:
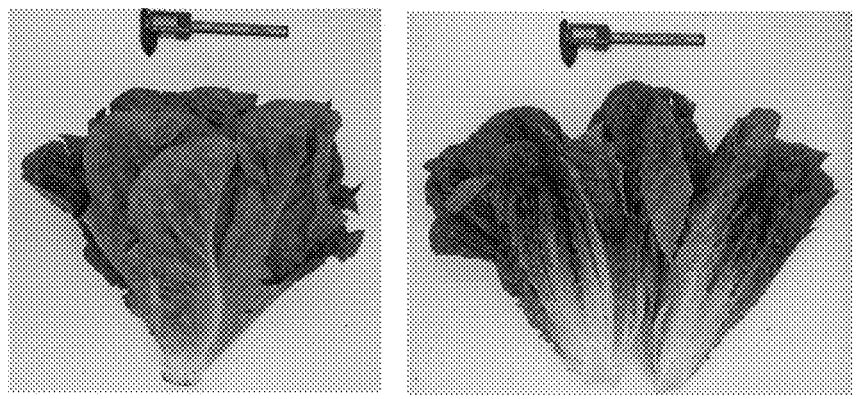
Figure 11E:
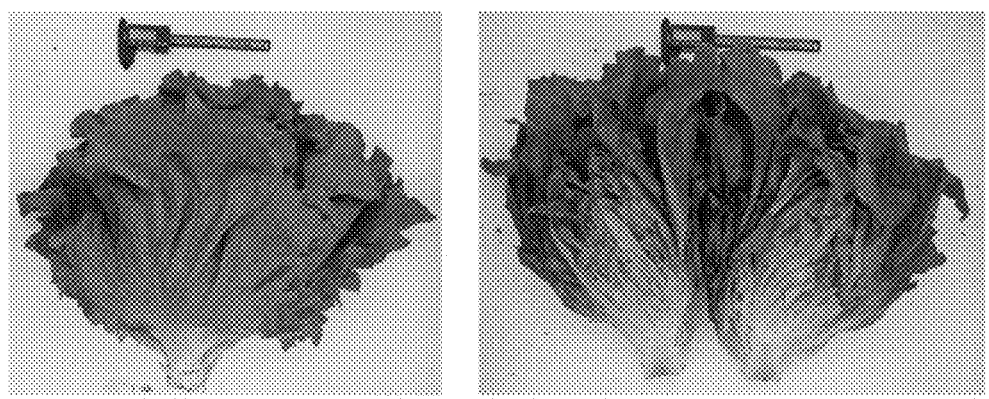
Figure 11F:
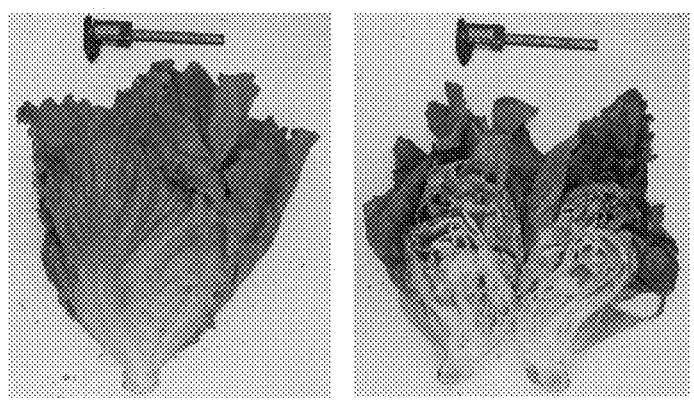
Figure 11G:
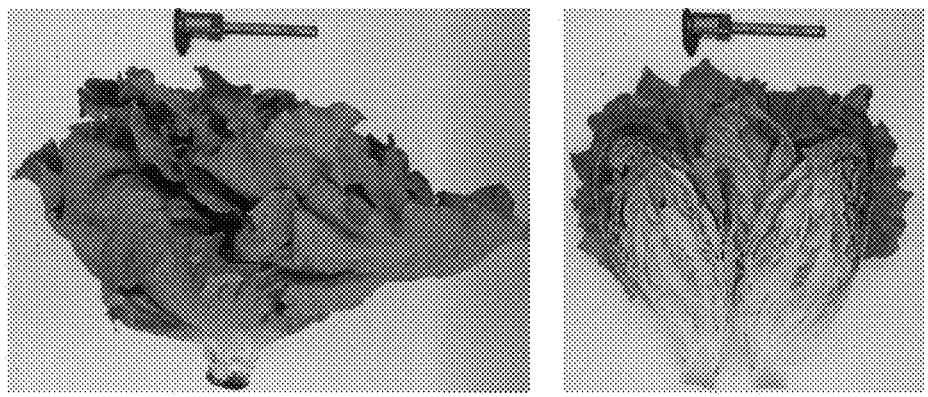
Figure 11H:
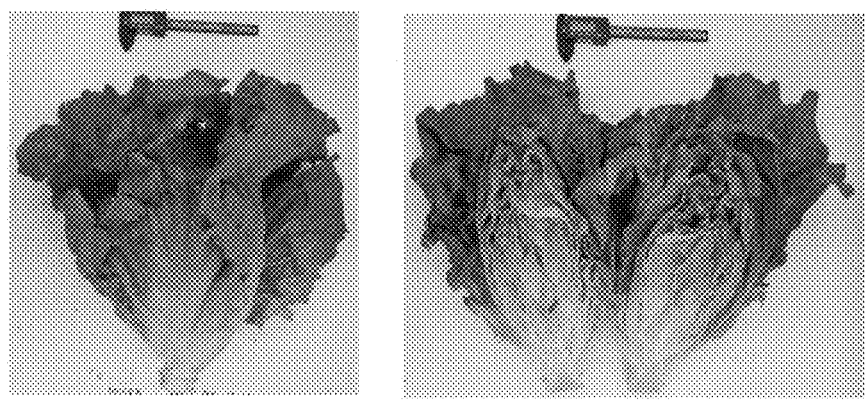
Figure 11I:
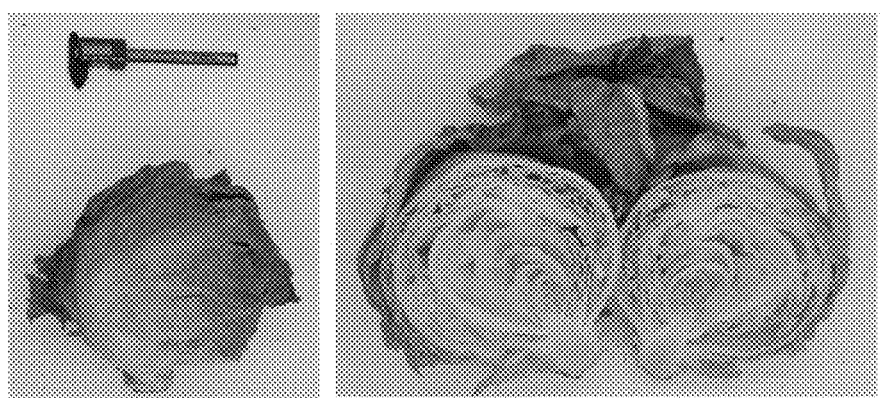
Figure 11J:
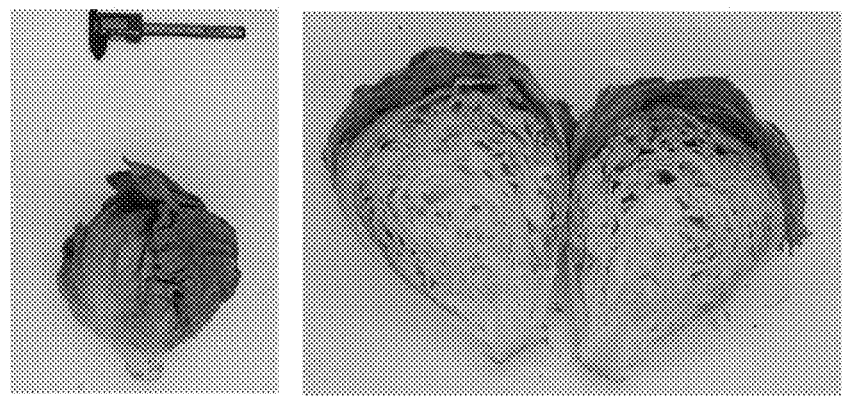
Figure 12A:
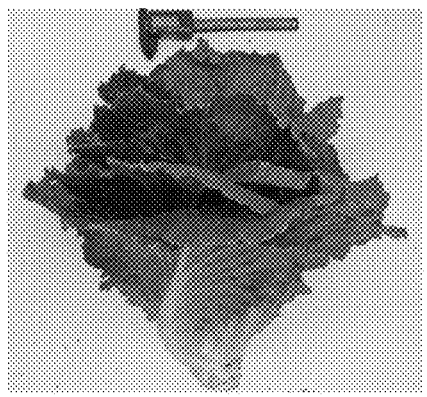
FIGS. 12A-12J show exemplary whole heads and vertical cross-sections of heads of lettuce varieties from Test 4.
Figure 12A:
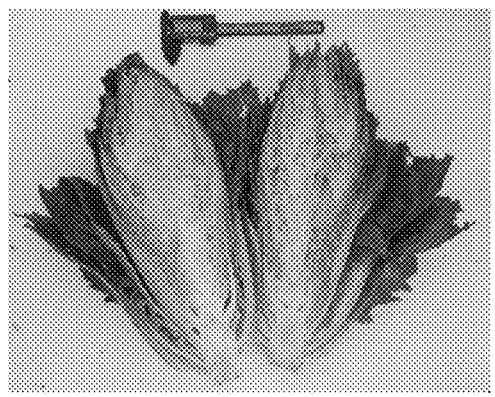
Figure 12B:
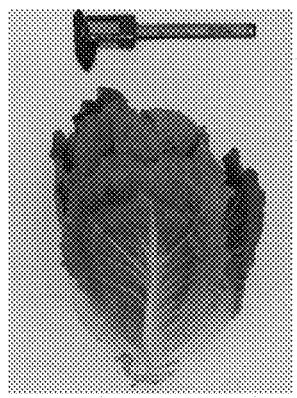
Figure 12B:
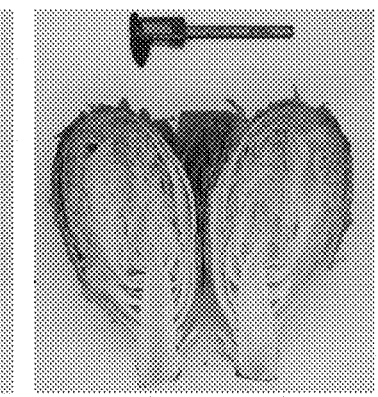
Figure 12C:
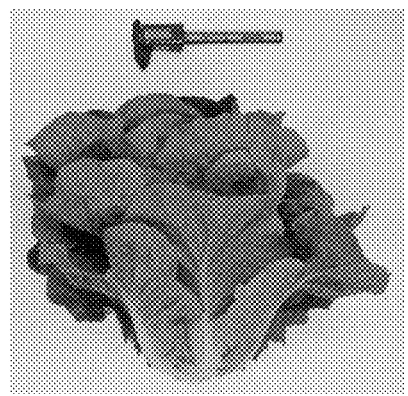
Figure 12C:
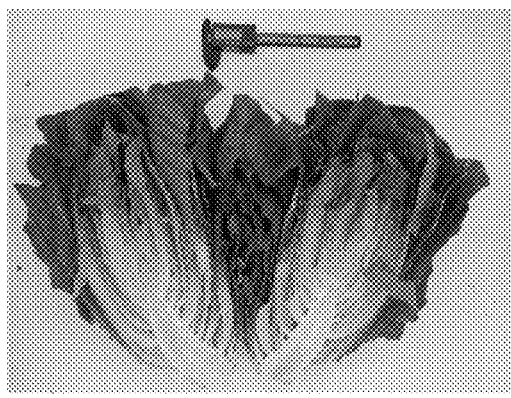
Figure 12D:
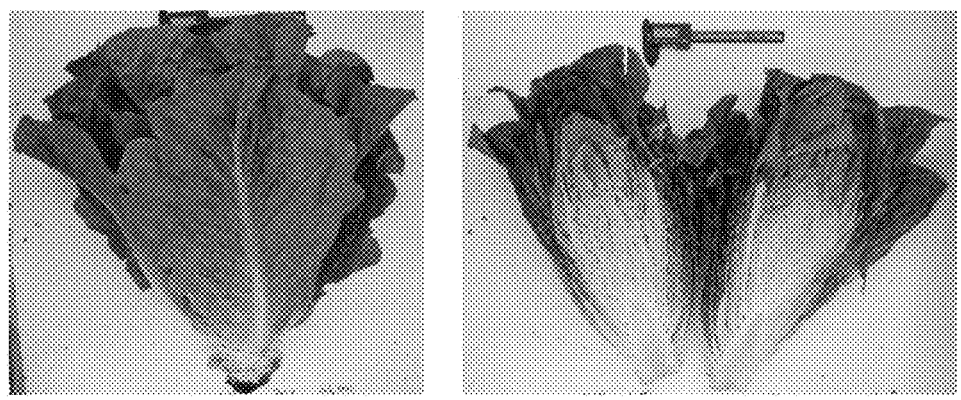
Figure 12E:
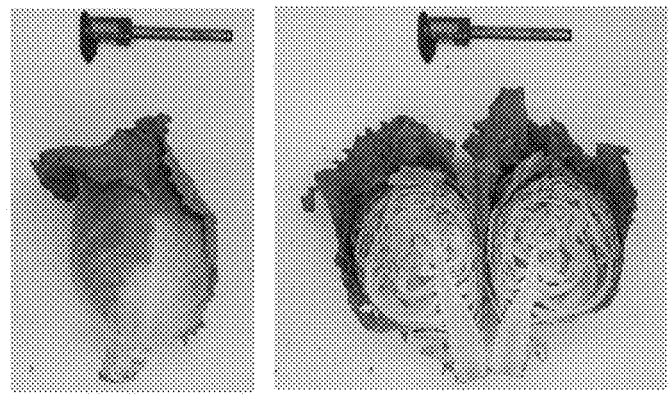
Figure 12F:
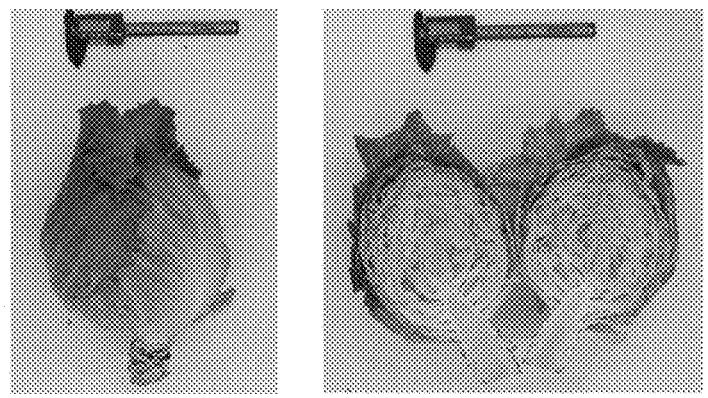
Figure 12G:
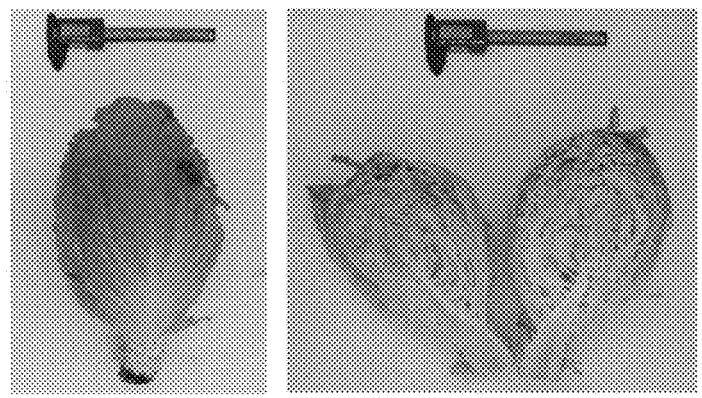
Figure 12H:
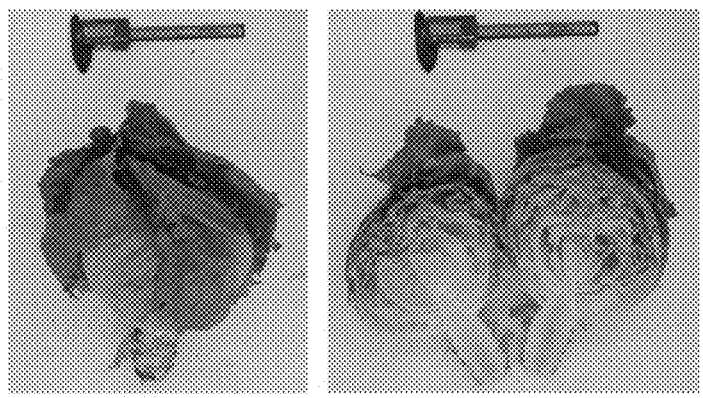
Figure 12I:
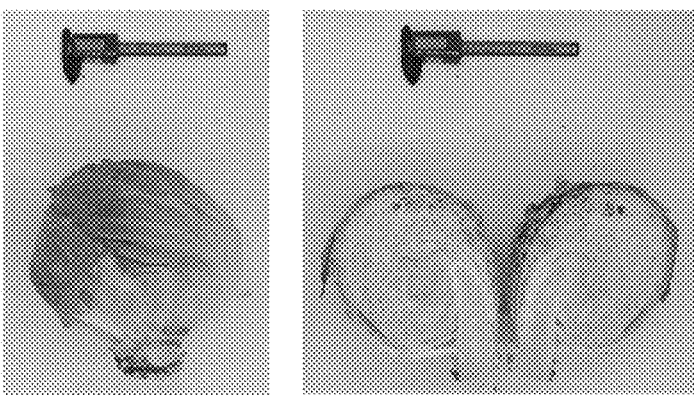
Figure 12J:
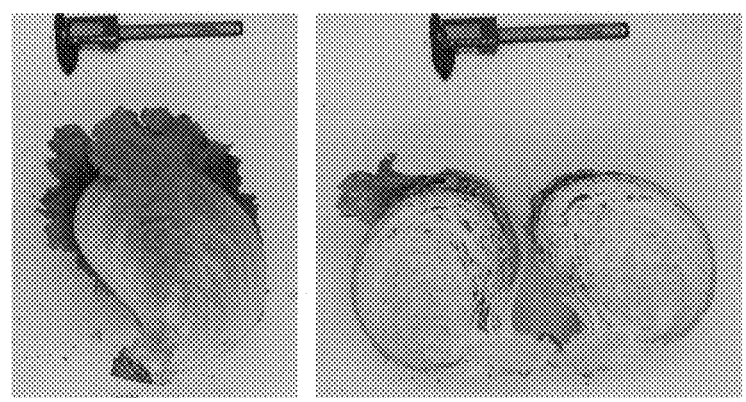

In some embodiments, the iceberg lettuce plant further includes one or more characteristics from the group of moderate leaf glossiness, moderate tendency to bolt, inner leaves paler than outer leaves, blanched inner leaves, green to greyish green outer leaves, outer leaves with a color ranging from about RHS146A to about RHS146B, inner leaves with a color ranging from RHS 145C to RHS 245D, leaves with an obovate shape, leaves with an elliptic shape, leaves with a broad obtrullate shape, leaves with a triangular shape, head with a narrow elliptic shape in longitudinal section, head with an elliptic shape in longitudinal section, head with a broad elliptic shape in longitudinal section, head with an oval shape in longitudinal section, head with an oblong shape in longitudinal section, medium degree of overlapping of upper part of leaves, strong degree of overlapping of upper part of leaves, absent or very few leaf divisions, leaf margin hardly to rather strongly incised, thick leaves, absent to medium undulation of leaf margin, semi-flabellate leaf venation, flabellate leaf venation, clear midrib, no clear midrib, heading, early heading, and medium heading. In other embodiments, the iceberg lettuce plant further includes one or more characteristics from the group of characteristics defining the upright heading iceberg lettuce plant type. Exemplary upright heading iceberg lettuce characteristics are illustrated in FIGS. 8A-8G. FIG. 8A illustrates the appearance of different degrees of overlapping of upper parts of leaves, including medium to strong degrees of overlapping. FIG. 8B illustrates the appearance of leaf divisions, including absent or very few leaf divisions. FIGS. 8C-8E illustrate different leaf shapes, including obovate, elliptic, and broad obtrullate. FIG. 8F illustrates leaf venation patterns, including flabellate venation. FIG. 8G illustrates the shape of the head in longitudinal section, including narrow elliptic and broad elliptic. For example, in some embodiments, an upright heading lettuce plant of the current disclosure may have a medium degree of overlapping of upper parts of leaves, absent or very few leaf divisions, obovate leaves, flabellate leaf venation, and a narrow elliptic shape of the head in longitudinal section. For example, in some embodiments, an upright heading lettuce plant of the current disclosure may have a strong degree of overlapping of upper parts of leaves, absent or very few leaf divisions, obovate leaves, flabellate leaf venation, and a broad elliptic shape of the head in longitudinal section.

In some embodiments, the height to diameter ratio of an upright heading iceberg plant of the present disclosure is greater than or equal to about 1.0, greater than or equal to about 1.1, greater than or equal to about 1.2, greater than or equal to about 1.3, greater than or equal to about 1.4, greater than or equal to about 1.5, greater than or equal to about 1.6, greater than or equal to about 1.7, greater than or equal to about 1.8, greater than or equal to about 1.9, greater than or equal to about 2.0, greater than or equal to about 2.1, greater than or equal to about 2.2, greater than or equal to about 2.3, greater than or equal to about 2.4, greater than or equal to about 2.5, greater than or equal to about 2.6, greater than or equal to about 2.7, greater than or equal to about 2.8, greater than or equal to about 2.9, greater than or equal to about 3.0, greater than or equal to about 3.1, greater than or equal to about 3.2, greater than or equal to about 3.3, greater than or equal to about 3.4, or greater than or equal to about 3.5. In some embodiments, the height to diameter ratio of an upright heading iceberg plant of the present disclosure is less than or equal to about 3.5, less than or equal to about 3.4, less than or equal to about 3.3, less than or equal to about 3.2, less than or equal to about 3.1, less than or equal to about 3.0, less than or equal to about 2.9, less than or equal to about 2.8, less than or equal to about 2.7, less than or equal to about 2.6, less than or equal to about 2.5, less than or equal to about 2.4, less than or equal to about 2.3, less than or equal to about 2.2, less than or equal to about 2.1, less than or equal to about 2.0, less than or equal to about 1.9, less than or equal to about 1.8, less than or equal to about 1.7, less than or equal to about 1.6, less than or equal to about 1.5, less than or equal to about 1.4, less than or equal to about 1.3, less than or equal to about 1.2, less than or equal to about 1.1, or less than or equal to about 1.0. In some embodiments, the height to diameter ratio of an upright heading iceberg plant of the present disclosure is greater than or equal to about any of the following ratios: 1.0, 1.5, 1.6, 1.7, 1.8, 1.9, 2.0, 2.1, 2.2, 2.3, 2.4, 2.5, 2.6, 2.7, 2.8, 2.9, 3.0, or 3.5. In some embodiments, the height to diameter ratio of an upright heading iceberg plant of the present disclosure is less than or equal to about any of the following ratios: 3.5, 3.0, 2.9, 2.8, 2.7, 2.6, 2.5, 2.4, 2.3, 2.2, 2.1, 2.0, 1.9, 1.8, 1.7, 1.6, 1.5, or 1.0. In some embodiments, the height to diameter ratio of an upright heading iceberg plant of the present disclosure can be any of a range of ratios having a lower limit of 1.0, 1.5, 1.6, 1.7, 1.8, 1.9, 2.0, 2.1, 2.2, 2.3, 2.4, 2.5, 2.6, 2.7, 2.8, 2.9, 3.0, or 3.5 and an independently selected upper limit of 3.5, 3.0, 2.9, 2.8, 2.7, 2.6, 2.5, 2.4, 2.3, 2.2, 2.1, 2.0, 1.9, 1.8, 1.7, 1.6, 1.5, or 1.0. For example, in some embodiments, the height to diameter ratio of an upright heading iceberg lettuce plant of the present disclosure is between about 1.5 and 3.0.

In some embodiments, the height of an upright heading iceberg plant of the present disclosure is greater than or equal to about 7.5 in, greater than or equal to about 8 in, greater than or equal to about 8.5 in, greater than or equal to about 9 in, greater than or equal to about 9.5 in, greater than or equal to about 10 in, greater than or equal to about 10.5 in, greater than or equal to about 11 in, greater than or equal to about 11.5 in, greater than or equal to about 12 in, greater than or equal to about 12.5 in, greater than or equal to about 13 in, greater than or equal to about 13.5 in, greater than or equal to about 14 in, greater than or equal to about 14.5 in, greater than or equal to about 15 in, greater than or equal to about 15.5 in, greater than or equal to about 16 in, greater than or equal to about 16.5 in, greater than or equal to about 17 in, greater than or equal to about 17.5 in, greater than or equal to about 18 in, greater than or equal to about 19 in, greater than or equal to about 20 in, greater than or equal to about 21 in, greater than or equal to about 22 in, greater than or equal to about 23 in, greater than or equal to about 24 in, or greater than or equal to about 25 in. In some embodiments, the height of an upright heading iceberg plant of the present disclosure is less than or equal to about 25 in, less than or equal to about 24 in, less than or equal to about 23 in, less than or equal to about 22 in, less than or equal to about 21 in, less than or equal to about 20 in, less than or equal to about 19 in, less than or equal to about 18 in, less than or equal to about 17.5 in, less than or equal to about 17 in, less than or equal to about 16.5 in, less than or equal to about 16 in, less than or equal to about 15.5 in, less than or equal to about 15 in, less than or equal to about 14.5 in, less than or equal to about 14 in, less than or equal to about 13.5 in, less than or equal to about 13 in, less than or equal to about 12.5 in, less than or equal to about 12 in, less than or equal to about 11.5 in, less than or equal to about 11 in, less than or equal to about 10.5 in, less than or equal to about 10 in, less than or equal to about 9.5 in, less than or equal to about 9 in, less than or equal to about 8.5 in, less than or equal to about 8 in, or less than or equal to about 7.5 in. In some embodiments, the height of an upright heading iceberg plant of the present disclosure is greater than or equal to about any of the following heights: 7.5 in, 8 in, 9 in, 10 in, 11 in, 12 in, 13 in, 14 in, 15 in, 16 in, 17 in, 18 in, 20 in, or 25 in. In some embodiments, the height of an upright heading iceberg plant of the present disclosure is less than or equal to about any of the following heights: 25 in, 20 in, 18 in, 17 in, 16 in, 15 in, 14 in, 13 in, 12 in, 11 in, 10 in, 9 in, 8 in, 7.5 in. In some embodiments, the height of an upright heading iceberg plant of the present disclosure can be any of a range of heights having a lower limit of 7.5 in, 8 in, 9 in, 10 in, 11 in, 12 in, 13 in, 14 in, 15 in, 16 in, 17 in, 18 in, 20 in, or 25 in and an independently selected upper limit of 5. For example, in some embodiments, the height of an upright heading iceberg lettuce plant of the present disclosure is between about 7.5 in and about 18 in.

In some embodiments, an iceberg lettuce plant is produced from a cross of a first iceberg lettuce plant with a second iceberg lettuce plant, wherein the first iceberg lettuce plant produces an upright heading iceberg lettuce plant with a height to diameter ratio greater than or equal to about 1.0, about 1.5 to about 3 times a height of a standard iceberg lettuce plant, a crisp leaf texture, and a closed head, the second iceberg lettuce plant produces an upright heading iceberg lettuce plant with a height to diameter ratio greater than or equal to about 1.0, about 1.5 to about 3 times a height of a standard iceberg lettuce plant, a crisp leaf texture, and a closed head, and wherein the iceberg lettuce plant produced from the cross has an upright heading iceberg lettuce plant with a height to diameter ratio greater than or equal to about 1.0, a height of about 1.5 to about 3 times a height of a standard iceberg lettuce plant, a crisp leaf texture, and a closed head. In some embodiments, the iceberg lettuce plant produced from the cross has a height to diameter ratio greater than or equal to about 1.5, a height greater than or equal to about 25.0 cm, and a closed head. In some embodiments, the first and second iceberg lettuce plants are 'E01E.70111' Lot A, 'E01E.70111' Lot B, 'E01E.70168' Lot A, or 'E01E.70168' Lot B lettuce plants, samples of each having been deposited under NCIMB Accession Numbers 42957, 42962, 42958, or 42963 respectively. In some embodiments, only one of the iceberg lettuce plants (i.e, the first or the second iceberg lettuce plant) is 'E01E.70111' Lot A, 'E01E.70111' Lot B, 'E01E.70168' Lot A, or 'E01E.70168' Lot B lettuce plants, samples of each having been deposited under NCIMB Accession Numbers 42957, 42962, 42958, or 42963 respectively. In one embodiment, the first lettuce plant and the second plant are from different lines (e.g., 'E01E.70111' Lot A and 'E01E.70111' Lot B). In another embodiment, the first lettuce plant and the second plant are from the same line (e.g., 'E01E.70111' Lot A). In some embodiments, the plants produced from these crosses have an upright heading iceberg lettuce plant with a height to diameter ratio greater than or equal to about 1.0, a height of about 1.5 to about 3 times a height of a standard iceberg lettuce plant, a crisp leaf texture, and a closed head.

In another embodiment, the present disclosure relates to one or more plant parts from any of the upright heading iceberg lettuce plants described herein. In some embodiments, the plant part is a head, a leaf, a seed, a cell, or any portion thereof. In some embodiments, the plant part is a head. In some embodiments, the head is upright heading. In some embodiments, the head has the characteristics of a height to diameter ratio greater than or equal to about 1.0, a height of about 1.5 to about 3 times a height of a standard iceberg lettuce plant, a crisp leaf texture, and a closed head. In some embodiments, the plant part is a stem, a root, a meristem, or a flower.

In some embodiments, the present disclosure relates to one or more pollen grains or one or more ovules from any of the upright heading iceberg lettuce plants described herein. In some embodiments, the present disclosure relates to a pollen grain from any of the upright heading iceberg lettuce plants described herein. In some embodiments, the present disclosure relates to an ovule from any of the upright heading iceberg lettuce plants described herein.

In some embodiments, the present disclosure relates to tissue culture produced from protoplasts or cells from any of the upright heading iceberg lettuce plants described herein. In some embodiments, the protoplasts and/or cells are produced from one or more plant parts from any of the upright heading iceberg lettuce plants described herein. In some embodiments, the plant part is one or more of leaf, anther, pistil, core, stem, root, root tip, flower, seed, cotyledon, hypocotyl, embryo, and meristematic cells. In some embodiments, the plants regenerated from the tissue culture have all the morphological and physiological characteristics of the plants of any of the upright heading iceberg lettuce plants described herein. In one embodiment, the plant regenerated from the tissue culture has all of the morphological and physiological characteristics of an iceberg lettuce plant produced by growing seed designated as 'E01E.70111' Lot A, representative sample of 'E01E.70111' Lot A lettuce seed having been deposited under NCIMB Accession Number 42957. In another embodiment, the plant regenerated from the tissue culture has all of the morphological and physiological characteristics of an iceberg lettuce plant produced by growing seed designated as 'E01E.70111' Lot B, representative sample of 'E01E.70111' Lot B lettuce seed having been deposited under NCIMB Accession Number 42962. In one embodiment, the plant regenerated from the tissue culture has all of the morphological and physiological characteristics of an iceberg lettuce plant produced by growing seed designated as 'E01E.70168' Lot A, representative sample of 'E01E.70168' Lot A lettuce seed having been deposited under NCIMB Accession Number 42958. In another embodiment, the plant regenerated from the tissue culture has all of the morphological and physiological characteristics of an iceberg lettuce plant produced by growing seed designated as 'E01E.70168' Lot B, representative sample of 'E01E.70168' Lot B lettuce seed having been deposited under NCIMB Accession Number 42963.

In certain aspects, the present disclosure relates to an upright heading iceberg lettuce plant including a space between a base of a head and a top of a ground (e.g., ground level). In some embodiments, said space includes an increased length of core outside of a processing material of a head (i.e., external stem). In some embodiments, the increased length of core outside of the processing material of the head (i.e., external stem) is about 3.5 cm or more, about 4 cm or more, about 4.5 cm or more, or about 5 cm or more. In some embodiments, the iceberg lettuce plant further includes one or more, two or more, three or more, four or more, five or more, six or more, seven or more, eight or more, or nine or more characteristics selected from the group of: a height to diameter ratio of about 1.3 to about 1.5, leaf strength between about 300 to 400 grams, about 40 to 50% overlapping leaves inside the processing material of the head, a short stem inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

In some embodiments, the increased length of core outside of the processing material of the head (i.e., external stem) of an upright heading iceberg plant of the present disclosure is greater than or equal to about 3.0 cm, greater than or equal to about 3.1 cm, greater than or equal to about 3.2 cm, greater than or equal to about 3.3 cm, greater than or equal to about 3.4 cm, greater than or equal to about 3.5 cm, greater than or equal to about 3.6 cm, greater than or equal to about 3.7 cm, greater than or equal to about 3.8 cm, greater than or equal to about 3.9 cm, greater than or equal to about 4.0 cm, greater than or equal to about 4.1 cm, greater than or equal to about 4.2 cm, greater than or equal to about 4.3 cm, greater than or equal to about 4.4 cm, greater than or equal to about 4.5 cm, greater than or equal to about 4.6 cm, greater than or equal to about 4.7 cm, greater than or equal to about 4.8 cm, greater than or equal to about 4.9 cm, greater than or equal to about 5.0 cm, greater than or equal to about 5.1 cm, greater than or equal to about 5.2 cm, greater than or equal to about 5.3 cm, greater than or equal to about 5.4 cm, or greater than or equal to about 5.5 cm. In some embodiments, the increased length of core outside of the processing material of the head (i.e., external stem) of an upright heading iceberg plant of the present disclosure is less than or equal to about 5.5 cm, less than or equal to about 5.4 cm, less than or equal to about 5.3 cm, less than or equal to about 5.2 cm, less than or equal to about 5.1 cm, less than or equal to about 5.0 cm, less than or equal to about 4.9 cm, less than or equal to about 4.8 cm, less than or equal to about 4.7 cm, less than or equal to about 4.6 cm, less than or equal to about 4.5 cm, less than or equal to about 4.4 cm, less than or equal to about 4.3 cm, less than or equal to about 4.2 cm, less than or equal to about 4.1 cm, less than or equal to about 4.0 cm, less than or equal to about 3.9 cm, less than or equal to about 3.8 cm, less than or equal to about 3.7 cm, less than or equal to about 3.6 cm, less than or equal to about 3.5 cm, less than or equal to about 3.4 cm, less than or equal to about 3.3 cm, less than or equal to about 3.2 cm, less than or equal to about 3.1 cm, or less than or equal to about 3.0 cm. In some embodiments, the increased length of core outside of the processing material of the head (i.e., external stem) of an upright heading iceberg plant of the present disclosure is greater than or equal to the following values in cm: 3.5, 3.7, 4.0, 4.2, 4.5, 4.7, or 5.0. In some embodiments, the increased length of core outside of the processing material of the head (i.e., external stem) of an upright heading iceberg plant of the present disclosure is less than or equal to about any of the following values in cm: 5.0, 4.7, 4.5, 4.2, 4.0, 3.7, or 3.5. In some embodiments, the increased length of core outside of the processing material of the head (i.e., external stem) of an upright heading iceberg lettuce plant of the present disclosure can be any of a range of values in cm having a lower limit of 3.5, 3.7, 4.0, 4.2, 4.5, 4.7, or 5.0 and an independently selected upper limit of 5.0, 4.7, 4.5, 4.2, 4.0, 3.7, or 3.5. For example, in some embodiments, the increased length of core outside of the processing material of the head (i.e., external stem) of an upright heading iceberg lettuce plant of the present disclosure is between about 3.5 and 5.0 cm.

In some embodiments, the height to diameter ratio of an upright heading iceberg plant of the present disclosure is greater than or equal to about 1.20, greater than or equal to about 1.21, greater than or equal to about 1.22, greater than or equal to about 1.23, greater than or equal to about 1.24, greater than or equal to about 1.25, greater than or equal to about 1.26, greater than or equal to about 1.27, greater than or equal to about 1.28, greater than or equal to about 1.29, greater than or equal to about 1.3, greater than or equal to about 1.31, greater than or equal to about 1.32, greater than or equal to about 1.33, greater than or equal to about 1.34, greater than or equal to about 1.35, greater than or equal to about 1.36, greater than or equal to about 1.37, greater than or equal to about 1.38, greater than or equal to about 1.39, greater than or equal to about 1.40, greater than or equal to about 1.41, greater than or equal to about 1.42, greater than or equal to about 1.43, greater than or equal to about 1.44, greater than or equal to about 1.45, greater than or equal to about 1.46, greater than or equal to about 1.47, greater than or equal to about 1.48, greater than or equal to about 1.49, greater than or equal to about 1.50, greater than or equal to about 1.51, greater than or equal to about 1.52, greater than or equal to about 1.53, greater than or equal to about 1.54, greater than or equal to about 1.55, greater than or equal to about 1.56, greater than or equal to about 1.57, greater than or equal to about 1.58, greater than or equal to about 1.59, or greater than or equal to about 1.60. In some embodiments, the height to diameter ratio of an upright heading iceberg plant of the present disclosure is less than or equal to about 1.60, less than or equal to about 1.59, less than or equal to about 1.58, less than or equal to about 1.57, less than or equal to about 1.56, less than or equal to about 1.55, less than or equal to about 1.54, less than or equal to about 1.53, less than or equal to about 1.52, less than or equal to about 1.51, less than or equal to about 1.50, less than or equal to about 1.49, less than or equal to about 1.48, less than or equal to about 1.47, less than or equal to about 1.46, less than or equal to about 1.45, less than or equal to about 1.44, less than or equal to about 1.43, less than or equal to about 1.42, less than or equal to about 1.41, less than or equal to about 1.40, less than or equal to about 1.39, less than or equal to about 1.38, less than or equal to about 1.37, less than or equal to about 1.36, less than or equal to about 1.35, less than or equal to about 1.34, less than or equal to about 1.33, less than or equal to about 1.32, less than or equal to about 1.31, less than or equal to about 1.30, less than or equal to about 1.29, less than or equal to about 1.28, less than or equal to about 1.27, less than or equal to about 1.26, less than or equal to about 1.25, less than or equal to about 1.24, less than or equal to about 1.23, less than or equal to about 1.22, less than or equal to about 1.21, or less than or equal to about 1.20. In some embodiments, the height to diameter ratio of an upright heading iceberg plant of the present disclosure is greater than or equal to about any of the following ratios: 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, or 1.50. In some embodiments, the height to diameter ratio of an upright heading iceberg plant of the present disclosure is less than or equal to about any of the following ratios: 1.50, 1.49, 1.48, 1.47, 1.46, 1.45, 1.44, 1.43, 1.42, 1.41, 1.40, 1.39, 1.38, 1.37, 1.36, 1.35, 1.34, 1.33, 1.32, 1.31, or 1.30. In some embodiments, the height to diameter ratio of an upright heading iceberg plant of the present disclosure can be any of a range of ratios having a lower limit of 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, or 1.50 and an independently selected upper limit of 1.50, 1.49, 1.48, 1.47, 1.46, 1.45, 1.44, 1.43, 1.42, 1.41, 1.40, 1.39, 1.38, 1.37, 1.36, 1.35, 1.34, 1.33, 1.32, 1.31, or 1.30. For example, in some embodiments, the height to diameter ratio of an upright heading iceberg lettuce plant of the present disclosure is between about 1.3 and 1.5.

In some embodiments, the leaf strength of an upright heading iceberg plant of the present disclosure is greater than or equal to about 250 grams, greater than or equal to about 260 grams, greater than or equal to about 270 grams, greater than or equal to about 280 grams, greater than or equal to about 290 grams, greater than or equal to about 300 grams, greater than or equal to about 305 grams, greater than or equal to about 310 grams, greater than or equal to about 315 grams, greater than or equal to about 320 grams, greater than or equal to about 325 grams, greater than or equal to about 330 grams, greater than or equal to about 335 grams, greater than or equal to about 340 grams, greater than or equal to about 345 grams, greater than or equal to about 350 grams, greater than or equal to about 355 grams, greater than or equal to about 360 grams, greater than or equal to about 365 grams, greater than or equal to about 370 grams, greater than or equal to about 375 grams, greater than or equal to about 380 grams, greater than or equal to about 385 grams, greater than or equal to about 390 grams, greater than or equal to about 395 grams, greater than or equal to about 400 grams, greater than or equal to about 410 grams, greater than or equal to about 420 grams, greater than or equal to about 430 grams, greater than or equal to about 440 grams, greater than or equal to about 450 grams, greater than or equal to about 460 grams, greater than or equal to about 470 grams, greater than or equal to about 480 grams, greater than or equal to about 490 grams, or greater than or equal to about 500 grams. In some embodiments, the leaf strength of an upright heading iceberg plant of the present disclosure is less than or equal to about 500 grams, less than or equal to about 490 grams, less than or equal to about 480 grams, less than or equal to about 470 grams, less than or equal to about 460 grams, less than or equal to about 450 grams, less than or equal to about 440 grams, less than or equal to about 430 grams, less than or equal to about 420 grams, less than or equal to about 410 grams, less than or equal to about 400 grams, less than or equal to about 395 grams, less than or equal to about 390 grams, less than or equal to about 385 grams, less than or equal to about 380 grams, less than or equal to about 375 grams, less than or equal to about 370 grams, less than or equal to about 365 grams, less than or equal to about 360 grams, less than or equal to about 355 grams, less than or equal to about 350 grams, less than or equal to about 345 grams, less than or equal to about 340 grams, less than or equal to about 335 grams, less than or equal to about 330 grams, less than or equal to about 325 grams, less than or equal to about 320 grams, less than or equal to about 315 grams, less than or equal to about 310 grams, less than or equal to about 305 grams, less than or equal to about 300 grams, less than or equal to about 290 grams, less than or equal to about 280 grams, less than or equal to about 270 grams, less than or equal to about 260 grams, less than or equal to about 250 grams, less than or equal to about 240 grams, less than or equal to about 230 grams, less than or equal to about 220 grams, less than or equal to about 210 grams, less than or equal to about 210 grams, or less than or equal to about 200 grams. In some embodiments, the leaf strength of an upright heading iceberg plant of the present disclosure is greater than or equal to about any of the following values in grams: 300, 310, 320, 330, 340, 350, 360, 370, 380, 390, or 400. In some embodiments, the leaf strength of an upright heading iceberg plant of the present disclosure is greater than or equal to about any of the following values in grams: 400, 390, 380, 370, 360, 350, 340, 330, 320, 310, or 300. In some embodiments, the leaf strength of an upright heading iceberg plant of the present disclosure can be any of a range of values in grams having a lower limit of 300, 310, 320, 330, 340, 350, 360, 370, 380, 390, or 400 and an independently selected upper limit of 400, 390, 380, 370, 360, 350, 340, 330, 320, 310, or 300. For example, in some embodiments, the leaf strength of an upright heading iceberg lettuce plant of the present disclosure is between about 300 and about 400 grams.

In some embodiments, the percent of overlapping leaves of an upright heading iceberg plant of the present disclosure is greater than or equal to about 35%, greater than or equal to about 36%, greater than or equal to about 37%, greater than or equal to about 38%, greater than or equal to about 39%, greater than or equal to about 40%, greater than or equal to about 41%, greater than or equal to about 42%, greater than or equal to about 43%, greater than or equal to about 44%, greater than or equal to about 45%, greater than or equal to about 46%, greater than or equal to about 47%, greater than or equal to about 48%, greater than or equal to about 49%, greater than or equal to about 50%, greater than or equal to about 51%, greater than or equal to about 52%, greater than or equal to about 53%, greater than or equal to about 54%, or greater than or equal to about 55%. In some embodiments, the percent of overlapping leaves of an upright heading iceberg plant of the present disclosure is less than or equal to about 55%, less than or equal to about 54%, less than or equal to about 53%, less than or equal to about 52%, less than or equal to about 51%, less than or equal to about 50%, less than or equal to about 49%, less than or equal to about 48%, less than or equal to about 47%, less than or equal to about 46%, less than or equal to about 45%, less than or equal to about 44%, less than or equal to about 43%, less than or equal to about 42%, less than or equal to about 41%, less than or equal to about 40%, less than or equal to about 39%, less than or equal to about 38%, less than or equal to about 37%, less than or equal to about 36%, or less than or equal to about 35%. In some embodiments, the percent of overlapping leaves of an upright heading iceberg plant of the present disclosure is greater than or equal to about any of the following percentages: 40%, 41%, 42%, 43%, 44%, 45%, 46%, 47%, 48%, 49%, or 50%. In some embodiments, the percent of overlapping leaves of an upright heading iceberg plant of the present disclosure is less than or equal to about any of the following percentages: 50%, 49%, 48%, 47%, 46%, 45%, 44%, 43%, 42%, 41%, or 40%. In some embodiments, the percent of overlapping leaves of an upright heading iceberg plant of the present disclosure can be any of a range of percentages having a lower limit of 40%, 41%, 42%, 43%, 44%, 45%, 46%, 47%, 48%, 49%, or 50% and an independently selected upper limit of 50%, 49%, 48%, 47%, 46%, 45%, 44%, 43%, 42%, 41%, or 40%. For example, in some embodiments, the percent of overlapping leaves of an upright heading iceberg lettuce plant of the present disclosure is between about 40% and 50%.

In some embodiments, the ° brix of leaves of an upright heading iceberg plant of the present disclosure is greater than or equal to about 4.5° brix, greater than or equal to about 4.6° brix, greater than or equal to about 4.7° brix, greater than or equal to about 4.8° brix, greater than or equal to about 4.85° brix, greater than or equal to about 4.9° brix, greater than or equal to about 4.95° brix, greater than or equal to about 5.0° brix, greater than or equal to about 5.05° brix, greater than or equal to about 5.1° brix, greater than or equal to about 5.15° brix, greater than or equal to about 5.2° brix, greater than or equal to about 5.25° brix, greater than or equal to about 5.3° brix, greater than or equal to about 5.4° brix, greater than or equal to about 5.5° brix, greater than or equal to about 5.6° brix, or greater than or equal to about 5.7° brix. In some embodiments, the ° brix of leaves of an upright heading iceberg plant of the present disclosure is less than or equal to about 5.7° brix, less than or equal to about 5.5° brix, less than or equal to about 5.4° brix, less than or equal to about 5.3° brix, less than or equal to about 5.25° brix, less than or equal to about 5.2° brix, less than or equal to about 5.15° brix, less than or equal to about 5.1° brix, less than or equal to about 5.05° brix, less than or equal to about 5.0° brix, less than or equal to about 4.95° brix, less than or equal to about 4.9° brix, less than or equal to about 4.85° brix, less than or equal to about 4.8° brix, less than or equal to about 4.7° brix, less than or equal to about 4.6° brix, or less than or equal to about 4.6° brix. In some embodiments, the ° brix of leaves of an upright heading iceberg plant of the present disclosure is greater than or equal to about any of the following values in ° brix: 4.8, 4.85, 4.9, 4.95, 5.0, 5.05, 5.1, 5.15, 5.2, 5.25, or 5.3. In some embodiments, the ° brix of an upright heading iceberg plant of the present disclosure is greater than or equal to about any of the following values in ° brix: 5.3, 5.25, 5.2, 5.15, 5.1, 5.05, 5.0, 4.95, 4.9, 4.85, or 4.8. In some embodiments, the ° brix of leaves of an upright heading iceberg plant of the present disclosure can be any of a range of values in ° brix having a lower limit of 4.8, 4.85, 4.9, 4.95, 5.0, 5.05, 5.1, 5.15, 5.2, 5.25, or 5.3 and an independently selected upper limit of 5.3, 5.25, 5.2, 5.15, 5.1, 5.05, 5.0, 4.95, 4.9, 4.85, or 4.8. For example, in some embodiments, the ° brix of leaves of an upright heading iceberg lettuce plant of the present disclosure is between about 4.8° brix and about 5.3° brix.

In some embodiments, the total sugars of leaves of an upright heading iceberg plant of the present disclosure are greater than or equal to about 20 g/l, greater than or equal to about 21 g/l, greater than or equal to about 22 g/l, greater than or equal to about 23 g/l, greater than or equal to about 24 g/l, greater than or equal to about 25 g/l, greater than or equal to about 26 g/l, greater than or equal to about 27 g/l, greater than or equal to about 28 g/l, greater than or equal to about 29 g/l, greater than or equal to about 30 g/l, greater than or equal to about 31 g/l, greater than or equal to about 32 g/l, greater than or equal to about 33 g/l, greater than or equal to about 34 g/l, greater than or equal to about 35 g/l, greater than or equal to about 36 g/l, greater than or equal to about 37 g/l, greater than or equal to about 38 g/l, greater than or equal to about 39 g/l, greater than or equal to about 40 g/l, greater than or equal to about 41 g/l, greater than or equal to about 42 g/l, greater than or equal to about 43 g/l, greater than or equal to about 44 g/l, or greater than or equal to about 45 g/l. In some embodiments, the total sugars of leaves of an upright heading iceberg plant of the present disclosure are less than or equal to about 45 g/l, less than or equal to about 44 g/l, less than or equal to about 43 g/l, less than or equal to about 42 g/l, less than or equal to about 41 g/l, less than or equal to about 40 g/l, less than or equal to about 39 g/l, less than or equal to about 38 g/l, less than or equal to about 37 g/l, less than or equal to about 36 g/l, less than or equal to about 35 g/l, less than or equal to about 34 g/l, less than or equal to about 33 g/l, less than or equal to about 32 g/l, less than or equal to about 31 g/l, less than or equal to about 30 g/l, less than or equal to about 29 g/l, less than or equal to about 28 g/l, less than or equal to about 27 g/l, less than or equal to about 26 g/l, less than or equal to about 25 g/l, less than or equal to about 24 g/l, less than or equal to about 23 g/l, less than or equal to about 22 g/l, less than or equal to about 21 g/l, or less than or equal to about 20 g/l. In some embodiments, the total sugars of leaves of an upright heading iceberg plant of the present disclosure are greater than or equal to about any of the following values in g/l: 25, 27, 30, 32, 35, 37, or 40. In some embodiments, the total sugars of leaves of an upright heading iceberg plant of the present disclosure are greater than or equal to about any of the following values in g/l: 40, 37, 35, 32, 30, 27, or 25. In some embodiments, the total sugars of leaves of an upright heading iceberg plant of the present disclosure can be any of a range of values in g/l having a lower limit of 25, 27, 30, 32, 35, 37, or 40 and an independently selected upper limit of 40, 37, 35, 32, 30, 27, or 25. For example, in some embodiments, the total sugars of leaves of an upright heading iceberg lettuce plant of the present disclosure are between about 25 g/l and about 40 g/l.

In some embodiments, the percent of dry matter weight of an upright heading iceberg plant of the present disclosure is greater than or equal to about 4.0%, greater than or equal to about 4.1%, greater than or equal to about 4.2%, greater than or equal to about 4.3%, greater than or equal to about 4.4%, greater than or equal to about 4.5%, greater than or equal to about 4.55%, greater than or equal to about 4.6%, greater than or equal to about 4.65%, greater than or equal to about 4.7%, greater than or equal to about 4.75%, greater than or equal to about 4.8%, greater than or equal to about 4.85%, greater than or equal to about 4.9%, greater than or equal to about 4.95%, greater than or equal to about 5.0%, greater than or equal to about 5.1%, greater than or equal to about 5.2%, greater than or equal to about 5.3%, greater than or equal to about 5.4%, or greater than or equal to about 5.5%. In some embodiments, the percent of dry matter weight of an upright heading iceberg plant of the present disclosure is less than or equal to about 5.5%, less than or equal to about 5.4%, less than or equal to about 5.3%, less than or equal to about 5.2%, less than or equal to about 5.1%, less than or equal to about 5.0%, less than or equal to about 4.95%, less than or equal to about 4.9%, less than or equal to about 4.85%, less than or equal to about 4.8%, less than or equal to about 4.75%, less than or equal to about 4.7%, less than or equal to about 4.65%, less than or equal to about 4.6%, less than or equal to about 4.55%, less than or equal to about 4.5%, less than or equal to about 4.4%, less than or equal to about 4.3%, less than or equal to about 4.2%, less than or equal to about 4.1%, or less than or equal to about 4.0%. In some embodiments, the percent of dry matter weight of an upright heading iceberg plant of the present disclosure is greater than or equal to about any of the following percentages: 4.5%, 4.55%, 4.6%, 4.65%, 4.7%, 4.75%, 4.8%, 4.85%, 4.9%, 4.95%, or 5.0%. In some embodiments, the percent of dry matter weight of an upright heading iceberg plant of the present disclosure is less than or equal to about any of the following percentages: 5.0%, 4.95%, 4.9%, 4.85%, 4.8%, 4.75%, 4.7%, 4.65%, 4.6%, 4.55%, or 4.5%. In some embodiments, the percent of dry matter weight of an upright heading iceberg plant of the present disclosure can be any of a range of percentages having a lower limit of 4.5%, 4.55%, 4.6%, 4.65%, 4.7%, 4.75%, 4.8%, 4.85%, 4.9%, 4.95%, or 5.0% and an independently selected upper limit of 5.0%, 4.95%, 4.9%, 4.85%, 4.8%, 4.75%, 4.7%, 4.65%, 4.6%, 4.55%, or 4.5%. For example, in some embodiments, the percent of dry matter weight of an upright heading iceberg lettuce plant of the present disclosure is between about 4.5% and 5%.

In some embodiments, the processing damage per bag of processed plant material of an upright heading iceberg plant of the present disclosure is greater than or equal to about 4.0%, greater than or equal to about 0%, greater than or equal to about 1%, greater than or equal to about 2%, greater than or equal to about 3%, greater than or equal to about 4%, greater than or equal to about 5%, greater than or equal to about 6%, greater than or equal to about 7%, greater than or equal to about 8%, greater than or equal to about 9%, greater than or equal to about 10%, greater than or equal to about 11%, or greater than or equal to about 12%. In some embodiments, the processing damage per bag of processed plant material of an upright heading iceberg plant of the present disclosure is less than or equal to about 12%, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2%, less than or equal to about 1%, or less than or equal to about 0%. In some embodiments, the processing damage per bag of processed plant material of an upright heading iceberg plant of the present disclosure is greater than or equal to about any of the following percentages: 5%, 6%, 7%, 8%, 9%, or 10%. In some embodiments, the processing damage per bag of processed plant material of an upright heading iceberg plant of the present disclosure is less than or equal to about any of the following percentages: 10%, 9%, 8%, 7%, 6%, or 5%. In some embodiments, the processing damage per bag of processed plant material of an upright heading iceberg plant of the present disclosure can be any of a range of percentages having a lower limit of %, 6%, 7%, 8%, 9%, or 10% and an independently selected upper limit of 10%, 9%, 8%, 7%, 6%, or 5%. For example, in some embodiments, the processing damage per bag of processed plant material of an upright heading iceberg lettuce plant of the present disclosure is between about 5% and 10%.

In some embodiments, the days of shelf life of processed and packaged plant material of an upright heading iceberg plant of the present disclosure are greater than or equal to about greater than or equal to about 30 days, greater than or equal to about 31 days, greater than or equal to about 32 days, greater than or equal to about 33 days, greater than or equal to about 34 days, greater than or equal to about 35 days, greater than or equal to about 36 days, greater than or equal to about 37 days, greater than or equal to about 38 days, greater than or equal to about 39 days, greater than or equal to about 40 days, greater than or equal to about 41 days, greater than or equal to about 42 days, greater than or equal to about 43 days, greater than or equal to about 44 days, greater than or equal to about 45 days, greater than or equal to about 46 days, greater than or equal to about 47 days, greater than or equal to about 48 days, greater than or equal to about 49 days, or greater than or equal to about 50 days. In some embodiments, the days of shelf life of processed and packaged plant material of an upright heading iceberg plant of the present disclosure are less than or equal to about 50 days, less than or equal to about 49 days, less than or equal to about 48 days, less than or equal to about 47 days, less than or equal to about 46 days, less than or equal to about 45 days, less than or equal to about 44 days, less than or equal to about 43 days, less than or equal to about 42 days, less than or equal to about 41 days, less than or equal to about 40 days, less than or equal to about 39 days, less than or equal to about 38 days, less than or equal to about 37 days, less than or equal to about 36 days, less than or equal to about 35 days, less than or equal to about 34 days, less than or equal to about 33 days, less than or equal to about 32 days, less than or equal to about 31 days, or less than or equal to about 30 days. In some embodiments, the days of shelf life of processed and packaged plant material of an upright heading iceberg plant of the present disclosure are greater than or equal to about any of the following values in days: 35, 36, 37, 38, 39, 40, 41, or 42. In some embodiments, the days of shelf life of processed and packaged plant material of an upright heading iceberg plant of the present disclosure are greater than or equal to about any of the following values in days: 42, 41, 40, 39, 38, 37, 36, or 35. In some embodiments, the days of shelf life of processed and packaged plant material of an upright heading iceberg plant of the present disclosure can be any of a range of values in days having a lower limit of 35, 36, 37, 38, 39, 40, 41, or 42 and an independently selected upper limit of 42, 41, 40, 39, 38, 37, 36, or 35. For example, in some embodiments, the days of shelf life of processed and packaged plant material of an upright heading iceberg lettuce plant of the present disclosure are between about 35 days and about 42 days.

Certain aspects of the present disclosure relate to an iceberg lettuce seed, wherein the seed produces an iceberg lettuce plant with an upright stature phenotype. In some embodiments, the upright stature phenotype includes a space between a base of a head and a top of a ground (e.g., ground level). In some embodiments, said space includes an increased length of core outside of a processing material of a head (i.e., external stem). In some embodiments, the increased length of core outside of the processing material of the head (i.e., external stem) is about 3.5 cm or more, about 4 cm or more, about 4.5 cm or more, or about 5 cm or more. In some embodiments, the upright stature phenotype further includes one or more characteristics selected from the group of: a height to diameter ratio of about 1.3 to about 1.5, leaf strength between about 300 to 400 grams, about 40 to 50% overlapping leaves inside the processing material of the head, a short stem inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

Certain aspects of the present disclosure relate to an iceberg lettuce plant produced from a cross of a first iceberg lettuce plant with a second iceberg lettuce plant, wherein the first iceberg lettuce plant is an upright heading iceberg lettuce plant including a space between a base of a head and a top of a ground, wherein said space includes an increased length of core outside of a processing material of a head (i.e., external stem), the second iceberg lettuce plant is an upright heading iceberg lettuce plant including a space between a base of a head and a top of a ground, wherein said space includes an increased length of core outside of a processing material of a head (i.e., external stem), and wherein the iceberg lettuce plant produced from the cross is an upright heading iceberg lettuce plant including a space between a base of a head and a top of a ground, wherein said space includes an increased length of core outside of a processing material of a head (i.e., external stem). In some embodiments, the first and second iceberg lettuce plants are 'E01E.70111' Lot A lettuce plants, a sample of 'E01E.70111' Lot A lettuce seed having been deposited under NCIMB Accession Number 42957. In some embodiments, the first and second iceberg lettuce plants are 'E01E.70111' Lot B lettuce plants, a sample of 'E01E.70111' Lot B lettuce seed having been deposited under NCIMB Accession Number 42962. In some embodiments, the first and second iceberg lettuce plants are 'E01E.70168' Lot A lettuce plants, a sample of 'E01E.70168' Lot A lettuce seed having been deposited under NCIMB Accession Number 42958. In some embodiments, the first and second iceberg lettuce plants are 'E01E.70168' Lot B lettuce plants, a sample of 'E01E.70168' Lot B lettuce seed having been deposited under NCIMB Accession Number 42963. In some embodiments, the first iceberg lettuce plant is an 'E01E.70111' Lot A lettuce plant, a sample of 'E01E.70111' Lot A lettuce seed having been deposited under NCIMB Accession Number 42957. In some embodiments, the second iceberg lettuce plant is an 'E01E.70168' Lot A lettuce plant, a sample of 'E01E.70168' Lot A lettuce seed having been deposited under NCIMB Accession Number 42958.

Certain aspects of the present disclosure relate to an iceberg lettuce plant produced from a cross of an 'E01E.70111' Lot A plant with a second 'E01E.70111' Lot A plant, a sample of 'E01E.70111' Lot A lettuce seed having been deposited under NCIMB Accession Number 42957, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce plant produced from a cross of an 'E01E.70111' Lot B plant with a second 'E01E.70111' Lot B plant, a sample of 'E01E.70111' Lot B lettuce seed having been deposited under NCIMB Accession Number 42962, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce plant produced from a cross of an 'E01E.70168' Lot A plant with a second 'E01E.70168' Lot A plant, a sample of 'E01E.70168' Lot A lettuce seed having been deposited under NCIMB Accession Number 42958, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce plant produced from a cross of an 'E01E.70168' Lot B plant with a second 'E01E.70168' Lot B plant, a sample of 'E01E.70168' Lot B lettuce seed having been deposited under NCIMB Accession Number 42963, wherein the iceberg lettuce plant produced from the cross includes a space between a base of a head and a top of a ground, and wherein said space includes an increased length of core outside of a processing material of a head (i.e., external stem).

Certain aspects of the present disclosure relate to an iceberg lettuce plant produced from a cross of an 'E01E.70111' Lot A plant with a second 'E01E.70168' Lot A plant, a sample of 'E01E.70111' Lot A lettuce seed having been deposited under NCIMB Accession Number 42957, and a sample of 'E01E.70168' Lot A lettuce seed having been deposited under NCIMB Accession Number 42958, wherein the iceberg lettuce plant produced from the cross includes a space between a base of a head and a top of a ground, and wherein said space includes an increased length of core outside of a processing material of a head (i.e., external stem).

In some embodiments that may be combined with any of the above embodiments, the external stem length allows for a harvest by machine. In some embodiments, the harvest by machine does not remove a substantial portion of processing material of a head. In some embodiments, the harvest by machine is more efficient (i.e., removes less processing material of the head) than for iceberg varieties 'Reliant' and 'Steamboat', cosberg varieties 'Cosmopolitan' and 'Crunchita', and romaine varieties 'True Heart' and 'Solid King'.

Lettuce plant parts include lettuce heads, lettuce leaves, parts of lettuce leaves, pollen, ovules, flowers, and the like. In another embodiment, the present disclosure is directed to a plant part of the plants of any of the above embodiments. In another embodiment, the present disclosure is further directed to heads, leaves, parts of leaves, stems, roots, meristems, flowers, pollen, and ovules of the plants of any of the above embodiments. In another embodiment, the present disclosure is further directed to tissue culture of the plants of any of the above embodiments, and to plants regenerated from the tissue culture, where the plant has all the morphological and physiological characteristics of the plants of any of the above embodiments. In one embodiment, the plant regenerated from the tissue culture has all of the morphological and physiological characteristics of an iceberg lettuce plant produced by growing seed designated as 'E01E.70111' Lot A, representative sample of 'E01E.70111' Lot A lettuce seed having been deposited under NCIMB Accession Number 42957. In another embodiment, the plant regenerated from the tissue culture has all of the morphological and physiological characteristics of an iceberg lettuce plant produced by growing seed designated as 'E01E.70111' Lot B, representative sample of 'E01E.70111' Lot B lettuce seed having been deposited under NCIMB Accession Number 42962. In one embodiment, the plant regenerated from the tissue culture has all of the morphological and physiological characteristics of an iceberg lettuce plant produced by growing seed designated as 'E01E.70168' Lot A, representative sample of 'E01E.70168' Lot A lettuce seed having been deposited under NCIMB Accession Number 42958. In another embodiment, the plant regenerated from the tissue culture has all of the morphological and physiological characteristics of an iceberg lettuce plant produced by growing seed designated as 'E01E.70168' Lot B, representative sample of 'E01E.70168' Lot B lettuce seed having been deposited under NCIMB Accession Number 42963. In some embodiments, the present disclosure is directed to a plant part of any of the above embodiments of plants regenerated from tissue culture. In some embodiments, the present disclosure is further directed to heads, leaves, parts of leaves, stems, roots, meristems, flowers, pollen, and ovules of any of the above embodiments of plants regenerated from tissue culture.

Seeds

Certain aspects of the present disclosure relate to one or more seeds that produce upright heading iceberg lettuce plants described herein. Certain aspects of the present disclosure relate to one or more seeds, wherein the seed produces an iceberg lettuce plant with an upright stature phenotype. In some embodiments, the upright stature phenotype includes a height to diameter ratio greater than or equal to about 1.0, a height of about 1.5 to about 3 times a height of a standard iceberg lettuce plant, a crisp leaf texture, and a closed head. In some embodiments, the iceberg lettuce plant further includes one or more characteristics from the group of a short core, a low level of internal tipburn, a low level of bottom rot, an increased number of leaves, a fast fill rate of leaves in a head, and a space between a base of a head and a top of a ground.

Certain aspects of the present disclosure relate to an iceberg lettuce seed containing an upright stature allele at locus A, wherein the seed produces upright heading iceberg lettuce plants described herein. Certain aspects of the present disclosure relate to an iceberg lettuce seed comprising an upright stature allele at locus A, wherein the seed produces an iceberg lettuce with an upright stature phenotype. In some embodiments, the upright stature phenotype includes a height to diameter ratio greater than or equal to about 1.0, a height of about 1.5 to about 3 times a height of a standard iceberg lettuce plant, a crisp leaf texture, and a closed head. In another embodiment, the iceberg lettuce further includes one or more characteristics from the group of: a short core, a low level of internal tipburn, a low level of bottom rot, an increased number of leaves, a fast fill rate of leaves in a head, and a space between a base of a head and a top of a ground.

The upright heading iceberg lettuce plants of the present disclosure may be produced from seed containing an upright stature allele (e.g. upright stature allele at locus A). In some embodiments, the allele is dominant. In some embodiments, the allele is recessive. In some embodiments, the allele is semi-dominant. In some embodiments, more than one allele contributes to the upright stature phenotype (e.g., a multi-gene trait, a polygenic trait, etc.). In some embodiments, the expression of one or more alleles is upregulated to produce the upright stature phenotype. In some embodiments, the expression of one or more alleles is downregulated to produce the upright stature phenotype. In some embodiments, the upright stature phenotype is the result of gene expression and environmental conditions (e.g., heat). In some embodiments, the upright stature phenotype is the result of gene expression and cultivation conditions (e.g., close planting). In some embodiments, specific characteristics of upright stature can be linked to specific alleles (e.g., increased height to height allele at locus B). In some embodiments, linked markers can be used to identify these alleles.

Certain aspects of the present disclosure relate to one or more seeds that produce upright heading iceberg lettuce plants described herein. Certain aspects of the present disclosure relate to an iceberg lettuce seed comprising an upright stature allele at locus A, wherein the seed produces upright heading iceberg lettuce plants described herein. Certain aspects of the present disclosure relate to an iceberg lettuce seed comprising an upright stature allele at locus A, wherein the seed produces an iceberg lettuce with an upright stature phenotype. In one embodiment, the upright stature phenotype includes a height to diameter ratio greater than or equal to about 1.0, a height of about 1.5 to about 3 times a height of a standard iceberg lettuce plant, a crisp leaf texture, and a closed head. In another embodiment, the iceberg lettuce further includes one or more characteristics from the group of a short core, a low level of internal tipburn, a low level of bottom rot, an increased number of leaves, a fast fill rate of leaves in a head, and a space between a base of a head and a top of a ground.

The upright heading iceberg lettuce plants of the present disclosure may be produced from seed containing an upright stature allele (e.g. upright stature allele at locus A). In some embodiments, the allele is dominant. In some embodiments, the allele is recessive. In some embodiments, the allele is semi-dominant. In some embodiments, more than one allele contributes to the upright stature phenotype (e.g., a multi-gene trait, a polygenic trait, etc.). In some embodiments, the expression of one or more alleles is upregulated to produce the upright stature phenotype. In some embodiments, the expression of one or more alleles is downregulated to produce the upright stature phenotype. In some embodiments, the upright stature phenotype is the result of gene expression and environmental conditions (e.g., heat). In some embodiments, the upright stature phenotype is the result of gene expression and cultivation conditions (e.g., close planting). In some embodiments, specific characteristics of upright stature can be linked to specific alleles (e.g., increased height to height allele at locus B). In some embodiments, linked markers can be used to identify these alleles.

Certain aspects of the present disclosure relate to an iceberg lettuce seed from the plants of any of the above embodiments. In another embodiment, the present disclosure is directed to iceberg lettuce plants grown from the seed of any of the above embodiments. In some embodiments of any of the above embodiments, the iceberg lettuce plant includes a space between a base of a head and a top of a ground, and said space includes an increased length of core outside of a processing material of a head (i.e., external stem). In some embodiments, the increased length of core outside of the processing material of the head (i.e., external stem) is about 3.5 cm or more, about 4 cm or more, about 4.5 cm or more, or about 5 cm or more. In some embodiments, the iceberg lettuce plant further includes one or more characteristics from the group of a height to diameter ratio of about 1.3 to about 1.5, leaf strength between about 300 to 400 grams, about 40 to 50% overlapping leaves inside the processing material of the head, a short stem inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

In another embodiment, the present disclosure is directed to methods of producing an herbicide resistant lettuce plant by introducing a gene conferring herbicide resistance, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile, into a lettuce plant produced by growing lettuce seed of any of the above embodiments, and to herbicide resistant lettuce plants produced by such methods. In another embodiment, the present disclosure is directed to methods of producing a pest or insect resistant lettuce plan by introducing a gene conferring pest or insect resistance (e.g., a gene encoding a *Bacillus thuringiensis* endotoxin) into a lettuce plant produced by growing lettuce seed of any of the above embodiments, and to pest or insect resistant lettuce plants produced by such methods. In another embodiment, the present disclosure is directed to methods of producing a disease resistant lettuce plant by introducing a gene conferring disease resistance into a lettuce plant produced by growing lettuce seed of any of the above embodiments, and to disease resistant lettuce plants produced by such methods. In another embodiment, the present disclosure is directed to methods of producing a lettuce plant with a value-added trait by introducing a gene conferring a value-added trait, where the gene encodes a protein selected from a ferritin, a nitrate reductase, and a monellin into a lettuce plant produced by growing lettuce seed of any of the above embodiments, and to value-added lettuce plants produced by such methods. In another embodiment, the present disclosure is directed to methods of producing a lettuce plant adapted to specific environmental conditions (e.g., drought, flooding, salinity, low nitrogen, high heat, high $CO_2$, etc.), into a lettuce plant produced by growing lettuce seed of any of the above embodiments, and to lettuce plants adapted to specific environmental conditions produced by such methods. In another embodiment, the present disclosure provides for single gene converted plants of any of the above embodiments. The single transferred gene may preferably be a dominant or recessive allele. Preferably, the single transferred gene will confer such traits as male sterility, herbicide resistance, and insect or pest resistance, modified fatty acid metabolism, modified carbohydrate metabolism, resistance for bacterial, fungal, or viral disease, male fertility, enhanced nutritional quality, and industrial usage. The single gene may be a naturally occurring lettuce gene.

Methods of Generating and Selecting Upright Heading Iceberg Lettuce Plants

Certain aspects of the present disclosure relate to methods of generating and selecting upright heading iceberg lettuce plants, and the seeds that produce the upright heading iceberg lettuce plants described herein.

In some embodiments, the method of generating and selecting upright heading iceberg lettuce plants involved crossing a first parental iceberg lettuce plant and a second parental iceberg lettuce plant. In some embodiments, the first parental iceberg lettuce plant is the male parental iceberg lettuce plant and the second parental iceberg lettuce plant is the female parental iceberg lettuce plant. In some embodiments, the first parental iceberg lettuce plant is the female parental iceberg lettuce plant and the second parental iceberg lettuce plant is the male parental iceberg lettuce plant. In some embodiments, the first parental iceberg lettuce plant and the second iceberg lettuce plant are plants from inbred iceberg lettuce plant lines. In some embodiments, the first parental iceberg lettuce plant and the second iceberg lettuce plant are off-types (e.g., rogues) from inbred iceberg lettuce plant lines. In some embodiments, the iceberg lettuce plant lines are the same. In other embodiments, the iceberg lettuce plant lines are different. In some embodiments, one of the parental iceberg lettuce plants is a plant of any of the above embodiments and the other parental iceberg lettuce plant is another iceberg lettuce plant. In some embodiments, both of the parental iceberg lettuce plants are a plant of any of the above embodiments. In some embodiments, one of the parental iceberg lettuce plants is 'E01E.70111' Lot A, 'E01E.70111' Lot B, 'E01E.70168' Lot A, or 'E01E.70168' Lot B. In some embodiments, one of the parental iceberg lettuce plants and the other parental iceberg lettuce plant are from different lines (e.g., 'E01E.70111' Lot A and 'E01E.70111' Lot B). In another embodiment, one of the parental iceberg lettuce plants and the other parental iceberg lettuce plant are from the same line (e.g., 'E01E.70111' Lot A). In still another embodiment, the present disclosure is further directed to lettuce plants, lettuce parts from the lettuce plants, and seeds produced therefrom where the lettuce plant is isolated by the breeding method of the disclosure.

In another embodiment, the present disclosure is further directed to a method of selecting lettuce plants with an upright stature, by a) crossing a first lettuce plant with a height to diameter ratio greater than or equal to about 1.0, a height of about 1.5 to about 3 times a height of a standard iceberg lettuce plant, a crisp leaf texture, and a closed head with a second lettuce plant with a height to diameter ratio greater than or equal to about 1.0, a height of about 1.5 to about 3 times a height of a standard iceberg lettuce plant, a crisp leaf texture, and a closed head, b) selecting offspring with an improved set of characteristics including a height to diameter ratio greater than or equal to about 1.5, a height greater than or equal to about 2 to about 3 times a height of a standard iceberg lettuce plant, a crisp leaf texture, and a more tightly closed head, c) selfing or sib-crossing (i.e. sobbing) the offspring, and d) repeating steps b) and c) for multiple generations to produce inbred lines with the improved set of characteristics. In one embodiment, the characteristics used for selection in step b) further include one or more characteristics from the group of: a short core, a low level of internal tipburn, a low level of bottom rot, an increased number of leaves, a fast fill rate of leaves in a head, and a space between a base of a head and a top of a ground. In another embodiment, the space between the base of the head and the top of the ground is achieved by an increased length of core or an increased number of frame leaves outside of the processing material of the head. In some embodiments, the characteristics used for selection in step b) further include one or more characteristics from the group of: moderate leaf glossiness, moderate tendency to bolt, inner leaves paler than outer leaves, blanched inner leaves, green to greyish green outer leaves, outer leaves with a color ranging from about RHS146A to about RHS146B, inner leaves with a color ranging from RHS 145C to RHS 245D, leaves with an obovate shape, leaves with an elliptic shape, leaves with a broad obtrullate shape, leaves with a triangular shape, head with a narrow elliptic shape in longitudinal section, head with an elliptic shape in longitudinal section, head with a broad elliptic shape in longitudinal section, head with an oval shape in longitudinal section, head with an oblong shape in longitudinal section, medium degree of overlapping of upper part of leaves, strong degree of overlapping of upper part of leaves, absent or very few leaf divisions, leaf margin hardly to rather strongly incised, thick leaves, absent to medium undulation of leaf margin, semi-flabellate leaf venation, flabellate leaf venation, clear midrib, no clear midrib, heading, early heading, and medium heading. In other embodiments, the iceberg lettuce plant further includes one or more characteristics from the group of characteristics defining the upright heading iceberg lettuce plant type. In still another embodiment, the present disclosure is further directed to lettuce plants, lettuce parts from the lettuce plants, and seeds produced therefrom where the lettuce plant is isolated by the breeding method of the disclosure.

In another embodiment, the present disclosure is further directed to a method of making upright heading iceberg lettuce plants, by a) crossing a first upright heading iceberg lettuce plant including a space between a base of a head and a top of a ground, wherein said space includes an increased length of core outside of a processing material of a head (i.e., external stem) with a second upright heading iceberg lettuce plant including a space between a base of a head and a top of a ground, wherein said space includes an increased length of core outside of a processing material of a head (i.e., external stem); b) selecting offspring lettuce plants including a space between a base of a head and a top of a ground, wherein said space includes an increased length of core outside of a processing material of a head (i.e., external stem); c) selfing or sibbing the offspring, and d) repeating steps b) and c) for multiple generations to produce inbred lines with the improved set of characteristics. In some embodiments, the increased length of core outside of the processing material of the head (i.e., external stem) is about 3.5 cm or more, about 4 cm or more, about 4.5 cm or more, or about 5 cm or more. In one embodiment, the characteristics used for selection in step b) further include one or more characteristics from the group of a height to diameter ratio of about 1.3 to about 1.5, leaf strength between about 300 to 400 grams, about 40 to 50% overlapping leaves inside the processing material of the head, a short stem inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

In a further embodiment, the present disclosure relates to methods for developing lettuce plants in a lettuce plant breeding program using plant breeding techniques including recurrent selection, backcrossing, pedigree breeding, restriction fragment length polymorphism enhanced selection, genetic marker enhanced selection, and transformation. Seeds, lettuce plants, and parts thereof, produced by such breeding methods are also part of the disclosure.

Further Embodiments

Gene Conversions

When the term "lettuce plant" is used in the context of the present invention, this also includes any gene conversions of that variety. The term "gene converted plant" as used herein refers to those lettuce plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental lettuce plant which contributes the gene for the desired characteristic is termed the "nonrecurrent" or "donor parent." This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol. Perlman & Sleeper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a lettuce plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of lettuce and regeneration of plants therefrom is well known and widely published. For example, reference may be had to Tang, et al., HortScience, 27:9, 1030-1032 (1992); Teng, et al., HortScience, 28:6, 669-1671 (1993); Zhang, et al., *Journal of Genetics and Breeding*, 46:3, 287-290 (1992); Webb, et al., *Plant Cell Tissue and Organ Culture*, 38:1, 77-79 (1994); Curtis, et al., *Journal of Experimental Botany*, 45:279, 1441-1449 (1994); Nagata, et al., *Journal for the American Society for Horticultural Science*, 125:6, 669-672 (2000); and Ibrahim, et al., *Plant Cell Tissue and Organ Culture*, 28(2), 139-145 (1992). It is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of variety 'E01E.70111'. A further aspect of this invention is to provide cells which upon growth and differentiation produce lettuce plants having the physiological and morphological characteristics of variety 'E01E.70168'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, the disclosures of which are incorporated herein by reference.

Additional Breeding Methods

The invention is also directed to methods for producing a lettuce plant by crossing a first parent lettuce plant with a second parent lettuce plant where the first or second parent lettuce plant is a lettuce plant of variety 'E01E.70111' Lot A. Further, both first and second parent lettuce plants can come from lettuce variety 'E01E.70111' Lot A. Thus, any such methods using lettuce variety 'E01E.70111' Lot A are part of the invention: selfing, backcrosses, hybrid production, crosses to populations, and the like. All plants produced using lettuce variety 'E01E.70111' Lot A as at least one parent are within the scope of this invention, including those developed from varieties derived from lettuce variety 'E01E.70111' Lot A. Advantageously, this lettuce variety could be used in crosses with other, different, lettuce plants to produce the first generation ($F_1$) lettuce hybrid seeds and plants with superior characteristics. The variety of the invention can also be used for transformation where exogenous genes are introduced and expressed by the variety of the invention. Genetic variants created either through traditional breeding methods using lettuce variety 'E01E.70111' Lot A, or through transformation of variety 'E01E.70111' Lot A by any of a number of protocols known to those of skill in the art are intended to be within the scope of this invention.

The following describes breeding methods that may be used with lettuce variety 'E01E.70111' Lot A in the development of further lettuce plants. One such embodiment is a method for developing variety 'E01E.70111' Lot A progeny lettuce plants in a lettuce plant breeding program, by: obtaining the lettuce plant, or apart thereof, of variety 'E01E.70111' Lot A, utilizing said plant or plant part as a source of breeding material, and selecting a lettuce variety 'E01E.70111' Lot A progeny plant with molecular markers in common with variety 'E01E.70111' Lot A and/or with morphological and/or physiological characteristics selected from the characteristics listed in the section entitled "Objective description of the variety 'E01E.70111' Lot A" Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce variety 'E01E.70111' Lot A progeny lettuce plants, by crossing variety 'E01E.70111' Lot A with another lettuce plant, thereby producing a population of lettuce plants, which, on average, derive 50% of their alleles from lettuce variety 'E01E.70111' Lot A. A plant of this population may be selected and repeatedly selfed or sibbed with a lettuce variety resulting from these successive filial generations. One embodiment of this invention is the lettuce variety produced by this method and that has obtained at least 50% of its alleles from lettuce variety 'E01E.70111' Lot A. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus the invention includes lettuce variety 'E01E.70111' Lot A progeny lettuce plants containing a combination of at least two variety 'E01E.70111' Lot A traits selected from those listed in the section entitled "Objective description of the variety 'E01E.70111' Lot A", or the variety 'E01E.70111' Lot A combination of traits listed in the Summary of the Invention, so that said progeny lettuce plant is not significantly different for said traits than lettuce variety 'E01E.70111' Lot A as determined at the 5% significance level when grown in the same environmental conditions. Using techniques described herein, molecular markers may be used to identify said progeny plant as a lettuce variety 'E01E.70111' Lot A progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce variety 'E01E.70111' Lot A may also be characterized through their filial relationship with lettuce variety 'E01E.70111' Lot A, as for example, being within a certain number of breeding crosses of lettuce variety 'E01E.70111' Lot A. A breeding cross is across made to introduce new genetics into the progeny, and is distinguished from a cross, such as a self or a sib cross, made to select among existing genetic alleles. The lower the number of breeding crosses in the pedigree, the closer the relationship between lettuce variety 'E01E.70111' Lot A and its progeny. For example, progeny produced by the methods described herein may be within 1, 2, 3, 4, or 5 breeding crosses of lettuce variety 'E01E.70111' Lot A.

The invention is also directed to methods for producing a lettuce plant by crossing a first parent lettuce plant with a second parent lettuce plant where the first or second parent lettuce plant is a lettuce plant of variety 'E01E.70111' Lot B. Further, both first and second parent lettuce plants can come from lettuce variety 'E01E.70111' Lot B. Thus, any such methods using lettuce variety 'E01E.70111' Lot B are part of the invention: selfing, backcrosses, hybrid production, crosses to populations, and the like. All plants produced using lettuce variety 'E01E.70111' Lot B as at least one parent are within the scope of this invention, including those developed from varieties derived from lettuce variety 'E01E.70111' Lot B. Advantageously, this lettuce variety could be used in crosses with other, different, lettuce plants to produce the first generation ($F_1$) lettuce hybrid seeds and plants with superior characteristics. The variety of the invention can also be used for transformation where exogenous genes are introduced and expressed by the variety of the invention. Genetic variants created either through traditional breeding methods using lettuce variety 'E01E.70111' Lot B, or through transformation of variety 'E01E.70111' Lot B by any of a number of protocols known to those of skill in the art are intended to be within the scope of this invention.

The following describes breeding methods that may be used with lettuce variety 'E01E.70111' Lot B in the development of further lettuce plants. One such embodiment is a method for developing variety 'E01E.70111' Lot B progeny lettuce plants in a lettuce plant breeding program, by: obtaining the lettuce plant, or apart thereof, of variety 'E01E.70111' Lot B, utilizing said plant or plant part as a source of breeding material, and selecting a lettuce variety 'E01E.70111' Lot B progeny plant with molecular markers in common with variety 'E01E.70111' Lot B and/or with morphological and/or physiological characteristics selected from the characteristics listed in the section entitled "Objective description of the variety 'E01E.70111' Lot B" Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce variety 'E01E.70111' Lot B progeny lettuce plants, by crossing variety 'E01E.70111' Lot B with another lettuce plant, thereby producing a population of lettuce plants, which, on average, derive 50% of their alleles from lettuce variety 'E01E.70111' Lot B. A plant of this population may be selected and repeatedly selfed or sibbed with a lettuce variety resulting from these successive filial generations. One embodiment of this invention is the lettuce variety produced by this method and that has obtained at least 50% of its alleles from lettuce variety 'E01E.70111' Lot B. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus the invention includes lettuce variety 'E01E.70111' Lot B progeny lettuce plants containing a combination of at least two variety 'E01E.70111' Lot B traits selected from those listed in the section entitled "Objective description of the variety 'E01E.70111' Lot B", or the variety 'E01E.70111' Lot B combination of traits listed in the Summary of the Invention, so that said progeny lettuce plant is not significantly different for said traits than lettuce variety 'E01E.70111' Lot B as determined at the 5% significance level when grown in the same environmental conditions. Using techniques described herein, molecular markers may be used to identify said progeny plant as a lettuce variety 'E01E.70111' Lot B progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce variety 'E01E.70111' Lot B may also be characterized through their filial relationship with lettuce variety 'E01E.70111' Lot B, as for example, being within a certain number of breeding crosses of lettuce variety 'E01E.70111' Lot B. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce variety 'E01E.70111' Lot B and its progeny. For example, progeny produced by the methods described herein may be within 1, 2, 3, 4, or 5 breeding crosses of lettuce variety 'E01E.70111' Lot B.

The invention is also directed to methods for producing a lettuce plant by crossing a first parent lettuce plant with a second parent lettuce plant where the first or second parent lettuce plant is a lettuce plant of variety 'E01E.70168' Lot A. Further, both first and second parent lettuce plants can come from lettuce variety "E01E.70168' Lot A'. Thus, any such methods using lettuce variety 'E01E.70168' Lot A are part of the invention: selfing, backcrosses, hybrid production, crosses to populations, and the like. All plants produced using lettuce variety 'E01E.70168' Lot A as at least one parent are within the scope of this invention, including those developed from varieties derived from lettuce variety 'E01E.70168' Lot A. Advantageously, this lettuce variety could be used in crosses with other, different, lettuce plants to produce the first generation ($F_1$) lettuce hybrid seeds and plants with superior characteristics. The variety of the invention can also be used for transformation where exogenous genes are introduced and expressed by the variety of the invention. Genetic variants created either through traditional breeding methods using lettuce variety 'E01E.70168' Lot A, or through transformation of variety 'E01E.70168' Lot A by any of a number of protocols known to those of skill in the art are intended to be within the scope of this invention.

The following describes breeding methods that may be used with lettuce variety 'E01E.70168' Lot A in the development of further lettuce plants. One such embodiment is a method for developing variety 'E01E.70168' Lot A progeny lettuce plants in a lettuce plant breeding program, by: obtaining the lettuce plant, or apart thereof, of variety 'E01E.70168' Lot A, utilizing said plant or plant part as a source of breeding material, and selecting a lettuce variety 'E01E.70168' Lot A progeny plant with molecular markers in common with variety 'E01E.70168' Lot A and/or with morphological and/or physiological characteristics selected from the characteristics listed in the section entitled "Objective description of the variety 'E01E.70168' Lot A". Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce variety 'E01E.70168' Lot A progeny lettuce plants, by crossing variety 'E01E.70168' Lot A with another lettuce plant, thereby producing a population of lettuce plants, which, on average, derive 50% of their alleles from lettuce variety 'E01E.70168' Lot A. A plant of this population may be selected and repeatedly selfed or sibbed with a lettuce variety resulting from these successive filial generations. One embodiment of this invention is the lettuce variety produced by this method and that has obtained at least 50% of its alleles from lettuce variety 'E01E.70168' Lot A. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus the invention includes lettuce variety 'E01E.70168' Lot A progeny lettuce plants containing a combination of at least two variety 'E01E.70168' Lot A traits selected from those listed in the section entitled "Objective description of the variety 'E01E.70168' Lot A", or the variety 'E01E.70168' Lot A combination of traits listed in the Summary of the Invention, so that said progeny lettuce plant is not significantly different for said traits than lettuce variety 'E01E.70168' Lot A as determined at the 5% significance level when grown in the same environmental conditions. Using techniques described herein, molecular markers may be used to identify said progeny plant as a lettuce variety 'E01E.70168' Lot A progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce variety 'E01E.70168' Lot A may also be characterized through their filial relationship with lettuce variety 'E01E.70168' Lot A, as for example, being within a certain number of breeding crosses of lettuce variety 'E01E.70168' Lot A. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce variety 'E01E.70168' Lot A and its progeny. For example, progeny produced by the methods described herein may be within 1, 2, 3, 4, or 5 breeding crosses of lettuce variety 'E01E.70168' Lot A.

The invention is also directed to methods for producing a lettuce plant by crossing a first parent lettuce plant with a second parent lettuce plant where the first or second parent lettuce plant is a lettuce plant of variety 'E01E.70168' Lot B. Further, both first and second parent lettuce plants can come from lettuce variety "E01E.70168' Lot B'. Thus, any such methods using lettuce variety 'E01E.70168' Lot B are part of the invention: selfing, backcrosses, hybrid production, crosses to populations, and the like. All plants produced using lettuce variety 'E01E.70168' Lot B as at least one parent are within the scope of this invention, including those developed from varieties derived from lettuce variety 'E01E.70168' Lot B. Advantageously, this lettuce variety could be used in crosses with other, different, lettuce plants to produce the first generation ($F_1$) lettuce hybrid seeds and plants with superior characteristics. The variety of the invention can also be used for transformation where exogenous genes are introduced and expressed by the variety of the invention. Genetic variants created either through traditional breeding methods using lettuce variety 'E01E.70168' Lot B, or through transformation of variety 'E01E.70168' Lot B by any of a number of protocols known to those of skill in the art are intended to be within the scope of this invention.

The following describes breeding methods that may be used with lettuce variety 'E01E.70168' Lot B in the development of further lettuce plants. One such embodiment is a method for developing variety 'E01E.70168' Lot B progeny lettuce plants in a lettuce plant breeding program, by: obtaining the lettuce plant, or apart thereof, of variety 'E01E.70168' Lot B, utilizing said plant or plant part as a source of breeding material, and selecting a lettuce variety 'E01E.70168' Lot B progeny plant with molecular markers in common with variety 'E01E.70168' Lot B and/or with morphological and/or physiological characteristics selected from the characteristics listed in the section entitled "Objective description of the variety 'E01E.70168' Lot B". Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce variety 'E01E.70168' Lot B progeny lettuce plants, by crossing variety 'E01E.70168' Lot B with another lettuce plant, thereby producing a population of lettuce plants, which, on average, derive 50% of their alleles from lettuce variety 'E01E.70168' Lot B. A plant of this population may be selected and repeatedly selfed or sibbed with a lettuce variety resulting from these successive filial generations. One embodiment of this invention is the lettuce variety produced by this method and that has obtained at least 50% of its alleles from lettuce variety 'E01E.70168' Lot B. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus the invention includes lettuce variety 'E01E.70168' Lot B progeny lettuce plants containing a combination of at least two variety 'E01E.70168' Lot B traits selected from those listed in the section entitled "Objective description of the variety 'E01E.70168' Lot B", or the variety 'E01E.70168' Lot B combination of traits listed in the Summary of the Invention, so that said progeny lettuce plant is not significantly different for said traits than lettuce variety 'E01E.70168' Lot B as determined at the 5% significance level when grown in the same environmental conditions. Using techniques described herein, molecular markers may be used to identify said progeny plant as a lettuce variety 'E01E.70168' Lot B progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce variety 'E01E.70168' Lot B may also be characterized through their filial relationship with lettuce variety 'E01E.70168' Lot B, as for example, being within a certain number of breeding crosses of lettuce variety 'E01E.70168' Lot B. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce variety 'E01E.70168' Lot B and its progeny. For example, progeny produced by the methods described herein may be within 1, 2, 3, 4, or 5 breeding crosses of lettuce variety 'E01E.70168' Lot B.

As used herein, the term "plant" includes plant cells, plant protoplasts, plant cell tissue cultures from which lettuce plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

Overview of the Variety 'E01E.70111' Lot A

'E01E.70111' Lot A is an inbred line from an original cross between two iceberg rogues. 'E01E.70111' and 'E01E.70168' are inbred lines from the same original cross. 'E01E.70111' Lot A and 'E01E.70111' Lot B are sister lines from the same parent in the previous generation.

Lettuce variety 'E01E.70111' Lot A is the result of numerous generations of plant selections chosen for its oblong to oval shape, taller height, crisp leaf texture, and closed head. Further traits of interest included its tighter filling head, short core, lower level of internal tip-burn, lower level of bottom rot, and the elevation of its base from the ground.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'E01E.70111' Lot A.

The data which define these characteristics is based on observations taken in San Juan Bautista, Calif. Color references are primarily to the RHS Colour Chart of The Royal Horticultural Society of London (RHS) (2007 edition). Descriptive terminology follows the *Plant Identification Terminology, An Illustrated Glossary,* 2nd edition by James G. Harris and Melinda Woolf Harris, unless where otherwise defined.

Objective Description of the Variety 'E01E.70111' Lot A

Lettuce variety 'E01E.70111' Lot A has the following morphologic and other characteristics:

Plant:
Type: Upright heading iceberg
Shape: Oblong to oval
Height: Tall
Diameter: Narrow
Core length: Relatively short under cool conditions; long cores under high heat conditions
Leaves:
Heading:
Outer leaves: Curl over, less tight wrap than iceberg
Inner leaves: Blanched
Color:
Outer leaves: Medium green
Inner leaves: Yellow-green
Mature leaf texture: Crisp Comparisons to Other Lettuce Varieties Table 1 below compares the characteristics of lettuce variety 'E01E.70111' Lot A with the most similar varieties 'Pueblo' (iceberg type, U.S. patent application Ser. No. 15/448,038), 'True Heart' (romaine type, U.S. Pat. No. 7,468,473), and 'Crunchita' (cosberg type, U.S. Pat. No. 9,119,366). Table 2 below compares the qualities of the harvested material of these varieties, including shelf life, maturity index, and other qualities.

TABLE 1

| Characteristic | 'E01E.70111' Lot A | 'Pueblo' | 'True Heart' | 'Crunchita' |
| --- | --- | --- | --- | --- |
| Head shape | Oval to oblong | Round | V-shaped/Deep V-shaped | Oval to oblong |
| Leaf shape | Fan-shaped to V-shaped/Deep V-shaped (more Fan-shaped) | Fan-shaped | V-shaped/Deep V-shaped | Fan-shaped to V-shaped/Deep V-shaped (more V-shaped) |

TABLE 2

| Characteristic | 'E01E.70111' Lot A | 'Pueblo' | 'True Heart' | 'Crunchita' |
| --- | --- | --- | --- | --- |
| Shelf life (days post harvest) | 22 | 22 | 16 | 16 |
| Odor (days post harvest) | 22 | 22 | 14 | 14 |
| Browning (days post harvest) | 22 | 22 | 16 | 16 |
| Rotting (days post harvest) | 20 | 20 | 14 | 14 |
| Maturity index (1 to 9) | 2.4 ± 0.5 | 4.1 ± 0.7 | 38.8 ± 17.7 | 36.8 ± 12.6 |
| Processing efficiency (%) | 82.3 ± 2.1 | 91.6 ± 4.1 | 84.7 ± 3.3 | 89.7 ± 2.7 |
| Internal tipburn (1 to 9) | 8.3 | 7.3 | 7.8 | 8.6 |
| Bremia (1 to 9) | 9.0 | 7.7 | 9.0 | 9.0 |
| Splitting (1 to 9) | 7.5 | 4.3 | 6.0 | 8.6 |
| Side shoot (1 to 9) | 9.0 | 9.0 | 9.0 | 9.0 |

Overview of the Variety 'E01E.70111' Lot B

'E01E.70111' Lot B is an inbred line from an original cross between two iceberg rogues. 'E01E.70111' and 'E01E.70168' are inbred lines from the same original cross. 'E01E.70111' Lot A and 'E01E.70111' Lot B are sister lines from the same parent in the previous generation.

Lettuce variety 'E01E.70111' Lot B is the result of numerous generations of plant selections chosen for its oblong to oval shape, taller height, crisp leaf texture, and closed head. Further traits of interest included its tighter filling head, short core, lower level of internal tip-burn, lower level of bottom rot, and the elevation of its base from the ground.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'E01E.70111' Lot B.

The data which define these characteristics is based on observations taken in San Juan Bautista, Calif. Color references are primarily to the RHS Colour Chart of The Royal Horticultural Society of London (RHS) (2007 edition). Descriptive terminology follows the *Plant Identification Terminology, An Illustrated Glossary,* 2nd edition by James G. Harris and Melinda Woolf Harris, unless where otherwise defined.

Objective Description of the Variety 'E01E.70111' Lot B

Lettuce variety 'E01E.70111' Lot B has the following morphologic and other characteristics:

Plant:
 Type: Upright heading iceberg
 Shape: Oblong to oval
 Height: Tall
 Diameter: Narrow
 Core length: Relatively short under cool conditions; long cores under high heat conditions
Leaves:
 Heading:
  Outer leaves: Curl over, less tight wrap than iceberg
  Inner leaves: Blanched
 Color:
  Outer leaves: Medium green
  Inner leaves: Yellow-green
 Mature leaf texture: Crisp
Comparisons to Other Lettuce Varieties Table 3 below compares the characteristics of lettuce variety 'E01E.70111' Lot B with the most similar varieties 'Pueblo' (iceberg type),'True Heart' (romaine type), and 'Crunchita' (cosberg type). Table 4 below compares the qualities of the harvested material of these varieties, including shelf life, maturity index, and other qualities.

TABLE 3

| Characteristic | 'E01E.70111' Lot B | 'Pueblo' | 'True Heart' | 'Crunchita' |
| --- | --- | --- | --- | --- |
| Head shape | Oval to oblong | Round | V-shaped/ Deep V-shaped | Oval to oblong |
| Leaf shape | Fan-shaped to V-shaped/Deep V-shaped (more Fan-shaped) | Fan-shaped | V-shaped/ Deep V-shaped | Fan-shaped to V-shaped/Deep V-shaped (more V-shaped) |

TABLE 4

| Characteristic | 'E01E.70111' Lot B | 'Pueblo' | 'True Heart' | 'Crunchita' |
| --- | --- | --- | --- | --- |
| Shelf life (days post harvest) | 20 | 22 | 16 | 16 |
| Odor (days post harvest) | 20 | 22 | 14 | 14 |
| Browning (days post harvest) | 18 | 22 | 16 | 16 |
| Rotting (days post harvest) | 18 | 20 | 14 | 14 |
| Maturity index (1 to 9) | 1.8 ± 0.7 | 4.1 ± 0.7 | 38.8 ± 17.7 | 36.8 ± 12.6 |
| Processing efficiency (%) | 81.1 ± 2.2 | 91.6 ± 4.1 | 84.7 ± 3.3 | 89.7 ± 2.7 |

TABLE 4-continued

| Characteristic | 'E01E.70111' Lot B | 'Pueblo' | 'True Heart' | 'Crunchita' |
| --- | --- | --- | --- | --- |
| Internal tipburn (1 to 9) | 6.8 | 7.3 | 7.8 | 8.6 |
| Bremia (1 to 9) | 9.0 | 7.7 | 9.0 | 9.0 |
| Splitting (1 to 9) | 7.1 | 4.3 | 6.0 | 8.6 |
| Side shoot (1 to 9) | 9.0 | 9.0 | 9.0 | 9.0 |

Overview of the Variety 'E01E.70168' Lot A

'E01E.70168' Lot A is an inbred line from an original cross between two iceberg rogues. 'E01E.70111' and 'E01E.70168' are inbred lines from the same original cross. 'E01E.70168' Lot A and 'E01E.70168' Lot B are sister lines from the same parent in the previous generation.

Lettuce variety 'E01E.70168' Lot A is the result of numerous generations of plant selections chosen for its oblong to oval shape, taller height, crisp leaf texture, and closed head. Further traits of interest included its tighter filling head, short core, lower level of internal tip-burn, lower level of bottom rot, and the elevation of its base from the ground.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'E01E.70168' Lot A.

The data which define these characteristics is based on observations taken in San Juan Bautista, Calif. Color references are primarily to the RHS Colour Chart of The Royal Horticultural Society of London (RHS) (2007 edition). Descriptive terminology follows the *Plant Identification Terminology, An Illustrated Glossary,* 2nd edition by James G. Harris and Melinda Woolf Harris, unless where otherwise defined.

Objective Description of the Variety 'E01E.70168' Lot A

Lettuce variety 'E01E.70168' Lot A has the following morphologic and other characteristics:

Plant:
 Type: Upright heading iceberg
 Shape: Oblong to oval
 Height: Tall
 Diameter: Narrow
 Core length: Relatively short under cool conditions; long cores under high heat conditions
Leaves:
 Heading:
  Outer leaves: Curl over, less tight wrap than iceberg
  Inner leaves: Blanched
 Color:
  Outer leaves: Medium green
  Inner leaves: Yellow-green
 Mature leaf texture: Crisp
Comparisons to Other Lettuce Varieties Table 5 below compares the characteristics of lettuce variety 'E01E.70168' Lot A with the most similar varieties 'Pueblo' (iceberg type),'True Heart' (romaine type), and 'Crunchita' (cosberg type). Table 6 below compares the qualities of the harvested material of these varieties, including shelf life, maturity index, and other qualities.

TABLE 5

| Characteristic | 'E01E.70168' Lot A | 'Pueblo' | 'True Heart' | 'Crunchita' |
|---|---|---|---|---|
| Plant shape | Oval to oblong | Round | V-shaped/Deep V-shaped | Oval to oblong |
| Leaf shape | Fan-shaped to V-shaped/Deep V-shaped (more Fan-shaped) | Fan-shaped | V-shaped/Deep V-shaped | Fan-shaped to V-shaped/Deep V-shaped (more V-shaped) |

TABLE 6

| Characteristic | 'E01E.70168' Lot A | 'Pueblo' | 'True Heart' | 'Crunchita' |
|---|---|---|---|---|
| Shelf life (days post harvest) | 18 | 22 | 16 | 16 |
| Odor (days post harvest) | 18 | 22 | 14 | 14 |
| Browning (days post harvest) | 18 | 22 | 16 | 16 |
| Rotting (days post harvest) | 16 | 20 | 14 | 14 |
| Maturity index (1 to 9) | 3.0 ± 0.5 | 4.1 ± 0.7 | 38.8 ± 17.7 | 36.8 ± 12.6 |
| Processing efficiency (%) | 93.2 ± 2.3 | 91.6 ± 4.1 | 84.7 ± 3.3 | 89.7 ± 2.7 |
| Internal tipburn (1 to 9) | 6.8 | 7.3 | 7.8 | 8.6 |
| Bremia (1 to 9) | 7.9 | 7.7 | 9.0 | 9.0 |
| Splitting (1 to 9) | 4.5 | 4.3 | 6.0 | 8.6 |
| Side shoot (1 to 9) | 8.6 | 9.0 | 9.0 | 9.0 |

Overview of the Variety 'E01E.70168' Lot B

'E01E.70168' Lot B is an inbred line from an original cross between two iceberg rogues. 'E01E.70111' and 'E01E.70168' are inbred lines from the same original cross. 'E01E.70168' Lot A and 'E01E.70168' Lot B are sister lines from the same parent in the previous generation.

Lettuce variety 'E01E.70168' Lot B is the result of numerous generations of plant selections chosen for its oblong to oval shape, taller height, crisp leaf texture, and closed head. Further traits of interest included its tighter filling head, short core, lower level of internal tip-burn, lower level of bottom rot, and the elevation of its base from the ground.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'E01E.70168' Lot B.

The data which define these characteristics is based on observations taken in San Juan Bautista, Calif. Color references are primarily to the RHS Colour Chart of The Royal Horticultural Society of London (RHS) (2007 edition). Descriptive terminology follows the *Plant Identification Terminology, An Illustrated Glossary*, 2nd edition by James G. Harris and Melinda Woolf Harris, unless where otherwise defined.

Objective Description of the Variety 'E01E.70168' Lot B

Lettuce variety 'E01E.70168' Lot B has the following morphologic and other characteristics:
Plant:
  Type: Upright heading iceberg
  Shape: Oblong to oval
  Height: Tall
  Diameter: Narrow
  Core length: Relatively short under cool conditions; long cores under high heat conditions
Leaves:
  Heading:
  Outer leaves: Curl over, less tight wrap than iceberg
  Inner leaves: Blanched
  Color:
  Outer leaves: Medium green
  Inner leaves: Yellow-green
  Mature leaf texture: Crisp
Comparisons to Other Lettuce Varieties Table 7 below compares the characteristics of lettuce variety 'E01E.70168' Lot B with the most similar varieties 'Pueblo' (iceberg type), 'True Heart' (romaine type), and 'Crunchita' (cosberg type). Table 8 below compares the qualities of the harvested material of these varieties, including shelf life, maturity index, and other qualities.

TABLE 7

| Characteristic | 'E01E.70168' Lot B | 'Pueblo' | 'True Heart' | 'Crunchita' |
|---|---|---|---|---|
| Plant shape | Oval to oblong | Round | V-shaped/Deep V-shaped | Oval to oblong |
| Leaf shape | Fan-shaped to V-shaped/Deep V-shaped (more Fan-shaped) | Fan-shaped | V-shaped/Deep V-shaped | Fan-shaped to V-shaped/Deep V-shaped (more V-shaped) |

TABLE 8

| Characteristic | 'E01E.70168' Lot B | 'Pueblo' | 'True Heart' | 'Crunchita' |
|---|---|---|---|---|
| Shelf life (days post harvest) | 16 | 22 | 16 | 16 |
| Odor (days post harvest) | 16 | 22 | 14 | 14 |
| Browning (days post harvest) | 16 | 22 | 16 | 16 |
| Rotting (days post harvest) | 16 | 20 | 14 | 14 |
| Maturity index (1 to 9) | 3.4 ± 0.7 | 4.1 ± 0.7 | 38.8 ± 17.7 | 36.8 ± 12.6 |
| Processing efficiency (%) | 93.4 ± 1.3 | 91.6 ± 4.1 | 84.7 ± 3.3 | 89.7 ± 2.7 |
| Internal tipburn (1 to 9) | 6.8 | 7.3 | 7.8 | 8.6 |
| Bremia (1 to 9) | 7.9 | 7.7 | 9.0 | 9.0 |
| Splitting (1 to 9) | 6.0 | 4.3 | 6.0 | 8.6 |
| Side shoot (1 to 9) | 8.6 | 9.0 | 9.0 | 9.0 |

DEPOSIT INFORMATION

A deposit of the lettuce variety 'E01E.70111' Lot A is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of lettuce variety 'E01E.70111' Lot A were deposited on Jan. 5, 2018 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 42957. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

A deposit of the lettuce variety 'E01E.70111' Lot B is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of lettuce variety 'E01E.70111' Lot B were deposited on Jan. 22, 2018 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 42962. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

A deposit of the lettuce variety 'E01E.70168' Lot A is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of lettuce variety 'E01E.70168' Lot A were deposited on Jan. 5, 2018 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 42958. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

A deposit of the lettuce variety 'E01E.70168' Lot B is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of lettuce variety 'E01E.70168' Lot B were deposited on Jan. 22, 2018 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 42963. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Enumerated Embodiments

The following enumerated embodiments are representative of some aspects of the invention.
1. An upright heading iceberg lettuce plant comprising a height to diameter ratio greater than or equal to about 1.0, a height of about 1.5 to about 3 times a height of a standard iceberg lettuce plant, a crisp leaf texture, and a closed head.
2. The plant of embodiment 1, wherein the iceberg lettuce plant further comprises one or more characteristics selected from the group consisting of: a short core, a low level of internal tipburn, a low level of bottom rot, an increased number of leaves, a fast fill rate of leaves in a head, and a space between a base of a head and a top of a ground.
3. The plant of embodiment 2, wherein said space is achieved by an increased length of core or an increased number of frame leaves outside of a processing material of a head.
4. An iceberg lettuce seed, wherein the seed produces an iceberg lettuce plant with an upright stature phenotype.
5. The seed of embodiment 4, wherein the upright stature phenotype comprises a height to diameter ratio greater than or equal to about 1.0, a height of about 1.5 to about 3 times a height of a standard iceberg lettuce plant, a crisp leaf texture, and a closed head.
6. The seed of embodiment 5, wherein the iceberg lettuce plant further comprises one or more characteristics selected from the group consisting of: a short core, a low level of internal tipburn, a low level of bottom rot, an increased number of leaves, a fast fill rate of leaves in a head, and a space between a base of a head and a top of a ground.
7. An iceberg lettuce seed comprising an upright stature allele at locus A, wherein the seed produces an iceberg lettuce plant with an upright stature phenotype.
8. The seed of embodiment 7, wherein the upright stature phenotype comprises a height to diameter ratio greater than or equal to about 1.0, a height of about 1.5 to about 3 times a height of a standard iceberg lettuce plant, a crisp leaf texture, and a closed head.
9. The seed of embodiment 8, wherein the iceberg lettuce plant further comprises one or more characteristics selected from the group consisting of: a short core, a low level of internal tipburn, a low level of bottom rot, an increased number of leaves, a fast fill rate of leaves in a head, and a space between a base of a head and a top of a ground.
10. An iceberg lettuce plant produced from a cross of a first iceberg lettuce plant with a second iceberg lettuce plant, wherein the first iceberg lettuce plant produces an upright heading iceberg lettuce plant with a height to diameter ratio greater than or equal to about 1.0, a height of about 1.5 to about 3 times a height of a standard iceberg lettuce plant, a crisp leaf texture, and a closed head, the second iceberg lettuce plant produces an upright heading iceberg lettuce plant with a height to diameter ratio greater than or equal to about 1.0, a height of about 1.5 to about 3 times a height of a standard iceberg lettuce plant, a crisp leaf texture, and a closed head, and wherein the iceberg lettuce plant produced from the cross has a height to diameter ratio greater than or equal to about 1.0, a height of about 1.5 to about 3 times a height of a standard iceberg lettuce plant, a crisp leaf texture, and a closed head.
11. The plant of embodiment 10, wherein the first and second iceberg lettuce plants are 'E01E.70111' Lot A lettuce plants, a sample of 'E01E.70111' Lot A lettuce seed having been deposited under NCIMB Accession Number 42957.
12. The plant of embodiment 10, wherein the first and second iceberg lettuce plants are 'E01E.70111' Lot B lettuce plants, a sample of 'E01E.70111' Lot B lettuce seed having been deposited under NCIMB Accession Number 42962.
13. The plant of embodiment 10, wherein the first and second iceberg lettuce plants are 'E01E.70168' Lot A lettuce plants, a sample of 'E01E.70168' Lot A lettuce seed having been deposited under NCIMB Accession Number 42958.
14. The plant of embodiment 10, wherein the first and second iceberg lettuce plants are 'E01E.70168' Lot B lettuce plants, a sample of 'E01E.70168' Lot B lettuce seed having been deposited under NCIMB Accession Number 42963.
15. The plant of embodiment 10, wherein the first iceberg lettuce plant is an 'E01E.70111' Lot A lettuce plant, a sample of 'E01E.70111' Lot A lettuce seed having been deposited under NCIMB Accession Number 42957.
16. The plant of embodiment 10, wherein the second iceberg lettuce plant is an 'E01E.70168' Lot A lettuce plant, a sample of 'E01E.70168' Lot A lettuce seed having been deposited under NCIMB Accession Number 42958.
17. An iceberg lettuce plant produced from a cross of an 'E01E.70111' Lot A plant with a second 'E01E.70111' Lot A plant, a sample of 'E01E.70111' Lot A lettuce seed having been deposited under NCIMB Accession Number 42957, wherein the iceberg lettuce plant produced from the cross has a height to diameter ratio greater than or equal to about 1.0, a height of about 1.5 to about 3 times a height of a standard iceberg lettuce plant, a crisp leaf texture, and a closed head.
18. An iceberg lettuce plant produced from a cross of an 'E01E.70111' Lot B plant with a second 'E01E.70111' Lot B plant, a sample of 'E01E.70111' Lot B lettuce seed having been deposited under NCIMB Accession Number 42962, wherein the iceberg lettuce plant produced from the cross has a height to diameter ratio greater than or equal to about 1.0, a height of about 1.5 to about 3 times a height of a standard iceberg lettuce plant, a crisp leaf texture, and a closed head.
19. An iceberg lettuce plant produced from a cross of an 'E01E.70168' Lot A plant with a second 'E01E.70168' Lot A plant, a sample of 'E01E.70168' Lot A lettuce seed having been deposited under NCIMB Accession Number 42958, wherein the iceberg lettuce plant produced from the cross has a height to diameter ratio greater than or equal to about 1.0, a height of about 1.5 to about 3 times a height of a standard iceberg lettuce plant, a crisp leaf texture, and a closed head.
20. An iceberg lettuce plant produced from a cross of an 'E01E.70168' Lot B plant with a second 'E01E.70168' Lot B plant, a sample of 'E01E.70168' Lot B lettuce seed having been deposited under NCIMB Accession Number 42963, wherein the iceberg lettuce plant produced from the cross has a height to diameter ratio greater than or equal to about 1.0, a height of about 1.5 to about 3 times a height of a standard iceberg lettuce plant, a crisp leaf texture, and a closed head.
21. An iceberg lettuce plant produced from a cross of an 'E01E.70111' Lot A plant with a second 'E01E.70168' Lot A plant, a sample of 'E01E.70111' Lot A lettuce seed having been deposited under NCIMB Accession Number 42957, and a sample of 'E01E.70168' Lot A lettuce seed having been deposited under NCIMB Accession Number 42958, wherein the iceberg lettuce seed produced from the cross produces an iceberg lettuce with a height to diameter ratio greater than or equal to about 1.0, a height of about 1.5 to about 3 times a height of a standard iceberg lettuce plant, a crisp leaf texture, and a closed head.
22. An iceberg lettuce seed from the plants of any one of embodiments 1 to 21.

23. The plant of any one of embodiments 1 to 21, wherein the iceberg lettuce plant has a height to diameter ratio greater than or equal to about 1.0, a height of about 1.5 to about 3 times a height of a standard iceberg lettuce plant, a crisp leaf texture, and a closed head.

24. A plant part from the plant of embodiment 23.

25. The plant part of embodiment 24, wherein said part is a head, a seed, a leaf, or a portion thereof.

26. The plant part of embodiment 25, wherein said part is a head.

27. An iceberg lettuce plant having all the physiological and morphological characteristics of the iceberg lettuce plant of embodiment 23.

28. A plant part from the plant of embodiment 27.

29. The plant part of embodiment 28 wherein said part is a head, a leaf, or a portion thereof.

30. The plant part of embodiment 29, wherein said part is a head.

31. A pollen grain or an ovule of the plant of embodiment 27.

32. A tissue culture produced from the plant of embodiment 27.

33. An iceberg lettuce plant regenerated from the tissue culture of embodiment 33, wherein the plant has all of the morphological and physiological characteristics of an iceberg lettuce plant produced by growing seed designated as 'E01E.70111' Lot A, representative sample of 'E01E.70111' Lot A lettuce seed having been deposited under NCIMB Accession Number 42957.

34. An iceberg lettuce plant regenerated from the tissue culture of embodiment 33, wherein the plant has all of the morphological and physiological characteristics of an iceberg lettuce plant produced by growing seed designated as 'E01E.70111' Lot B, representative sample of 'E01E.70111' Lot B lettuce seed having been deposited under NCIMB Accession Number 42962.

35. An iceberg lettuce plant regenerated from the tissue culture of embodiment 33, wherein the plant has all of the morphological and physiological characteristics of an iceberg lettuce plant produced by growing seed designated as 'E01E.70168' Lot A, representative sample of 'E01E.70168' Lot A lettuce seed having been deposited under NCIMB Accession Number 42958.

36. An iceberg lettuce plant regenerated from the tissue culture of embodiment 33, wherein the plant has all of the morphological and physiological characteristics of an iceberg lettuce plant produced by growing seed designated as 'E01E.70168' Lot B, representative sample of 'E01E.70168' Lot B lettuce seed having been deposited under NCIMB Accession Number 42963.

37. A method of making iceberg lettuce seeds, said method comprising crossing the plant of embodiment 23 with another iceberg lettuce plant and harvesting seed therefrom.

38. A method of making iceberg lettuce seeds, said method comprising crossing the plant of embodiment 27 with another iceberg lettuce plant and harvesting seed therefrom.

39. A method of selecting an iceberg lettuce plant with upright stature, the method comprising:
　a) crossing a first iceberg lettuce plant with a height to diameter ratio greater than or equal to about 1.0, a height of about 1.5 to about 3 times a height of a standard iceberg lettuce plant, a crisp leaf texture, and a closed head with a second iceberg lettuce plant with a height to diameter ratio greater than or equal to about 1.0, a height of about 1.5 to about 3 times a height of a standard iceberg lettuce plant, a crisp leaf texture, and a closed head;
　b) selecting offspring with an improved set of characteristics comprising a height to diameter ratio greater than or equal to about 1.5, a height greater than or equal to about 2 to about 3 times a height of a standard iceberg lettuce plant, a crisp leaf texture, and a more tightly closed head;
　c) selfing or sibbing said offspring;
　d) repeating steps b) and c) for multiple generations to produce inbred lines with the improved set of characteristics.

40. The method of embodiment 39, wherein the characteristics used for selection in step b) further comprise one or more characteristics selected from the group consisting of: one or more characteristics selected from the group consisting of: a short core, a low level of internal tipburn, a low level of bottom rot, an increased number of leaves, a fast fill rate of leaves in a head, and a space between a base of a head and a top of a ground.

41. The method of embodiment 40, wherein said space between the base of the head and the top of the ground is achieved by an increased length of core or an increased number of frame leaves outside of a processing material of a head.

42. An iceberg lettuce (*Lactuca sativa*) plant comprising a genetic determinant that leads to the iceberg lettuce plant having an upright stature, which genetic determinant is as comprised in a lettuce plant representative seed of which was deposited with the NCIMB under accession numbers 42957, 42962, 42958, and 42963.

43. The plant of embodiment 42, wherein the genetic determinant is homozygously present.

44. The plant of embodiment 42, wherein the genetic determinant is heterozygously present.

45. The plant of embodiment 42, wherein the upright stature comprises one or more characteristics selected from the group consisting of: a ratio of plant height to diameter greater than about 1, a height of about 1.5 to about 3 times a height of a standard iceberg lettuce plant, a crisp leaf texture, and a closed head.

46. The plant of embodiment 42, wherein the lettuce further comprises one or more characteristics selected from the group consisting of: a short core, a low level of internal tipburn, a low level of bottom rot, an increased number of leaves, a fast fill rate of leaves in a head, and a space between a base of a head and a top of a ground.

47. An iceberg lettuce (*Lactuca sativa*) plant comprising a genetic determinant that leads to the iceberg lettuce plant having an upright stature, wherein the upright stature comprises one or more characteristics selected from the group consisting of: a ratio of plant height to diameter greater than about 1, a height of about 1.5 to about 3 times a height of a standard iceberg lettuce plant, a crisp leaf texture, and a closed head, and wherein the genetic determinant is as comprised in a lettuce plant representative seed of which was deposited with the NCIMB under accession numbers 42957, 42962, 42958, and 42963.

48. The plant of embodiment 47, wherein the genetic determinant is homozygously present.

49. The plant of embodiment 47, wherein the genetic determinant is heterozygously present.

50. The plant of embodiment 47, wherein the lettuce further comprises one or more characteristics selected from the group consisting of: a short core, a low level of internal tipburn, a low level of bottom rot, an increased number of leaves, a fast fill rate of leaves in a head, and a space between a base of a head and a top of a ground.

51. The plant of any one of embodiments 42 to 50, obtainable by crossing a first iceberg lettuce plant with a second iceberg lettuce plant, wherein at least one of the said plants comprises the genetic determinant as comprised in a lettuce plant representative seed of which was deposited with the NCIMB under accession numbers 42957, 42962, 42958, and 42963, or a progeny plant thereof carrying the genetic determinant, and selecting, preferably in the $F_2$ generation, for plants having an upright stature.

52. A seed of the plant of any one of embodiments 42 to 50, wherein the seed comprises the genetic determinant as present in seeds of which a representative sample was deposited with the NCIMB under accession numbers 42957, 42962, 42958, and 42963.

53. A progeny plant of the plant as embodied in embodiment 51, wherein the plant comprises the genetic determinant as present in seeds of which a representative sample was deposited with the NCIMB under accession numbers 42957, 42962, 42958, or 42963.

54. The progeny plant as embodied in embodiment 53, wherein the genetic determinant is homozygously present.

55. The progeny plant as embodied in embodiment 53, wherein the genetic determinant is heterozygously present.

56. A progeny plant of the seed as embodied in embodiment 52, wherein the plant comprises the genetic determinant as present in seeds of which a representative sample was deposited with the NCIMB under accession numbers 42957, 42962, 42958, or 42963.

57. The progeny plant as embodied in embodiment 56, wherein the genetic determinant is homozygously present.

58. The progeny plant as embodied in embodiment 56, wherein the genetic determinant is heterozygously present.

59. A propagation material derived from the plant as embodied in embodiment 51, wherein the plant comprises the genetic determinant as present in seeds of which a representative sample was deposited with the NCIMB under accession numbers 42957, 42962, 42958, and 42963.

60. A propagation material derived from the seed as embodied in embodiment 52, wherein the plant comprises the genetic determinant as present in seeds of which a representative sample was deposited with the NCIMB under accession numbers 42957, 42962, 42958, and 42963.

61. A propagation material capable of growing into a plant as embodied in embodiment 42.

62. A propagation material capable of growing into a plant as embodied in embodiment 47.

63. The propagation material as embodied in embodiments 61 or 62, wherein the propagation material comprises a microspore, pollen, ovary, ovule, embryo, embryo sac, egg cell, cutting, root, root tip, hypocotyl, cotyledon, stem, leaf, flower, anther, seed, meristem, protoplast, callus, or cell.

64. A tissue culture of the propagation material as embodied in embodiments 61 or 62.

65. A plant part of the plant as embodied in embodiment 42, wherein said part is a head, a leaf, or a portion thereof.

66. A plant part of the plant as embodied in embodiment 47, wherein said part is a head, a leaf, or a portion thereof.

67. The plant part of embodiments 65 or 66, wherein said part is a head.

68. A method for producing an iceberg lettuce plant comprising an upright stature phenotype, the method comprising:
(a) crossing the lettuce plant of embodiment 42 with a second iceberg lettuce plant, wherein said second iceberg lettuce plant is a non-upright stature iceberg lettuce plant, to produce progeny;
(b) using said progeny of (a) in a back-crossing breeding program with the iceberg lettuce plant of embodiment 42 as the recurrent parent for one or more generations, to produce a progeny iceberg lettuce plant comprising the upright stature phenotype.

69. A method for producing an iceberg lettuce plant comprising an upright stature phenotype, the method comprising:
(a) crossing the iceberg lettuce plant of embodiment 47 with a second iceberg lettuce plant, wherein said second iceberg lettuce plant is a non-upright stature iceberg lettuce plant, to produce progeny;
(b) using said progeny of (a) in a back-crossing breeding program with the iceberg lettuce plant of embodiment 47 as the recurrent parent for one or more generations, to produce a progeny iceberg lettuce plant comprising the upright stature phenotype.

70. The method of embodiments 68 or 69, wherein the upright stature phenotype further comprises one or more characteristics selected from the group consisting of: a ratio of plant height to diameter greater than about 1, a height of about 1.5 to about 3 times a height of a standard iceberg lettuce plant, a crisp leaf texture, a closed head, a short core, a low level of internal tipburn, a low level of bottom rot, an increased number of leaves, a fast fill rate of leaves in a head, and a space between a base of a head and a top of a ground.

71. An upright heading iceberg lettuce plant comprising a space between a base of a head and a top of a ground.

72. The plant of embodiment 71, wherein said space comprises an increased length of core outside of a processing material of a head (i.e., external stem).

73. The plant of embodiment 72, wherein the upright heading iceberg lettuce plant further comprises one or more characteristics selected from the group consisting of: a height to diameter ratio of about 1.3 to about 1.5, leaf strength between about 300 to 400 grams, about 40 to 50% overlapping leaves inside the processing material of the head, a short core inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

74. An iceberg lettuce seed, wherein the seed produces an iceberg lettuce plant with an upright stature phenotype.

75. The seed of embodiment 74, wherein the upright stature phenotype comprises a space between a base of a head and a top of a ground.

76. The seed of embodiment 75, wherein said space comprises an increased length of core outside of a processing material of a head (i.e., external stem).

77. The seed of embodiment 76, wherein the upright stature phenotype further comprises one or more characteristics selected from the group consisting of: a height to diameter ratio of about 1.3 to about 1.5, leaf strength between about 300 to 400 grams, about 40 to 50% overlapping leaves inside the processing material of the head, a short core inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

78. An iceberg lettuce plant produced from a cross of a first iceberg lettuce plant with a second iceberg lettuce plant, wherein the first iceberg lettuce plant is an upright heading iceberg lettuce plant comprising a space between a base of a head and a top of a ground, wherein said space comprises an increased length of core outside of a processing material of a head (i.e., external stem), the second iceberg lettuce plant is an upright heading iceberg lettuce plant comprising a space between a base of a head and a top of a ground, wherein said space comprises an increased length of core outside of a processing material of a head (i.e., external stem), and wherein the iceberg lettuce plant produced from the cross is an upright heading iceberg lettuce plant comprising a space between a base of a head and a top of a ground, wherein said space comprises an increased length of core outside of a processing material of a head (i.e., external stem).

79. The plant of embodiment 78, wherein the first and second iceberg lettuce plants are 'E01E.70111' Lot A lettuce plants, a sample of 'E01E.70111' Lot A lettuce seed having been deposited under NCIMB Accession Number 42957.

80. The plant of embodiment 78, wherein the first and second iceberg lettuce plants are 'E01E.70111' Lot B lettuce plants, a sample of 'E01E.70111' Lot B lettuce seed having been deposited under NCIMB Accession Number 42962.

81. The plant of embodiment 78, wherein the first and second iceberg lettuce plants are 'E01E.70168' Lot A lettuce plants, a sample of 'E01E.70168' Lot A lettuce seed having been deposited under NCIMB Accession Number 42958.

82. The plant of embodiment 78, wherein the first and second iceberg lettuce plants are 'E01E.70168' Lot B lettuce plants, a sample of 'E01E.70168' Lot B lettuce seed having been deposited under NCIMB Accession Number 42963.

83. The plant of embodiment 78, wherein the first iceberg lettuce plant is an 'E01E.70111' Lot A lettuce plant, a sample of 'E01E.70111' Lot A lettuce seed having been deposited under NCIMB Accession Number 42957.

84. The plant of embodiment 78, wherein the second iceberg lettuce plant is an 'E01E.70168' Lot A lettuce plant, a sample of 'E01E.70168' Lot A lettuce seed having been deposited under NCIMB Accession Number 42958.

85. An iceberg lettuce plant produced from a cross of an 'E01E.70111' Lot A plant with a second 'E01E.70111' Lot A plant, a sample of 'E01E.70111' Lot A lettuce seed having been deposited under NCIMB Accession Number 42957, wherein the iceberg lettuce plant produced from the cross comprises a space between a base of a head and a top of a ground, and wherein said space comprises an increased length of core outside of a processing material of a head.

86. An iceberg lettuce plant produced from a cross of an 'E01E.70111' Lot B plant with a second 'E01E.70111' Lot B plant, a sample of 'E01E.70111' Lot B lettuce seed having been deposited under NCIMB Accession Number 42962, wherein the iceberg lettuce plant produced from the cross comprises a space between a base of a head and a top of a ground, and wherein said space comprises an increased length of core outside of a processing material of a head (i.e., external stem).

87. An iceberg lettuce plant produced from a cross of an 'E01E.70168' Lot A plant with a second 'E01E.70168' Lot A plant, a sample of 'E01E.70168' Lot A lettuce seed having been deposited under NCIMB Accession Number 42958, wherein the iceberg lettuce plant produced from the cross comprises a space between a base of a head and a top of a ground, and wherein said space comprises an increased length of core outside of a processing material of a head (i.e., external stem).

88. An iceberg lettuce plant produced from a cross of an 'E01E.70168' Lot B plant with a second 'E01E.70168' Lot B plant, a sample of 'E01E.70168' Lot B lettuce seed having been deposited under NCIMB Accession Number 42963, wherein the iceberg lettuce plant produced from the cross comprises a space between a base of a head and a top of a ground, and wherein said space comprises an increased length of core outside of a processing material of a head (i.e., external stem).

89. An iceberg lettuce plant produced from a cross of an 'E01E.70111' Lot A plant with a second 'E01E.70168' Lot A plant, a sample of 'E01E.70111' Lot A lettuce seed having been deposited under NCIMB Accession Number 42957, and a sample of 'E01E.70168' Lot A lettuce seed having been deposited under NCIMB Accession Number 42958, wherein the iceberg lettuce plant produced from the cross comprises a space between a base of a head and a top of a ground, and wherein said space comprises an increased length of core outside of a processing material of a head (i.e., external stem).

90. An iceberg lettuce seed from the plants of any one of embodiments 71 to 89.

91. The plant of any one of embodiments 71 to 89, wherein the iceberg lettuce plant comprises a space between a base of a head and a top of a ground, and wherein said space comprises an increased length of core outside of a processing material of a head (i.e., external stem).

92. The plant of embodiment 91, wherein the iceberg lettuce plant further comprises one or more characteristics selected from the group consisting of: a height to diameter ratio of about 1.3 to about 1.5, leaf strength between about 300 to 400 grams, about 40 to 50% overlapping leaves inside the processing material of the head, a short core inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

93. A plant part from the plant of embodiment 92.

94. The plant part of embodiment 93, wherein said part is a head, a seed, a leaf, or a portion thereof.

95. The plant part of embodiment 94, wherein said part is a head.

96. An iceberg lettuce plant having all the physiological and morphological characteristics of the iceberg lettuce plant of embodiment 92.

97. A plant part from the plant of embodiment 96.

98. The plant part of embodiment 97 wherein said part is a head, a leaf, or a portion thereof.

99. The plant part of embodiment 98, wherein said part is a head.

100. A pollen grain or an ovule of the plant of embodiment 96.

101. A tissue culture produced from the plant of embodiment 96.

102. An iceberg lettuce plant regenerated from the tissue culture of embodiment 101, wherein the plant has all of the morphological and physiological characteristics of an iceberg lettuce plant produced by growing seed designated as 'E01E.70111' Lot A, representative sample of 'E01E.70111' Lot A lettuce seed having been deposited under NCIMB Accession Number 42957.

103. An iceberg lettuce plant regenerated from the tissue culture of embodiment 101, wherein the plant has all of the morphological and physiological characteristics of an iceberg lettuce plant produced by growing seed designated as 'E01E.70111' Lot B, representative sample of 'E01E.70111' Lot B lettuce seed having been deposited under NCIMB Accession Number 42962.

104. An iceberg lettuce plant regenerated from the tissue culture of embodiment 101, wherein the plant has all of the morphological and physiological characteristics of an iceberg lettuce plant produced by growing seed designated as 'E01E.70168' Lot A, representative sample of 'E01E.70168' Lot A lettuce seed having been deposited under NCIMB Accession Number 42958.

105. An iceberg lettuce plant regenerated from the tissue culture of embodiment 101, wherein the plant has all of the morphological and physiological characteristics of an iceberg lettuce plant produced by growing seed designated as 'E01E.70168' Lot B, representative sample of 'E01E.70168' Lot B lettuce seed having been deposited under NCIMB Accession Number 42963.

106. A method of making iceberg lettuce seeds, said method comprising crossing the plant of embodiment 92 with another iceberg lettuce plant and harvesting seed therefrom.

107. A method of making iceberg lettuce seeds, said method comprising crossing the plant of embodiment 96 with another iceberg lettuce plant and harvesting seed therefrom.

108. A method of making upright heading iceberg lettuce plants, the method comprising:
  a) crossing a first upright heading iceberg lettuce plant comprising a space between a base of a head and a top of a ground, wherein said space comprises an increased length of core outside of a processing material of a head (i.e., external stem) with a second upright heading iceberg lettuce plant comprising a space between a base of a head and a top of a ground, wherein said space comprises an increased length of core outside of a processing material of a head (i.e., external stem);
  b) selecting offspring lettuce plants comprising a space between a base of a head and a top of a ground, wherein said space comprises an increased length of core outside of a processing material of a head (i.e., external stem);
  c) selfing or sibbing said offspring;
  d) repeating steps b) and c) for multiple generations to produce inbred lines.

109. The method of embodiment 108, wherein the characteristics used for selection in step b) further comprise one or more characteristics selected from the group consisting of: a height to diameter ratio of about 1.3 to about 1.5, leaf strength between about 300 to 400 grams, about 40 to 50% overlapping leaves inside the processing material of the head, a short core inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

110. An upright heading iceberg lettuce plant comprising a space between a base of a head and a top of a ground.

111. The plant of embodiment 110, wherein said space comprises an increased length of core outside of a processing material of a head (i.e., external stem).

112. The plant of embodiment 111, wherein the increased length of core outside of the processing material of the head (i.e., external stem) is about 3.5 cm or more, about 4 cm or more, about 4.5 cm or more, or about 5 cm or more.

113. The plant of embodiment 111 or embodiment 112, wherein the upright heading iceberg lettuce plant further comprises one or more characteristics selected from the group consisting of: a height to diameter ratio of about 1.3 to about 1.5, leaf strength between about 300 to 400 grams, about 40 to 50% overlapping leaves inside the processing material of the head, a short core inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

114. An upright heading iceberg lettuce seed, wherein the seed produces an upright heading iceberg lettuce plant with an upright stature phenotype.

115. The seed of embodiment 114, wherein the upright stature phenotype comprises a space between a base of a head and a top of a ground.

116. The seed of embodiment 115, wherein said space comprises an increased length of core outside of a processing material of a head (i.e., external stem).

117. The seed of embodiment 116, wherein the increased length of core outside of the processing material of the head (i.e., external stem) is about 3.5 cm or more, about 4 cm or more, about 4.5 cm or more, or about 5 cm or more.

118. The seed of embodiment 116 or embodiment 117, wherein the upright stature phenotype further comprises one or more characteristics selected from the group consisting of: a height to diameter ratio of about 1.3 to about 1.5, leaf strength between about 300 to 400 grams, about 40 to 50% overlapping leaves inside the processing material of the head, a short core inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

119. An upright heading iceberg lettuce plant produced from a cross of a first iceberg lettuce plant with a second iceberg lettuce plant, wherein the first iceberg lettuce plant is an upright heading iceberg lettuce plant comprising a space between a base of a head and a top of a ground, wherein said space comprises an increased length of core outside of a processing material of a head (i.e., external stem), the second iceberg lettuce plant is an upright heading iceberg lettuce plant comprising a space between a base of a head and a top of a ground, wherein said space comprises an increased length of core outside of a processing material of a head (i.e., external stem), and wherein the iceberg lettuce plant produced from the cross is an upright heading iceberg lettuce plant comprising a space between a base of a head and a top of a ground, wherein said space comprises an increased length of core outside of a processing material of a head (i.e., external stem).

120. The plant of embodiment 119, wherein the first and second upright heading iceberg lettuce plants are 'E01E.70111' Lot A lettuce plants, a sample of 'E01E.70111' Lot A lettuce seed having been deposited under NCIMB Accession Number 42957.

121. The plant of embodiment 119, wherein the first and second upright heading iceberg lettuce plants are 'E01E.70111' Lot B lettuce plants, a sample of 'E01E.70111' Lot B lettuce seed having been deposited under NCIMB Accession Number 42962.

122. The plant of embodiment 119, wherein the first and second upright heading iceberg lettuce plants are 'E01E.70168' Lot A lettuce plants, a sample of 'E01E.70168' Lot A lettuce seed having been deposited under NCIMB Accession Number 42958.

123. The plant of embodiment 119, wherein the first and second upright heading iceberg lettuce plants are 'E01E.70168' Lot B lettuce plants, a sample of 'E01E.70168' Lot B lettuce seed having been deposited under NCIMB Accession Number 42963.

124. The plant of embodiment 119, wherein the first upright heading iceberg lettuce plant is an 'E01E.70111' Lot A lettuce plant, a sample of 'E01E.70111' Lot A lettuce seed having been deposited under NCIMB Accession Number 42957.

125. The plant of embodiment 78, wherein the second upright heading iceberg lettuce plant is an 'E01E.70168' Lot A lettuce plant, a sample of 'E01E.70168' Lot A lettuce seed having been deposited under NCIMB Accession Number 42958.

126. An upright heading iceberg lettuce plant produced from a cross of an 'E01E.70111' Lot A plant with a second 'E01E.70111' Lot A plant, a sample of 'E01E.70111' Lot A lettuce seed having been deposited under NCIMB Accession Number 42957, wherein the upright heading iceberg lettuce plant produced from the cross comprises a space between a base of a head and a top of a ground, and wherein said space comprises an increased length of core outside of a processing material of a head.

127. An upright heading iceberg lettuce plant produced from a cross of an 'E01E.70111' Lot B plant with a second 'E01E.70111' Lot B plant, a sample of 'E01E.70111' Lot B lettuce seed having been deposited under NCIMB Accession Number 42962, wherein the upright heading iceberg lettuce plant produced from the cross comprises a space between a base of a head and a top of a ground, and wherein said space comprises an increased length of core outside of a processing material of a head (i.e., external stem).

128. An upright heading iceberg lettuce plant produced from a cross of an 'E01E.70168' Lot A plant with a second 'E01E.70168' Lot A plant, a sample of 'E01E.70168' Lot A lettuce seed having been deposited under NCIMB Accession Number 42958, wherein the upright heading iceberg lettuce plant produced from the cross comprises a space between a base of a head and a top of a ground, and wherein said space comprises an increased length of core outside of a processing material of a head (i.e., external stem).

129. An upright heading iceberg lettuce plant produced from a cross of an 'E01E.70168' Lot B plant with a second 'E01E.70168' Lot B plant, a sample of 'E01E.70168' Lot B lettuce seed having been deposited under NCIMB Accession Number 42963, wherein the upright heading iceberg lettuce plant produced from the cross comprises a space between a base of a head and a top of a ground, and wherein said space comprises an increased length of core outside of a processing material of a head (i.e., external stem).

130. An upright heading iceberg lettuce plant produced from a cross of an 'E01E.70111' Lot A plant with a second 'E01E.70168' Lot A plant, a sample of 'E01E.70111' Lot A lettuce seed having been deposited under NCIMB Accession Number 42957, and a sample of 'E01E.70168' Lot A lettuce seed having been deposited under NCIMB Accession Number 42958, wherein the upright heading iceberg lettuce plant produced from the cross comprises a space between a base of a head and a top of a ground, and wherein said space comprises an increased length of core outside of a processing material of a head (i.e., external stem).

131. An upright heading iceberg lettuce seed from the upright heading lettuce plants of any one of embodiments 110 to 130.

132. The upright heading iceberg lettuce plant of any one of embodiments 110 to 130, wherein the iceberg lettuce plant comprises a space between a base of a head and a top of a ground, and wherein said space comprises an increased length of core outside of a processing material of a head (i.e., external stem).

133. The upright heading iceberg lettuce plant of any one of embodiments 110 to 130, wherein the increased length of core outside of the processing material of the head (i.e., external stem) is about 3.5 cm or more, about 4 cm or more, about 4.5 cm or more, or about 5 cm or more.

134. The plant of embodiment 132 or embodiment 133, wherein the iceberg lettuce plant further comprises one or more characteristics selected from the group consisting of: a height to diameter ratio of about 1.3 to about 1.5, leaf strength between about 300 to 400 grams, about 40 to 50% overlapping leaves inside the processing material of the head, a short core inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

135. The plant of any one of embodiments 132 to 134, wherein the external stem length allows for a harvest by machine.

136. The plant of embodiment 135, wherein the harvest by machine does not remove a substantial portion of processing material of a head.

137. The plant of embodiment 136, wherein the harvest by machine is more efficient than for iceberg varieties 'Reliant' and 'Steamboat', cosberg varieties 'Cosmopolitan' and 'Crunchita', and romaine varieties 'True Heart' and 'Solid King'.

138. A plant part from the plant of any one of embodiments 134 to 137.

139. The plant part of embodiment 138, wherein said part is a head, a seed, a leaf, or a portion thereof.

140. The plant part of embodiment 139, wherein said part is a head.

141. An iceberg lettuce plant having all the physiological and morphological characteristics of the iceberg lettuce plant of any one of embodiments 134 to 137.

142. A plant part from the plant of embodiment 141.

143. The plant part of embodiment 142 wherein said part is a head, a leaf, or a portion thereof.

144. The plant part of embodiment 143, wherein said part is a head.

145. A pollen grain or an ovule of the plant of embodiment 141.

146. A tissue culture produced from the plant of embodiment 141.

147. An iceberg lettuce plant regenerated from the tissue culture of embodiment 146, wherein the plant has all of the morphological and physiological characteristics of an iceberg lettuce plant produced by growing seed designated as 'E01E.70111' Lot A, representative sample of 'E01E.70111' Lot A lettuce seed having been deposited under NCIMB Accession Number 42957.

148. An iceberg lettuce plant regenerated from the tissue culture of embodiment 146, wherein the plant has all of the morphological and physiological characteristics of an iceberg lettuce plant produced by growing seed designated as 'E01E.70111' Lot B, representative sample of 'E01E.70111' Lot B lettuce seed having been deposited under NCIMB Accession Number 42962.

149. An iceberg lettuce plant regenerated from the tissue culture of embodiment 146, wherein the plant has all of the morphological and physiological characteristics of an iceberg lettuce plant produced by growing seed designated as 'E01E.70168' Lot A, representative sample of 'E01E.70168' Lot A lettuce seed having been deposited under NCIMB Accession Number 42958.

150. An iceberg lettuce plant regenerated from the tissue culture of embodiment 146, wherein the plant has all of the morphological and physiological characteristics of an iceberg lettuce plant produced by growing seed designated as 'E01E.70168' Lot B, representative sample of 'E01E.70168' Lot B lettuce seed having been deposited under NCIMB Accession Number 42963.

151. A method of making iceberg lettuce seeds, said method comprising crossing the plant of any one of embodiments 134 to 137 with another iceberg lettuce plant and harvesting seed therefrom.

152. A method of making iceberg lettuce seeds, said method comprising crossing the plant of embodiment 141 with another iceberg lettuce plant and harvesting seed therefrom.

153. A method of making upright heading iceberg lettuce plants, the method comprising:
   a) crossing a first upright heading iceberg lettuce plant comprising a space between a base of a head and a top of a ground, wherein said space comprises an increased length of core outside of a processing material of a head (i.e., external stem) with a second upright heading iceberg lettuce plant comprising a space between a base of a head and a top of a ground, wherein said space comprises an increased length of core outside of a processing material of a head (i.e., external stem);
   b) selecting offspring lettuce plants comprising a space between a base of a head and a top of a ground, wherein said space comprises an increased length of core outside of a processing material of a head (i.e., external stem);
   c) selfing or sibbing said offspring;
   d) repeating steps b) and c) for multiple generations to produce inbred lines.

154. The method of embodiment 153, wherein the increased length of core outside of the processing material of the head (i.e., external stem) is about 3.5 cm or more, about 4 cm or more, about 4.5 cm or more, or about 5 cm or more.

155. The method of embodiment 153 or embodiment 154, wherein the characteristics used for selection in step b) further comprise one or more characteristics selected from the group consisting of: a height to diameter ratio of about 1.3 to about 1.5, leaf strength between about 300 to 400 grams, about 40 to 50% overlapping leaves inside the processing material of the head, a short core inside of the processing material of the head (i.e., internal stem), leaves with about 4.8 to 5.3° Brix, leaves with about 25 to 40 g/l total sugars, leaves with about 4.5 to 5% dry matter weight, 5-10% processing damage per bag of processed plant material, and a range of about 35 to 42 days of shelf life of processed and packaged plant material.

EXAMPLES

The present disclosure will be more fully understood by reference to the following examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Shelf Life Trial

The following example describes a trial comparing the shelf life capabilities of eight lettuce varieties of different types (e.g., iceberg, romaine, and upright heading iceberg). 'E01E.70111' and 'E01E.70168' are inbred lines from the same original cross. 'E01E.70111' Lot A and 'E01E.70111' Lot B are sister lines from the same parent in the previous generation. 'E01E.70168' Lot A and 'E01E.70168' Lot B are also sister lines from the same parent in the previous generation.

Materials and Methods

Lettuce varieties: The lettuce varieties and types used in the study are presented in Table 9.

TABLE 9

Lettuce varieties and types tested in the shelf life trial

| Lettuce Variety | Lettuce Type |
|---|---|
| True Heart | Romaine |
| Crunchita | Cosberg |
| Pueblo | Iceberg |
| Steamboat | Iceberg |
| E01E.70111 Lot A | Upright heading iceberg |
| E01E.70111 Lot B | Upright heading iceberg |
| E01E.70168 Lot A | Upright heading iceberg |
| E01E.70168 Lot B | Upright heading iceberg |

Procedure: This was a small plot trial, and plants were planted by individuals with simple push planters using raw seed. The lettuce plants were grown in San Juan Bautista, Calif., USA, and harvested on Jul. 21, 2017. The harvested material was kept at 41° F. for two days before processing. Plastic bags (30 PA 200*300 unperforated) were used to store the harvested material (135 g plant material per bag) under MAP conditions (e.g., cold storage). Beginning on day 6 after harvest, the appearance and smell of the harvested material in the bags were evaluated every 2 days. In addition, other qualities of the harvested material were evaluated, including processing efficiency, internal tipburn, and splitting. A minimum of 2 bags per variety was opened at each evaluation point. Evaluation of the harvested material continued until the material was fully decayed.

Results

The results of the appearance and smell evaluation are presented below in Table 10. The number under the heading "Shelf Life" was the number of days from harvest time to visually not acceptable. The number under the heading "Odor" was the number of days from harvest time to bad odor. The number under the heading "Browning" was the number of days from harvest time to first browning. The number under the heading "Rotting" was the number of days from harvest time to first significant rotting symptoms.

TABLE 10

Appearance and smell evaluation

| Lettuce Variety | Shelf Life (days post harvest) | Odor (days post harvest) | Browning (days post harvest) | Rotting (days post harvest) |
|---|---|---|---|---|
| True Heart | 16 | 14 | 16 | 14 |
| Crunchita | 16 | 14 | 16 | 14 |
| Pueblo | 22 | 22 | 22 | 20 |
| Steamboat | 32 | 30 | 32 | 28 |
| E01E.70111 Lot A | 22 | 22 | 22 | 20 |
| E01E.70111 Lot B | 20 | 20 | 18 | 18 |
| E01E.70168 Lot A | 18 | 18 | 18 | 16 |
| E01E.70168 Lot B | 16 | 16 | 16 | 16 |

As can be seen in Table 10, the romaine and cosberg varieties 'True Heart' and 'Crunchita' developed bad odor and first significant rotting symptoms two weeks after harvest. These varieties were also visually unacceptable and developed first browning symptoms within 16 days after harvest. Similarly, both lines of 'E01E.70168' (Lot A and Lot B) began exhibiting significant rotting symptoms at 16 days after harvest, and began browning, developed bad odor, and became visually unacceptable at 16 to 18 days after harvest.

In contrast, the iceberg variety 'Pueblo' began exhibiting these characteristics 20 to 22 days after harvest. The iceberg variety 'Steamboat' (U.S. Pat. No. 7,977,536) exhibited first significant rotting symptoms 28 days after harvest, and became visually unacceptable, began browning, and developed bad odor 2 to 4 days after that (at 30 to 32 days after harvest). Similarly, both lines of 'E01E.70111' (Lot A and Lot B) began exhibiting significant rotting symptoms at 18 to 20 days after harvest, and began browning, developed bad odor, and became visually unacceptable at 18 to 22 days after harvest. 'E01E.70111' Lot A developed these qualities 2 to 4 days after 'E01E.70111' Lot B (consistently at 22 days after harvest, in comparison to 18 or 20 days after harvest).

Figure 2:
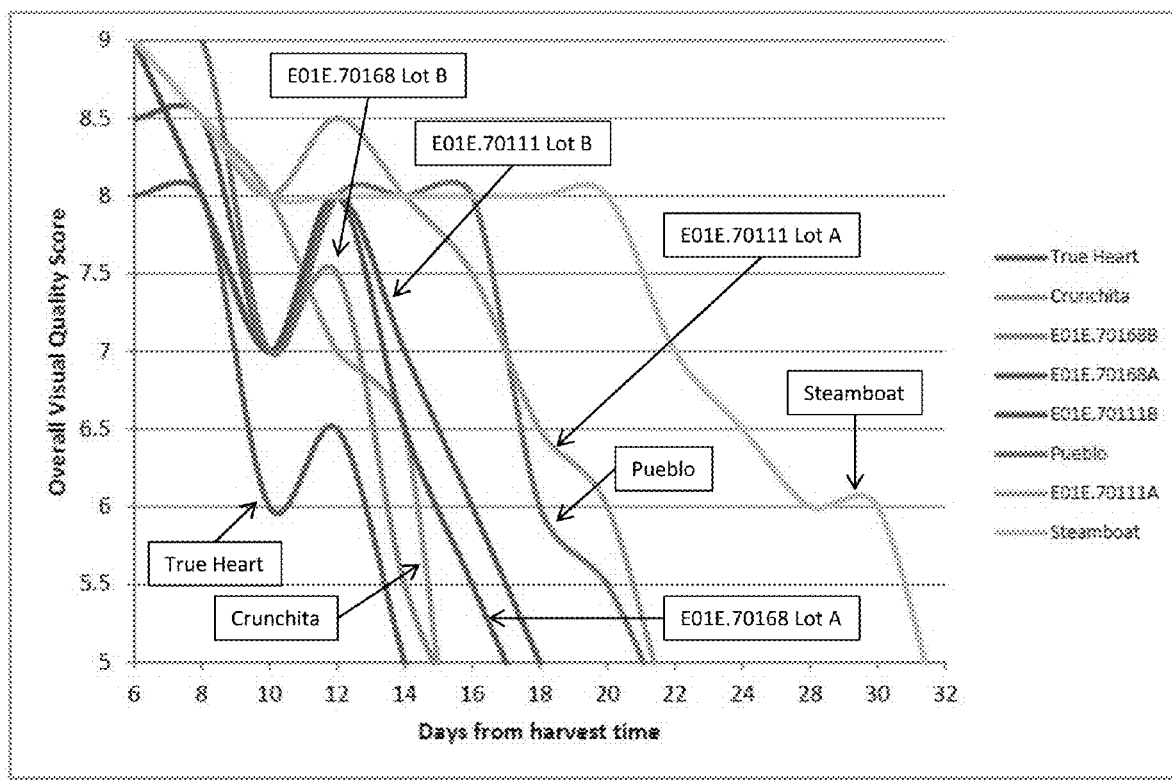
FIG. 2 shows visual quality scores of multiple lettuce varieties during storage.

FIG. 2 illustrates the visual quality scores of each of the lettuce varieties over the evaluation period. The variety 'True Heart' (dark blue line) rapidly declined in visual quality from days 8 to 10, and the varieties 'Crunchita' (pink line) as well as both 'E01E.70168' lines (Lot A and Lot B, red and orange lines respectively) declined at a similarly rapid rate. 'E01E.70111' Lot B (purple line) also had a rapid decrease in visual quality during storage. In contrast, 'Pueblo' and 'E01E.70111' Lot A (teal and light blue lines respectively) maintained good visual quality. 'Steamboat' (green line) maintained good visual quality for the longest time of any of the varieties, and in fact showed little decrease in visual quality for a span of 10 days (day 10 to day 20 from harvest time).

Figure 3:
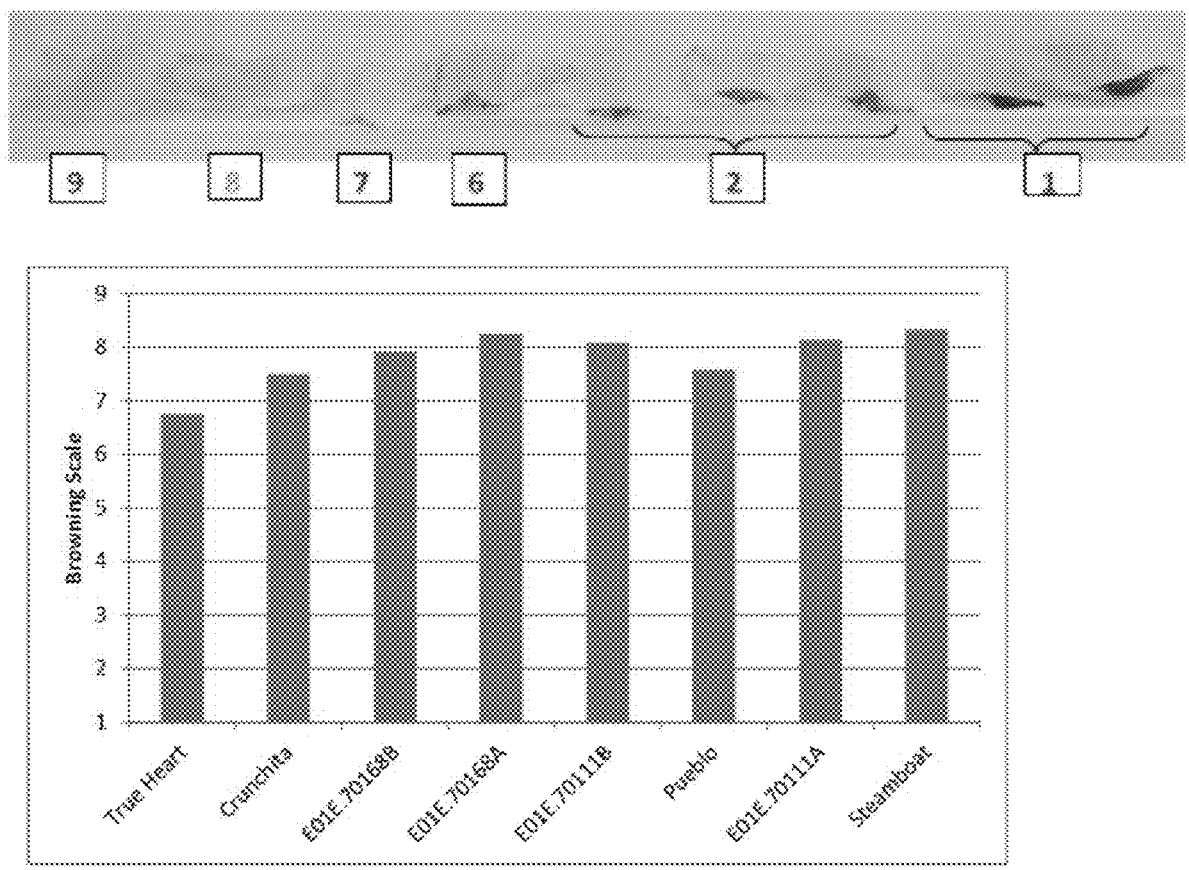
FIG. 3 shows browning scores of multiple lettuce varieties.

FIG. 3 illustrates the intensity of browning of each of the lettuce varieties. At the top of FIG. 3, a visual representation of the ratings is provided. A rating of 1 (see top of FIG. 3, right-most image) was given when the veins were completely brown. A rating of 9 (see top of FIG. 3, left-most image) was given when the veins were white and clean. As can be seen in the bar chart at the bottom of FIG. 3, 'True Heart', 'Crunchita', and 'Pueblo' showed a higher intensity of browning than the other varieties. None of the varieties showed strong browning symptoms during storage. In addition, the intensity of pinking was very low in 'E01E.70168', 'E01E.70111', and 'Steamboat'.

Figure 4:
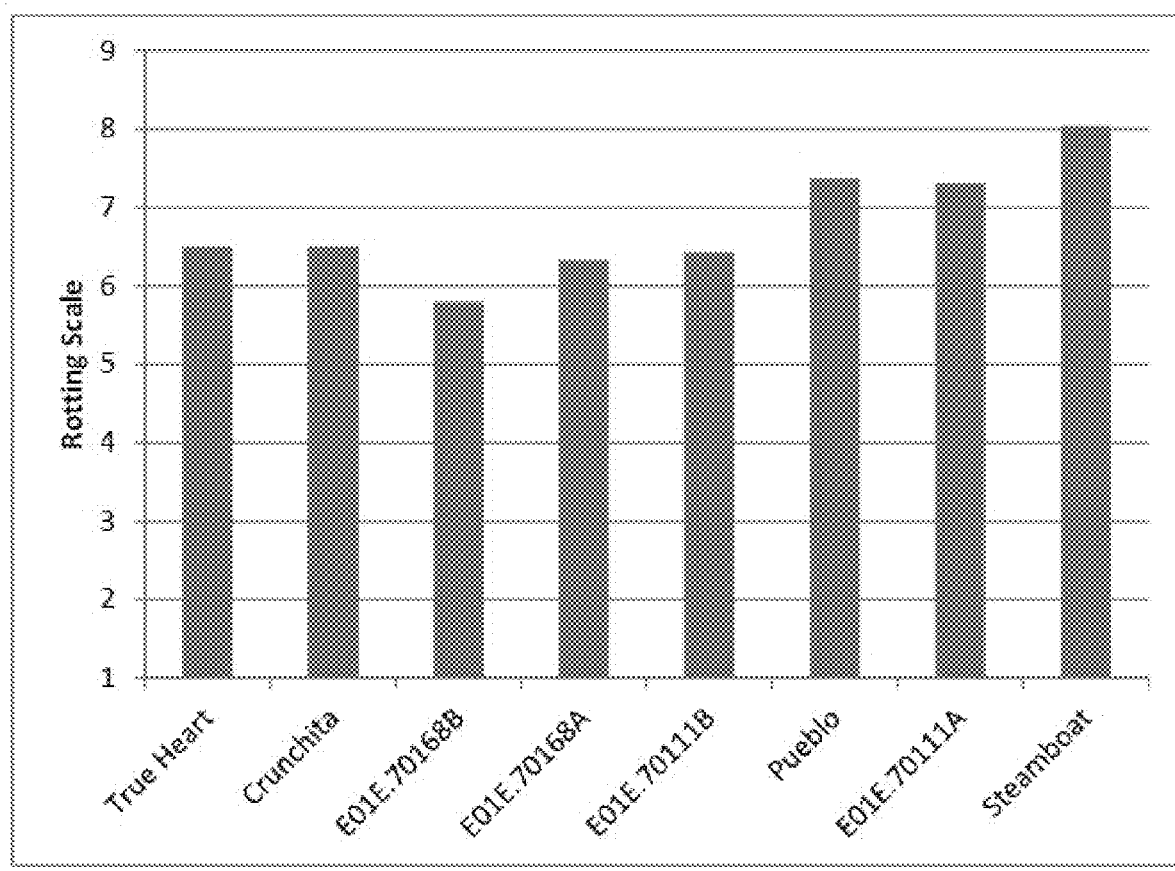
FIG. 4 shows rotting scores of multiple lettuce varieties.

In FIG. 4, the intensity of rotting for each of the lettuce varieties is illustrated. A rating of 1 on the rotting scale indicated that the harvested material of the lettuce varieties was completely rotten, while a rating of 9 indicated that no rotting was present. 'E01E.70168' (Lot A and Lot B), 'True Heart', and 'Crunchita' showed more rotting intensity than the other lettuce varieties at an early storage time. In contrast, 'E01E.70111' (Lot A and Lot B), 'Pueblo', and 'Steamboat' had very low rotting intensity.

Figure 5:
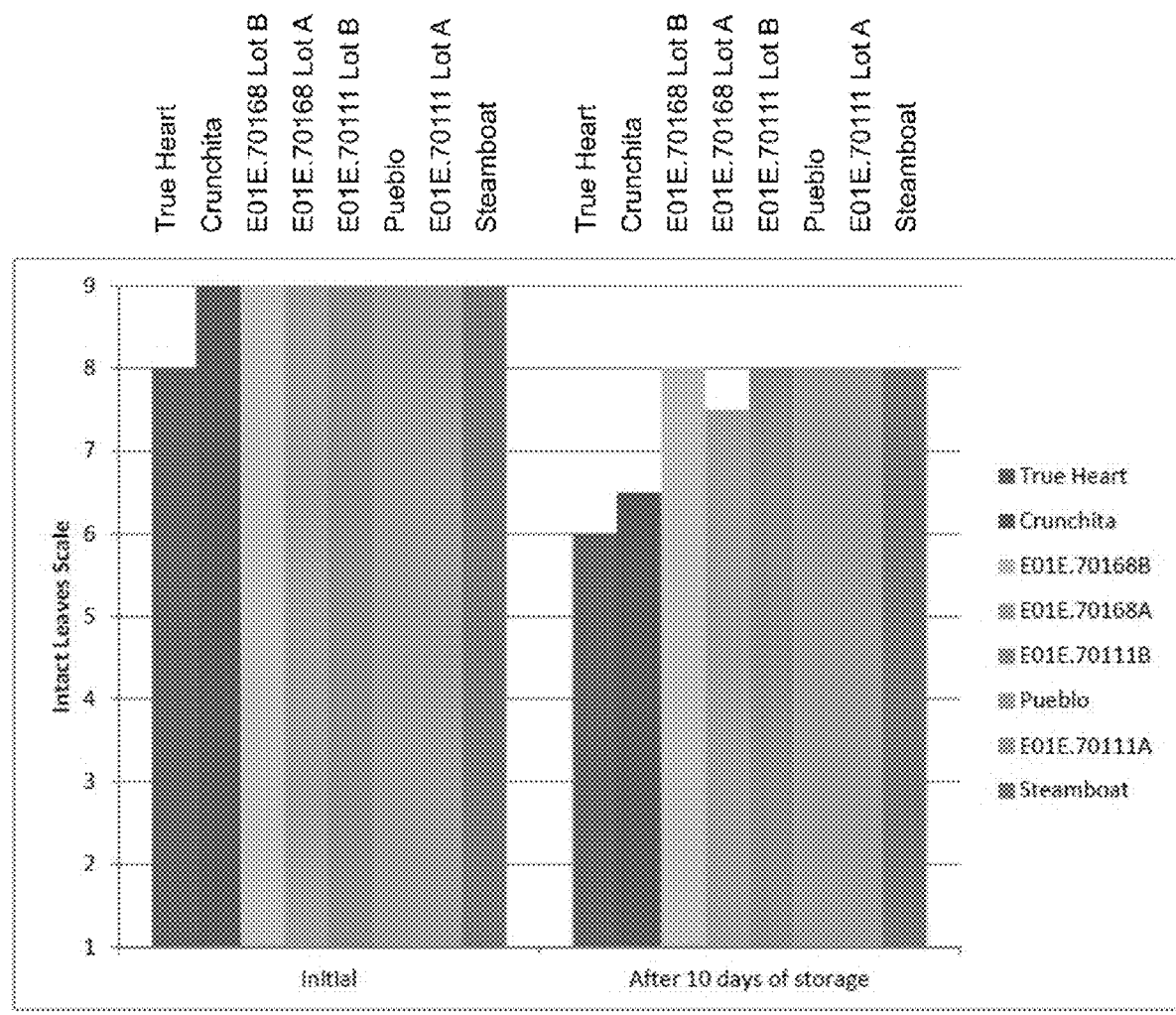
FIG. 5 shows intact leaves scores of multiple lettuce varieties initially and after 10 days of storage.

FIG. 5 illustrates the leaf intactness for each of the lettuce varieties. A rating of 1 on the scale indicated completely damaged leaves, while a rating of 9 indicated intact leaves. 'True Heart' appeared more damaged than other varieties during processing. The three varieties that were significantly deteriorated during cold storage, namely 'True Heart', 'Crunchita', and 'E01E.70168', also had the shortest shelf life of the varieties in the study. Those with longer shelf life, such as 'E01E.70111', 'Pueblo', and 'Steamboat', did not show significant bruises after 10 days in storage.

In Table 11, the maturity index for each of the varieties is shown.

TABLE 11

Maturity index for each of the varieties

| | Maturity Index | |
|---|---|---|
| Lettuce Variety | Average | Standard Deviation |
| True Heart | 38.8 | 17.7 |
| Crunchita | 36.8 | 12.6 |
| Pueblo | 4.1 | 0.7 |
| Steamboat | 3.4 | 0.9 |
| E01E.70111 A | 2.4 | 0.5 |
| E01E.70111 B | 1.8 | 0.7 |
| E01E.70168 A | 3.0 | 0.5 |
| E01E.70168 B | 3.4 | 0.7 |

Figure 6:
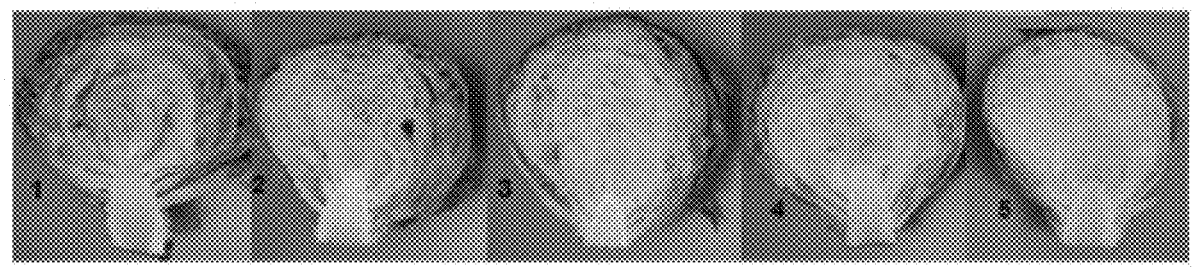
FIG. 6 shows the maturity index of iceberg lettuce.

FIG. 6 shows the stages of the maturity index for iceberg lettuce, wherein stages 3 and 4 are considered ideal for processing.

In Table 12, the results of the evaluation of other qualities of the harvested material are shown. The processing efficiency percentage was the percentage of harvested plant material viable for processing. The remaining categories were all measured on a scale of 1 to 9. For Internal tipburn and *Bremia* (i.e., infection with the downy mildew pathogen *Bremia lactucae*), a rating of 9 meant there was no tipburn or *Bremia*, and a rating of 1 meant the harvested material was full of tipburn or *Bremia*. For splitting, a rating of 9 meant the harvested material was soft splitting and a rating of 1 meant it was hard splitting. Finally, for side shoots, a rating of 9 meant the harvested material had no side shoots and a rating of 1 meant the harvested material was full of side shoots.

TABLE 12

Evaluation of other qualities of the harvested material

| | Processing Efficiency (%) | | | | | |
|---|---|---|---|---|---|---|
| Lettuce Variety | Average | Standard Deviation | Internal Tipburn | Bremia | Splitting | Side Shoot |
| True Heart | 84.7 | 3.3 | 7.8 | 9.0 | 6.0 | 9.0 |
| Crunchita | 89.7 | 2.7 | 8.6 | 9.0 | 8.6 | 9.0 |
| Pueblo | 91.6 | 4.1 | 7.3 | 7.7 | 4.3 | 9.0 |
| Steamboat | 94.5 | 1.1 | 7.8 | 7.8 | 6.0 | 9.0 |
| E01E.70111 A | 82.3 | 2.1 | 8.3 | 9.0 | 7.5 | 9.0 |
| E01E.70111 B | 81.1 | 2.2 | 6.8 | 9.0 | 7.1 | 9.0 |

TABLE 12-continued

Evaluation of other qualities of the harvested material

| | Processing Efficiency (%) | | | | | |
|---|---|---|---|---|---|---|
| Lettuce Variety | Average | Standard Deviation | Internal Tipburn | Bremia | Splitting | Side Shoot |
| E01E.70168 A | 93.2 | 2.3 | 6.8 | 7.9 | 4.5 | 8.6 |
| E01E.70168 B | 93.4 | 1.3 | 6.8 | 7.9 | 6.0 | 8.6 |

As can be seen in Table 12, the processing efficiency of the romaine and cosberg varieties 'True Heart' and 'Crunchita' was lower (84.7% and 89.7%, respectively) than that of the iceberg varieties 'Pueblo' and 'Steamboat' (91.6% and 94.5%, respectively). The processing efficiency of both lines of 'E01E.70111' (Lot A and Lot B) was lower than either 'True Heart' or 'Crunchita' (82.3% and 81.1%). In contrast, the processing efficiency of both lines of 'E01E.70168' (Lot A and Lot B) was intermediate between the two iceberg varieties (93.2% and 93.4%).

The cosberg variety 'Crunchita' had the lowest level of internal tipburn (rated 8.6 out of 9, where 9 is no internal tipburn), and 'E01E.70111' Lot A had the second-lowest level (rated 8.3 out of 9). The romaine variety 'True Heart', as well as the two iceberg varieties 'Pueblo' and 'Steamboat', had intermediate levels of internal tipburn (rated 7.8, 7.3, and 7.8 out of 9, respectively). The varieties 'E01E.70111' Lot B, 'E01.70168' A, and 'E01.70168' B had the highest levels of internal tipburn (rated 6.8 out of 9).

'True Heart', 'Crunchita', and both Lots of 'E01E.70111' had no measurable infection with the downy mildew pathogen *B. lactucae*. In contrast, both iceberg varieties and both Lots of 'E01E.70168' had measurable *B. lactucae* infection.

Of the varieties, the iceberg variety 'Pueblo' was the variety with the most hard splitting (rated 4.3 out of 9, where 9 was soft splitting and 1 was hard splitting), and 'E01E.70168' Lot A was the variety with the second-most hard splitting (rated 4.5 out of 9). The cosberg variety 'Crunchita' was the variety with the most soft splitting (rated 8.6 out of 9). The remaining varieties had intermediate splitting levels/types, with ratings ranging from 6.0 to 7.5.

Most of the lettuce varieties evaluated had no side shoots. Both lines of 'E01E.70168' (Lot A and Lot B), however, had a small number of side shoots (rated 8.6 out of 9, where 9 was no side shoot and 1 was full of side shoots).

Example 2: Trial Including Chop Test

This was a small plot trial to compare 'E01E.70111' Lot A and 'E01E.70111' Lot B characteristics. In addition, the harvested material was compared to a standard iceberg variety in a chop test. The chop test was designed to test the qualities of chopped processing material/product (i.e. a measurement of "chunking" or how easily the chopped sections of processing material/product separate). Product that separated easily when chopped would also mix more easily in a bag (e.g., of prepared salad), while product that did not separate easily (i.e. the chopped sections stuck together) would mix less easily.

Materials and Methods

The plants were grown on 80 inch beds with 5 lines to abed and thinned to 10 inches between plants. Plants were planted by individuals with simple push planters using raw seed.

Results

Figure 7A:
FIG. 7A shows a cross-section of lettuce variety 'E01E.70111' Lot B.

FIG. 7A illustrates the vertical cross-section of ahead of lettuce variety 'E01E.70111' Lot B. From the cross-section, it can be seen that the head was cupped in, and the interior leaves were blanching, and had relatively short cores. There was fairly loose fill at this growing stage, and the plants were not yet completely mature.

Figure 7B:
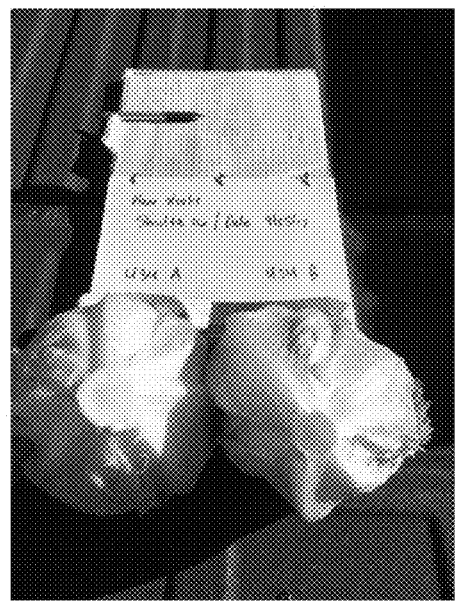
FIG. 7B shows a comparison of the bottom of 'E01E.70111' Lot A and 'E01E.70111' Lot B.

In FIG. 7B, a side-by-side comparison of 'E01E.70111' Lot A and 'E01E.70111' Lot B is shown. The core of the Lot A head (on the left) appeared to be larger in diameter than the core of the Lot B head (on the right), but these characteristics may not be generally applicable to these lines. In general, larger diameter cores would help the plant stand up better in the field (more sturdy), but it could also mean that the core was longer which would not be as advantageous.

When an upright heading iceberg lettuce variety (e.g., 'E01E.70111' Lot A) was compared to a standard iceberg lettuce variety in a chop test, the results were comparable (i.e., perhaps there was a slight color difference) and could not be clearly distinguished by visual assessment. Therefore, it appeared that upright heading iceberg lettuce and standard iceberg lettuce had similar chunking characteristics.

Example 3: Genome-Wide Association Mapping

Molecular analysis will be performed on 'E01E.70111' Lot A, 'E01E.70111' Lot B, 'E01E.70168' Lot A, and 'E01E.70168' Lot B. A genome-wide association mapping procedure will be used (e.g., GMAS, GWAS, etc.). This analysis aims to determine the genetic control of the physiological type (i.e., upright heading iceberg lettuce).

Example 4: Size, Weight, Etc. Measurements

Large scale replicated trials will be planted. Plants will be seeded with a tractor and mechanical implements using pelleted seed. Planting procedure will be similar to commercial productions.

Measurements on head length, diameter, weight, maturity, and core length will be taken. Additional measurements will also be taken, such as calculated weight of harvested product per acre at different plant spacing.

Example 5: Large Scale Field Trial—Morphological Characterization

The following example describes a large scale trial comparing the morphological characteristics of ten lettuce varieties of different types (e.g., cosberg, romaine, upright heading iceberg, and iceberg). The large scale trial included four separate tests conducted over the spring and summer of 2018 in California, USA.

Materials and Methods

Lettuce varieties and tests: The lettuce varieties and types that were used in the study are presented in Table 13. The four tests were conducted in Soledad, Calif., USA, San Juan Bautista, Calif., USA, and Salinas, Calif., USA over spring and summer of 2018. The plant dates, harvest dates, days to harvest, season, and estimated trial maturity for the four tests in the large scale trial are presented in Table 14.

TABLE 13

Lettuce varieties and types tested in the large scale trial

| Lettuce Variety | Lettuce Type |
|---|---|
| Cosmopolitan | Cosberg |
| Crunchita | Cosberg |
| True Heart | Romaine |
| Solid King | Romaine |
| E01E.70111 Lot A | Upright heading iceberg |
| E01E.70111 Lot B | Upright heading iceberg |
| E01E.70168 Lot A | Upright heading iceberg |
| E01E.70168 Lot B | Upright heading iceberg |
| Reliant | Iceberg |
| Steamboat | Iceberg |

TABLE 14

Parameters of the four tests in the large scale trial

| Test | Planting Date | Harvest Date | Days to Harvest | Season California Central Coast | Estimated trial maturity | Location |
|---|---|---|---|---|---|---|
| Test 1 | Feb. 22, 2018 | May 18, 2018 | 85 | Spring | 85% | Soledad, CA, USA |
| Test 2 | Feb. 28, 2018 | Jun. 5, 2018 | 97 | Spring | 95% | San Juan Bautista, CA, USA |
| Test 3 | May 7, 2018 | Jul. 10, 2018 | 64 | Summer | 80% | Salinas, CA, USA |
| Test 4 | May 8, 2018 | Jul. 24, 2018 | 77 | Summer | 100% | San Juan Bautista, CA, USA |

Growth and harvesting: All ten lettuce varieties were seeded, grown, and harvested in the same way across all four tests. Plants were seeded with an EarthWay Garden Seeder (Model 1001-B) using pelleted ('True Heart', 'Solid King', and 'Reliant') and raw seed ('Cosmopolitan', 'Crunchita', 'E01E.70111' Lot A, 'E01E.70111' Lot B, 'E01E.70168' Lot A, 'E01E.70168' Lot B, and 'Steamboat'). The harvest/postharvest procedures were identical across all ten lettuce varieties across all four tests. Lettuces were cut manually by expert lettuce cutters at commercial maturity, and following industry standards. Lettuces were harvested that appeared healthy and without external damage in the field. Every block was harvested around the same time of day, and all varieties were cut simultaneously to ensure no variety remained in the sun for a much longer time than the other varieties. Twelve lettuce plants were harvested per variety per test.

After harvest, lettuces were put immediately into boxes without removing the external leaves. All boxes from one harvest were loaded in a random order onto the same truck for transport. The boxes were then transported within two hours to a cold room kept at 41° F. (5° C.). For cold room storage, the harvested material was covered using plastic bags with perforations. Then, the material was stored for 48 hours before processing.

Morphological characterization: Six of the twelve plants were used for morphological characterization. At the beginning of each test, every variety received a random lab number that was used for all evaluations in order to guarantee unbiased assessments. On the day of processing, external leaves were carefully removed. Morphological evaluations were performed under natural light and at room temperature (68° F.; 20° C.). For each test, evaluations of all lettuce varieties were conducted in a random order over a period not longer than 30 hours. In order to maintain the lettuces in optimal conditions between evaluations, lettuces were kept at 41° F. (5° C.), and then brought to room temperature. Data was taken by a postharvest researcher and immediately transferred to a computer for use in preparing analytical graphs and conducting statistical analyses.

Data analysis: Analytical graphs were prepared as box and whisker charts or bar charts. Box and whisker charts were used to show the distribution of the data into quartiles, and to highlight the mean and outliers. The mean of the data was shown by an "x" symbol within the box. Some of the boxes had lines extending vertically (i.e., "whiskers"), which indicated variability outside the upper and lower quartiles. Any point that fell outside of the whiskers was considered an outlier, and was indicated by a dot symbol separate from both box and whiskers.

Bar charts were used to show the results of Analysis of Variance (ANOVA) statistical analyses. The bars in the bar charts depicted the means, and each lettuce variety was shown as a differently-patterned bar (keys were included at bottom of graphs; from left to right, bars corresponded to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'). ANOVA was used to determine whether there were any significant differences between the means of independent (i.e., unrelated) groups, and the probability level of alpha 5% was used in these analyses. If the difference between two means was found to be significant (i.e., the differences between lettuces from the same variety (variance within the same variety) were smaller than the differences between varieties), the means were labeled with different letters on the bar graph showing the results (letters were shown at top of the bars on the graph). A result of a significant difference showed that the compared varieties were different in regard to the characteristics of that trait. If the difference between two means was not found to be significant (i.e., the differences between lettuces from the same variety (variance within the same variety) were similar or higher than the differences between varieties), the means were labeled with the same letters on the bar graph showing the results (letters were shown at top of the bars on the graph). A result of no significant difference showed that the varieties were the same in regard to the characteristics of that trait. All ANOVAs were performed with the software XLStat (Addinsoft 1995-2018, version 2018.5) with the specifications: 2 interactions levels, 95% confidence interval, zero constraints, and pairwise comparison performed with Tukey test.

Figure 13A:
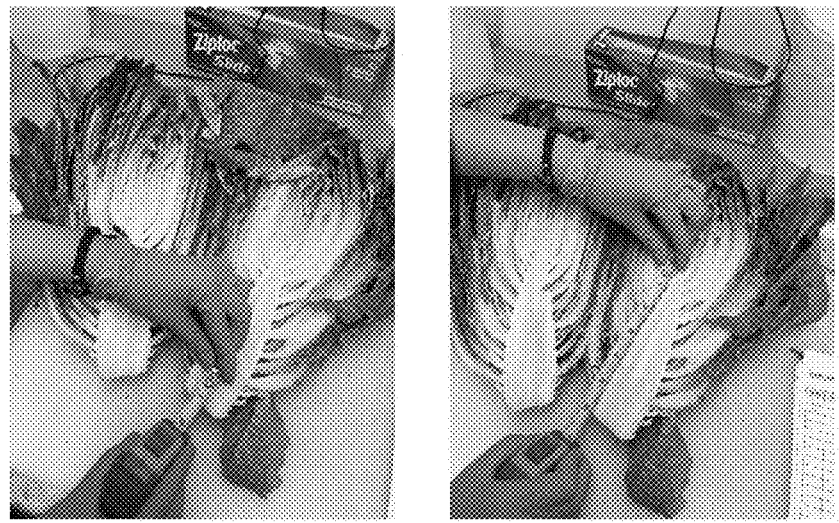
FIGS. 13A-13P show the stem length measurement procedure and the analysis of stem length measurement data from Tests 1-4.
Figure 13B:
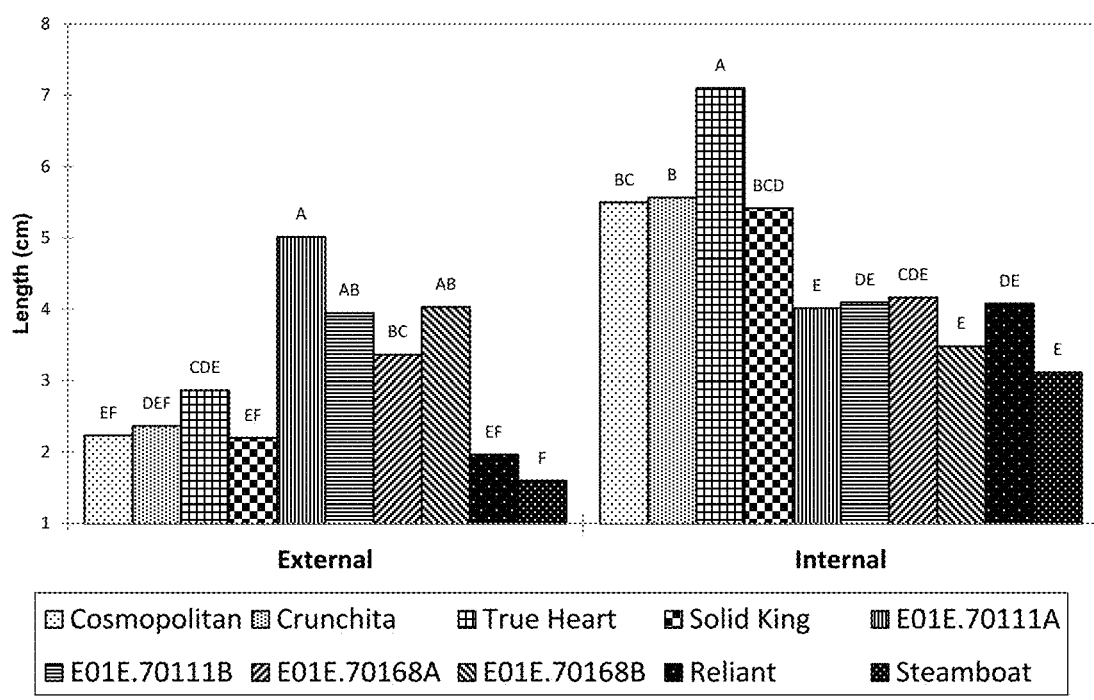
FIGS. 13B, 13E, 13H, 13K, and 13N show ANOVA analysis of the means of external and internal stem length measurement data in cm from Test 1 (FIG. 13B), Test 2 (FIG. 13E), Test 3 (FIG. 13H), Test 4 (FIG. 13K), and all tests (i.e., Tests 1-4.
Figure 13C:
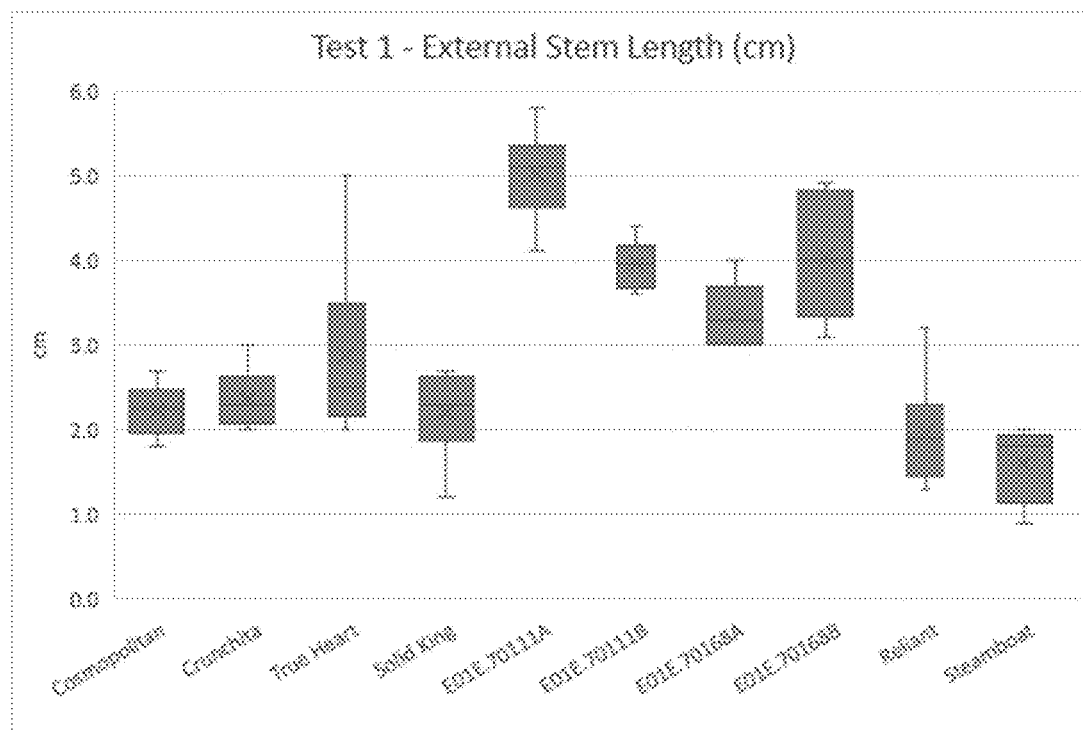
FIGS. 13C, 13F, 13I, 13L, and 13O show box and whisker charts of external stem length data in cm from Test 1 (FIG. 13C), Test 2 (FIG. 13F), Test 3 (FIG. 13I), Test 4 (FIG. 13L), and all tests (i.e., Tests 1-4.
Figure 13D:
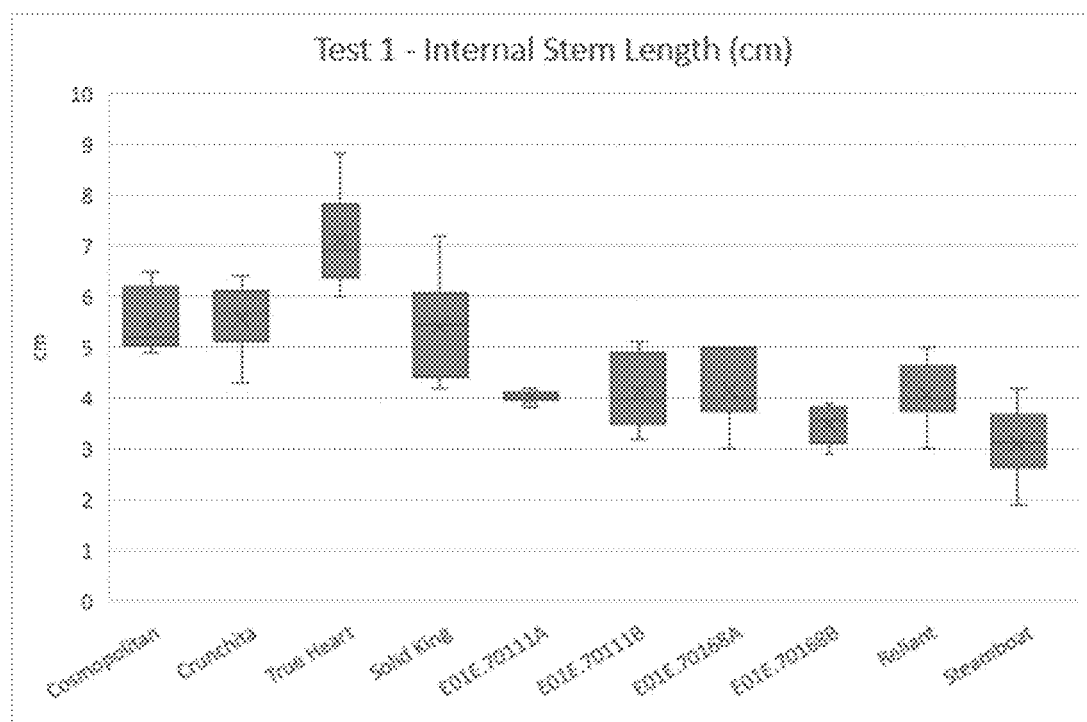
FIGS. 13D, 13G, 13J, 13M, and show box and whisker charts of internal stem length data in cm from Test 1 (FIG. 13D), Test 2 (FIG. 13G), Test 3 (FIG. 13J), Test 4 (FIG. 13M), and all tests (i.e., Tests 1-4.
Figure 13E:
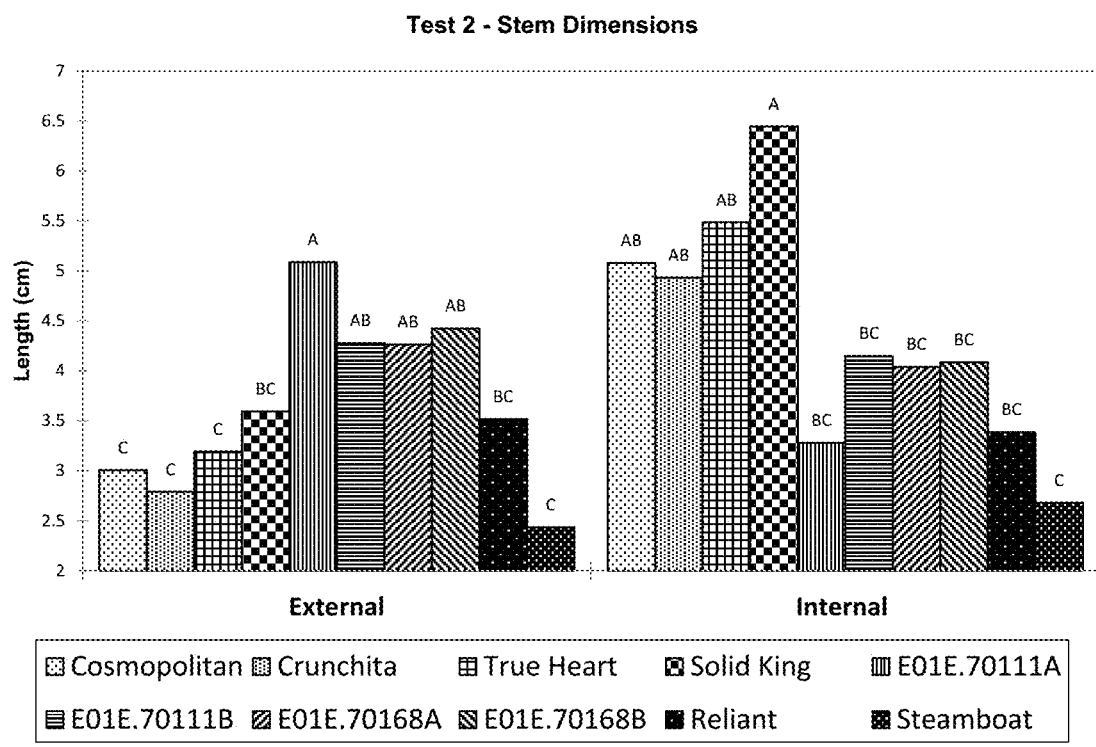
Figure 13F:
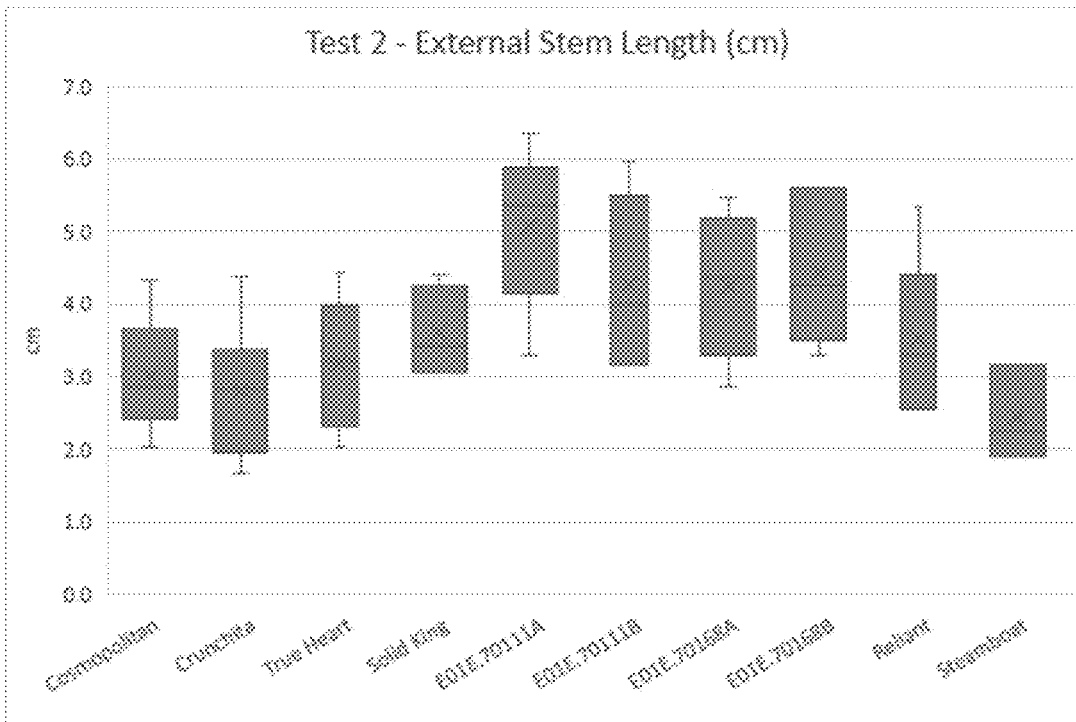
Figure 13G:
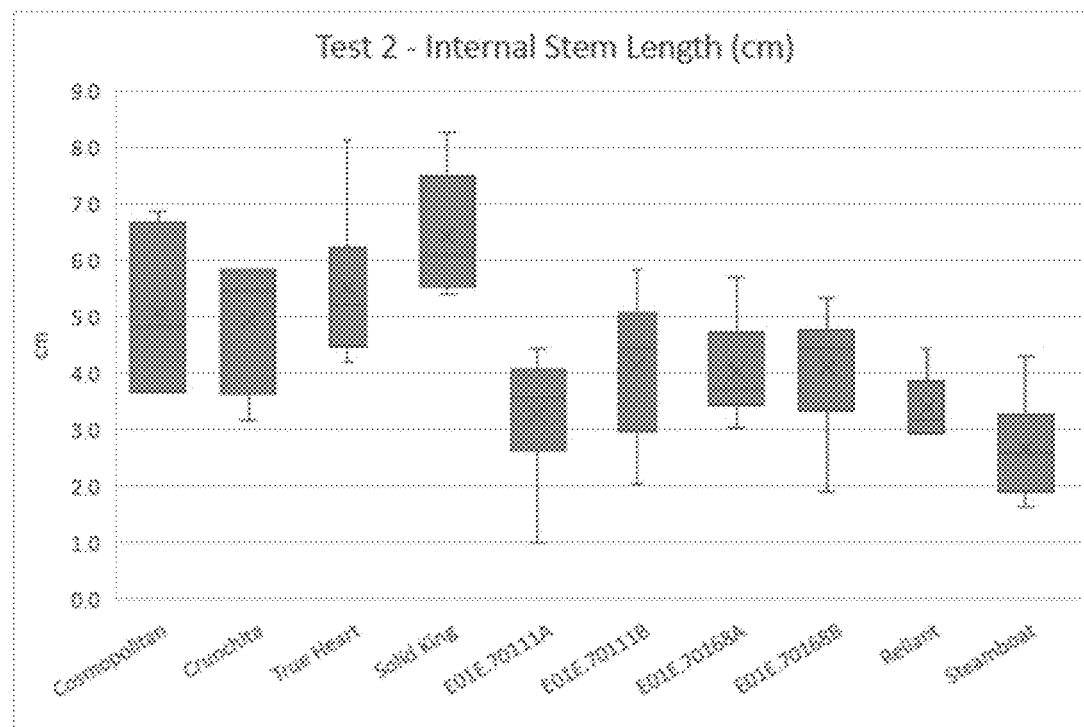
Figure 13H:
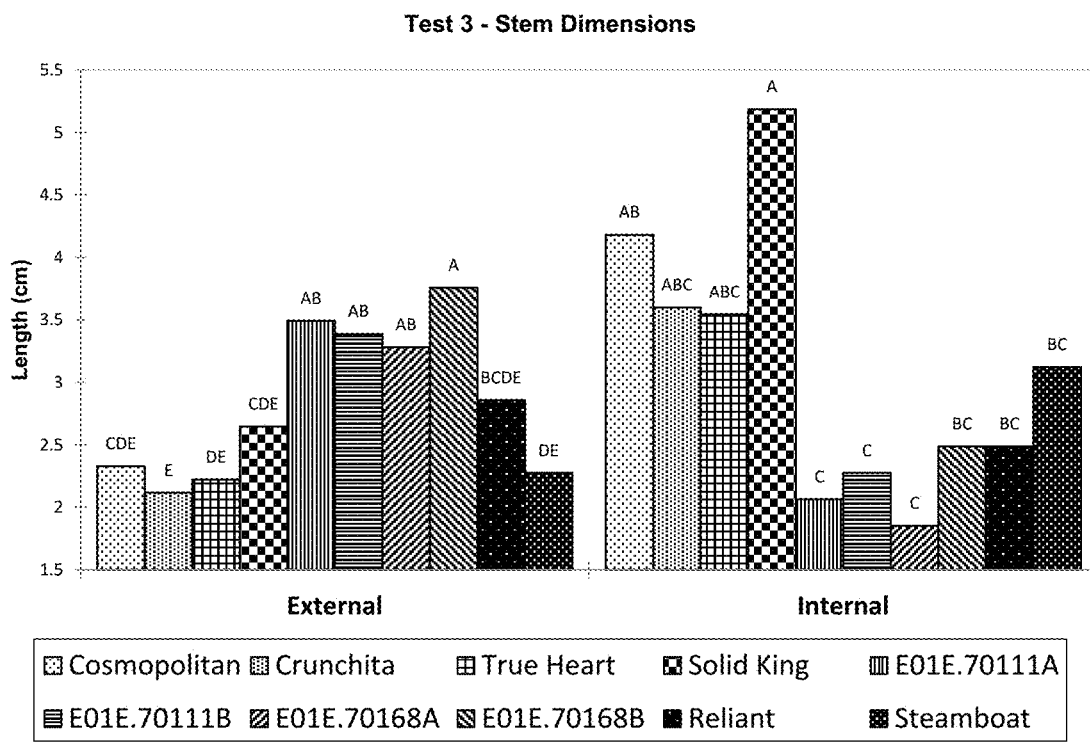
Figure 13I:
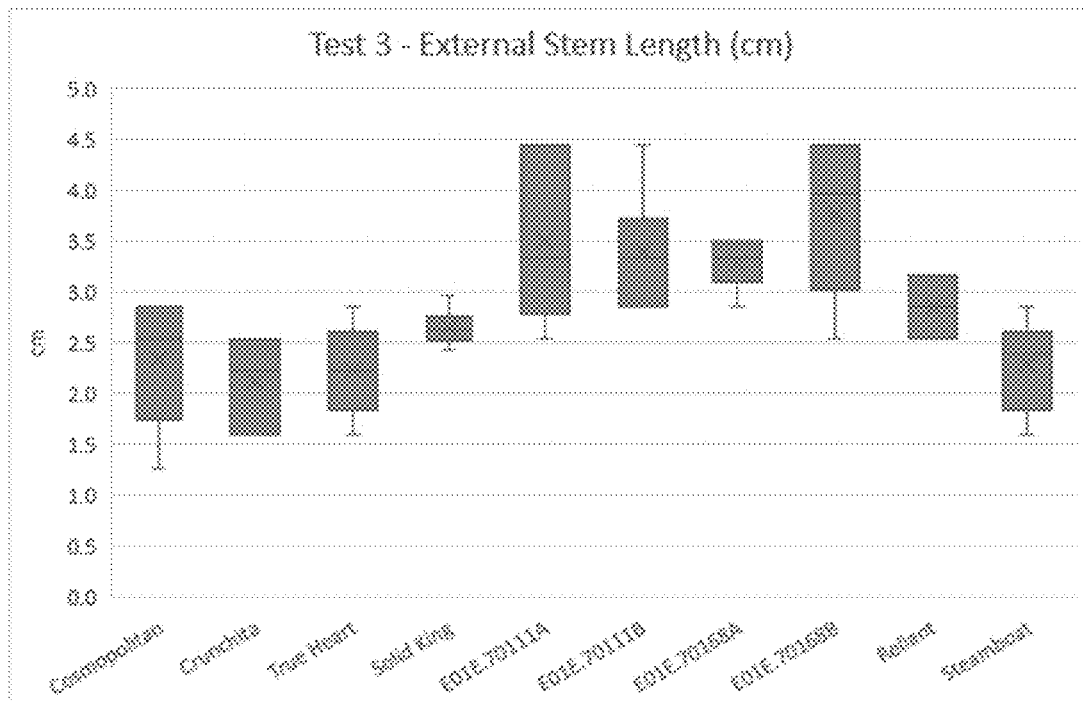
Figure 13J:
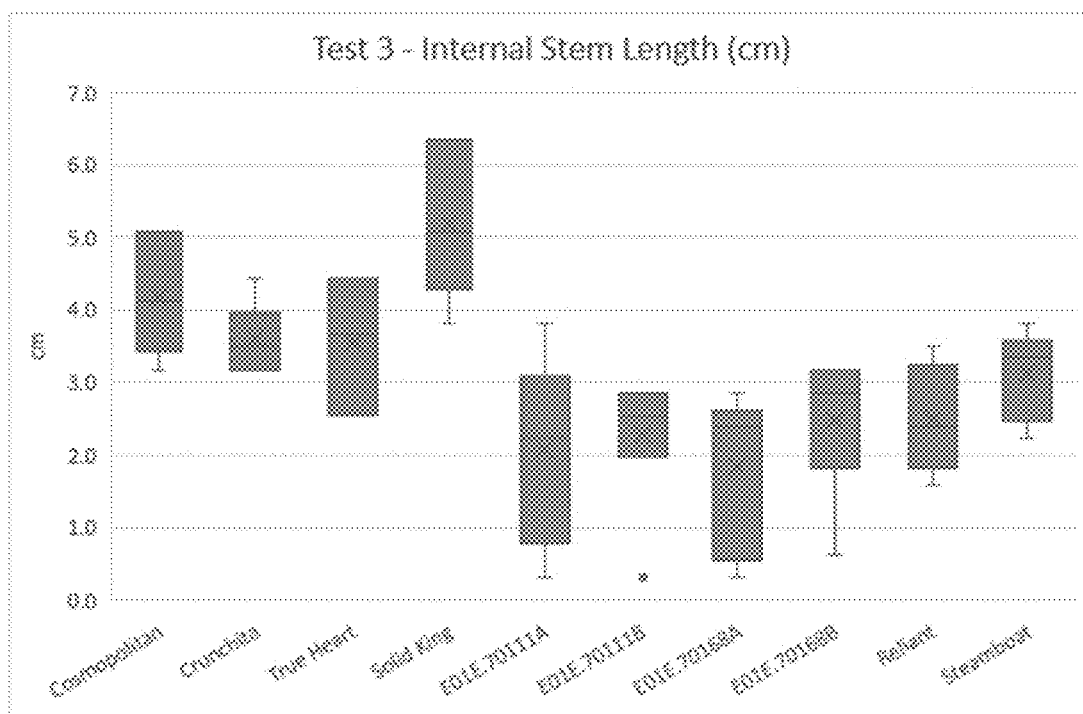
Figure 13K:
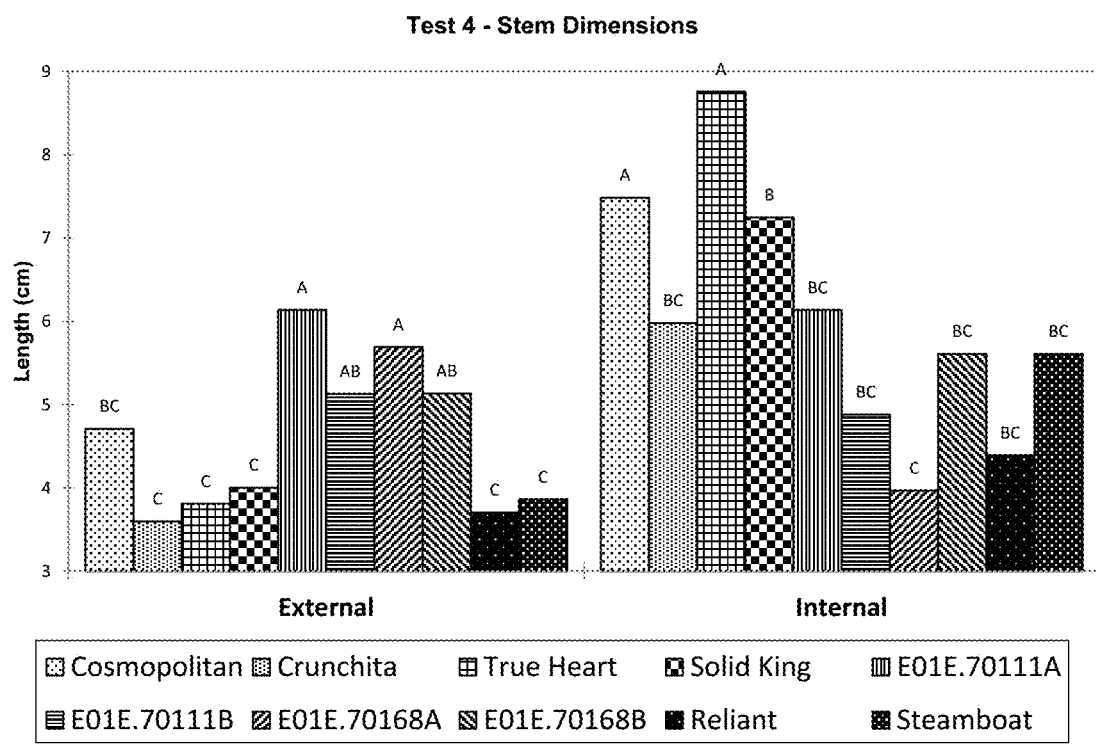
Figure 13L:
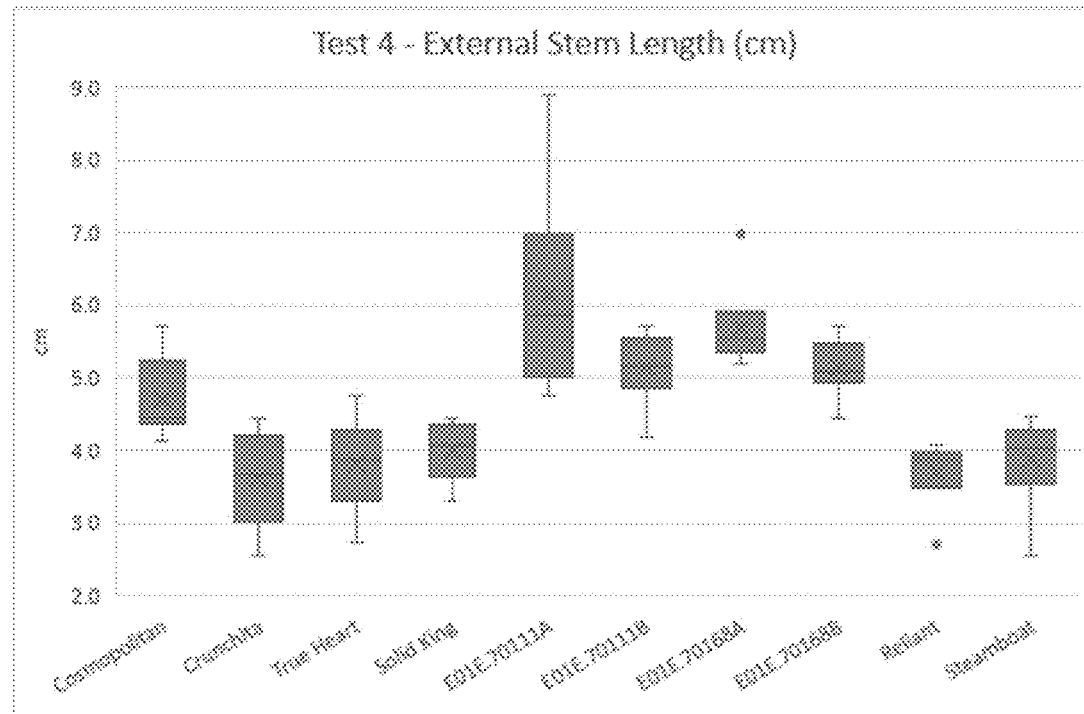
Figure 13M:
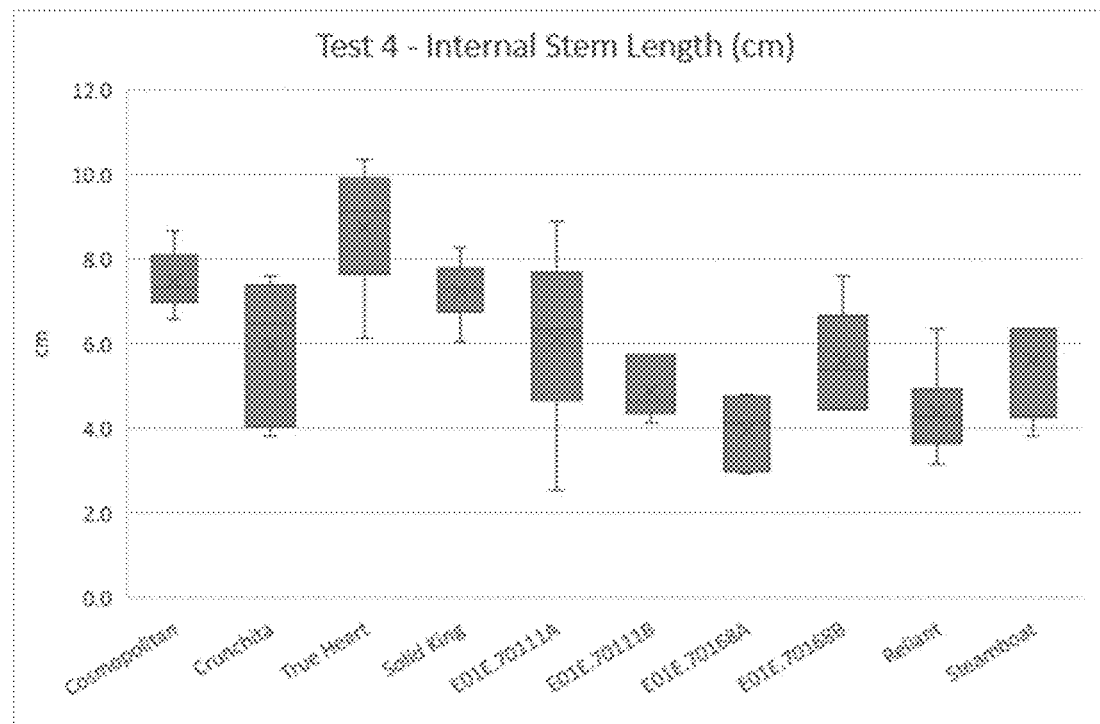

Measurement of stem length: Stem length measurements were taken with a standard metric tape in inches. Measurements were later converted into centimeters (cm) for statistical analyses. Two different stem length measurements were taken: external stem length and internal stem length. External stem was measured from the harvest cut point at base of head to the first frame leaf of the head, and internal stem was measured from the first frame leaf of the head to the end of the stem at the center of the head (locations of external and internal stems are shown in FIG. 29). FIG. 13A shows exemplary images of the external (left image) and internal (right image) stem length measurement procedures.

Figure 14A:
FIGS. 14A-14F show the lettuce head weight measurement procedure and the analysis of lettuce head weight measurement data in grams (g) from Tests 1-4.
Figure 14B:
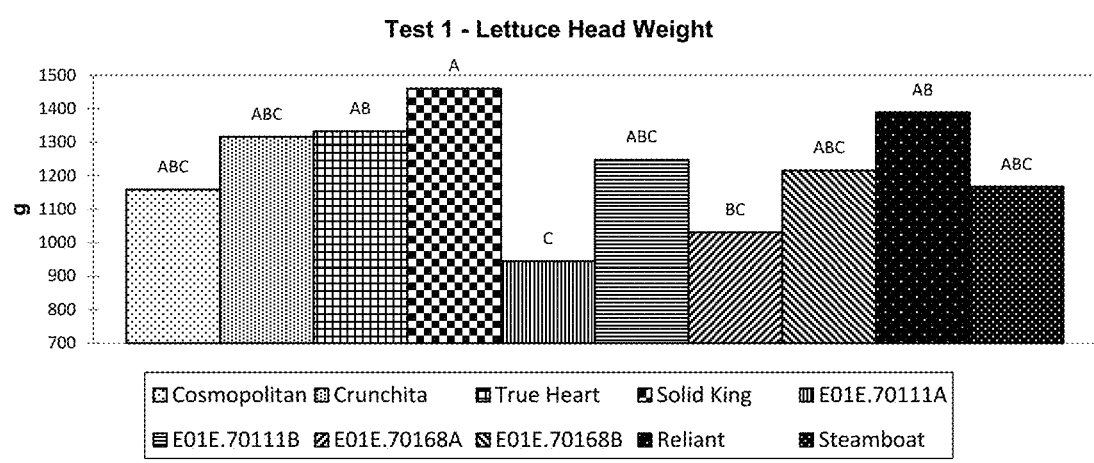
Figure 14C:
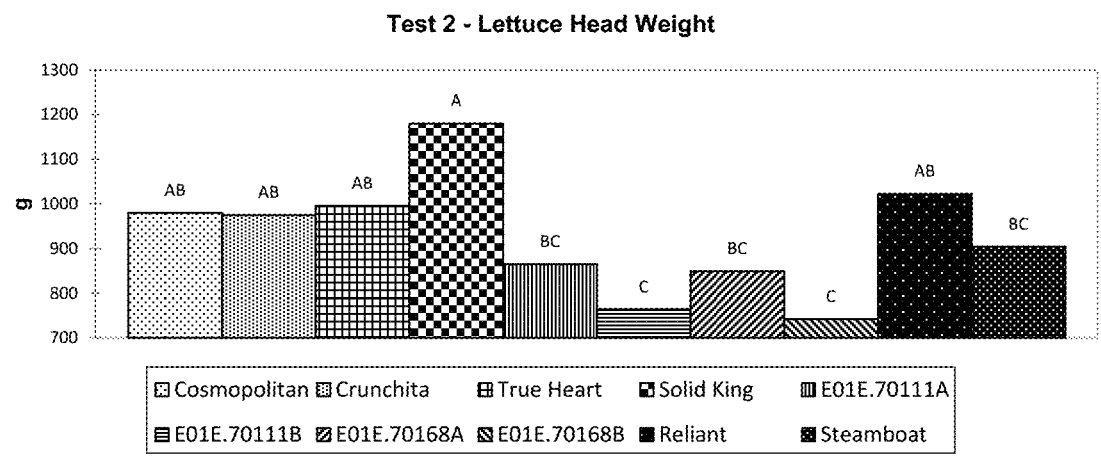
Figure 14D:
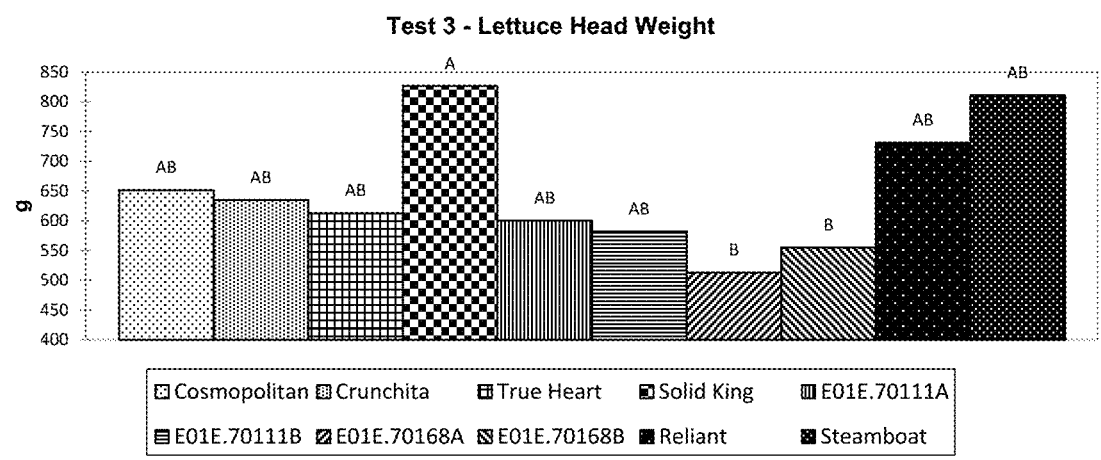
Figure 14E:
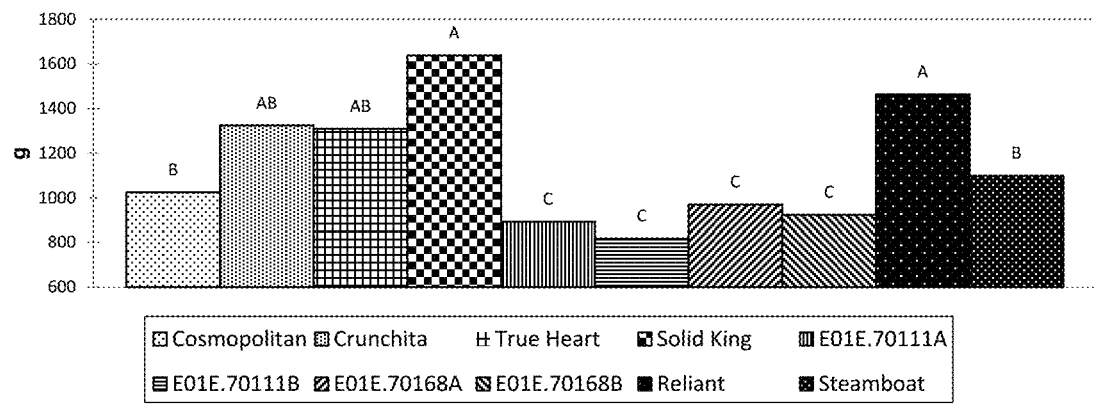

Measurement of lettuce head weight: Lettuce head weight measurements were taken with an Ohaus NV2101 Precision Balance (2100 g capacity, 0.1 g readability). Weight was measured in grams. An exemplary image of the lettuce head weight measurement procedure is shown in FIG. 14A.

Figure 15A:
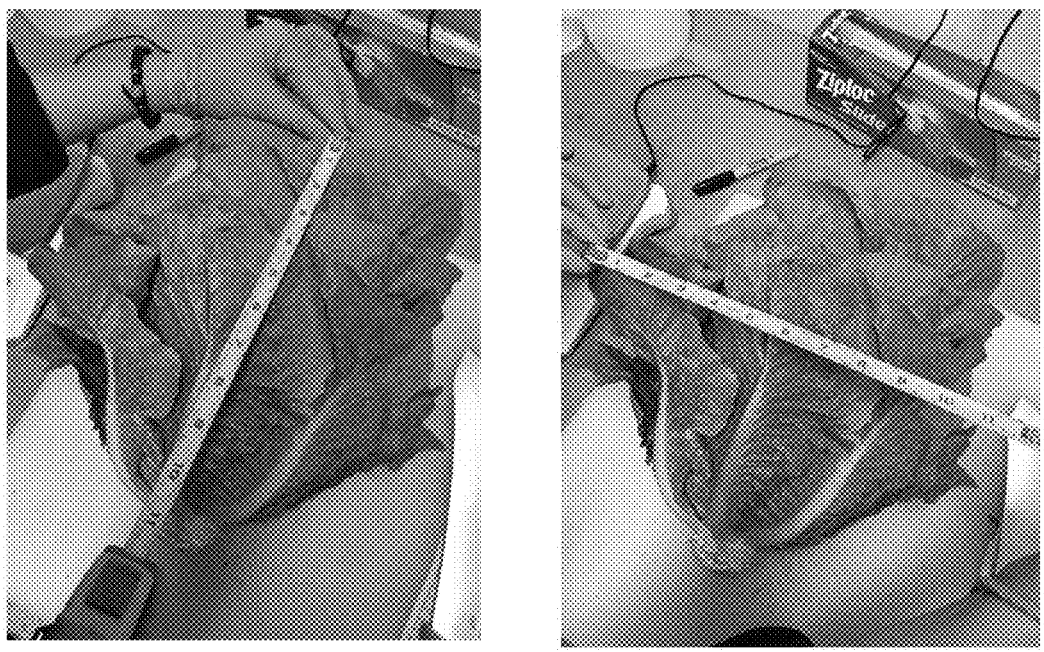
FIGS. 15A-15F show the lettuce head height and lettuce head width measurement procedures and the analysis of lettuce head height and width measurement data in cm from Tests 1-4.
Figure 15B:
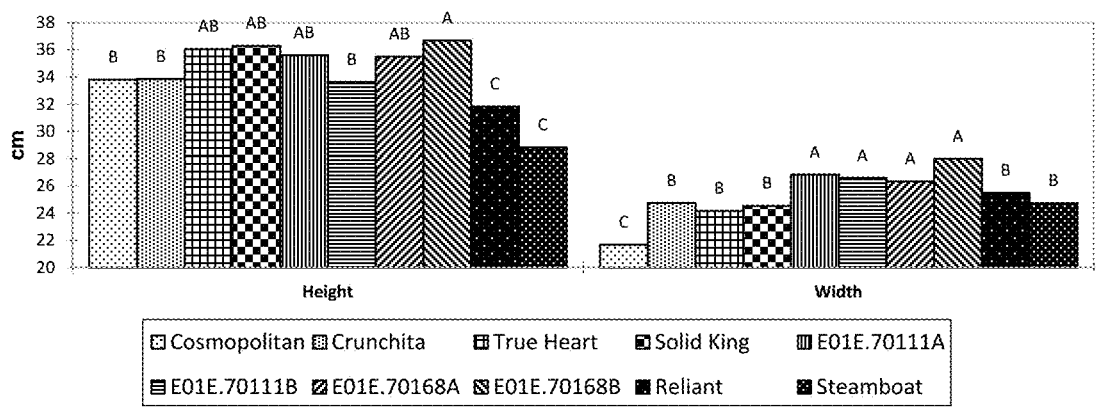
Figure 15C:
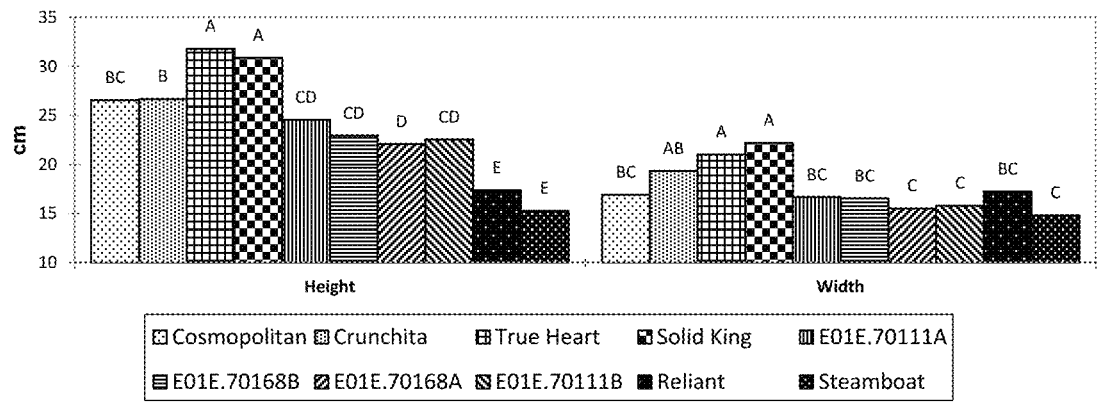
Figure 15D:
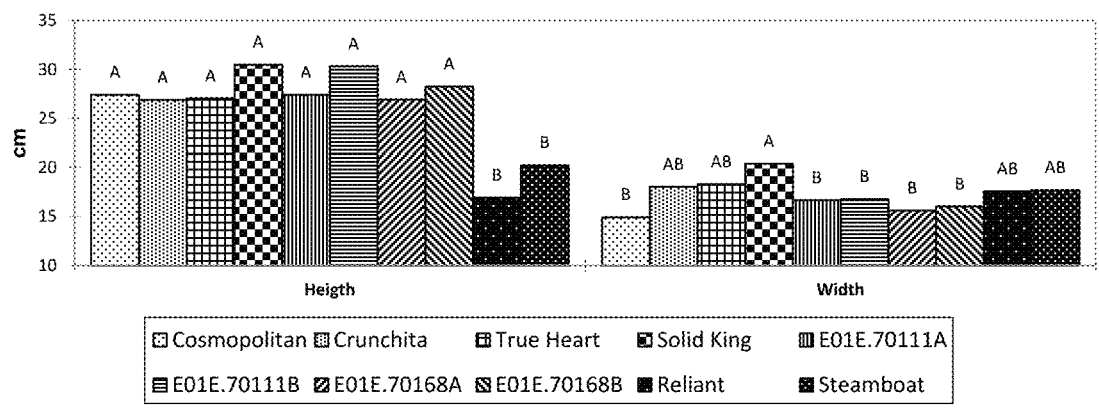
Figure 15E:
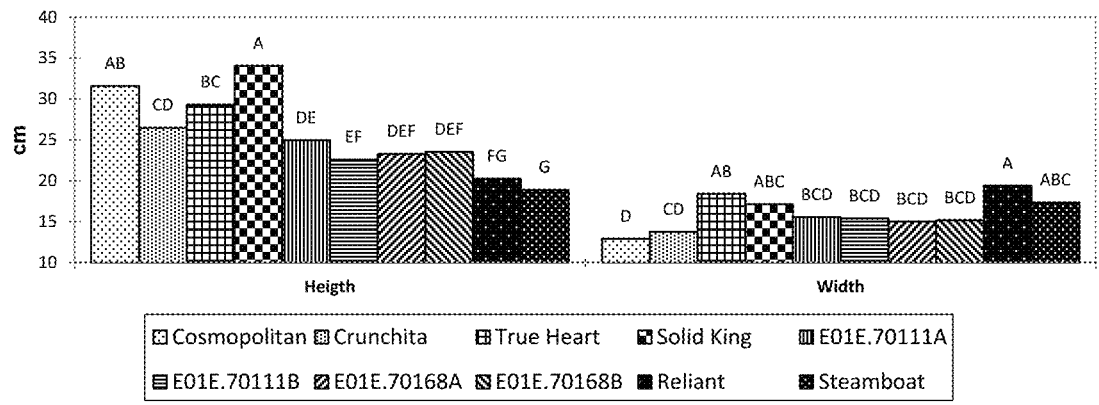

Measurement of lettuce head height and width: Lettuce head dimensions were taken with a standard metric tape in inches. Measurements were later converted into centimeters (cm) for statistical analyses. Exemplary images of the lettuce head height (left image) and lettuce head width (right image) measurement procedures are shown in FIGS. 15A-15B.

Figure 16A:
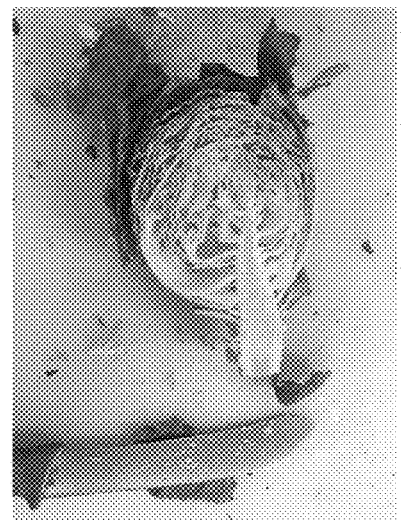
FIGS. 16A-16F show the evaluation of the percentage of overlapping leaves procedure and the analysis of the percentage of overlapping leaves data from Tests 1-4.
Figure 16B:
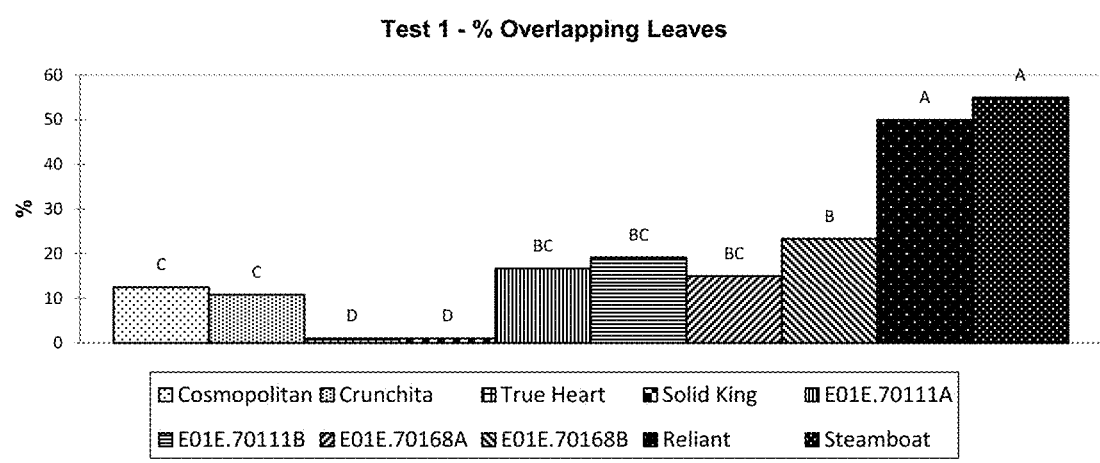
Figure 16C:
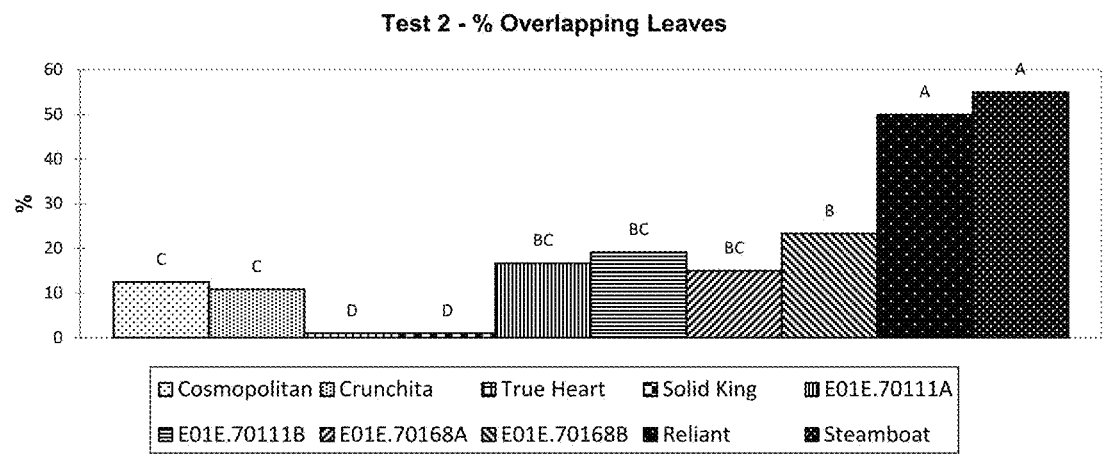
Figure 16D:
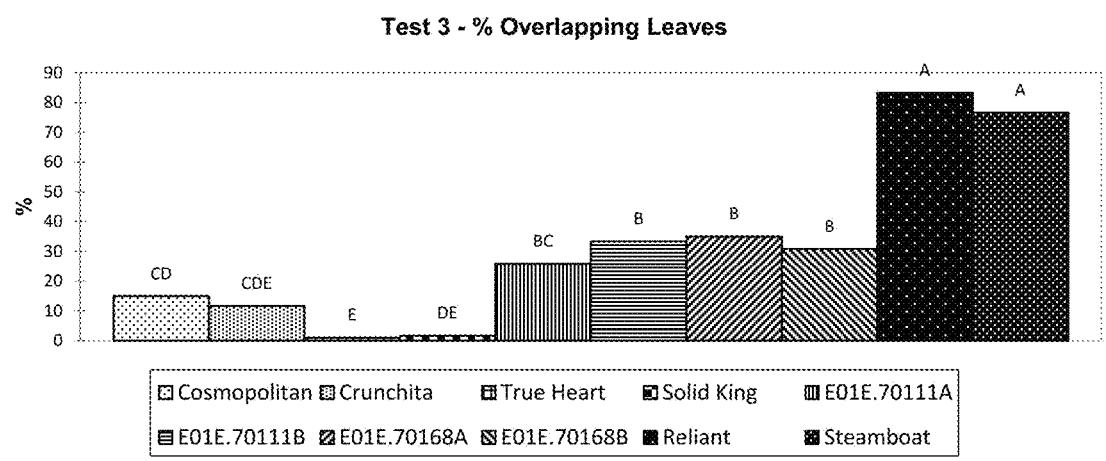
Figure 16E:
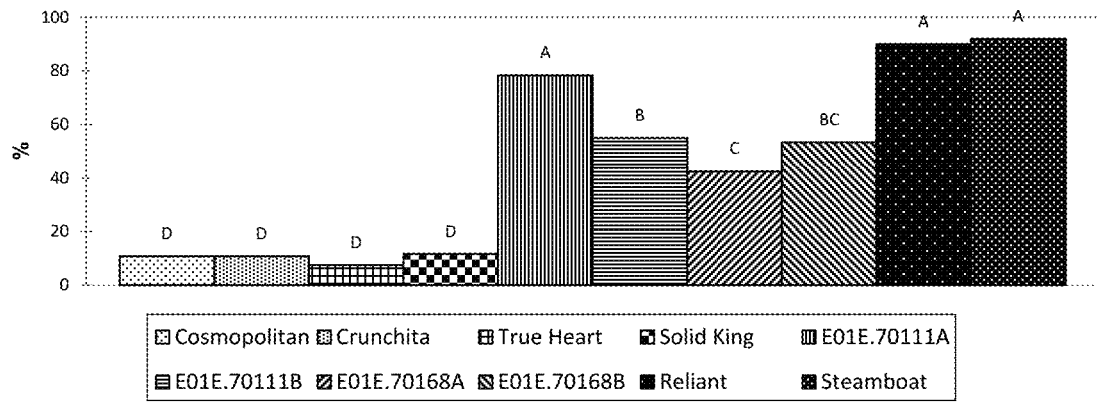
Figure 16F:
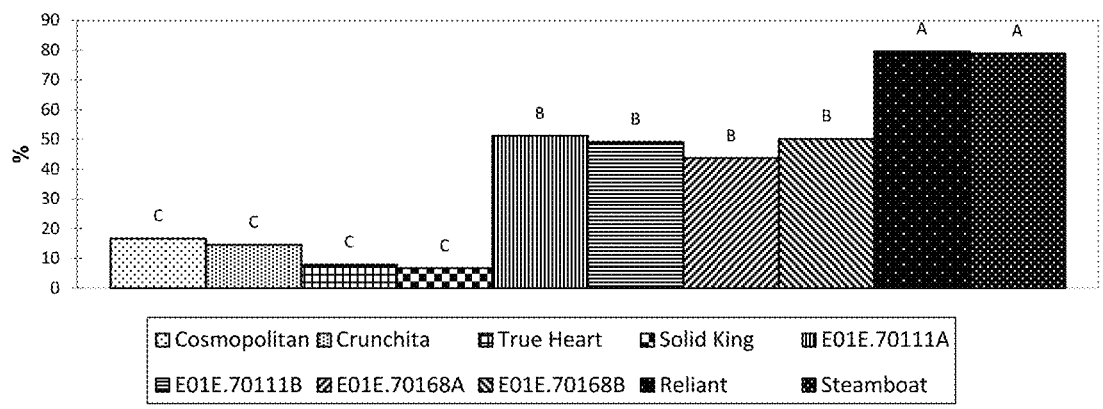

Evaluation of the percentage of overlapping leaves: Evaluation of the percentage of overlapping leaves was done by visually evaluating individual lettuce heads. The lettuce heads were first cut in half, and then in quarters for the evaluation. All evaluations were performed by the same expert evaluator under direct light. An exemplary image of a lettuce head cut in half for use in the evaluation of the percentage of overlapping leaves procedure is shown in FIG. 16A.

Figure 17A:
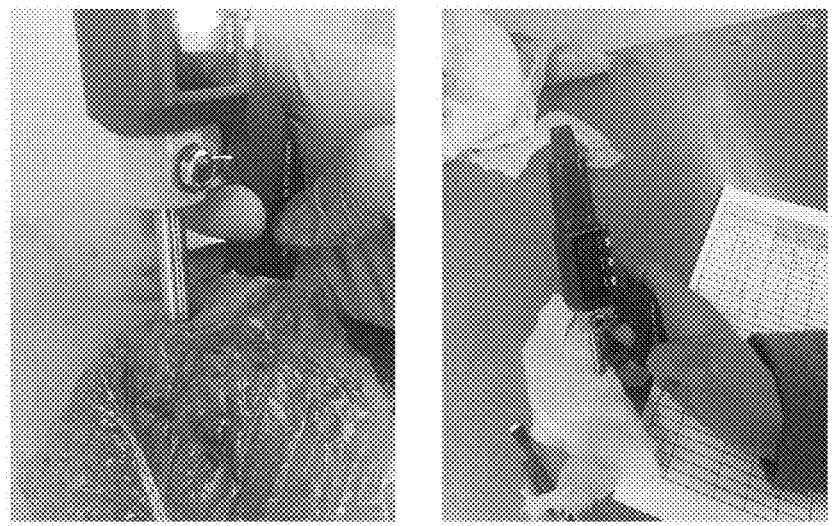
FIGS. 17A-17F show the leaf thickness measurement procedure and the analysis of lettuce leaf thickness measurement data in millimeters (mm) from Tests 1-4.
Figure 17B:
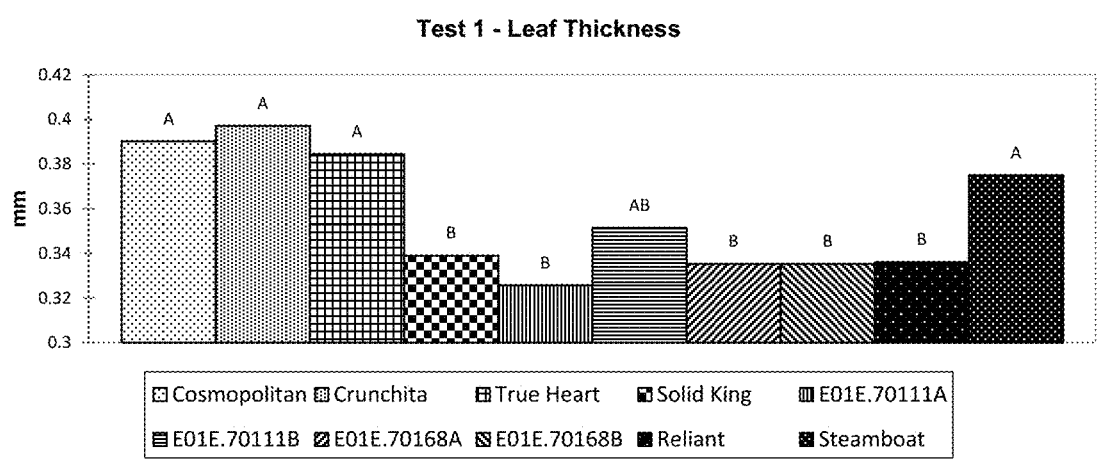
Figure 17C:
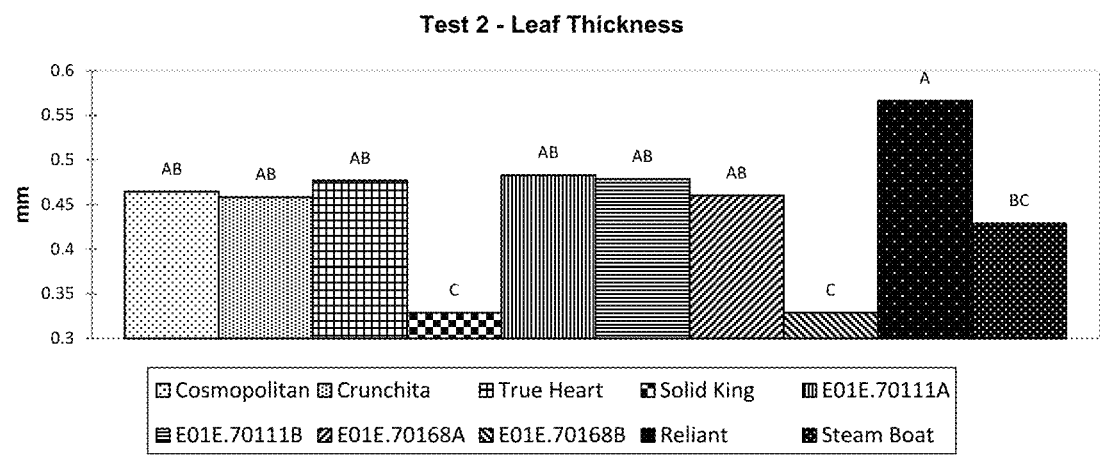
Figure 17D:
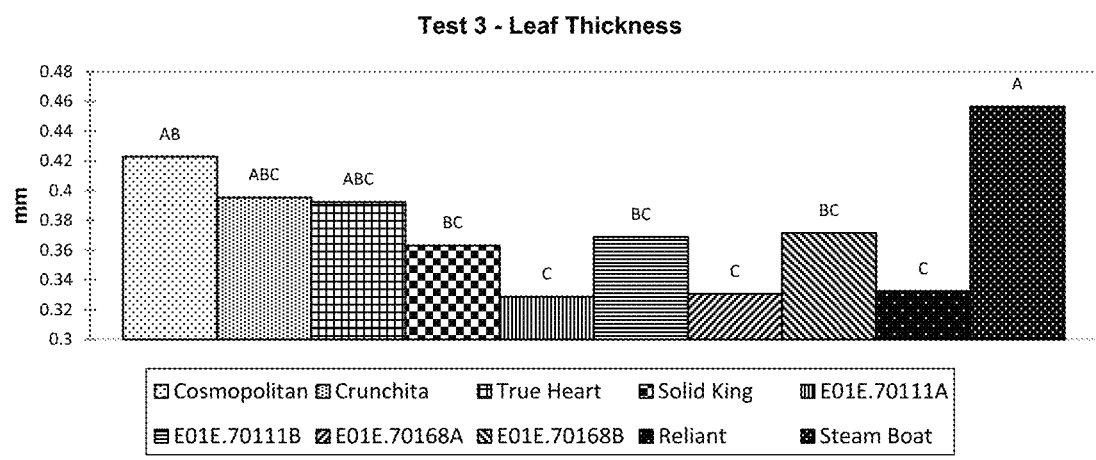
Figure 17E:
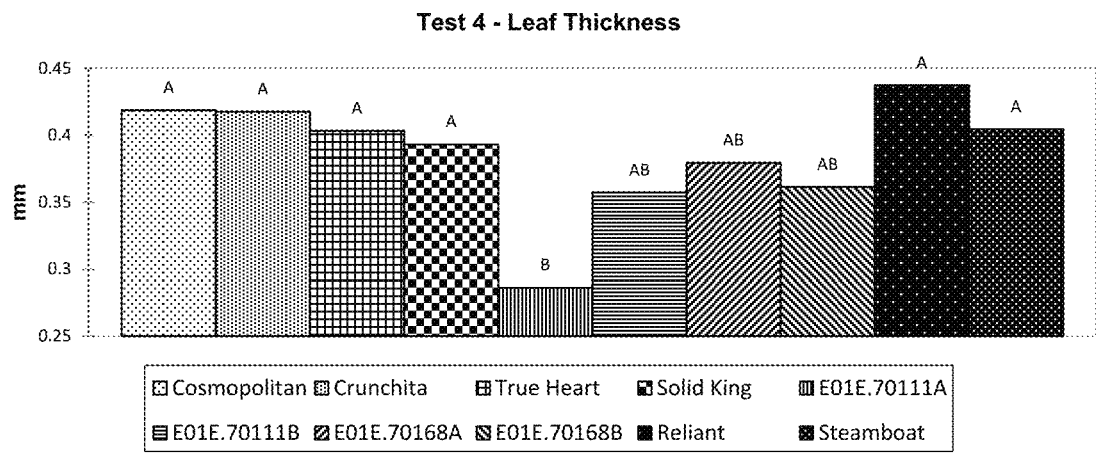

Measurement of leaf thickness: Leaf thickness was measured with an electronic 0-1 inch digital micrometer caliper with 0.00005 inch/0.001 mm resolution (RexBeTi). Six data points were taken for each lettuce of each variety per test in order to get a representative average of leaf thickness. These measurements were taken at the top and bottom of external, mid, and internal leaves. Leaf thickness was measured in millimeters (mm). Exemplary images of the leaf thickness measurement procedure are shown in FIG. 17A.

Figure 18A:
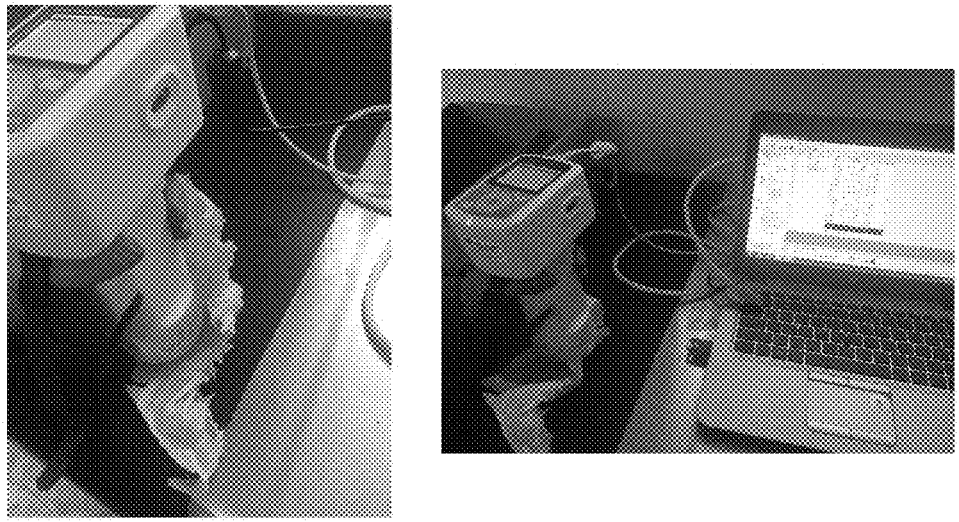
FIGS. 18A-18P show the measurement of leaf color using the spectrophotometer procedure and the analysis of color lightness data, color hue angle data, and leaf gloss data from Tests 1-4.
Figure 18B:
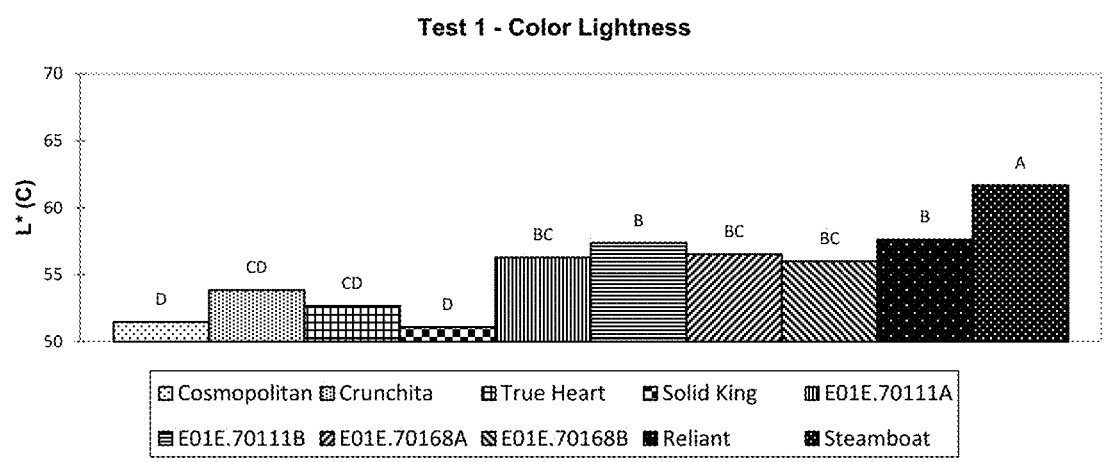
FIGS. 18B-18F show ANOVA analysis of the means of color lightness measurements from Test 1 (FIG. 18B), Test 2 (FIG. 18C), Test 3 (FIG. 18D), Test 4 (FIG. 18E), and all tests (i.e., Tests 1-4.
Figure 18C:
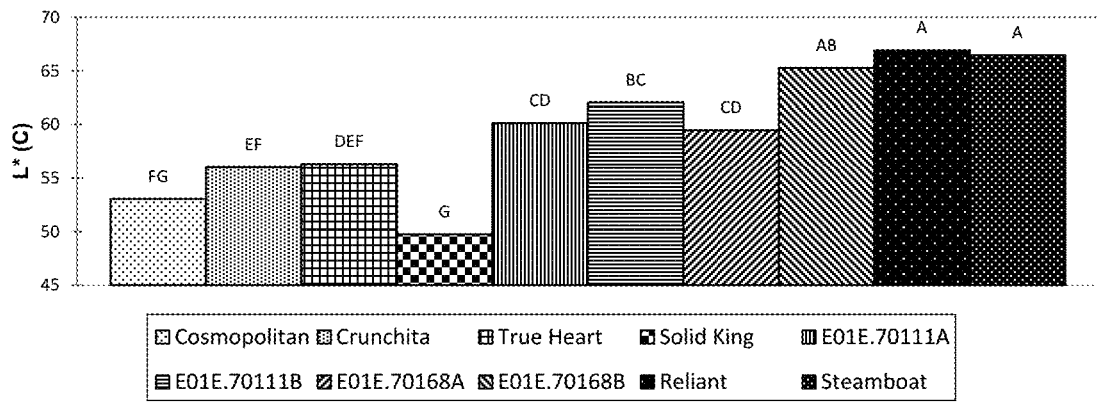
Figure 18D:
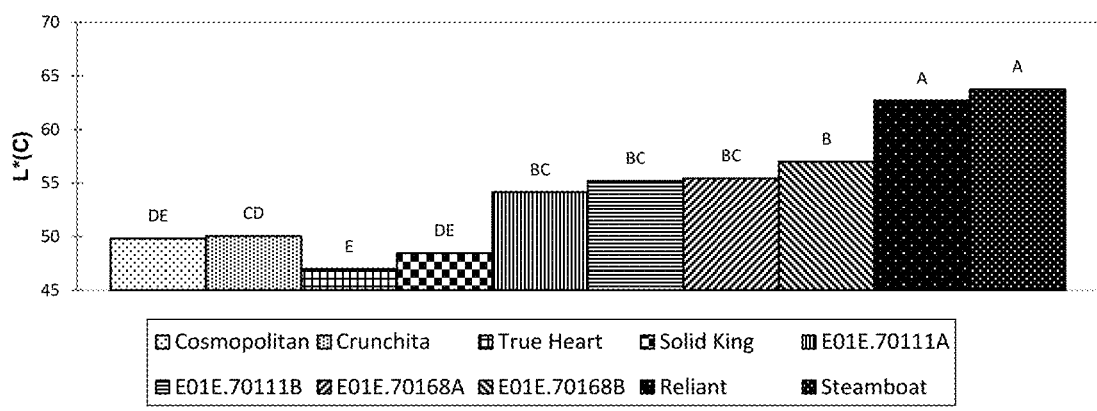
Figure 18E:
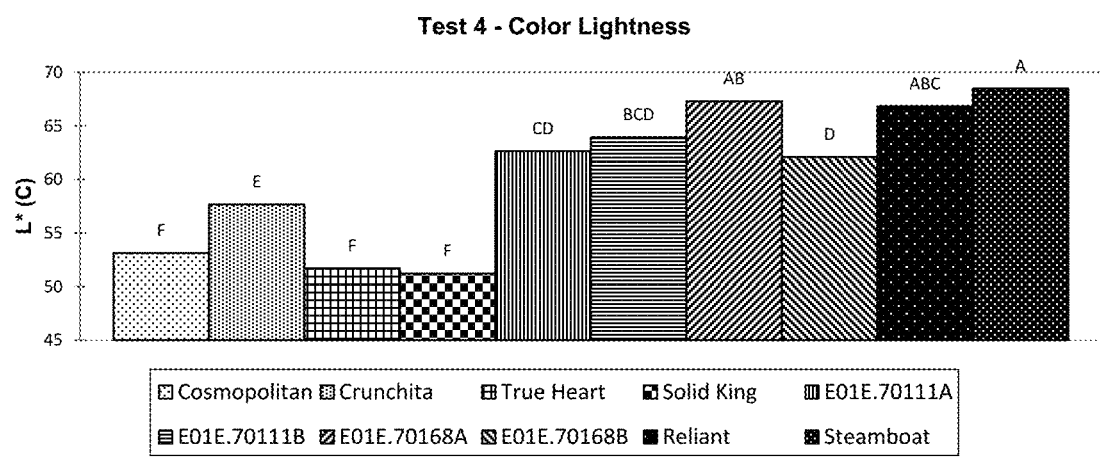

Measurement of leaf color: Two methods were used to measure the leaf color: Konica Minolta CM-700d Spectrophotometer (spectrophotometer) and the RHS Colour Chart of The Royal Horticultural Society of London, Sixth Edition 2015 (RHS Colour Chart). The spectrophotometer was set to measure reflectance in the CIELAB color space ($L^*$, $a^*$, $b^*$), 2 degree observer and C illuminant with a measurement area of 3 mm per measurement point (six measurements per lettuce, six lettuces per variety and test). The colorimeter was used in conjunction with SpectraMagic NX Professional software to record measurements and to provide a comprehensive color analysis. The spectrophotometer was used to measure three separate color components: lightness (i.e., brightness), hue angle (i.e., true color, arc tan ($b^*/a^*$, where $b^*$=blue-yellow component and $a^*$=green-red component))), and gloss (i.e., specular reflection at 8 degrees, shine). Exemplary images of the measurement of leaf color using the spectrophotometer are shown in FIG. 18A.

Figure 19:
FIG. 19 shows an exemplary image of the measurement of leaf color using the RHS color chart procedure.

The RHS Colour Chart was used because it is the standard reference used by horticulturists worldwide for recording plant colors. It has 920 colors, and each color has a unique number and letter code as well as a name. An exemplary image of the measurement of leaf color using the RHS colour chart is shown in FIG. 19.

For both color measurement methods, six data points were taken for each lettuce of each variety per test in order to get a representative average of leaf color. These measurements were taken at the top and bottom of external, mid, and internal leaves.

Figure 20A:
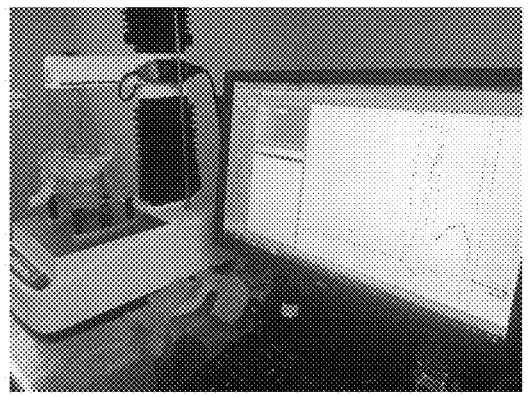
FIGS. 20A-20G show the measurement of leaf strength using the texturometer procedure and the analysis of leaf strength measurement data from Tests 1-4.
Figure 20B:
Figure 20B:
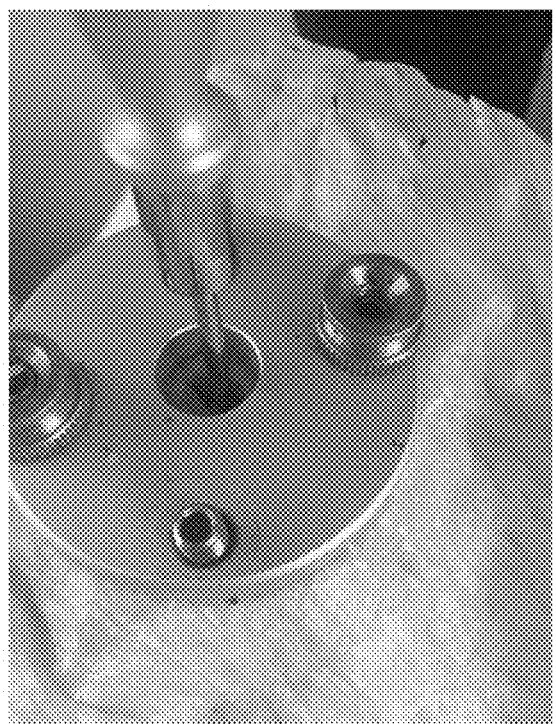
Figure 20C:
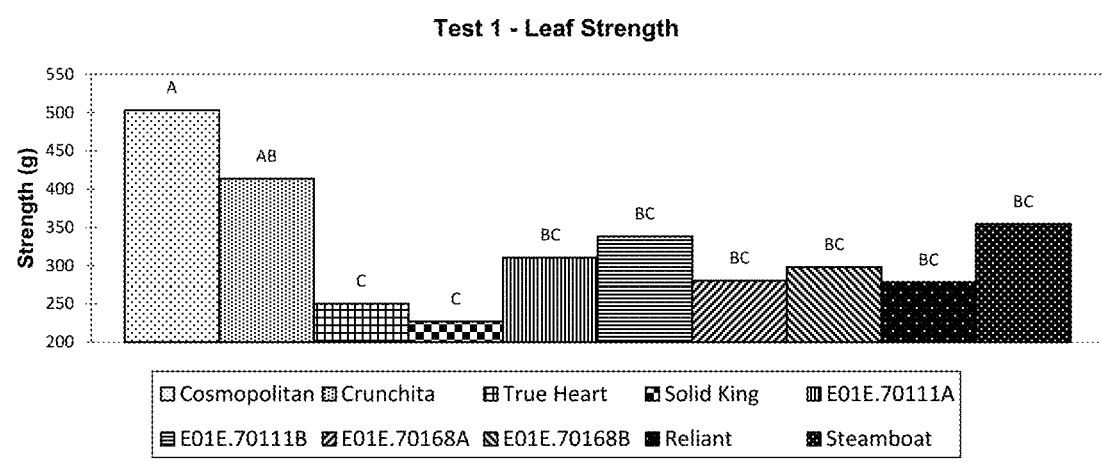
Figure 20D:
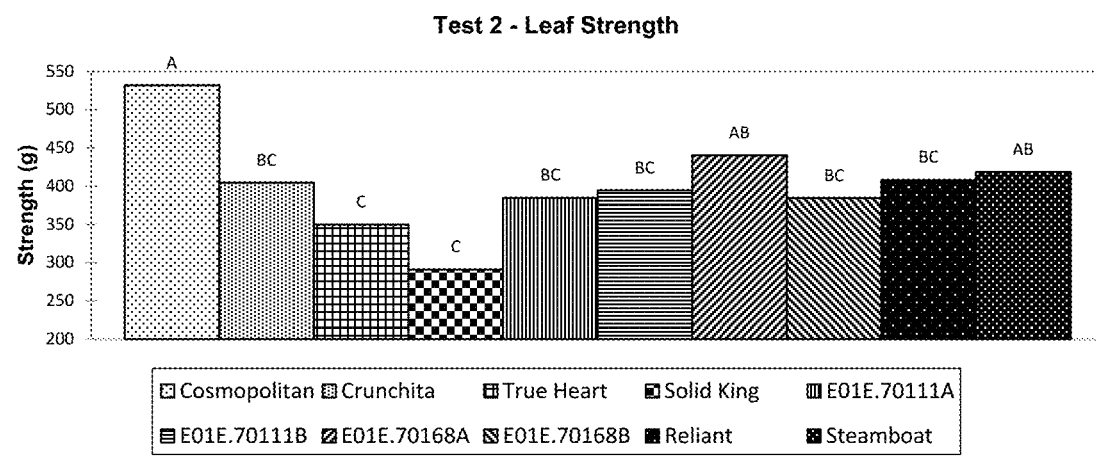
Figure 20E:
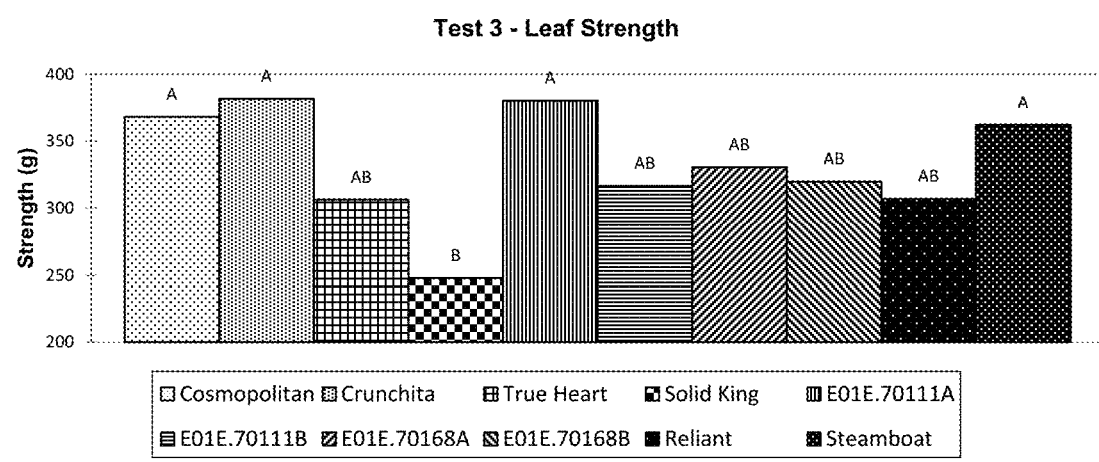
Figure 20F:
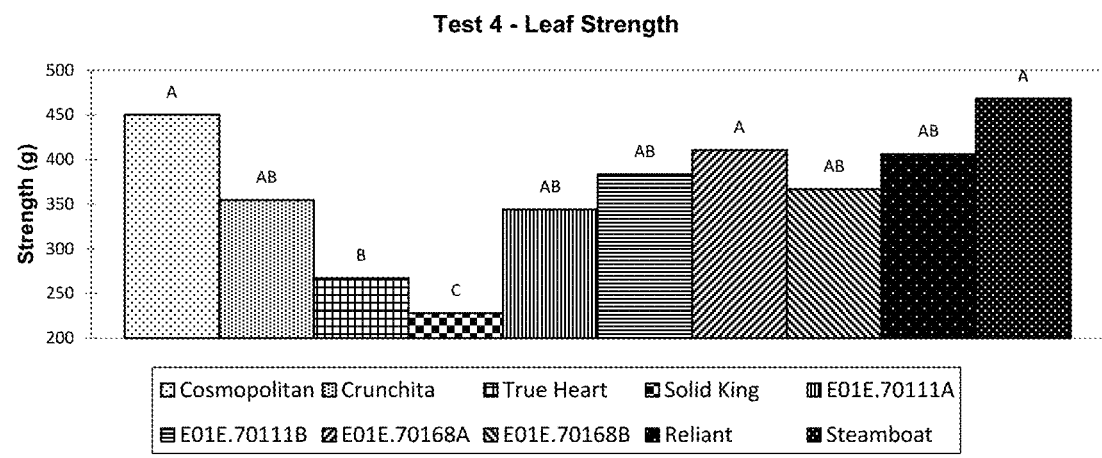

Measurement of leaf strength: Leaf strength was measured with the texture analyzer (texturometer) TA.XT Plus, which can measure forces from several hundredths of a gram up to 50 kilograms. In addition, the texturometer can travel at a speed ranging from 0.01 and 40 mm/second, has micron level distance resolution, and can be used with multiple probes and fixtures. For the measurement of leaf strength (force (g) needed to tear a leaf or leaf fragment), the TA-108s Single Small Film Extensibility Rig was attached. The procedure was set at a pre-test speed of 0.2 cm/sec, test speed of 0.1 cm/sec, post-test speed of 1 cm/sec, a distance of 1.5 cm and a trigger force of 5 g. Six data points were taken for each lettuce of each variety per test in order to get a representative average of leaf strength. These measurements were taken at the top and bottom of external, mid, and internal leaves. Exemplary images of the measurement of leaf strength using the texturometer are shown in FIGS. 20A-20B.

Results

Appearance of lettuce varieties: Whole head and whole head vertical cross section images were taken for each of the ten lettuce varieties in all four tests of the large scale trial. FIGS. 9A-9J show exemplary images from Test 1, FIGS. 10A-10J show exemplary images from Test 2, FIGS. 11A-11J show exemplary images from Test 3, and FIGS. 12A-12J show exemplary images from Test 4.

Figure 13N:
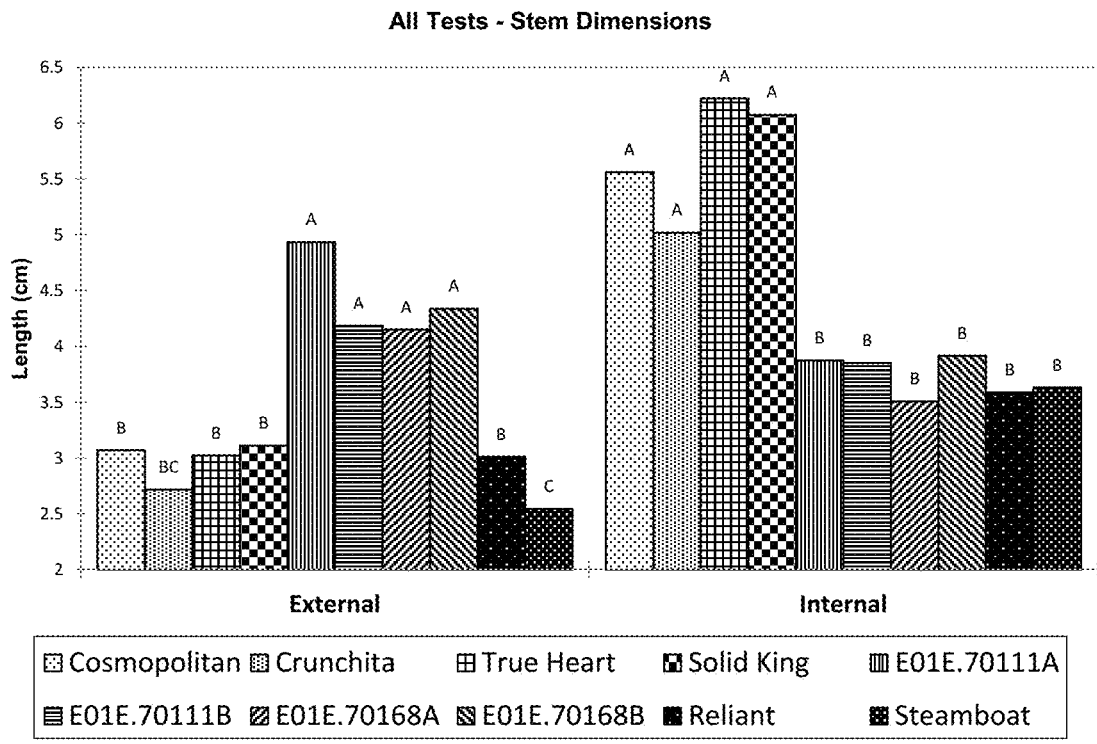
Figure 13O:
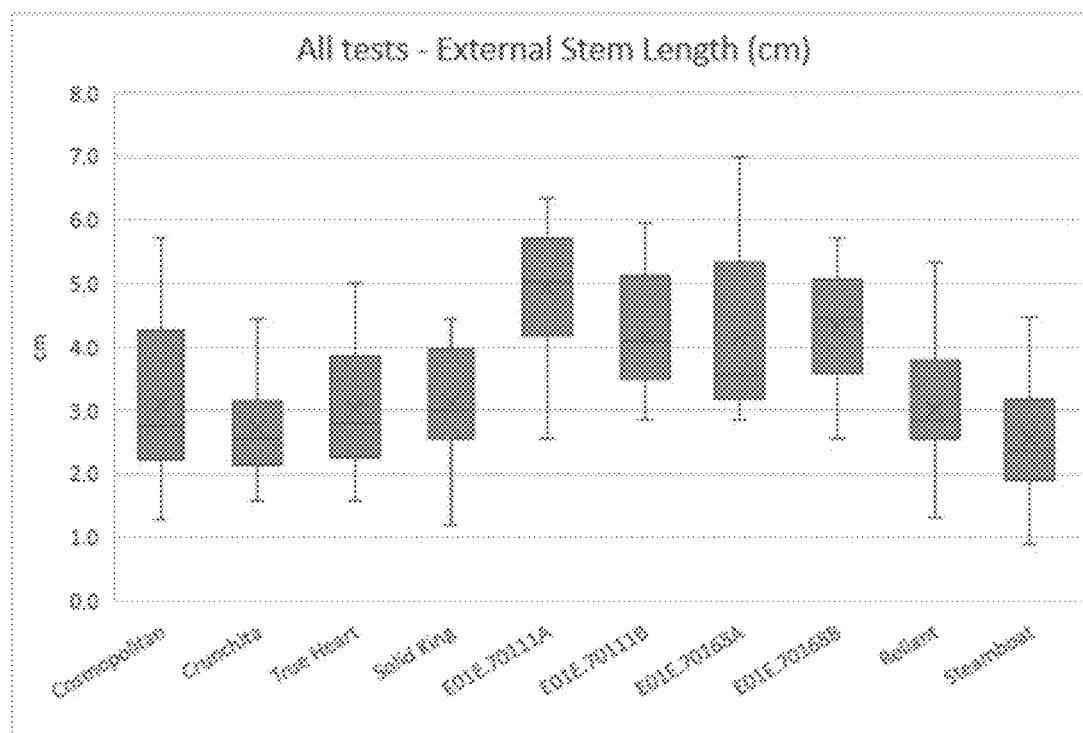
Figure 13P:
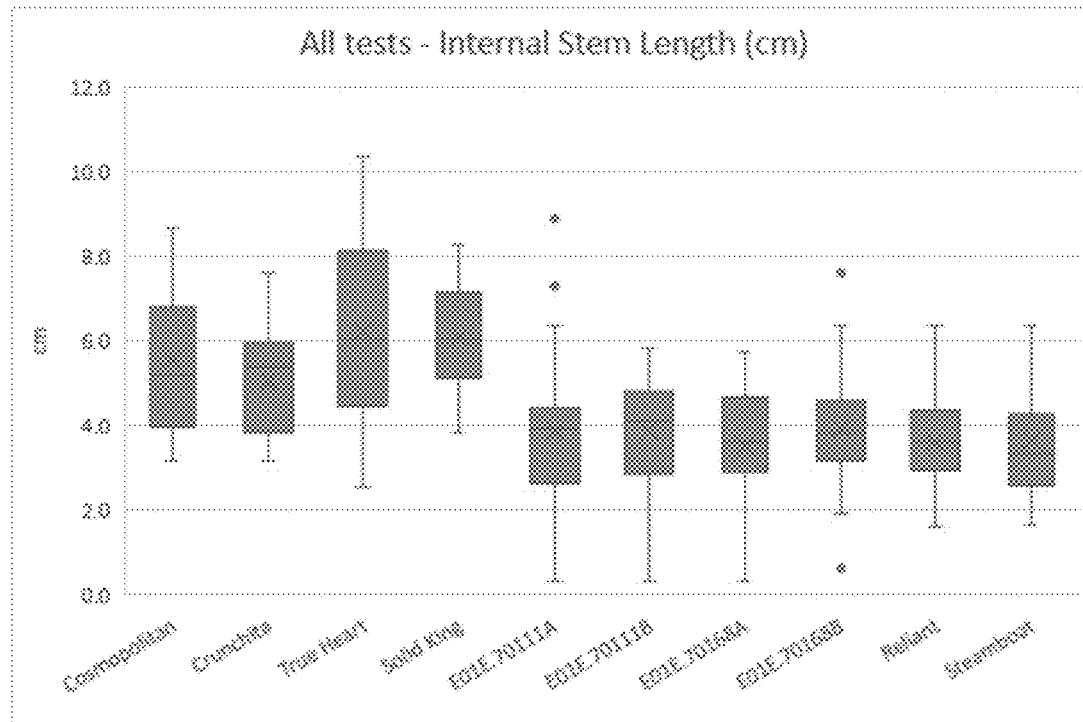

Measurement of stem length: ANOVA analysis results of the means of external and internal stem lengths in cm from the four tests are shown in FIGS. 13B, 13E, 13H, 13K, and 13N. FIGS. 13C, 13F, 13, 13L, and 13O show box and whisker charts of external stem length data in cm from all four tests, and FIGS. 13D, 13G, 13J, 13M, and 13P show box and whisker charts of internal stem length data in cm from all four tests. Internal stem lengths of romaine and cosberg varieties were significantly longer than internal stem lengths of upright heading iceberg and iceberg varieties (FIG. 13N). Both upright heading iceberg and iceberg varieties had comparatively short internal stem lengths that were an average of 3-4 cm, while romaine and cosberg varieties had long internal stem lengths of about 5-6.25 cm. In regard to external stem lengths, upright heading iceberg varieties had an external stem that was significantly longer than the other tested varieties (FIG. 13N). The external stem length of upright heading iceberg varieties was over 4 cm and up to almost 5 cm (for 'E01E.70111' Lot A), while that of the other lettuce varieties was about 2.5-3 cm.

Figure 14F:
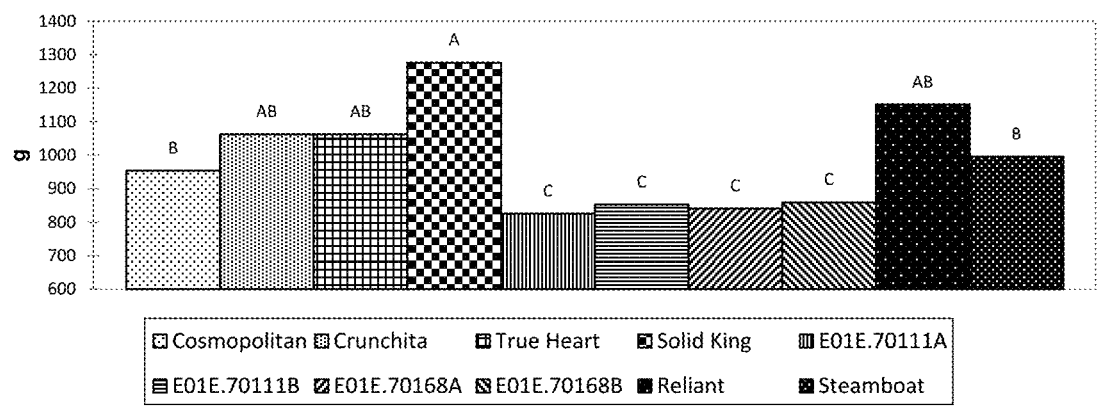

Measurement of lettuce head weight: ANOVA analysis results of the means of lettuce head weight measurement in g from the four tests are shown in FIGS. 14B-14F. Head weights for each variety varied across Tests 1-4. Overall, romaine variety 'Solid King' consistently had the heaviest heads. The other varieties differed from test to test, for example in Test 3 (FIG. 14D) the iceberg varieties had the next-heaviest heads, while in Test 1 (FIG. 14B), the romaine and cosberg varieties had the next-heaviest heads along with the iceberg varieties and a couple of the upright heading iceberg lettuce varieties. When all tests were combined, the upright heading iceberg varieties were lighter in weight than the other varieties (FIG. 14F).

Figure 15F:
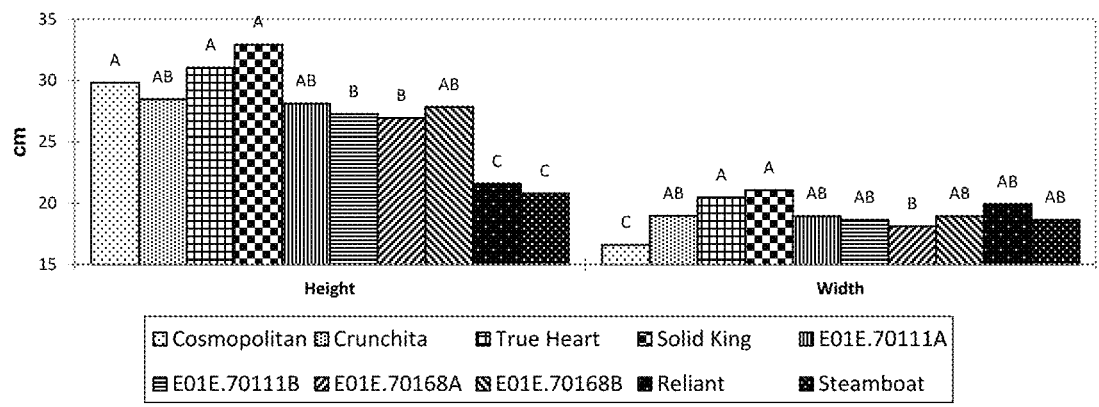

Measurement of lettuce head height and width: ANOVA analysis results of the means of lettuce head height and width measurements in cm from the four tests are shown in FIGS. 15B-15F. Overall, the heights of the cosberg, romaine, and machine harvestable iceberg lettuce varieties were comparable, while the iceberg lettuce varieties were significantly shorter in height (FIG. 15F). The widths of all of the varieties were comparable, with the exception of the cosberg variety 'Cosmopolitan' that was narrower than the rest of the varieties.

Evaluation of the percentage of overlapping leaves: ANOVA analysis results of the percentage of overlapping leaves from the four tests are shown in FIGS. 16B-16F. In each of the individual tests, as well as when all tests were combined (FIG. 16F), the romaine varieties had a very low percentage of overlapping leaves at less than 10%. The cosberg varieties had a slightly higher percentage of overlapping leaves, which was generally 10-20%. The upright heading iceberg varieties had an intermediate percentage of overlapping leaves, generally between 20-40%. Finally, the iceberg varieties had a very high percentage of overlapping leaves at 80% or more.

Figure 17F:
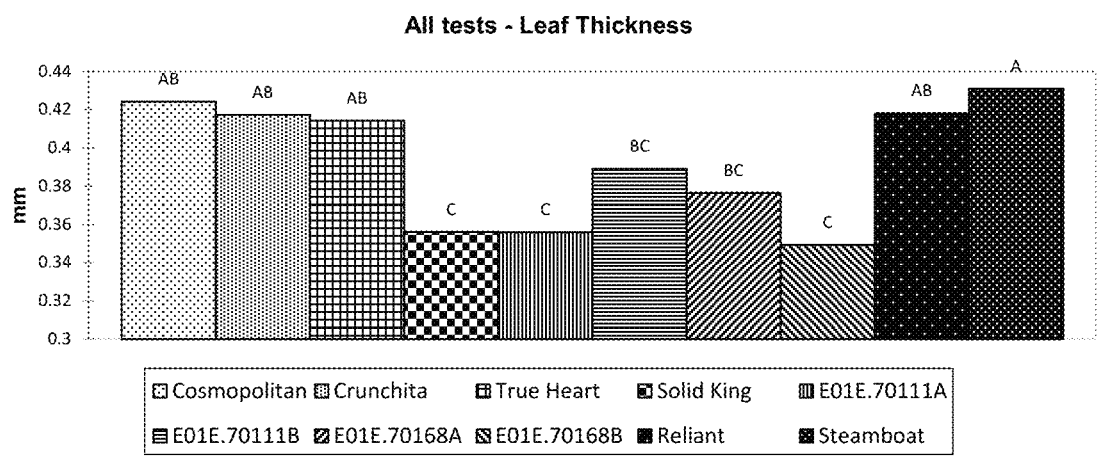

Measurement of leaf thickness: ANOVA analysis results of the means of leaf thickness measurements in cm from the four tests are shown in FIGS. 17B-17F. Leaf thicknesses were comparable across all tested varieties in all tests (FIG. 17F).

Figure 18F:
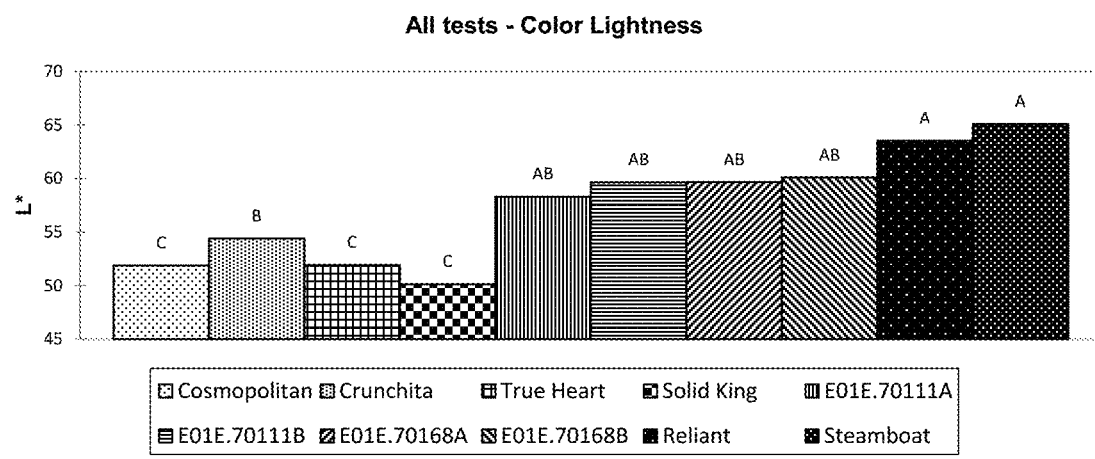
Figure 18G:
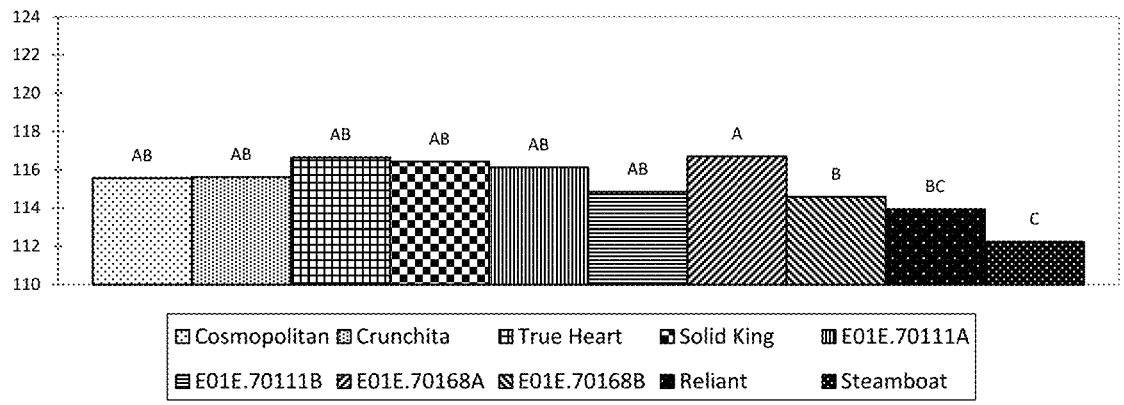
FIGS. 18G-18K show ANOVA analysis of the means of color hue angle measurements from Test 1 (FIG. 18G), Test 2 (FIG. 18H), Test 3 (FIG. 18I), Test 4 (FIG. 18J), and all tests (i.e., Tests 1-4.
Figure 18H:
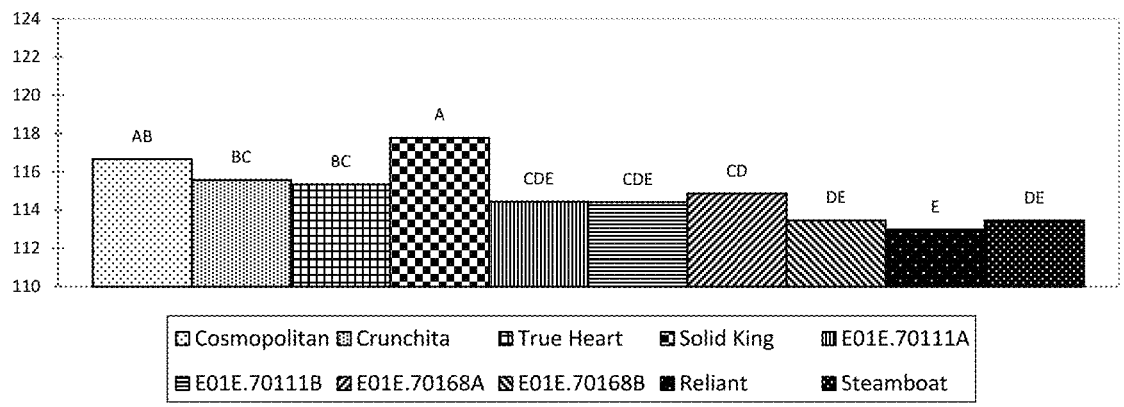
Figure 18I:
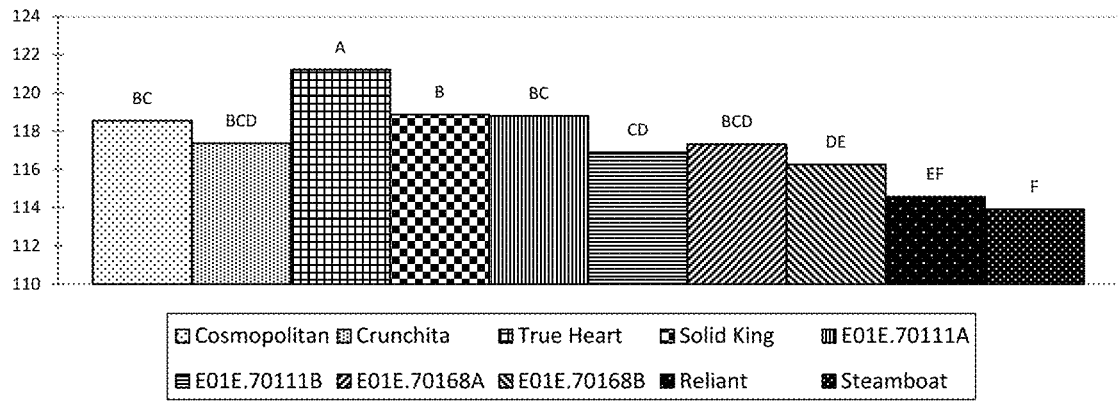
Figure 18J:
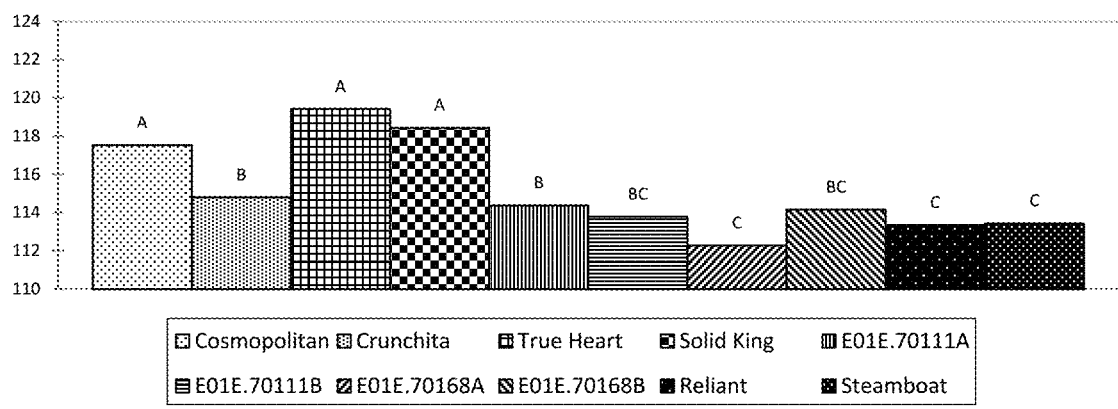
Figure 18K:
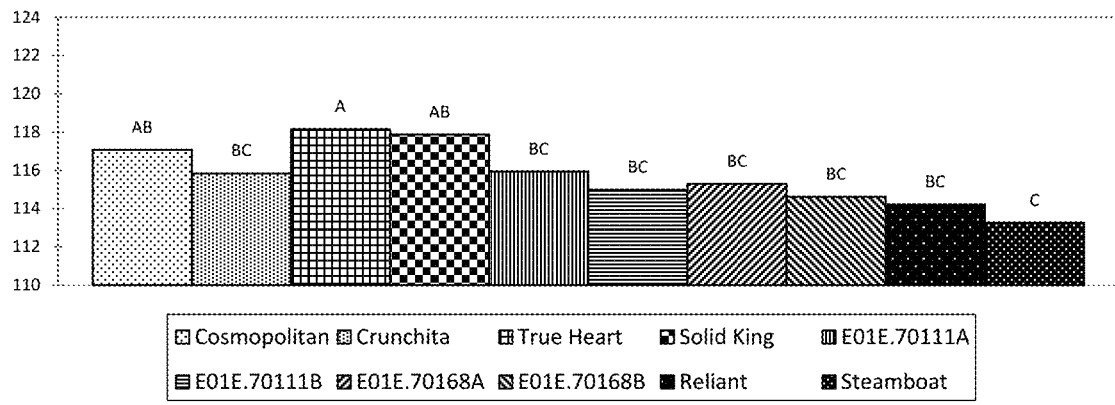
Figure 18L:
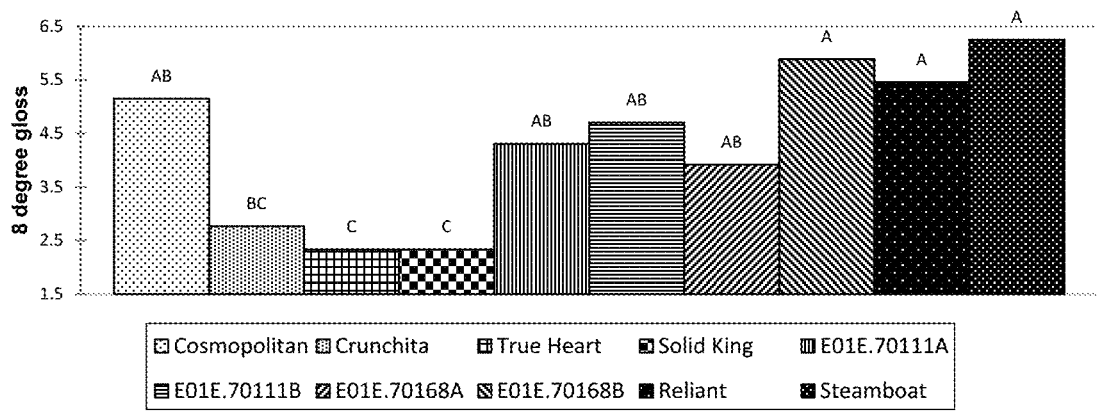
Figure 18M:
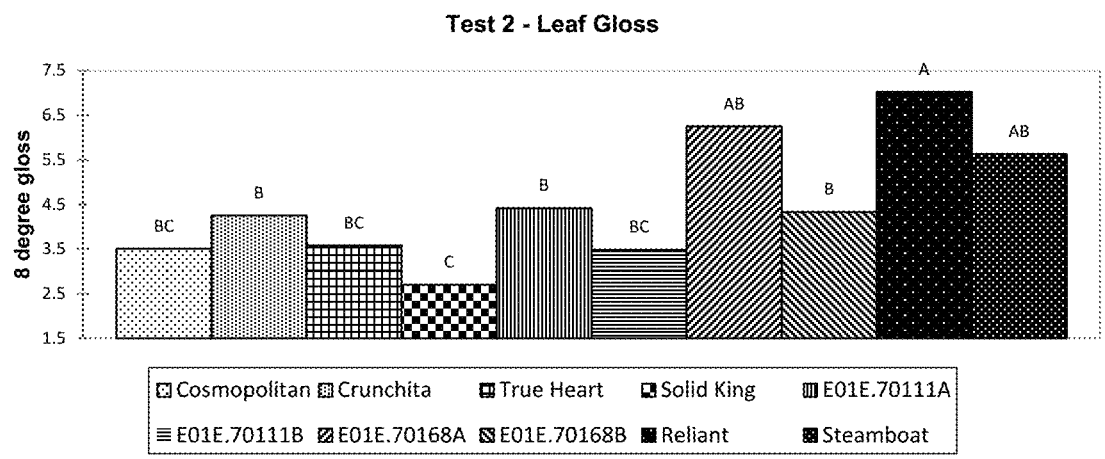
Figure 18N:
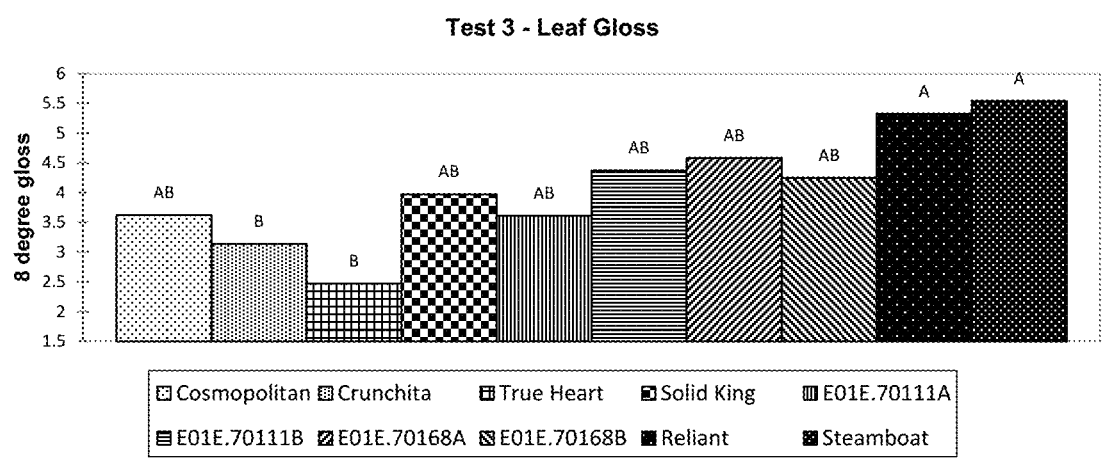
Figure 18O:
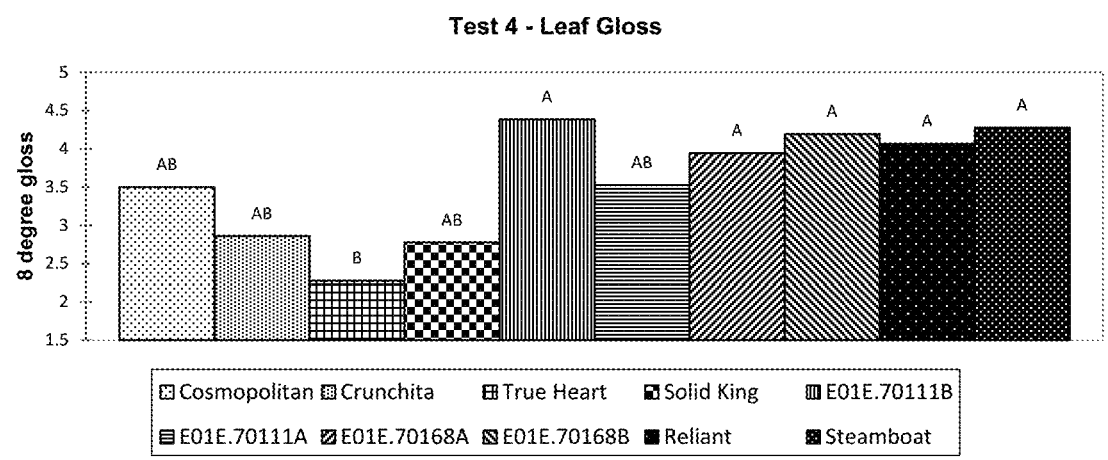
Figure 18P:
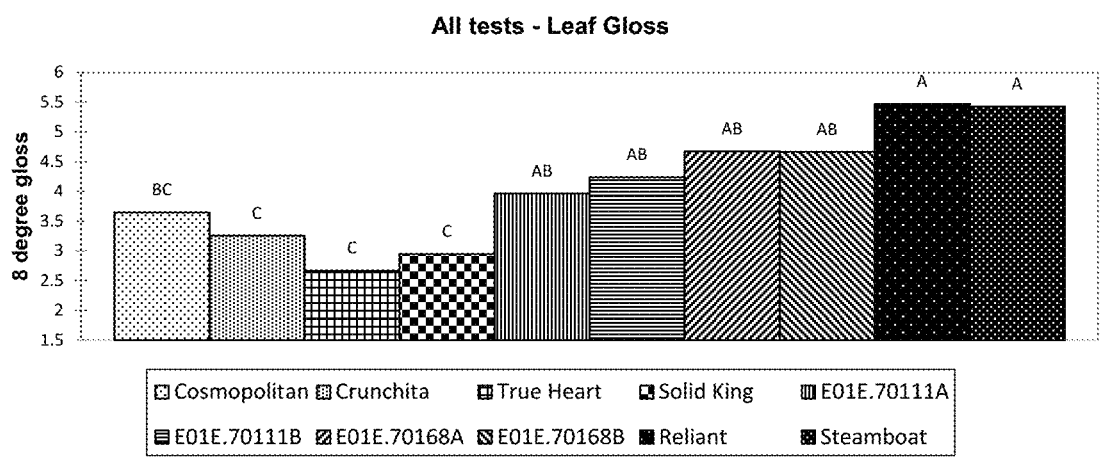

Measurement of leaf color using the spectrophotometer: ANOVA analysis results of the means of color lightness measurements from all four tests are shown in FIGS. 18B-18F. Color lightness was comparable between upright heading iceberg and iceberg varieties, and significantly different from color lightness of romaine and cosberg varieties (FIG. 18F). ANOVA analysis results of the means of color hue angle measurements from all four tests are shown in FIGS. 18G-18K. Color hue angle measurements were comparable across all of the varieties tested (FIG. 18K). ANOVA analysis results of the means of leaf gloss measurements from all four tests is shown in FIGS. 18L-18P. As with color lightness measurements, leaf gloss was comparable between upright heading iceberg and iceberg varieties, and significantly different from leaf gloss of romaine and cosberg varieties (FIG. 18L).

Measurement of leaf color using the RHS Colour Chart: Six measurements were taken from each of the six tested plants for each variety per test, resulting in a total of 36 observations for each variety per test. The mode of each group of 36 observations was then identified in order to determine the representative color of the variety. The mode colors of the ten tested varieties are listed in Table 15 for Test 1, Table 16 for Test 2, Table 17 for Test 3, Table 18 for Test 4, and Table 19 for all tests (i.e., Test 1-4).

TABLE 15

Mode colors of all varieties in Test 1

| Variety | Observations | Categories | Mode (RHS value) | Mode frequency | Color name |
|---|---|---|---|---|---|
| Cosmopolitan | 36 | 10 | 143 | 7 | Strong Yellow Green |
| Crunchita | 36 | 9 | 143 | 10 | Strong Yellow Green |
| True Heart | 36 | 9 | 144 | 6 | Strong Yellow Green |
| Solid King | 36 | 9 | 143 | 12 | Strong Yellow Green |
| E01E.70111A | 36 | 8 | 137 | 9 | Moderate Olive Green |
| E01E.70111B | 36 | 9 | 141 | 8 | Deep Yellowish Green |
| E01E.70168A | 36 | 8 | 145 | 12 | Light yellow Green |
| E01E.70168B | 36 | 7 | 144 | 10 | Strong Yellow Green |
| Reliant | 36 | 10 | 145 | 7 | Light Yellow Green |
| Steamboat | 36 | 10 | 149 | 8 | Brilliant Yellow Green |

TABLE 16

Mode colors of all varieties in Test 2

| Variety | Observations | Categories | Mode (RHS value) | Mode frequency | Color name |
|---|---|---|---|---|---|
| Cosmopolitan | 36 | 8 | 144 | 11 | Strong Yellow Green |
| Crunchita | 36 | 7 | 145 | 14 | Light Yellow Green |
| True Heart | 36 | 10 | 144 | 8 | Strong Yellow Green |
| Solid King | 36 | 7 | 143 | 9 | Strong Yellow Green |
| E01E.70111A | 36 | 7 | 145 | 13 | Light Yellow Green |
| E01E.70111B | 36 | 9 | 145 | 10 | Light Yellow Green |
| E01E.70168A | 36 | 11 | 144 | 7 | Strong Yellow Green |
| E01E.70168B | 36 | 7 | 145 | 13 | Light Yellow Green |
| Reliant | 36 | 9 | 145 | 12 | Light Yellow Green |
| Steamboat | 36 | 6 | 145 | 25 | Light Yellow Green |

TABLE 17

Mode colors of all varieties in Test 3

| Variety | Observations | Categories | Mode (RHS value) | Mode frequency | Color name |
|---|---|---|---|---|---|
| Cosmopolitan | 36 | 6 | 137 | 16 | Moderate Olive Green |
| Crunchita | 36 | 7 | 144 | 12 | Strong Yellow Green |
| True Heart | 36 | 5 | 137 | 17 | Moderate Olive Green |
| Solid King | 36 | 8 | 143 | 11 | Strong Yellow Green |
| E01E.70111A | 36 | 7 | 143 | 9 | Strong Yellow Green |

TABLE 17-continued

Mode colors of all varieties in Test 3

| Variety | Observations | Categories | Mode (RHS value) | Mode frequency | Color name |
|---|---|---|---|---|---|
| E01E.70111B | 36 | 7 | 145 | 9 | Light Yellow Green |
| E01E.70168A | 36 | 7 | 143 | 11 | Strong Yellow Green |
| E01E.70168B | 36 | 7 | 145 | 9 | Light Yellow Green |
| Reliant | 36 | 8 | 144 | 15 | Strong Yellow Green |
| Steamboat | 36 | 7 | 145 | 22 | Light Yellow Green |

TABLE 18

Mode colors of all varieties in Test 4

| Variety | Observations | Categories | Mode (RHS value) | Mode frequency | Color name |
|---|---|---|---|---|---|
| Cosmopolitan | 36 | 8 | 137 | 11 | Moderate Olive Green |
| Crunchita | 36 | 6 | 138 | 11 | Moderate Olive Green |
| True Heart | 36 | 7 | 137 | 12 | Moderate Olive Green |
| Solid King | 36 | 7 | 143 | 14 | Strong Yellow Green |
| E01E.70111A | 36 | 6 | 145 | 17 | Light Yellow Green |
| E01E.70111B | 36 | 8 | 145 | 11 | Light Yellow Green |
| E01E.70168A | 36 | 7 | 145 | 17 | Light Yellow Green |
| E01E.70168B | 36 | 7 | 144 | 11 | Strong Yellow Green |
| Reliant | 36 | 6 | 145 | 19 | Light Yellow Green |
| Steamboat | 36 | 4 | 145 | 22 | Light Yellow Green |

TABLE 19

Mode colors of all varieties in all tests (i.e., Test 1-4)

| Variety | Observations | Categories | Mode (RHS value) | Mode frequency | Color name |
|---|---|---|---|---|---|
| Cosmopolitan | 144 | 12 | 137 | 41 | Moderate Olive Green |
| Crunchita | 144 | 12 | 145 | 31 | Light Yellow Green |
| True Heart | 144 | 11 | 137 | 39 | Moderate Olive Green |
| Solid King | 144 | 11 | 143 | 46 | Strong Yellow Green |
| E01E.70111A | 144 | 9 | 145 | 38 | Light Yellow Green |
| E01E.70111B | 144 | 11 | 145 | 32 | Light Yellow Green |
| E01E.70168A | 144 | 12 | 145 | 41 | Light Yellow Green |
| E01E.70168B | 144 | 11 | 144 | 35 | Strong Yellow Green |
| Reliant | 144 | 13 | 145 | 46 | Light Yellow Green |
| Steamboat | 144 | 11 | 145 | 75 | Light Yellow Green |

These results showed that the iceberg varieties were clearly distinguished from the romaine varieties by their color. Over all four tests, the iceberg varieties were primarily evaluated to have the color light yellow green (RHS 145), while the romaine varieties were evaluated to have either the color moderate olive green (RHS 137) or the color strong yellow green (RHS 143) (Table 19). The upright heading iceberg lettuce varieties were evaluated to have the iceberg-type color of light yellow green (RHS 145) across all four tests, with the exception of 'E01E.70168' Lot B. Finally, the two cosberg varieties, 'Cosmopolitan' and 'Crunchita', were together evaluated as having colors intermediate between romaine and iceberg over all four tests.

Figure 20G:
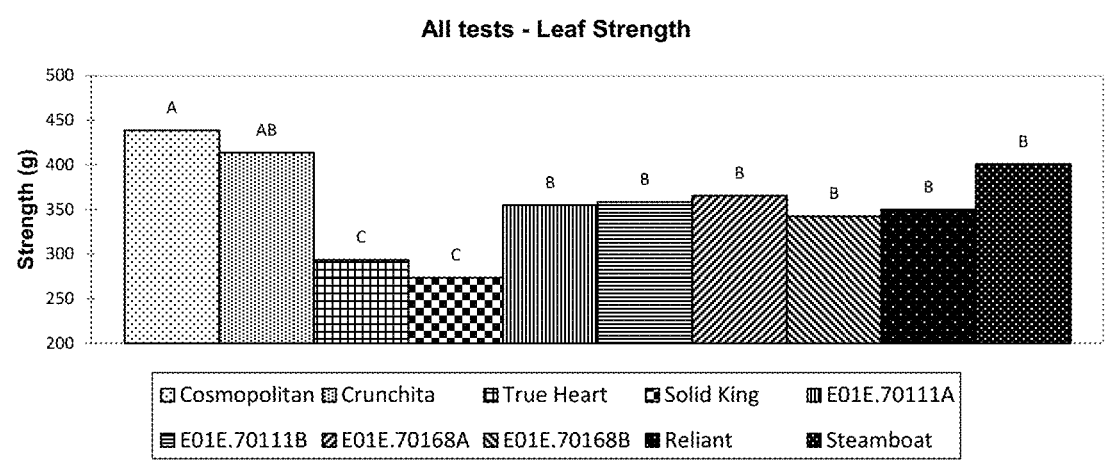

Measurement of leaf strength: ANOVA analysis results of the means of leaf strength measurements in cm are shown in FIGS. 20C-20G. Overall, the leaf strength of upright heading iceberg lettuce was comparable to the leaf strength of iceberg lettuce (FIG. 20G). Both types of iceberg lettuce were significantly different from romaine lettuce varieties, which had weaker leaves, and different from cosberg lettuce varieties, which had stronger leaves.

Summary

Figure 28:
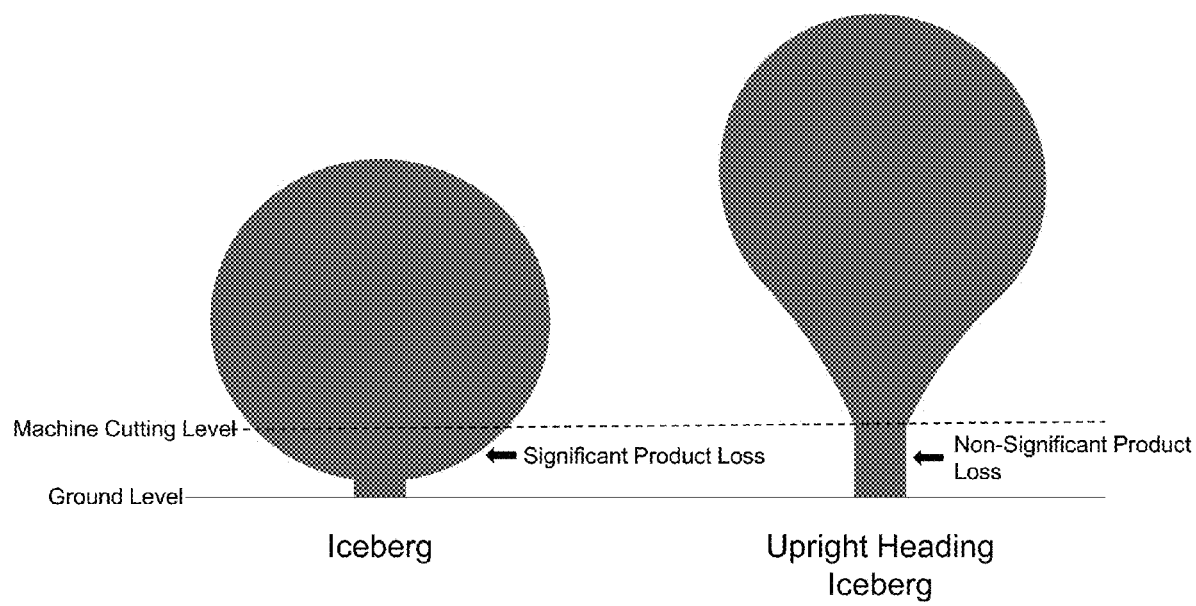
FIG. 28 shows a schematic of the machine cutting level on iceberg and upright heading iceberg lettuce varieties. Ground level is depicted by a solid line, machine cutting level is depicted by a dashed line, and the location of product loss (i.e., below the machine cutting level) for each lettuce variety is labeled and indicated with a thick black arrow.

In summary, the morphological characterization results showed that upright heading iceberg varieties had an external stem that was significantly longer than the other tested varieties (i.e., romaine, cosberg, iceberg). These longer external stems raised the upright heading iceberg variety heads off of the ground further than the heads of the other varieties, making these varieties suitable for mechanical harvest. The mechanical harvest process uses uniform beds with level ground to ensure uniform cutting, and cutting occurs about 2 inches above the bed. This elevated cutting is done to prevent soil or other debris (e.g., leaf debris) from contaminating the product and being taken up into the cutting machine. Traditional iceberg lettuce varieties have heads close to ground level, meaning that a large portion of the bottom of the head is cut off during mechanical harvest (FIG. 28). This cut both reduces yield and increases the risk of contaminating the product with other material (e.g., soil, leaf debris). Thus, the longer stem of the upright heading iceberg lettuce varieties situates the head at the correct height to be mechanically harvested without loss of head material used for processing.

Moreover, the longer external stems of upright heading iceberg varieties did not result in longer internal stems. Longer internal stems are a negative characteristic for lettuce varieties used in processing, because when product is harvested and the stem is removed, there is less product volume to use for processing. Further, the upright heading iceberg varieties had an intermediate percentage of overlapping leaves. The percentage of overlapping leaves is one way of assessing how clean the lettuce heads will be at harvest. The intermediate percentage of overlapping leaves of the upright heading iceberg varieties indicates that the heads of these varieties will be clean at harvest, similar to the cosberg varieties, and in contrast to the romaine varieties.

In addition, upright heading iceberg varieties were shown to have many of the same characteristics as iceberg varieties. These characteristics included a short internal stem length and comparable head size. Further, the quality of the leaves was similar, with both leaf thickness and leaf strength showing no significant differences between upright heading iceberg and iceberg varieties. Finally, leaf appearance was shown to be similar using multiple metrics. Overall, both the colorimeter (spectrophotometer) measurements and the RHS Colour Chart assessment showed that upright heading iceberg leaf color was comparable to iceberg leaf color. Therefore, upright heading iceberg varieties had many of the known and valued characteristics of iceberg varieties, while also having the new long external stem length characteristic that makes them suitable for mechanical harvest.

Example 6: Large Scale Field Trial—Nutritional Characterization

Figure 21:
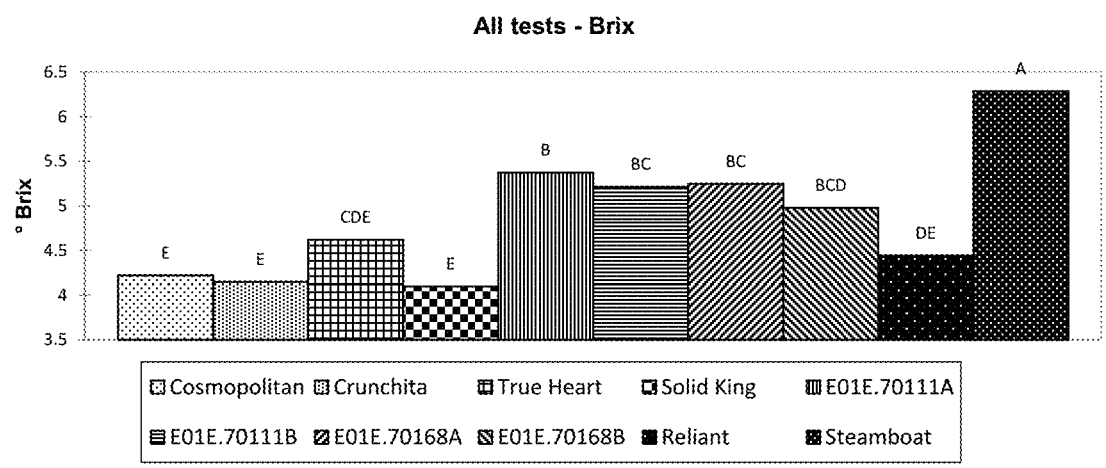
FIG. 21 shows ANOVA analysis of the means of ° Brix measurements from Tests 1-4. The bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.
Figure 22A:
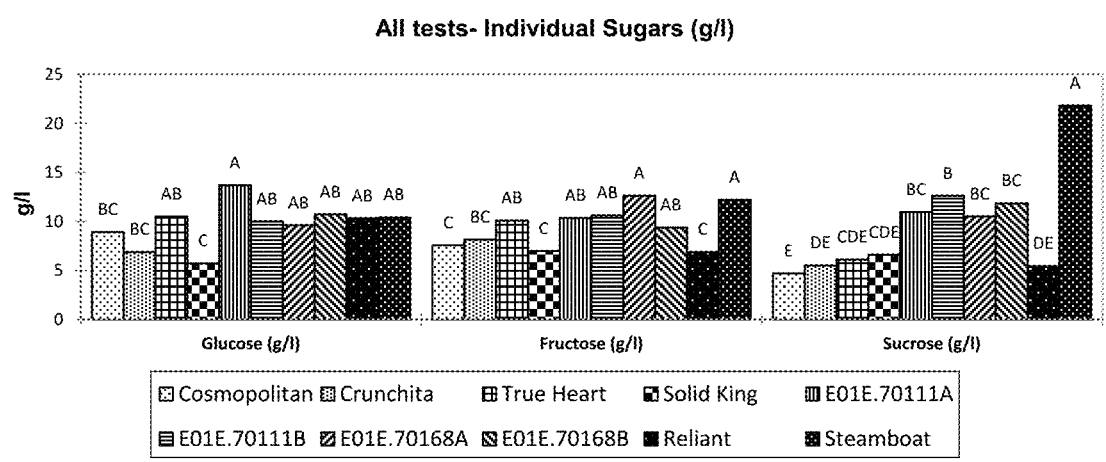
FIGS. 22A-22C show ANOVA analysis of the means of different sugar measurements across all tests (i.e., Tests 1-4).
Figure 22B:
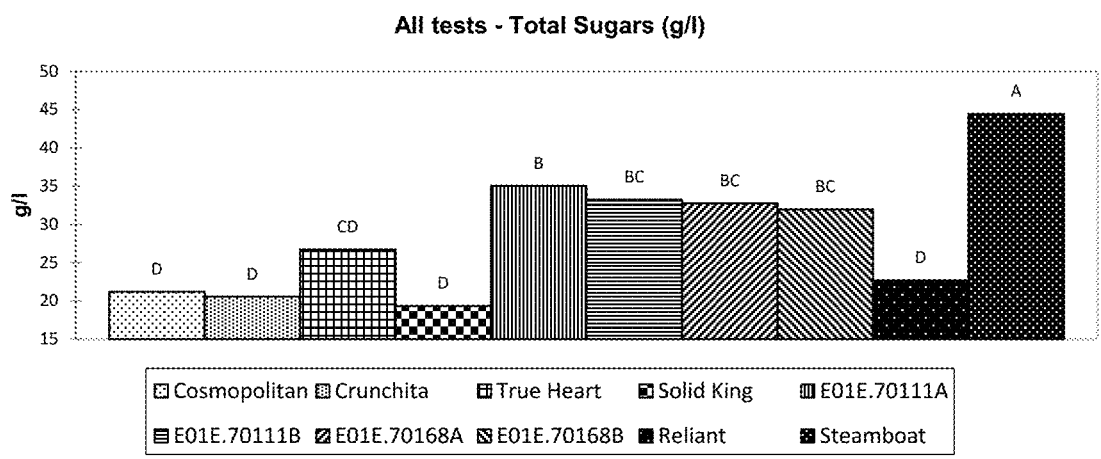
Figure 22C:
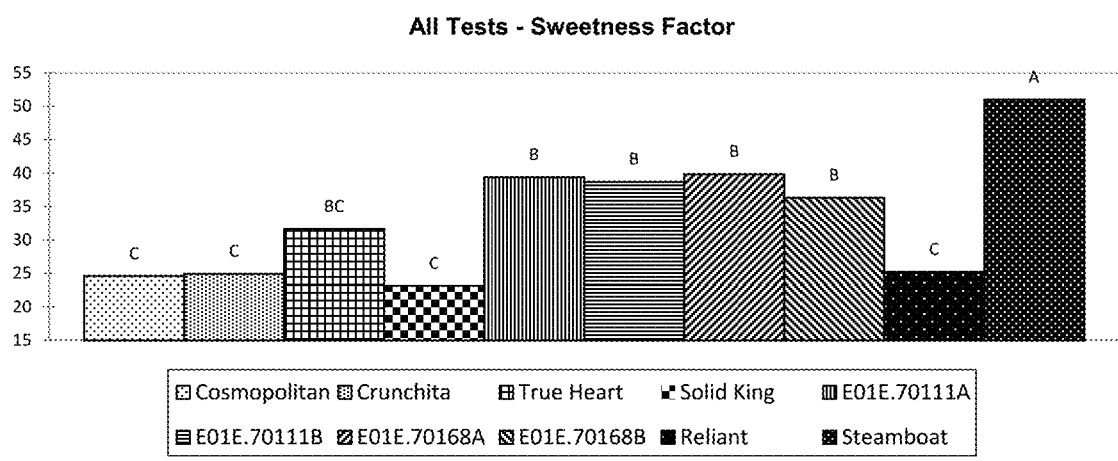

The large scale trial described in Example 5 was also used to evaluate the nutritional characteristics of the ten lettuce varieties of different types.
Materials and Methods
  Lettuce varieties and tests: Lettuce varieties and tests were as in Example 5.
  Growth and harvesting: Growth and harvesting were as in Example 5.
  Nutritional characterization: The same six of the twelve harvested plants (i.e., the same six plants used for morphological characterization in Example 5) were evaluated for nutritional characteristics. At the beginning of each test, every variety received a random lab number that was used for all evaluations in order to guarantee unbiased assessments. Morphological evaluations were performed under natural light and at room temperature (68° F.; 20° C.). For each test, evaluations of all lettuce varieties were conducted in a random order over a period not longer than 30 hours. In order to maintain the lettuces in optimal conditions between evaluations, lettuces were kept at 41° F. (5° C.), and then brought to room temperature. Data was taken by a postharvest researcher and immediately transferred to a computer for use in preparing analytical graphs and conducting statistical analyses.
  Measurement of ° brix: ° Brix measurement was done using the temperature-corrected Mettler Toledo Refractometer 30GS (0.1% brix resolution). Around 300 g of lettuce plant material (mix of lettuce tissues including external, mid, and internal leaves, and upper and lower parts of each leaf type) was cut and mixed. Approximately 200 g of this mix of lettuce tissues were juiced with a Nutribullet Pro 900 series (MagicBullet) and three drops of this juice were immediately analyzed for ° brix. The average of three ° brix measurements was considered the average ° brix of that lettuce. Six lettuces per variety and per test were analyzed in the study.
  Measurement of individual sugars: Around 300 g of lettuce plant material (mix of lettuce tissues including external, mid, and internal leaves, and upper and lower parts of each leaf type) was cut and mixed. Approximately 200 g of this mix of lettuce tissues were juiced with a Nutribullet Pro 900 series (MagicBullet) and 2 ml of juice was immediately analyzed for individual sugars using the Sucrose/Fructose/Glucose Assay Kit from Megazyme (UV-method, with spectrophotometer and 1.5 ml cuvettes). The average of the three technical repetitions of sugar measurements was considered the average sugars of that lettuce. Six lettuces per variety and per test were analyzed in the study. The sweetness factor formula was used to calculate the sweetness factor: Sweetness factor=0.75*glucose+1*sucrose+1.75*fructose.
  Measurement of percentage of dry matter weight: Around 300 g of lettuce plant material (mix of lettuce tissues including external, mid, and internal leaves, and upper and lower parts of each leaf type) was cut and mixed. Approximately 80 g of this mix were separated from the rest and three batches of 25 g were accurately weighed and then immediately put in an oven at 55° C. After 48 hours (or the point when final weight no longer changed), samples were weighed again. The percentage of dry matter weight was calculated as the ratio of dry weight to fresh weight multiplied by 100. The average of the three technical repetitions of dry matter measurements was considered the average dry matter weight of that lettuce. Six lettuces per variety and per test were analyzed in the study.
Results
  Measurement of ° Brix: ° Brix is generally used as an indicator of the sweetness of fruits and vegetables, as it is a simple method for measuring the percentage of total soluble solids concentration. A higher ° Brix value indicates a higher amount of dissolved solids such as sucrose, glucose, and fructose, as well as vitamins, minerals, amino acids, proteins, hormones and other nutrients in the vegetable. It is estimated that in a healthy fruit or vegetable, approximately 80% of the ° Brix is represented by the natural sugars (i.e., sucrose, glucose, and fructose). ° Brix analysis results for all ten tested varieties across all four tests are shown in FIG. 21. These results show that the romaine and cosberg varieties had a lower ° Brix of about 4-4.5, while the iceberg varieties had a range of ° Brix from about 4.5 ('Reliant') to over 6 ('Steamboat'). The upright heading iceberg varieties consistently had an intermediate ° Brix of about 5-5.5.
  Measurement of individual sugars: Although ° Brix provides a general overview, to evaluate the sweetness of a product, it is necessary to study the individual sugars. Reducing sugars (glucose and fructose) are the major components of the soluble solids measured by ° Brix; sucrose is also present, but in very small quantities. The sweetness factor (i.e., sweetness perceived by the consumer) is dependent on the percentage of each of these three sugars relative to the total sugar content, since not all sugars are perceived with the same intensity. The sweetness of fructose is perceived earlier than that of sucrose or glucose, and the taste sensation reaches a peak (higher than that of sucrose) and diminishes more quickly than that of sucrose. Fructose can also enhance other flavors in the system. The sweetness factor formula takes into account the different perceptions of sweetness elicited by each of the three sugars.
  FIG. 22A shows ANOVA analysis of the means of glucose, fructose, and sucrose measurements in g/l from all tests (i.e., Tests 1-4). Glucose amounts were comparable between all of the varieties, with romaine and cosberg varieties having the lowest amount of glucose (except romaine variety 'True Heart'). Fructose amounts were also comparable between all of the varieties, and again the romaine and cosberg varieties had the lowest amounts, as did one iceberg variety ('Reliant'). Sucrose amounts differed more clearly between the different lettuce varieties: romaine and cosberg, as well as iceberg 'Reliant', had the lowest sucrose levels of around 5 g/l, iceberg 'Steamboat' had the highest sucrose levels of around 20 g/l, and upright heading iceberg had intermediate sucrose levels around 10-15 g/l. Total sugar measurements, shown in FIG. 22B, were similarly distributed. Significant differences in amounts were seen between the romaine and cosberg varieties as well as iceberg 'Reliant' (about 20-25 g/l), iceberg 'Steamboat' (about 40 g/l), and upright heading iceberg (about 30-35 g/1). FIG. 22C shows that the calculated sweetness factor was similarly distributed between these three groups. Again, the upright heading iceberg varieties were intermediate, and had a sweetness factor of about 40.

Figure 23:
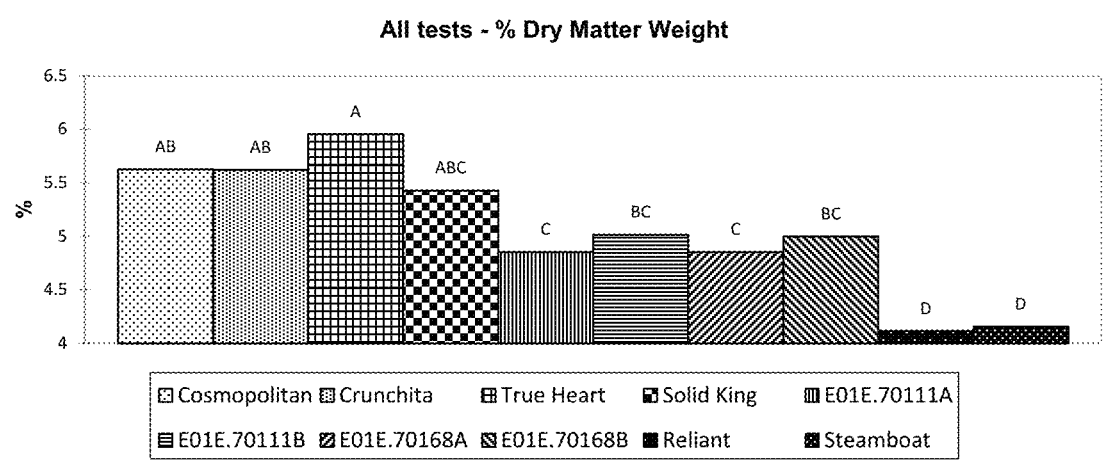
FIG. 23 shows ANOVA analysis of the means of percentage of dry matter weight measurements across all tests (i.e., Tests 1-4). The bars depict the means, each lettuce variety is shown as a differently-patterned bar (key at bottom of graph; from left to right, bars correspond to lettuce varieties 'Cosmopolitan', 'Crunchita', 'True Heart', 'Solid King', 'E01E.70111' Lot A, 'E01E.70111' Lot B, 'E01E.70168' Lot A, 'E01E.70168' Lot B, 'Reliant', and 'Steamboat'), and significantly different means between varieties are indicated by different letters at the top of the bar.

Measurement of percentage of dry matter weight: While total solid measurements as described above comprise only soluble solids (e.g., sugars, organic acids, lipids, minerals and pigments; measured with ° Brix), percent dry matter content includes soluble and insoluble solids (e.g., sugars, organic acids, lipids, minerals, pigments, proteins, cellulose, hemicellulose, pectins and polysaccharides). FIG. 23 shows ANOVA analysis of the means of percentage of dry matter weight from all tests (i.e., Tests 1-4). These results clearly show that the percentage of dry matter weight was significantly lower for the two iceberg varieties, at about 4%. Both romaine and cosberg varieties had the highest percentages, at over 5.25%. Upright heading iceberg varieties had intermediate percentages, at about 4.8-5%.

Summary

In summary, the nutritional characterization indicated that upright heading iceberg varieties had intermediate sweetness levels. These intermediate sweetness levels were similar to the sweetness levels of iceberg varieties, which are valued by consumers for their sweetness, and higher than the sweetness levels of romaine and cosberg varieties.

Further, upright heading iceberg varieties had an intermediate percentage of dry matter weight. Iceberg lettuce varieties tend to have lower dry matter weight values than romaine and cosberg varieties. This was seen in the dry matter weight percentage results, which showed romaine and cosberg varieties to have significantly higher percentages of dry matter weight than iceberg varieties. The intermediate percentage of dry matter weight of the upright heading iceberg varieties indicates that these varieties have a higher soluble and insoluble solids (sugars, organic acids, lipids, minerals, pigments, proteins, cellulose, hemicellulose, pectins and polysaccharides) than iceberg varieties.

Example 7: Large Scale Field Trial—Shelf Life Evaluations

The large scale trial described in Example 5 was also used to evaluate the shelf life of the ten lettuce varieties of different types.

Materials and Methods

Lettuce varieties and tests: Lettuce varieties and tests were as in Example 5.

Growth and harvesting: Lettuce varieties and tests were as in Example 5.

Shelf life evaluation: The other six of the twelve harvested plants (i.e., not the same six plants used for morphological and nutritional characterization in Examples 5 and 6) were used for shelf life evaluation. At the beginning of each test, every variety received a random lab number that was used for all evaluations in order to guarantee unbiased assessments. Plants were processed as described below. Standard lettuce packaging bags were used (30 PA 200*300 unperforated) with modified atmosphere conditions (around 2% oxygen inside the sealed bag), and 135 g plant material per bag. Bags were evaluated (i.e., visual evaluations and aroma evaluations) by opening a minimum of two bags per lab number every two days. The initial evaluation was done at day six after harvest and evaluation continued until the plant material was fully decayed.

Figure 24A:
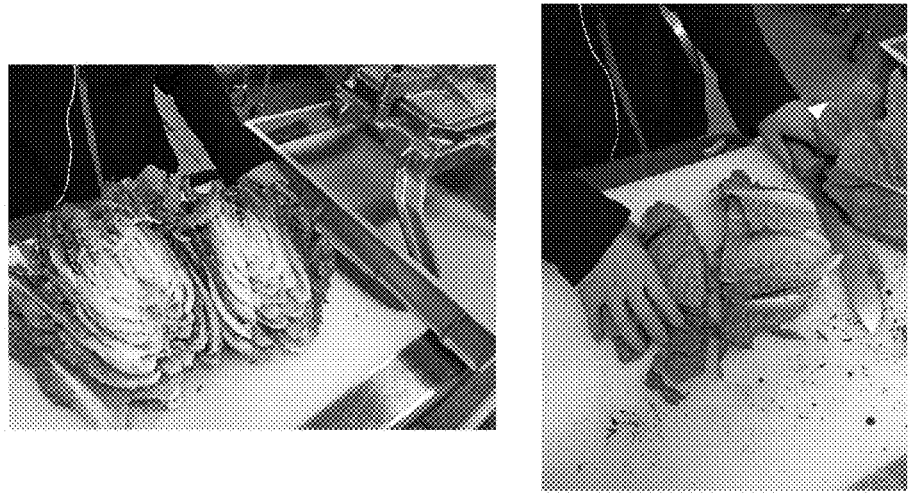
FIGS. 24A-24G show exemplary images of the plant material processing procedure for shelf life evaluation.
Figure 24B:
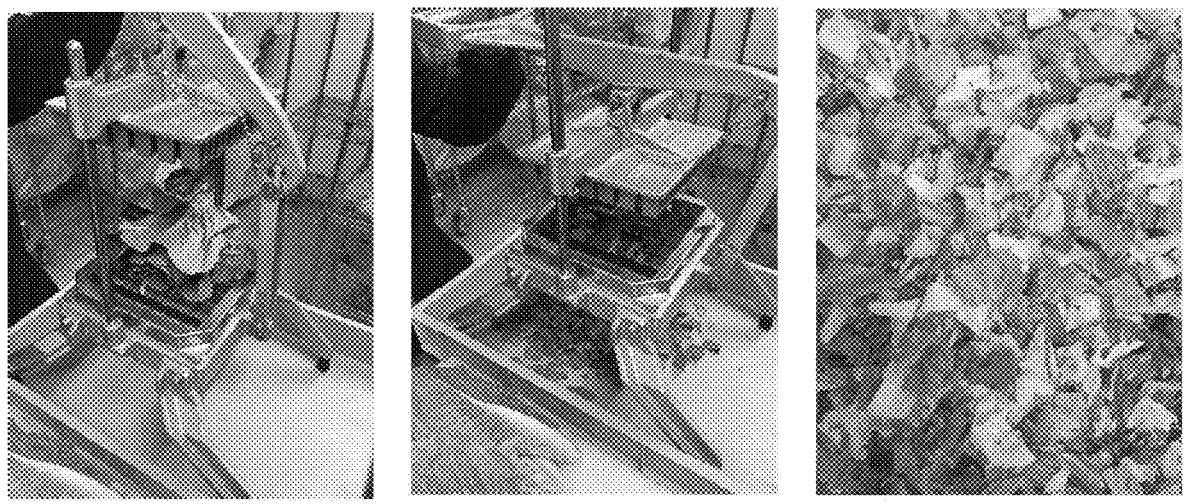
Figure 24C:

Preparation of plant material for shelf life evaluation: Individual lettuces were processed with the Nemco 55650-1½" Slice Easy lettuce cutter. The cutter was cleaned and disinfected between varieties to avoid mixing materials and/or spreading diseases. Exemplary images of plant material processing are shown in FIGS. 24A-24B. Immediately after cutting, plant material was disinfected and dried. First, the plant material was washed with bleach for 30 seconds (50 ppm NaOCl diluted in water at 41F (5° C.); the pH of the disinfection water was between 6 and 7 (lowered using HCl as needed)). Second, the plant material was rinsed with water at 41° F. (5° C.) for 30 seconds. Third, the plant material was collected in colanders to drain. Fourth, the plant material was centrifuged for 4 minutes in a Delfield SALD-1 Salad Dryer 20 Gallons to dry. Exemplary images of plant material disinfection and drying are shown in FIG. 24C.

Figure 24D:
Figure 24E:
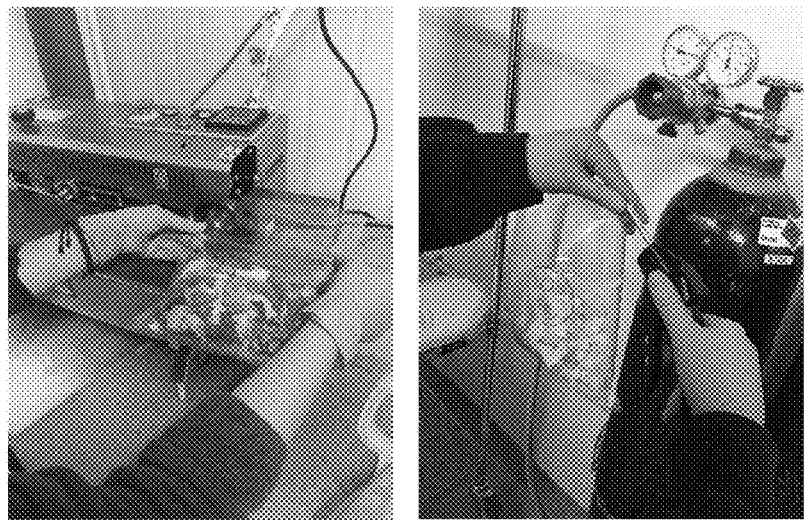
Figure 24F:

After drying, the plant material was filled into standard lettuce bags (30 PA 20429580 cm; suitable for modified atmospheric conditions). Plant material of each variety, consisting of material from a mixture of the lettuce heads from the same variety, washed and centrifuged together, was weighed and packaged to produce a total of 25 bags containing 135 g of plant material each. An exemplary image of plant material weighing and packaging is shown in FIG. 24D. Modified atmospheric conditions (MAP) were used in the bags, because MAP is the standard market practice (large cut surfaces need low oxygen to prevent oxidation and high respiring material needs air). MAP was achieved by sealing bags with a band sealer at 180-200° C. Next, a corner on the top of the bag was cut and used to vacuum the bags and then flush them with food grade nitrogen three consecutive times to reduce the oxygen content within the bag to less than 2%. This process was performed with a three-way valve with vacuum hoses on each side: one to connect with the nitrogen cylinder (provided by Airgas), one to connect to the vacuum pump, and one equipped with a hose connector or pipette tip to enter the bag. This setup was used to ensure that there was no leaking between the entrance of the bag and the tip. After this process, the bag was completely sealed again. Exemplary images of the process to achieve MAP and the sealed bags with MAP are shown in FIGS. 24E-24F.

Figure 24G:

Evaluation of percentage of processing damage: Evaluation of percentage of processing damage was based on visual quality evaluations. Blind tests were performed by the same expert evaluator in the same laboratory under the same light and at the same time of the day. Evaluations were performed at the beginning of storage, usually between 4 and 12 days after processing, five bags per variety were evaluated at a time. Processing damage was characterized as damage resulting directly from the plant material preparation process (i.e., cutting, disinfecting, and drying the plant material). Data was reported as percentage of physically damaged leaves in the bag, independent of the extent of the damage. An exemplary image of packaged plant material in storage is shown in FIG. 24G.

Evaluation of days of shelf life: Evaluation of days of shelf life was based on overall visual quality evaluations. Blind tests were performed by the same expert evaluator in the same laboratory under the same light and at the same time of the day. Evaluation was done every other day (e.g., days 8, 10, 12, 14, 16, etc.), and five bags per variety were evaluated at a time. Days were counted from the day of harvest to the day the lettuce bags were not marketable anymore. Characteristics including overall visual quality, decay, browning, loss of texture, and loss of freshness (including aroma deterioration) were taken into account. If aroma was being evaluated, bags were opened and allowed to equilibrate at room temperature for 15-30 minutes before evaluation. The end of shelf life was the day on which that individual bag of lettuce would no longer be accepted for consumption, and this could be on the basis of any one of these characteristics or a combination of one or more of these characteristics. Each bag was individually evaluated and scored for days of shelf life without information from previous days. At the end of the shelf life evaluation, after 50 days of storage, processed plant material of each variety was photographed from two bags, one was photographed inside the packaging and the other was photographed after plant material had been removed from the packaging (FIGS. 27A-27J).

Results

Figure 25A:
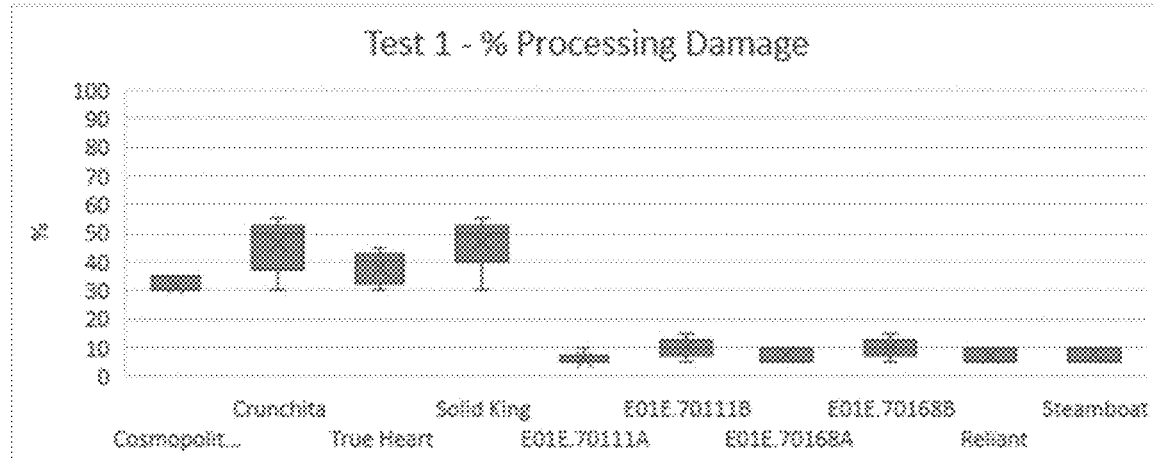
FIGS. 25A-25F show the analysis of the means of percentage of processing damage data from Tests 1-4.
Figure 25B:
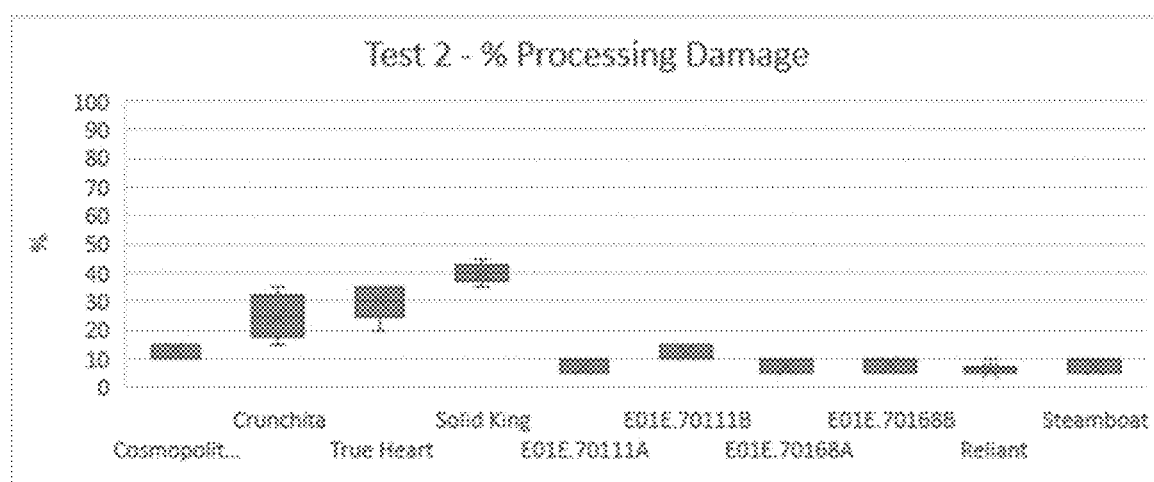
Figure 25C:
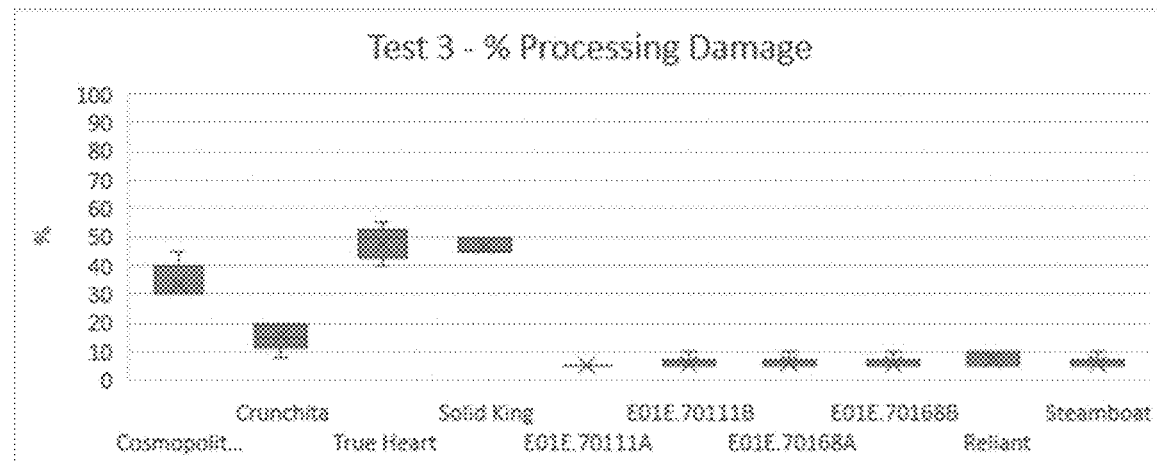
Figure 25D:
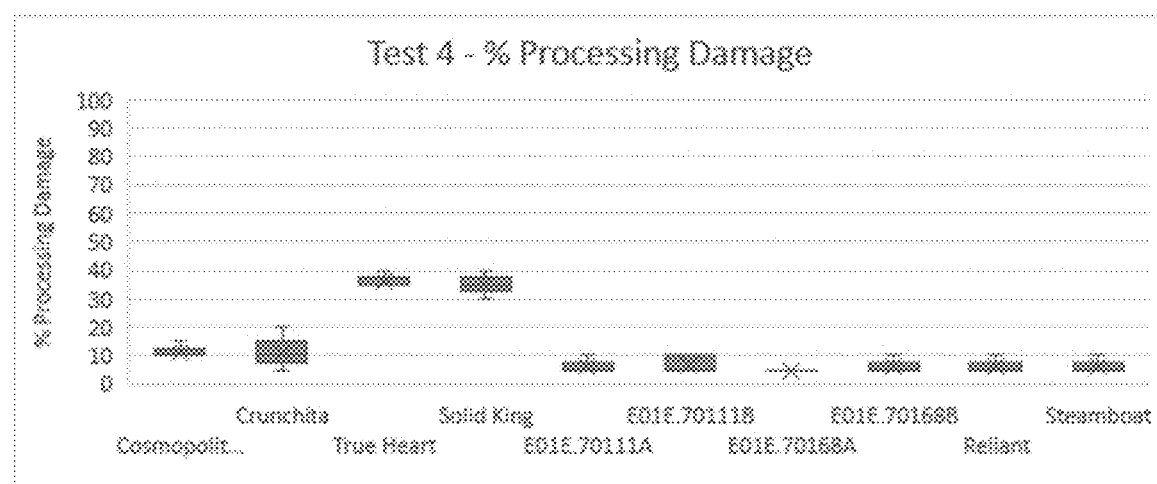
Figure 25E:
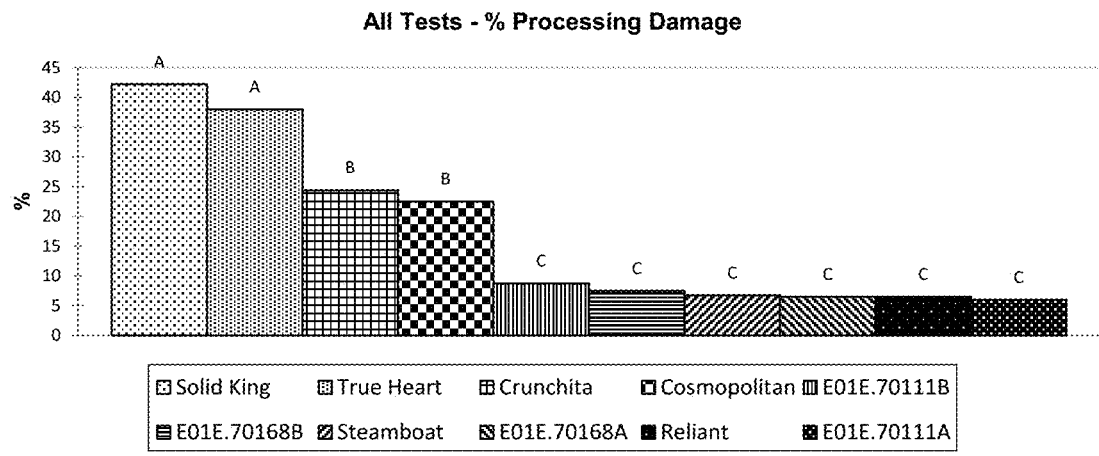
Figure 25F:
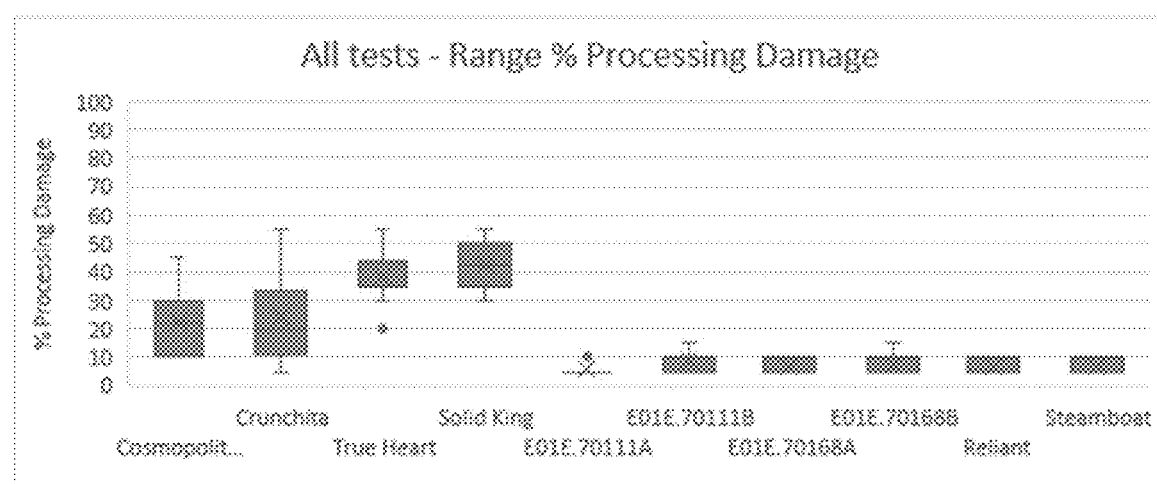

Evaluation of percentage of processing damage: FIGS. 25A-25D, and 25F show box and whisker charts of percentage of processing damage data from all four tests. ANOVA analysis results of the means of percentage of processing damage are shown in FIG. 25E. FIG. 25F, depicting the range of percentage of processing damage across Tests 1-4, clearly shows that romaine and cosberg varieties were more susceptible to processing damage, in some cases reaching values of over 50%. In contrast, iceberg and upright heading iceberg varieties were barely damaged during processing, and generally had 10% or less damage. In addition, iceberg and upright heading iceberg had a smaller range of percent processing damage across Tests 1-4. These differences in percent processing damage were statistically significant, and divided into three distinct categories (FIG. 25E). The romaine varieties had the highest percentage of processing damage, at about 37-42%. The cosberg varieties had an intermediate percentage of processing damage, at about 20-22%. The iceberg and upright heading iceberg varieties had a low percentage of processing damage, ranging from 5-10%. Notably, iceberg and upright heading iceberg formed one category; there was no clear difference between the two different iceberg types.

Figure 26A:
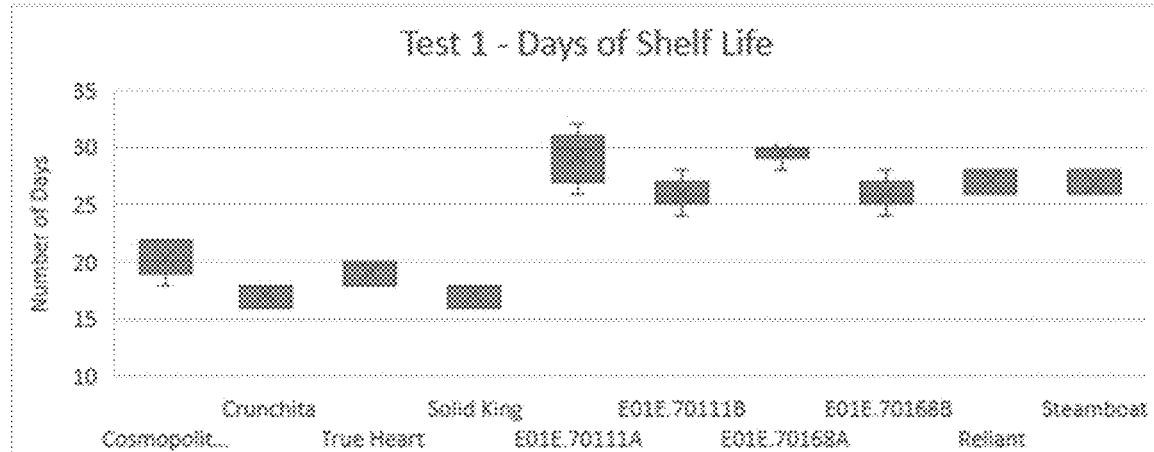
FIGS. 26A-26F show the analysis of the days of shelf life data from Tests 1-4.
Figure 26B:
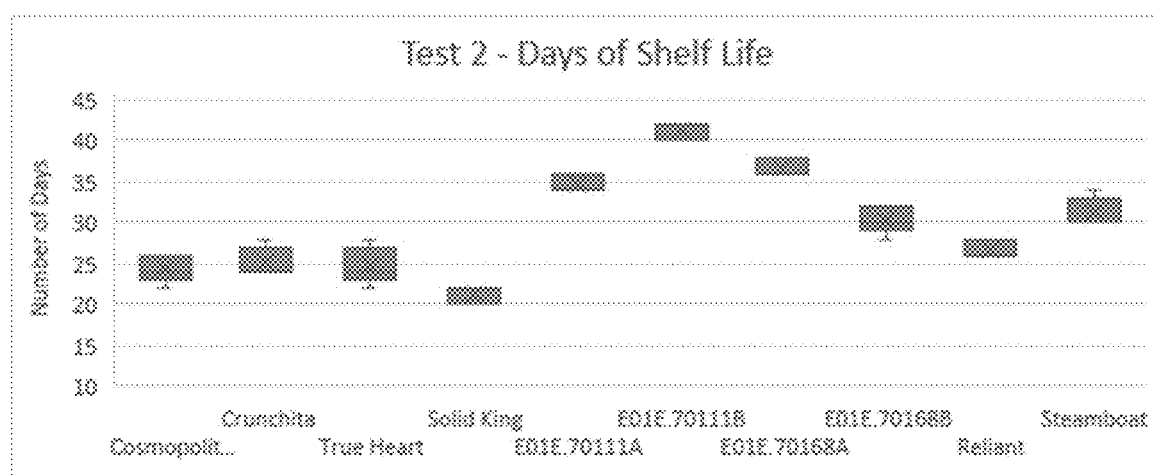
Figure 26C:
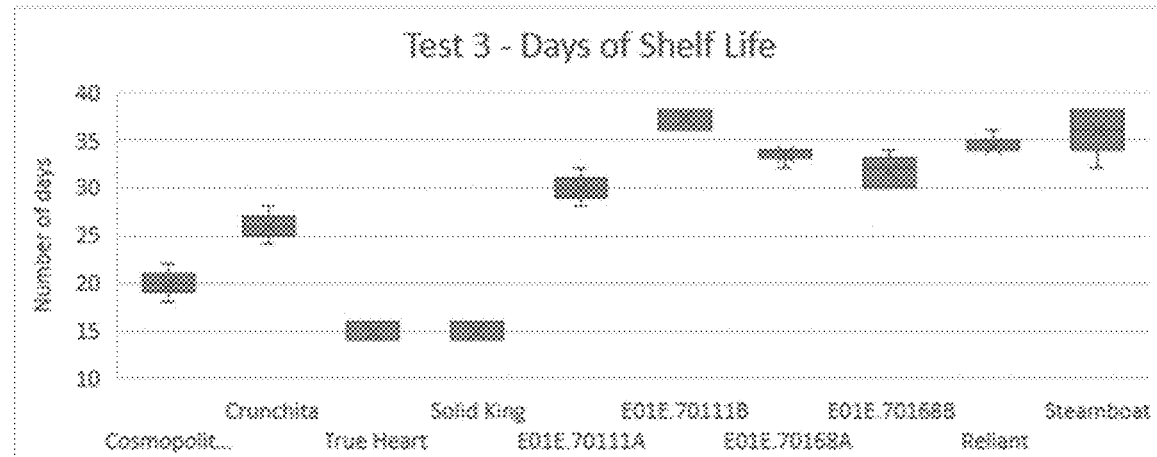
Figure 26D:
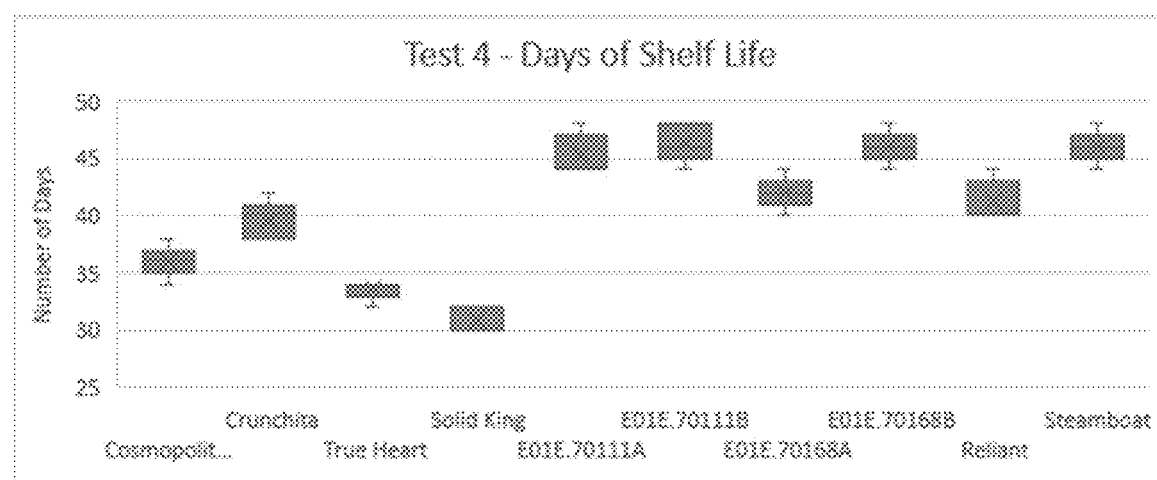
Figure 26E:
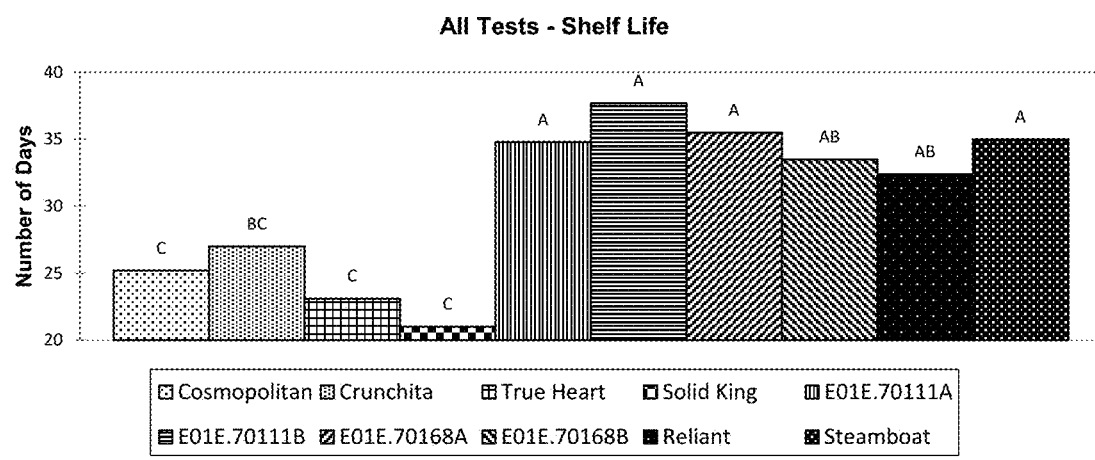
Figure 26F:
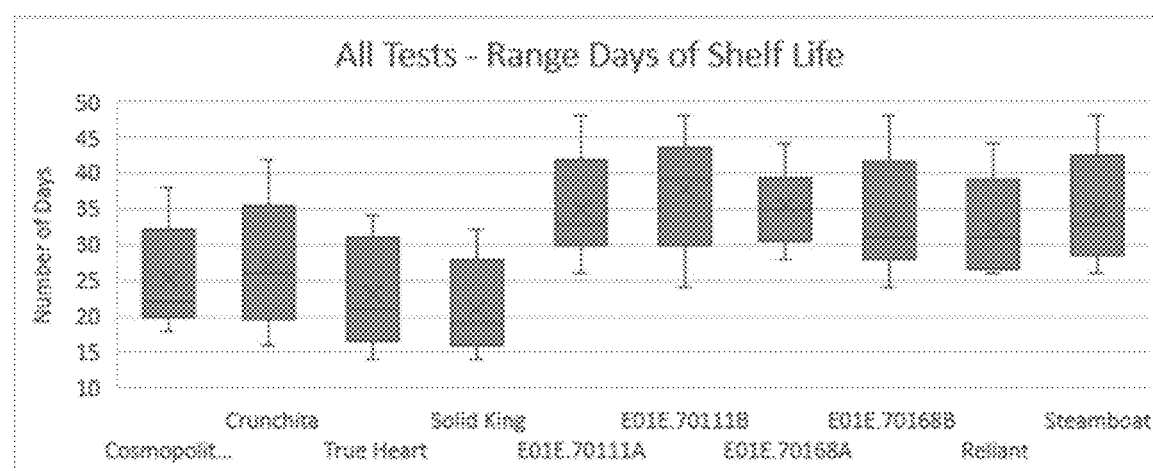

Evaluation of days of shelf life: FIGS. 26A-26D, and 26F show box and whisker charts of days of shelf life data from all four tests. ANOVA analysis results of the means of days of shelf life data are shown in FIG. 26E. FIG. 26F, depicting the range of days of shelf life across Tests 1-4, clearly shows that romaine and cosberg varieties had shorter shelf lives than iceberg and upright heading iceberg varieties. These differences in shelf life were statistically significant, and divided into two distinct categories (FIG. 26E). The romaine and cosberg varieties had relatively short shelf lives, with about 20-27 days passing before they were rated as no longer acceptable for consumption. In contrast, the iceberg and upright heading iceberg varieties had longer shelf lives of about 30-37 days. As with the percentage of processing damage evaluation, iceberg and upright heading iceberg formed one category.

Figure 27A:
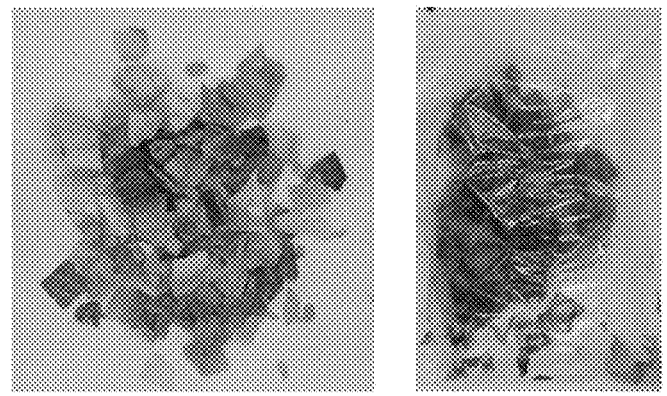
FIGS. 27A-27J show exemplary images of processed and packaged plant material after 50 days of storage.
Figure 27B:
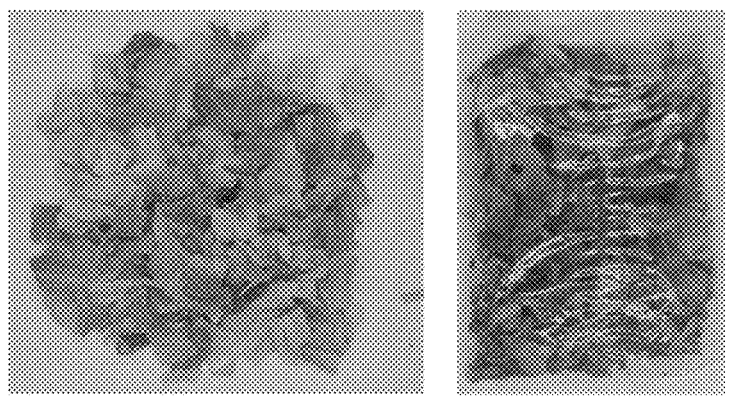
Figure 27C:
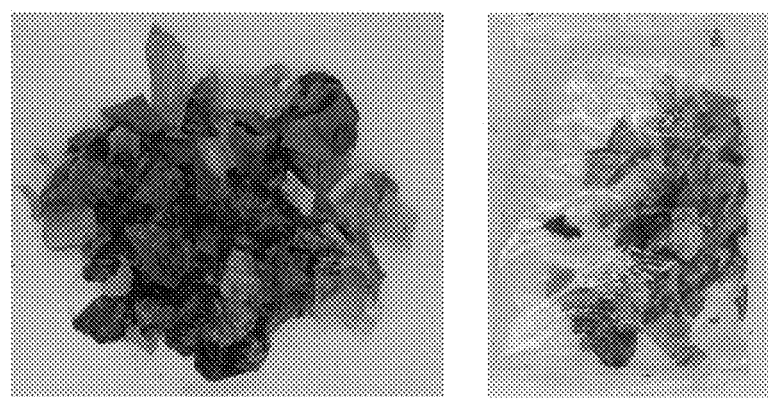
Figure 27D:
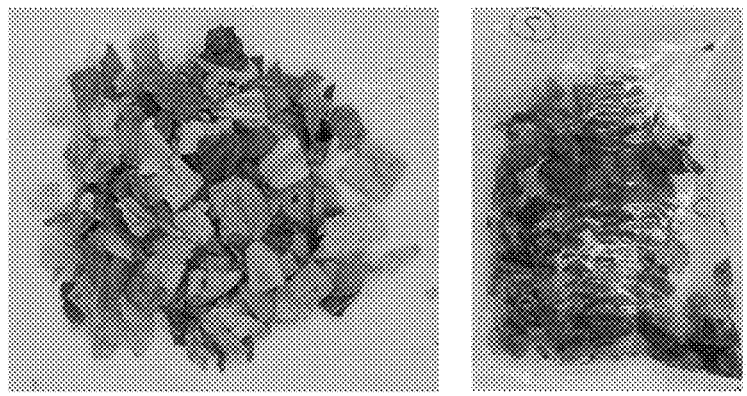
Figure 27E:
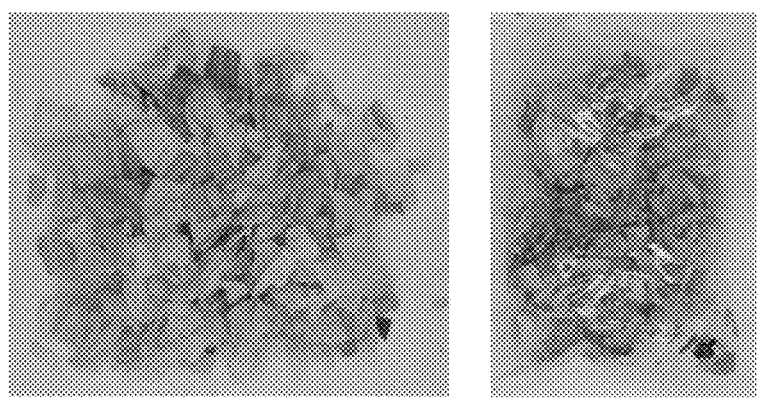
Figure 27F:
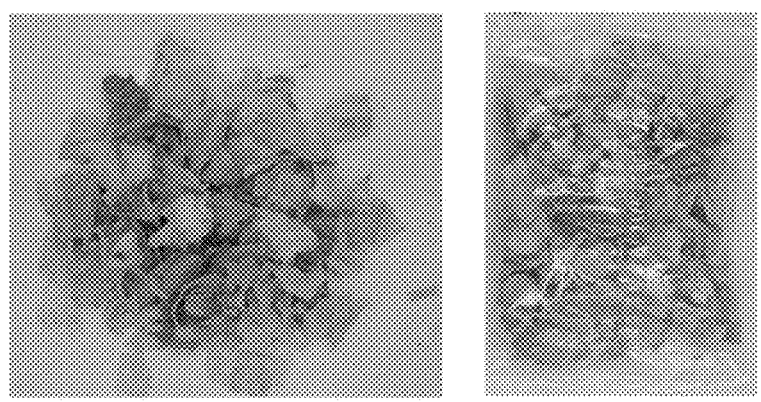
Figure 27G:
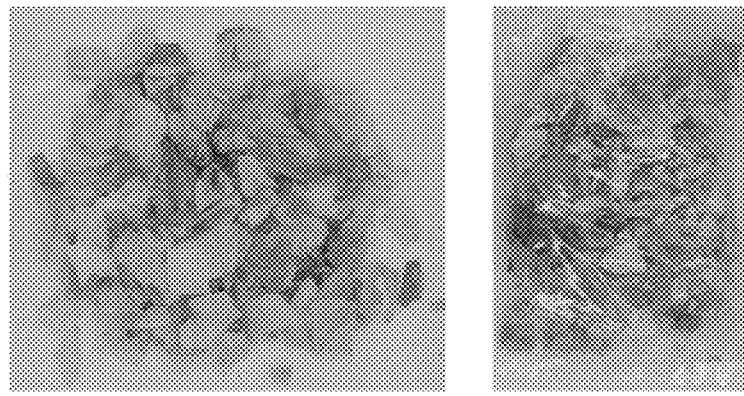
Figure 27H:
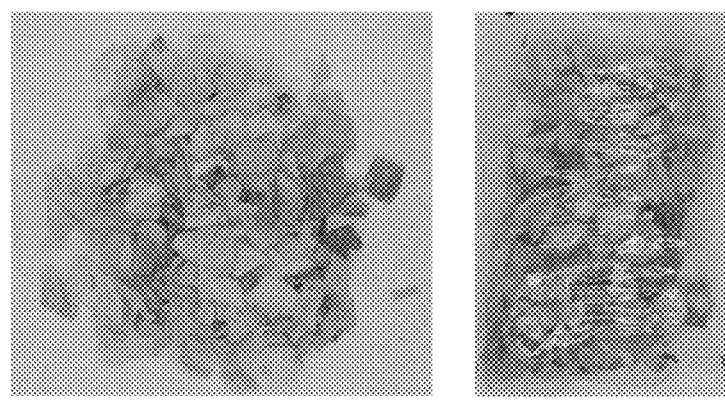
Figure 27I:
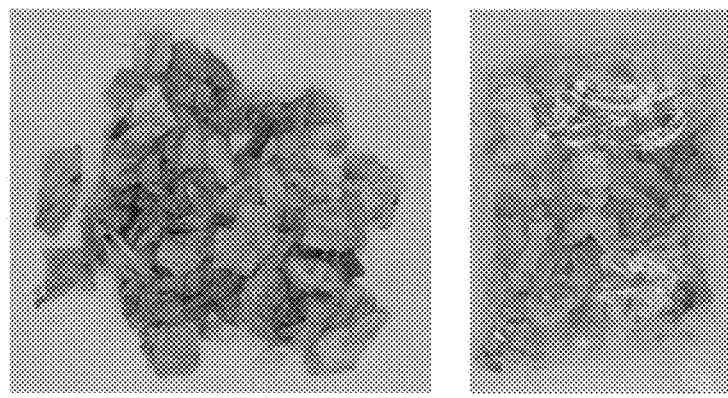
Figure 27J:
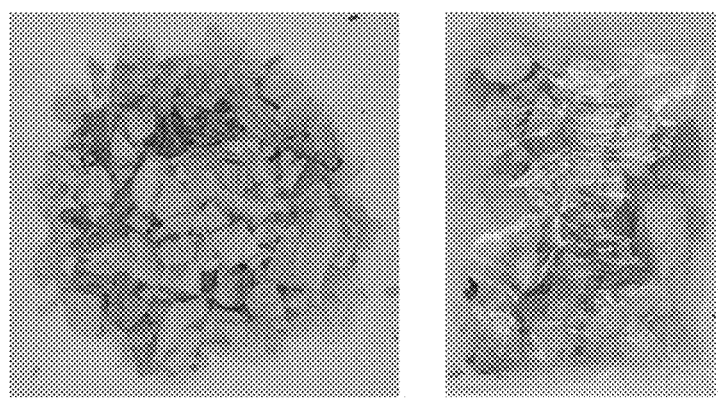

Clear differences in visual appearance were also seen at the end of the shelf life trial (i.e., after 50 days of storage). FIGS. 27C-27D show that the romaine varieties ('True Heart' and 'Solid King') had browning, wilting, and liquid development in the bag. One of the cosberg varieties ('Cosmopolitan', FIG. 27A) had a similar appearance, while the other cosberg variety ('Crunchita', FIG. 27B) appeared more green and fresh. Some samples of one of the iceberg varieties had clear browning on its leaves, but most of the bags appeared green and fresh ('Reliant', FIG. 27I). The remaining iceberg variety ('Steamboat', FIG. 27J), as well as all of the upright heading iceberg varieties (FIGS. 27E-27H), had a green and fresh appearance.

Summary

In summary, the shelf life evaluation results showed that upright heading iceberg varieties are suitable for industrial processing and packaging. For one, the upright heading iceberg varieties had a low percentage of processing damage, which was comparable to the iceberg varieties. For another, the upright heading iceberg varieties had a long shelf life. Moreover, in this study, most of the samples of the upright heading iceberg varieties maintained a green and fresh appearance even after 35 days of storage. These results indicate that upright heading iceberg varieties are sufficiently robust for industrial processing and packaging. Moreover, they have a long shelf life, making these varieties suitable for longer-term storage and distribution.

What is claimed is:

1. A lettuce seed selected from the group consisting of a lettuce seed designated as 'E01E.70111' Lot A, representative sample of seed having been deposited under NCIMB Accession Number 42957; a lettuce seed designated as 'E01E.70111' Lot B, representative sample of seed having been deposited under NCIMB Accession Number 42962; a lettuce seed designated as 'E01E.70168' Lot A, representative sample of seed having been deposited under NCIMB Accession Number 42958; and a lettuce seed designated as 'E01E.70168' Lot B, representative sample of seed having been deposited under NCIMB Accession Number 42963.

2. A lettuce plant produced by growing the seed of claim 1.

3. A plant part from the plant of claim 2.

4. The plant part of claim 3, wherein the part is a head, a leaf, or a portion thereof.

5. The plant part of claim 4, wherein the part is a head.

6. An $F_1$ hybrid lettuce plant having 'E01E.70111' Lot A as a parent, wherein 'E01E.70111' Lot A is grown from the seed of claim 1.

7. An $F_1$ hybrid lettuce plant having 'E01E.70111' Lot B as a parent, wherein 'E01E.70111' Lot B is grown from the seed of claim 1.

8. An $F_1$ hybrid lettuce plant having 'E01E.70168' Lot A as a parent, wherein 'E01E.70168' Lot A is grown from the seed of claim 1.

9. An $F_1$ hybrid lettuce plant having 'E01E.70168' Lot B as a parent, wherein 'E01E.70168' Lot B is grown from the seed of claim 1.

10. A pollen grain or an ovule of the plant of claim 2.

11. A tissue culture of the plant of claim 2.

12. A lettuce plant regenerated from the tissue culture of claim 11, wherein the plant has all of the morphological and physiological characteristics of a lettuce plant produced by growing seed designated as 'E01E.70111' Lot A, representative sample of seed having been deposited under NCIMB Accession Number 42957.

13. A lettuce plant regenerated from the tissue culture of claim 11, wherein the plant has all of the morphological and physiological characteristics of a lettuce plant produced by growing seed designated as 'E01E.70111' Lot B, representative sample of seed having been deposited under NCIMB Accession Number 42962.

14. A lettuce plant regenerated from the tissue culture of claim 11, wherein the plant has all of the morphological and physiological characteristics of a lettuce plant produced by growing seed designated as 'E01E.70168' Lot A, representative sample of seed having been deposited under NCIMB Accession Number 42958.

15. A lettuce plant regenerated from the tissue culture of claim 11, wherein the plant has all of the morphological and physiological characteristics of a lettuce plant produced by growing seed designated as 'E01E.70168' Lot B, representative sample of seed having been deposited under NCIMB Accession Number 42963.

* * * * *